(12) United States Patent
Connor

(10) Patent No.: US 11,850,052 B2
(45) Date of Patent: Dec. 26, 2023

(54) DRY EEG ELECTRODE FOR USE ON A HAIR-COVERED PORTION OF A PERSON'S HEAD

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 120 days.

(21) Appl. No.: 17/714,988

(22) Filed: Apr. 6, 2022

(65) Prior Publication Data

US 2022/0233124 A1    Jul. 28, 2022

Related U.S. Application Data

(63) Continuation-in-part of application No. 17/665,086, filed on Feb. 4, 2022, now Pat. No. 11,662,819, and a continuation-in-part of application No. 17/136,117, filed on Dec. 29, 2020, now abandoned, and a continuation-in-part of application No. 16/554,029, filed on Aug. 28, 2019, now abandoned, said application No. 17/136,117 is a continuation-in-part of application No. 16/554,029, filed on Aug. 28, 2019, now abandoned, which is a continuation-in-part of application No. 16/022,987, filed on Jun. 29, 2018, now Pat. No. 11,172,859, which is a continuation-in-part of application No. 15/136,948, filed on Apr. 24, 2016, now Pat. No. 10,234,942, which is a continuation-in-part of application No. 14/599,522, filed on Jan. 18, 2015, now Pat. No. 9,814,426.

(Continued)

(51) Int. Cl.
  *A61B 5/291* (2021.01)
  *A61B 5/00* (2006.01)
  *A61B 5/251* (2021.01)

(52) U.S. Cl.
  CPC .............. *A61B 5/291* (2021.01); *A61B 5/251* (2021.01); *A61B 5/6814* (2013.01)

(58) Field of Classification Search
  CPC ....... A61B 5/291; A61B 5/251; A61B 5/6814; A61B 5/268; A61B 2562/0209; A61B 5/256; A61B 5/257; A61B 5/6803; G06F 2203/0381; G06F 3/015; G06F 3/017; G16H 20/30; G16H 40/63; G02C 5/14; G02C 11/10
  See application file for complete search history.

(56) References Cited

U.S. PATENT DOCUMENTS 8,798,710 B2   8/2014  Chi
9,314,183 B2   4/2016  Chi et al.
(Continued)

OTHER PUBLICATIONS (Acar, 2019), "Wearable and Flexible Textile Electrodes for Biopotential Signal Monitoring: A Review," Electronics, 2019, 8(5), 479.

(Continued)

*Primary Examiner* — Jacqueline Cheng
*Assistant Examiner* — Tho Q Tran

(57) ABSTRACT

This invention is a dry EEG electrode with an articulated distal base and/or a plurality of articulated conductive proximal protrusions which penetrate between strands of hair for good electromagnetic contact without causing discomfort or skin irritation.

1 Claim, 36 Drawing Sheets

Related U.S. Application Data

(60) Provisional application No. 62/972,692, filed on Feb. 11, 2020, provisional application No. 62/851,904, filed on May 23, 2019, provisional application No. 62/796,901, filed on Jan. 25, 2019, provisional application No. 62/791,838, filed on Jan. 13, 2019, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015, provisional application No. 61/932,517, filed on Jan. 28, 2014.

(56) References Cited

U.S. PATENT DOCUMENTS

| | | |
|---|---|---|
| 10,842,404 B2 | 11/2020 | Mercier et al. |
| 2009/0134887 A1 | 5/2009 | Hu et al. |
| 2010/0198042 A1* | 8/2010 | Popescu ............... A61B 5/6814 600/383 |
| 2014/0107458 A1 | 4/2014 | Op De Beeck et al. |
| 2015/0088224 A1 | 3/2015 | Goldwasser et al. |
| 2015/0141788 A1 | 5/2015 | Chi et al. |
| 2015/0367122 A1 | 12/2015 | Morshed et al. |
| 2016/0089045 A1 | 3/2016 | Sadeghian-Motahar |
| 2016/0143554 A1 | 5/2016 | Lim et al. |
| 2016/0174859 A1 | 6/2016 | Oudenhoven et al. |
| 2017/0112444 A1 | 4/2017 | Lin et al. |
| 2017/0150925 A1 | 6/2017 | Jung |
| 2017/0172447 A1 | 6/2017 | Mitra et al. |
| 2017/0224990 A1 | 8/2017 | Goldwasser et al. |
| 2017/0258353 A1 | 9/2017 | Jovanovic et al. |
| 2017/0258400 A1 | 9/2017 | Jovanovic et al. |
| 2018/0028089 A1* | 2/2018 | Nishiwaki ............... A61B 5/369 |
| 2018/0049639 A1 | 2/2018 | Tian |
| 2018/0153470 A1 | 6/2018 | Gunasekar et al. |
| 2018/0192906 A1 | 7/2018 | Soulet De Brugiere et al. |
| 2018/0235499 A1 | 8/2018 | Zorman et al. |
| 2018/0235500 A1 | 8/2018 | Lee et al. |
| 2018/0348863 A1 | 12/2018 | Aimone et al. |
| 2018/0353096 A1 | 12/2018 | Mercier et al. |
| 2019/0000338 A1 | 1/2019 | Van Den Ende et al. |
| 2019/0239807 A1* | 8/2019 | Watson ............... A61B 5/0006 |
| 2019/0328261 A1 | 10/2019 | Shakour et al. |
| 2020/0019243 A1 | 1/2020 | Aimone et al. |
| 2020/0159324 A1 | 5/2020 | Keller et al. |
| 2020/0237249 A1 | 7/2020 | Gunasekar et al. |
| 2020/0281527 A1 | 9/2020 | Gunasekar et al. |
| 2021/0038106 A1 | 2/2021 | Ramakrishnan et al. |
| 2021/0109594 A1 | 4/2021 | Keller et al. |
| 2021/0200313 A1 | 7/2021 | Aimone et al. |
| 2021/0282695 A1 | 9/2021 | Goldstein et al. |
| 2021/0338128 A1 | 11/2021 | Le Lous et al. |
| 2022/0000407 A1 | 1/2022 | Ludwig et al. |
| 2022/0004257 A1 | 1/2022 | Keller et al. |
| 2022/0015701 A1 | 1/2022 | Gunasekar et al. |
| 2022/0022813 A1 | 1/2022 | Gunasekar et al. |

OTHER PUBLICATIONS (Casson, 2019), "Wearable EEG and Beyond," Biomedical Engineering Letters, Jan. 2019, 9(1), 53-71.
(Chen, 2014), "Soft, Comfortable Polymer Dry Electrodes for High Quality ECG and EEG Recording," Sensors, Dec. 10, 2014, 14(12), 23758-80.
(Chen, 2016), "Polymer-Based Dry Electrodes for Biopotential Measurements," Thesis, Arenberg Doctoral School, 2016.
(Chi, 2010), "Dry-Contact and Noncontact Biopotential Electrodes: Methodological Review," IEEE Reviews in Biomedical Engineering, 2010, 3, 106-119.
(Chlaihawi, 2018), "Development of Printed and Flexible Dry ECG Electrodes," Sensing and Bio-Sensing Research, 2018, 20, 9-15.
(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6). 1365.
(Fu, 2020), "Dry Electrodes for Human Bioelectrical Signal Monitoring," Sensors, Jun. 29, 2020, 20(13), 3651.
(Gao, 2018), "Soft Pin-Shaped Dry Electrode with Bristles for EEG Signal Measurements," Sensors and Actuators, 2018, vol. 283, 348-361.
(Hsu, 2014), "Developing Barbed Microtip-Based Electrode Arrays for Biopotential Measurement," Sensors, 2014, 14(7), 12370-12386.
(Kocturova, 2019), "Comparison of Dry Electrodes for Mobile EEG System," 2019.
(Krachunov, 2016), "3D Printed Dry EEG Electrodes," Sensors, 2016, 16(10), 1635.
(Lau-Zhu, 2019), "Mobile EEG in Research on Neurodevelopmental Disorders: Opportunities and Challenges," Developmental Cognitive Neuroscience, 2019, vol. 36.
(Lee, 2015), "Reverse-Curve-Arch-Shaped Dry EEG Electrode for Increased Skin-Electrode Contact Area on Hairy Scalps," Electronics Letters, Oct. 1, 2015.
(Lopez-Gordo, 2014), "Dry EEG Electrodes," Sensors, Jul. 18, 2014, 14(7), 12847-70.
(Mota, 2013), "Development of a Quasi-Dry Electrode for EEG Recording," Sensors and Actuators, 2013, vol. 199, 310-317.
(Olesen, 2020), "Development and Assessment of Electrodes and Instrumentation for Plantar Skin Impedance Measurements," Thesis, Master in Electronics, Informatics and Technology, University of Oslo Autumn. 2020.
(Ouyang, 2021), "Application of Intrinsically Conducting Polymers in Flexible Electronics," SmartMat, Aug. 18, 2021, 2.
(Ruffini, 2008), "First Human Trials of a Dry Electrophysiology Sensor Using a Carbon Nanotube Array Interface," Sensors and Actuators, Jun. 15, 2008, 144.
(Shad, 2020), "Impedance and Noise of Passive and Active Dry EEG Electrodes: A Review," IEEE Sensors Journal, Jul. 27, 2020.
(Sunwoo, 2020), "Advances in Soft Bioelectronics for Brain Research and Clinical Neuroengineering," Matter, 2020, 3(6) 1923-1947.
(Zhang, 2020), "Fully Organic Compliant Dry Electrodes Self-Adhesive to Skin for Long-Term Motion-Robust Epidermal Biopotential Monitoring," Nature Communications, 2020, 11, 4683.

* cited by examiner

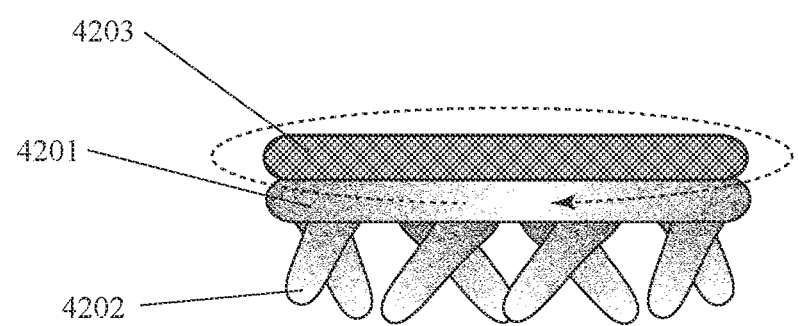
Fig. 42
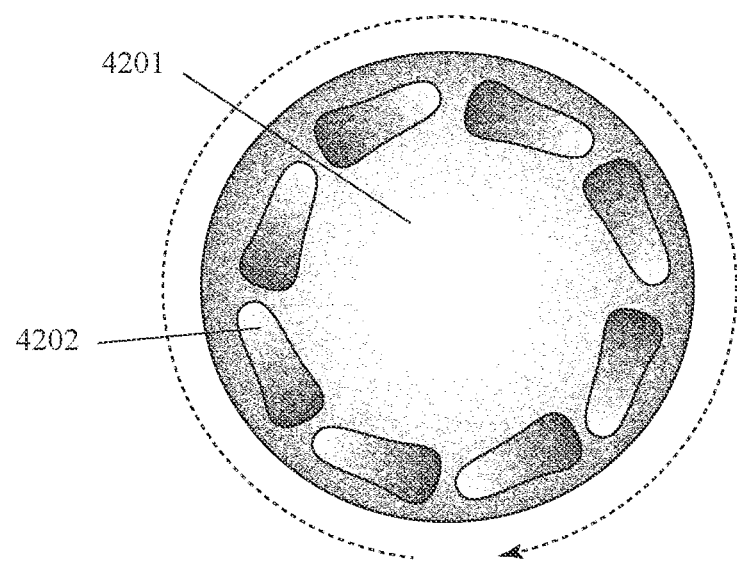

DRY EEG ELECTRODE FOR USE ON A HAIR-COVERED PORTION OF A PERSON'S HEAD

CROSS-REFERENCE TO RELATED APPLICATIONS

This application is a continuation-in-part of U.S. patent application Ser. No. 17/665,086 filed on Feb. 4, 2022. This application is a continuation-in-part of U.S. patent application Ser. No. 17/136,117 filed on Dec. 29, 2020. This application is a continuation-in-part of U.S. patent application Ser. No. 16/554,029 filed on Aug. 28, 2019.

U.S. patent application Ser. No. 17/136,117 claimed the priority benefit of U.S. provisional patent application 62/972,692 filed on Feb. 11, 2020. U.S. patent application Ser. No. 17/136,117 was a continuation-in-part of U.S. patent application Ser. No. 16/554,029 filed on Aug. 28, 2019.

U.S. patent application Ser. No. 16/554,029 claimed the priority benefit of U.S. provisional patent application 62/851,904 filed on May 23, 2019. U.S. patent application Ser. No. 16/554,029 claimed the priority benefit of U.S. provisional patent application 62/796,901 filed on Jan. 25, 2019. U.S. patent application Ser. No. 16/554,029 claimed the priority benefit of U.S. provisional patent application 62/791,838 filed on Jan. 13, 2019. U.S. patent application Ser. No. 16/554,029 was a continuation-in-part of U.S. patent application Ser. No. 16/022,987 filed on Jun. 29, 2018 which issued as U.S. Pat. No. 11,172,859 on Nov. 15, 2021.

U.S. patent application Ser. No. 16/022,987 was a continuation-in-part of U.S. patent application Ser. No. 15/136,948 filed on Apr. 24, 2016 which issued as U.S. Pat. No. 10,234,942 on Mar. 19, 2019.

U.S. patent application Ser. No. 15/136,948 claimed the priority benefit of U.S. provisional patent application 62/322,594 filed on Apr. 14, 2016. U.S. patent application Ser. No. 15/136,948 claimed the priority benefit of U.S. provisional patent application 62/303,126 filed on Mar. 3, 2016. U.S. patent application Ser. No. 15/136,948 claimed the priority benefit of U.S. provisional patent application 62/169,661 filed on Jun. 2, 2015. U.S. patent application Ser. No. 15/136,948 claimed the priority benefit of U.S. provisional patent application 62/160,172 filed on May 12, 2015. U.S. patent application Ser. No. 15/136,948 was a continuation-in-part of U.S. patent application Ser. No. 14/599,522 filed on Jan. 18, 2015 which issued as U.S. Pat. No. 9,814,426 on Nov. 14, 2017.

U.S. patent application Ser. No. 14/599,522 claimed the priority benefit of U.S. provisional patent application 61/932,517 filed on Jan. 28, 2014.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to dry EEG electrodes.

INTRODUCTION

There are numerous potential applications for incorporating EEG electrodes into wearable technology such as smart eyewear, smart earwear, smart headbands, and smart adhesive patches. However, wet EEG electrodes are not well-suited for use with such wearable technology and flat dry EEG electrodes do not work well on areas of a person's head which are covered by hair. There has been some creative innovation in the prior art in the development of dry electrodes with protrusions which penetrate between strands of hair. However, protrusions in the prior art which are sufficiently resilient and narrow to penetrate hair can be uncomfortable, cause skin irritation, and lack sufficient contact area to enable good electromagnetic communication with a person's head. There remains an unmet need for dry EEG electrodes which can be incorporated into wearable technology and work well on areas of a person's head which are covered by hair.

REVIEW OF THE RELEVANT ART

There is creative innovation underway with respect to dry EEG electrodes. For example, U.S. Pat. No. 8,798,710 (Chi, Aug. 5, 2014, "Apparatuses, Systems and Methods for Biopotential Sensing with Dry Electrodes") discloses an electrode for transferring electrical signals that includes an electrical conductor, a membrane selectively permeable to ionic conduction, and a conductive medium positioned in communication with a portion of the electrical conductor and a portion of the membrane. U.S. patent application 20150141788 (Chi et al., May 21, 2015, "Transducer Assemblies for Dry Applications of Transducers") and U.S. Pat. No. 9,314,183 (Chi et al., Apr. 19, 2016, "Transducer Assemblies for Dry Applications of Transducers") disclose a transducer with at least one probe which penetrates and slides through patches of hair.

U.S. patent application 20180353096 (Mercier et al., Dec. 13, 2018, "Electrode, Wearable Assembly and System") and U.S. patent Ser. No. 10/842,404 (Mercier et al., Nov. 24, 2020, "Electrode, Wearable Assembly and System") disclose an electrode for acquiring electroencephalogram signals which includes a base and a plurality of legs extending from the base. U.S. patent application 20190239807 (Watson et al., Aug. 8, 2019, "Hair Ratcheting Electroencephalogram Sensors") discloses a sensor housing defining a channel extending along a channel axis through the housing from a first side of the sensor housing to a second side of the sensor housing opposite the first side, at least one contact electrode extending from the first side of the housing, an electrically-conducting lead attached to the housing in electrical communication with the at least one contact electrode, and a locking mechanism located in the channel permitting one-way axial motion of a thread threaded through the channel from the first side to the second side.

U.S. patent application 20210338128 (Le Lous et al., Nov. 4, 2021, "Sensor for Measuring a Biological Potential") discloses a sensor for measuring a biological potential comprising a base and at least one leg. U.S. patent application 20160143554 (Lim et al., May 26, 2016, "Apparatus for Measuring Bioelectrical Signals") discloses an electrode with a tapering portion that narrows toward one end and a protruding portion that extends from the one end of the tapering portion. U.S. patent application 20160174859 (Oudenhoven et al., Jun. 23, 2016, "Electrode for Biopotential Sensing") discloses an electrode for biopotential sensing comprising a main electrode base and a plurality of contact pins protruding from the main electrode base.

U.S. patent applications 20200019243 (Aimone et al., Jan. 16, 2020, "Wearable Computing Device with Electrophysiological Sensors"), 20180348863 (Aimone et al., Dec. 6, 2018, "Wearable Computing Device with Electrophysiological Sensors"), and 20210200313 (Aimone et al., Jul. 1, 2021, "Wearable Computing Device with Electrophysiological Sensors") disclose an electrode which extends to contact a user's skin. U.S. patent application 20090134887 (Hu et al., May 28, 2009, "Contact Sensor") discloses a contact sensor with a main body and at least one conductor in an arc shape.

U.S. patent application 20180235500 (Lee et al., Aug. 23, 2018, "Dry Electrode for Detecting Biosignal and Method for Manufacturing Same") discloses a dry electrode comprising a body part; a protrusion part formed on one surface of the body part; and a coating. U.S. patent application 20160089045 (Sadeghian-Motahar et al., Mar. 31, 2016, "Bio-Potential Sensing Materials as Dry Electrodes and Devices") discloses a dry electrode that may be placed in contact with the skin of an animal to receive bio-potential signals. U.S. patent application 20170172447 (Mitra et al., Jun. 22, 2017, "Sensor, System, and Holder Arrangement for Biosignal Activity Measurement") discloses a sensor module with a plurality of pins protruding from a main electrode base.

U.S. patent application 20210282695 (Goldstein et al., Sep. 16, 2021, "Personal Apparatus for Conducting Electroencephalography") discloses an apparatus for conducting electroencephalography while allowing for secure and easy application to a human subject's forehead. U.S. patent applications 20150088224 (Goldwasser et al., Mar. 26, 2015, "Wearable Transdermal Electrical Stimulation Devices and Methods of Using Them") and 20170224990 (Goldwasser et al., Aug. 10, 2017, "Apparatuses and Methods for Neuromodulation") disclose apparatuses and methods for transdermal electrical stimulation (TES).

U.S. patent applications 20180153470 (Gunasekar et al., Jun. 7, 2018, "Electroencephalography Headset and System for Collecting Biosignal Data"), 20200281527 (Gunasekar et al., Sep. 10, 2020, "Electroencephalography Headset and System for Collecting Biosignal Data"), 20220015701 (Gunasekar et al., Jan. 20, 2022, "Electroencephalography Headset and System for Collecting Biosignal Data"), and 20220022813 (Gunasekar et al., Jan. 27, 2022, "Electroencephalography Headset and System for Collecting Biosignal Data") disclose a system for collecting biosignal data with multiple junctions and electrodes. U.S. patent application 20200237249 (Gunasekar et al., Jul. 30, 2020, "Headset and Electrodes for Sensing Bioelectrical Potential and Methods of Operation Thereof") discloses an electrode tip body, one or more deflectable electrode legs coupled to the electrode tip body, and a conductive cushioning material coupled to a segment of at least one of the one or more electrode legs.

U.S. patent application 20170258353 (Jovanovic et al., Sep. 14, 2017, "Headsets and Electrodes for Gathering Electroencephalographic Data") discloses electrodes with a housing, a spring, and a pin. U.S. patent application 20170258400 (Jovanovic et al., Sep. 14, 2017, "Headsets and Electrodes for Gathering Electroencephalographic Data") discloses an electrode which includes a ring disposed in an opening and an arm, where the arm has a first portion extending outward from the opening away from a housing. U.S. patent application 20170150925 (Jung, Jun. 1, 2017, "EEG Hair Band") discloses hair bands with EEG electrodes.

U.S. patent applications 20200159324 (Keller et al., May 21, 2020, "Headware for Computer Control"), 20210109594 (Keller et al., Apr. 15, 2021, "Headware for Computer Control"), and 20220004257 (Keller et al., Jan. 6, 2022, "Headware for Computer Control") disclose headware for computer control including an inner layer with a first surface and a second surface, an outer layer disposed on the first surface of the inner layer, and at least one sensor disposed on the second surface of the inner layer, and at least one sensor configured to measure electrical signals from a brain and extract meaning from the electrical signals. U.S. patent application 20170112444 (Lin et al., Apr. 27, 2017, "Bio-Signal Sensor") discloses a dry electrode having a plurality of probes.

U.S. patent application 20220000407 (Ludwig et al., Jan. 6, 2022, "Dry Electrodes") discloses an electrode with a substrate, electrically conductive particles with at least one point, in contact with the substrate, a supporting layer that envelopes the electrically conductive particles with points that protrude from the supporting layer, and an electrical connector. U.S. patent application 20150367122 (Morshed et al., Dec. 24, 2015, "Patterned Carbon Nanotube Electrode") discloses an electrode, including a substrate and a plurality of carbon nanotube pillars disposed on the substrate, wherein at least two of the carbon nanotube pillars are disposed at a predetermined distance from each other.

U.S. patent application 20140107458 (Op De Beeck et al., Apr. 17, 2014, "Resilient Sensor for Biopotential Measurements") discloses a sensor for biopotential measurement comprising an electrical contacting unit for establishing an electrical contact with an animal or human skin, the electrical contacting unit being resilient. U.S. patent application 20210038106 (Ramakrishnan et al., Feb. 11, 2021, "Mobile, Wearable EEG Device with High Quality Sensors") discloses sensor units with conductive segments disposed in a flexible sensing layer material. U.S. patent application 20190328261 (Shakour et al., Oct. 31, 2019, "Brush Electrode") discloses a plurality of strand electrodes which extend outward from an electrode base to contact a skin surface.

U.S. patent application 20180192906 (Soulet De Brugiere et al., Jul. 12, 2018, "Polymer Composition and Electrode for a Device for the Non-Invasive Measurement of Biological Electrical Signals") discloses a polymer matrix in which are dispersed carbon nanotubes and adsorbent elements selected from activated carbon particles and graphene nanoplatelets, as well as electrodes including such compositions. U.S. patent application 20180049639 (Tian, Feb. 22, 2018, "Dry Electrode, Its Manufacturing Method and Bio-Electromagnetic Wave Detecting Device and Sensor Element Comprising the Dry Electrode") discloses a dry electrode with at least one set of protruding structures arranged on a flexible substrate.

U.S. patent application 20190000338 (Van Den Ende et al., Jan. 3, 2019, "Method and System for Obtaining Signals From Dry EEG Electrodes") discloses an actuator operatively coupled to an EEG electrode and configured to move the electrode in at least two dimensions, including an axial dimension and a lateral dimension, to enable the EEG electrode to contact the skin at different locations. U.S. patent application 20180235499 (Zorman et al., Aug. 23, 2018, "Method for Measuring an Electrophysiological Parameter by Means of a Capacitive Electrode Sensor of Controlled Capacitance") discloses a sensor comprising: a body in an electrically insulating material, the body comprising a base and a plurality of protrusions projecting from the base.

There is also relevant art in the non-patent literature. (Acar, 2019), "Wearable and Flexible Textile Electrodes for Biopotential Signal Monitoring: A Review," Electronics, 2019, 8(5), 479, presents a systematic review of wearable textile electrodes for physiological signal monitoring. (Casson, 2019), "Wearable EEG and Beyond," Biomedical Engineering Letters, January, 2019, 9(1), 53-71, reviews recent progress on electrodes used to make connections to the head and the physical EEG hardware. (Chen, 2014), "Soft, Comfortable Polymer Dry Electrodes for High Quality ECG and EEG Recording," Sensors, Dec. 10, 2014, 14(12), 23758-80, discloses dry electrodes fabricated from EPDM rubber containing various additives for optimum conductivity, flexibility and ease of fabrication.

(Chen, 2016), "Polymer-Based Dry Electrodes for Biopotential Measurements," Thesis, Arenberg Doctoral School, 2016, investigates the mechanical properties of the polymer dry electrodes with compression tests for elastic modulus and compliance characterization. (Chi, 2010), "Dry-Contact and Noncontact Biopotential Electrodes: Methodological Review," IEEE Reviews in Biomedical Engineering, 2010, 3, 106-119, explores the use of dry/noncontact electrodes for clinical use by explaining the electrical models for dry, insulated and noncontact electrodes and showing performance limits, along with measured data. (Chlaihawi, 2018), "Development of Printed and Flexible Dry ECG Electrodes," Sensing and Bio-Sensing Research, 2018, 20, 9-15, discloses printed, flexible and wearable dry electrodes for monitoring electrocardiogram (ECG) signals without any skin preparation or wet gel.

(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6), 1365, compares three different dry electrode types: gold-coated single pin, multiple pins and solid-gel. (Fu, 2020), "Dry Electrodes for Human Bioelectrical Signal Monitoring," Sensors, Jun. 29, 2020, 20(13), 3651, gives a retrospective overview of the development of dry electrodes used for monitoring bioelectrical signals, including sensing principles, material selection, device preparation, and measurement performance. (Gao, 2018), "Soft Pin-Shaped Dry Electrode with Bristles for EEG Signal Measurements," Sensors and Actuators, 2018, Vol. 283, 348-361, presents a novel soft pin-shaped dry electrode for electroencephalography recording.

(Hsu, 2014), "Developing Barbed Microtip-Based Electrode Arrays for Biopotential Measurement," Sensors, 2014, 14(7), 12370-12386, discloses the fabrication of barbed microtip-based electrode arrays via silicon wet etching. (Kocturova, 2019), "Comparison of Dry Electrodes for Mobile EEG System," 2019, evaluates two types of comb electrodes: one based on a Ag—AgCl alloy and one based on a flexible conductive polymer. (Krachunov, 2016), "3D Printed Dry EEG Electrodes," Sensors, 2016, 16(10), 1635, presents a novel methodology for the design and manufacture of dry electrodes using low cost desktop 3D printers.

(Lau-Zhu, 2019), "Mobile EEG in Research on Neurodevelopmental Disorders: Opportunities and Challenges," Developmental Cognitive Neuroscience, 2019, Vol. 36, presents a brief overview of recent developments in mobile EEG technologies. (Lee, 2015), "Reverse-Curve-Arch-Shaped Dry EEG Electrode for Increased Skin-Electrode Contact Area on Hairy Scalps," Electronics Letters, Oct. 1, 2015, discloses reverse-curve-arch-shaped dry EEG electrodes for use in increasing the skin-electrode contact area on hairy scalps. (Lopez-Gordo, 2014), "Dry EEG Electrodes," Sensors, Jul. 18, 2014, 14(7), 12847-70, reviews current approaches to developing dry EEG electrodes for clinical and other applications.

(Mota, 2013), "Development of a Quasi-Dry Electrode for EEG Recording," Sensors and Actuators, 2013, Vol. 199, 310-317, reports on the development of a novel polymer-based electrode prototype for electroencephalography (EEG) between classic "wet" and "dry" electrodes. (Olesen, 2020), "Development and Assessment of Electrodes and Instrumentation for Plantar Skin Impedance Measurements," Thesis, Master in Electronics, Informatics and Technology, University of Oslo, Autumn, 2020, describes the development and testing of electrodes for plantar bioimpedance measurements. (Ouyang, 2021), "Application of Intrinsically Conducting Polymers in Flexible Electronics," SmartMat, Aug. 18, 2021, 2, discusses the use of intrinsically conducting polymers (ICPs), such as polyacetylene, polyaniline, polypyrrole, polythiophene, and poly(3,4-ethylenedioxythiophene) (PEDOT) for dry electrodes.

(Ruffini, 2008), "First Human Trials of a Dry Electrophysiology Sensor Using a Carbon Nanotube Array Interface," Sensors and Actuators, Jun. 15, 2008, 144, reports the results from the first human trials of a new dry electrode sensor for surface biopotential applications, wherein the contact surface of the electrode is covered with carbon nanotubes. (Shad, 2020), "Impedance and Noise of Passive and Active Dry EEG Electrodes: A Review," IEEE Sensors Journal, 7/27/2020, reviews the impedance and noise of passive and active dry EEG electrodes. (Sunwoo, 2020), "Advances in Soft Bioelectronics for Brain Research and Clinical Neuroengineering," Matter, 2020, 3(6) 1923-1947, reviews recent technological advances using unconventional soft materials, such as silicon/metal nanowires, functionalized hydrogels, and stretchable conductive nanocomposites. (Zhang, 2020), "Fully Organic Compliant Dry Electrodes Self-Adhesive to Skin for Long-Term Motion-Robust Epidermal Biopotential Monitoring," Nature Communications, 2020, 11, 4683, reports an intrinsically conductive polymer dry electrode with excellent self-adhesiveness, stretchability, and conductivity.

Despite the above creative innovation and progress in this field, there still remains a need for better dry EEG electrode designs which can more-effectively penetrate between strands of hair to ensure good contact with a person's head without being uncomfortable or irritating the person's skin.

SUMMARY OF THE INVENTION

Although there has been creative innovation and progress in the field of dry EEG electrodes, there remains a need for electrode designs which can penetrate more-effectively between strands of hair for good electromagnetic contact without causing discomfort or skin irritation. To address this need, disclosed herein are EEG electrodes for use on a hair-covered portion of a person's head with a plurality of conductive protrusions which extend out from a distal electrode base portion toward a person's head. In an example, these protrusions can be articulated so that they move laterally and slide between strands of hair as an electrode is pressed onto a person's head. In an example, an electrode base itself can be articulated so that a proximal portion of the base rotates relative to a distal portion of the base as the electrode is pressed onto a person's head, thereby causing protrusions to move laterally and slide between strands of hair.

INTRODUCTION TO THE FIGURES

FIG. 42 shows an EEG electrode with a rotatable ring of protrusions which extend out in a non-perpendicular manner.

DETAILED DESCRIPTION OF THE FIGURES

Figure 3:
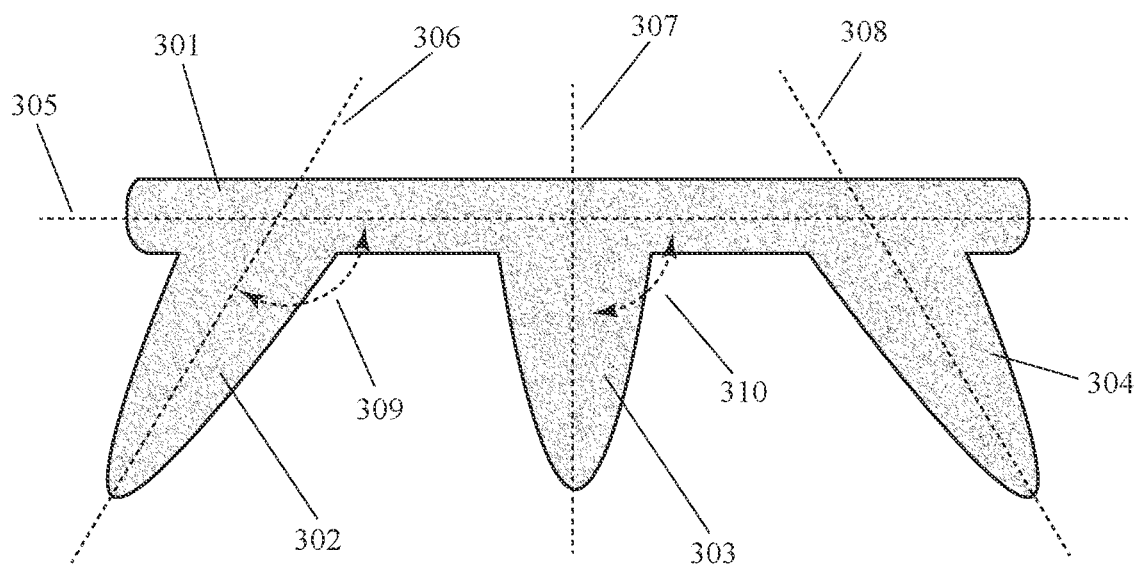
FIG. 3 shows an EEG electrode with protrusions which extend out from a base at different angles and in different directions.
Figure 69:
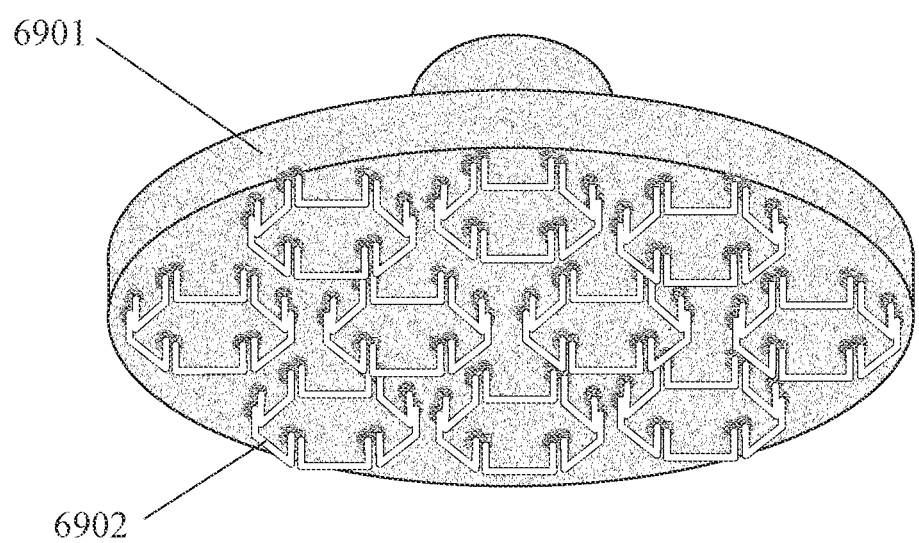
FIG. 69 shows an EEG electrode with rings of loops.

Before discussing the specific examples of dry EEG electrodes which are shown in FIGS. 3 through 69, it is useful to first discuss some general embodiment variations which can be applied later to these specific examples where relevant.

In an example, an EEG electrode for use on a hair-covered portion of a person's head can comprise: a distal portion; and a plurality of articulated conductive protrusions which extend out from the distal portion toward the person's head in order to penetrate between hairs and come into contact with the surface of the person's head; wherein each protrusion further comprises a first longitudinal segment which is movably attached to the distal portion by a first connection, joint, or axle; wherein each protrusion further comprises a second longitudinal segment which is movably attached to the distal portion by a second connection, joint, or axle; and wherein the first and second longitudinal segments are movably connected to each other by a third connection, joint, or axle.

In an example, an EEG electrode for use on a hair-covered portion of a person's head can comprise: a distal electrode portion; a proximal electrode portion which further comprises a plurality of electroconductive protrusions which extend toward the surface of the person's head; a plurality of articulated movable struts which connect the distal electrode portion to the proximal electrode portion; and one or more springs between the distal electrode portion and the proximal electrode portion; wherein pressure from the surface of a person's head on the protrusions pushes the proximal electrode portion toward the distal electrode portion, which rotates the proximal electrode portion relative to the distal electrode portion, which slides the protrusions laterally relative to the surface of the person's head, which enables the protrusions to slide and penetrate between hairs on the surface of the person's head.

In an example, an EEG electrode for use on a hair-covered portion of a person's head can comprise: an electrode base; and a plurality of sets of electroconductive loops; wherein an electroconductive loop in a set of electroconductive loops extends out from the electrode base toward the surface of a person's head; and wherein an electroconductive loop in a set of electroconductive loops is connected to the electrode base at two or more locations, including a central first location which is a first distance from the center of a set and a peripheral second location which is a second distance from the center of the set, wherein the second distance is greater than the first distance.

In an example, an EEG electrode for use on a hair-covered portion of a person's head can comprise: a (disk-shaped) distal portion with a central cross-sectional plane (which is substantially parallel to the surface of a person's head); and a plurality of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein each protrusion in the plurality of electroconductive proximal protrusions has a central longitudinal axis, including axes; wherein a linear extension of a first central longitudinal axis of a first protrusion in the plurality of conductive proximal protrusions intersects the central cross-sectional plane of the distal portion at a first distance (which can be zero) from a center of the distal portion; wherein a linear extension of a second central longitudinal axis of a second protrusion in the plurality of conductive proximal protrusions intersects the central cross-sectional plane of the distal portion at a second distance from the center of the distal portion; wherein the second distance is greater than the first distance; wherein a protrusion angle is the angle of intersection between a linear extension of a central longitudinal axis of a protrusion and the cross-sectional plane of the distal portion which faces toward, or aligns with, the center of the cross-sectional plane of the distal portion; wherein a second protrusion angle of the second protrusion is greater than a first protrusion angle of the first protrusion.

In an example, a distal portion of an electrode can have a circular and/or disk shape. In an example, the distal portion can have an oblong, oval, or elliptical shape. In an example, the distal portion can have a square or rectangular shape. In an example, the distal portion can have a rounded square or rounded rectangular shape. In an example, the distal portion can have a hexagonal shape. In an example, the distal portion of the electrode can have non-uniform thickness. In an example, the center of the distal portion can be thicker than the periphery of the distal portion. In an example, the center of the distal portion can be thinner than the periphery of the distal portion. In an example, the distal portion of the electrode can be electroconductive. In an example, a distal portion of an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, a plurality of electroconductive proximal protrusions (e.g. pins, prongs, teeth, spikes, fingers, and/or protrusions) can include a protrusion from the center of a distal portion of an electrode. In an example, the protrusion angle of a protrusion at the center of the distal portion can be 90 degrees. In an example, the protrusion angle of non-central protrusion can be in the range of 100 to 145 degrees. In an example, the protrusion angle of non-central protrusion can be in the range of 130 to 160 degrees. In an example, the protrusion angle of non-central protrusion can be at least 10 degrees greater than the protrusion angle of a protrusion at the center of the distal portion. In an example, the protrusion angle of non-central protrusion can be at least 30 degrees greater than the protrusion angle of a protrusion at the center of the distal portion. In an example, protrusions which are farther from the center of the electrode can tilt, point, bow, or curve away from the center of the electrode.

In an example, protrusions which are closer to the center of a distal portion of an electrode can be longer than protrusions which are farther from the center of the distal portion. In an example, protrusions which are farther from the center of a distal portion of an electrode can be longer than protrusions which are closer to the center of the distal portion. In an example, protrusions which are closer to the center of a distal portion of an electrode can be more flexible, be more elastic, have a higher Young's modulus, be more compressible, and/or have a lower durometer than protrusions which are farther from the center of the distal portion. In an example, protrusions which are farther from the center of a distal portion of an electrode can be more flexible, be more elastic, have a higher Young's modulus, be more compressible, and/or have a lower durometer than protrusions which are closer to the center of the distal portion.

In an example, a plurality of electroconductive proximal protrusions (e.g. pins, prongs, teeth, spikes, fingers, and/or protrusions) can comprise at least two nested (e.g. concentric) rings of protrusions. In an example, the protrusion angles of protrusions in an outer ring can be greater than the protrusion angles of protrusions in an inner ring. In an example, the protrusion angles of protrusions in an outer ring can be less than the protrusion angles of protrusions in an inner ring. In an example, there can be differences and/or variation in protrusion angles and/or protrusion directions of different protrusions around the circumference of a ring of protrusions. In an example, a plurality of electroconductive proximal protrusions (e.g. pins, prongs, teeth, spikes, fingers, and/or protrusions) can comprise a hub-and-spoke array of protrusions.

In an example, an EEG electrode can comprise a distal portion, a conductive protrusion which extends out from the center of the distal portion toward a person's head, and a ring of conductive protrusions around the central protrusion which also extend out from the distal portion toward the person's head. In an example, an EEG electrode can comprise a distal portion, a conductive protrusion which extends out from the center of the distal portion toward a person's head, and a ring of conductive protrusions around the periphery of the distal portion which also extend out from the distal portion toward the person's head. In an example, an EEG electrode can comprise a distal portion, a conductive protrusion which extends out from the center of the distal portion toward a person's head, and two rings of conductive protrusions around the central protrusion which also extend out from the distal portion toward the person's head. In an example, an EEG electrode can comprise a distal portion and two or more nested rings of conductive protrusions which extend out from the distal portion toward the person's head, wherein protrusions in an outer ring protrude from the distal portion at a greater center-facing angle than protrusions in an inner ring.

In an example, a plurality of electroconductive proximal protrusions (e.g. pins, prongs, teeth, spikes, fingers, and/or protrusions) can comprise an orthogonal grid (e.g. with at least two sets of orthogonal rows and columns) of protrusions. In an example, there can be differences and/or variation in protrusion angles and/or protrusion directions of different protrusions along a row or column of protrusions. In an example, a plurality of electroconductive proximal protrusions (e.g. pins, prongs, teeth, spikes, fingers, and/or protrusions) can comprise a hexagonal grid (e.g. a honeycomb-shaped array) of protrusions.

In an example, a protrusion can have a columnar shape. In an example, a protrusion can have a conic shape. In an example, a protrusion can have a conic section shape. In an example, a protrusion can have a frustal shape. In an example, a protrusion can have a parabolic shape. In an example, a protrusion can have an ellipsoidal shape. In an example, a protrusion can have a crescent and/or banana shape. In an example, a protrusion can have a pyramidic shape. In an example, a protrusion can have a hemispherical shape. In an example, a protrusion can have a distal (farther from head) hemispherical portion and a proximal (closer to head) frustum-shaped portion. In an example, a protrusion can have a distal hemispherical portion and a proximal paraboloid-shaped portion.

In an example, a hair-penetrating protrusion on an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, EEG electrodes can be incorporated into a set of head phones or a hairband. In an example, a mobile brain activity monitor can extend under a layer of hair, slide between hair layers, slide between hair strands, slide into or under hair, and/or slide under a layer of hair. In an example, a mobile brain activity monitor can have multiple protrusions, prongs, and/or teeth which extend under a layer of hair, slide between hair layers, slide between hair strands, slide into or under hair, and/or slide under a layer of hair). In an example, a mobile brain activity monitor can have a plurality of longitudinal protrusions, prongs, and/or teeth whose longitudinal axes are substantially parallel to the surface of the person's head.

In an example, data concerning a person's brain activity can be collected by one or more electrodes at one or multiple selected recording sites. In another example, the locations of one or more electrodes can be selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In another example, one or more reference places can be selected from the group of sites consisting of A1 and A2.

In an example, a brain activity monitor can have five electrodes. In another example, electrodes can be at AFz, F3, F4, CP5, and CP6; or F3, F4, Cz, P3, and P4; or T3/T7, Cz, T4/T8, CP3, and CP4. In another example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, a brain activity monitor can have ten electrodes. In another example, these electrodes can be at the following sites FP', FP2, F3, F4, T3/T7, T4/T8, P3, P4, O1, and O2. In another example, a brain activity monitor can have eight electrodes. In another example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In another example, a brain activity monitor can have seven electrodes. In another example, these electrodes can be at: FP1, FP2, Fz, C3, C4, Cz, and Pz; or F3, F4, Cz, P3, P4, O1, and O2. In another example, a brain activity monitor can have six electrodes. In another example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2.

In an example, an electrode can be a dry electrode. In another example, an EEG electrode can be made from low-conductivity material which has been doped, impregnated, or coated with a high-conductivity material. In another example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper.

In an example, an EEG electrode can be made from low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In another example, an EEG electrode can be made from high-conductivity material selected from the group consisting of: aluminum or aluminum alloy; carbon nanotubes, graphene, or other carbon-based material; copper or copper alloy; gold; nickel; silver; and steel. In another example, an EEG electrode can be made with polydimethylsiloxane (PDMS) which has been doped or impregnated with aluminum, carbon (in one or more various configurations and formulations), copper, gold, nickel, silver, or steel. In another example, an EEG electrode can be made from polydimethylsiloxane (PDMS) and carbon nanotubes. In another example, an EEG electrode can be made from polydimethylsiloxane (PDMS) and silver.

In an example, an electrode can have protrusions, prongs, and/or teeth which extend under a layer of hair for better electromagnetic communication with a person's brain. In another example, an EEG electrode can be made from conductive elastomeric material which is created by doping, impregnating, or embedding conductive material into an otherwise non-conductive elastomeric polymer or hydrogel. In another example, an EEG electrode can be made from elastomeric material (such as an elastomeric polymer) which is doped, impregnated, or embedded with conductive particles or microstructures (such as metal particles or microstructures). In another example, an EEG electrode can be made from silicone material which has been impregnated, doped, or embedded with carbon particles or microstructures. In another example, an EEG electrode can be made from polydimethylsiloxane (PDMS) which has been impregnated, doped, or embedded with carbon nanotubes. In another example, an EEG electrode can be made from hydroxypropyl methylcellulose (HPMC) which has been impregnated, doped, or embedded with silver chloride.

In an example, an EEG electrode can be made from polystyrene (PST) which has been impregnated, doped, or embedded with carbon particles or microstructures. In another example, an EEG electrode can be made from polyvinyl alcohol (PVOH) which has been impregnated, doped, or embedded with carbon nanotubes. In another example, an EEG electrode can be made from thermoplastic elastomer (TPE) which has been impregnated, doped, or embedded with graphene. In another example, an EEG electrode can be made from thermoplastic polyurethane (TPU) which has been impregnated, doped, or embedded with tungsten particles or pieces. In another example, an EEG electrode can be made from polydimethylsiloxane (PDMS) which has been impregnated, doped, or embedded with niobium. In another example, an EEG electrode can be made from cellulose which has been impregnated, doped, or embedded with gold or gold alloy particles or pieces. In another example, an EEG electrode can be made from cellulose which has been impregnated, doped, or embedded with aluminum or aluminum alloy particles or pieces.

In an example, an EEG electrode can be made from styrene ethylene butylene streyene (SEBS) which has been impregnated, doped, or embedded with tungsten particles or pieces. In another example, an EEG electrode can be made from SEBS which has been impregnated, doped, or embedded with tungsten particles or pieces. In another example, an EEG electrode can be made from polypropylene glycol material which has been impregnated, doped, or embedded with silver chloride. In another example, an EEG electrode can be made from polyurethane which has been impregnated, doped, or embedded with niobium. In another example, an EEG electrode can be made from polyvinyl alcohol (PVOH) which has been impregnated, doped, or embedded with graphene. In another example, an EEG electrode can be made from cellulose which has been impregnated, doped, or embedded with carbon particles or microstructures. In another example, an EEG electrode can be made from hydroxypropyl methylcellulose (HPMC) which has been impregnated, doped, or embedded with carbon nanotubes. In another example, an EEG electrode can be made from rubber which has been impregnated, doped, or embedded with gold or gold alloy particles or pieces.

In an example, an EEG electrode can be made from styrene ethylene butylene streyene (SEBS) which has been impregnated, doped, or embedded with carbon nanotubes. In another example, an EEG electrode can be made from polyethylene glycol (PEG) which has been impregnated, doped, or embedded with aluminum or aluminum alloy particles or pieces. In another example, an EEG electrode can be made from polystyrenesulfonate (PEDOT/PSS) which has been impregnated, doped, or embedded with graphite. In another example, an EEG electrode can be made from thermoplastic elastomer (TPE) which has been impregnated, doped, or embedded with silver chloride. In another example, an EEG electrode can be made from elastomeric polymer material which has been impregnated, doped, or embedded with gold or gold alloy particles or pieces. In another example, an EEG electrode can be made from silicone rubber which has been impregnated, doped, or embedded with steel particles or pieces.

In an example, an EEG electrode can be made from cellulose which has been impregnated, doped, or embedded with graphene. In another example, an EEG electrode can be made from polyethylene glycol (PEG) which has been impregnated, doped, or embedded with silver or sliver alloy particles or pieces. In another example, electrodes can be made from polystyrenesulfonate (PEDOT/PSS) which has been impregnated, doped, or embedded with aluminum or aluminum alloy particles or pieces. In another example, an EEG electrode can be made from polyvinyl alcohol (PVOH) which has been impregnated, doped, or embedded with gold or gold alloy particles or pieces. In another example, an EEG electrode can be made from polyvinyl alcohol (PVOH) which has been impregnated, doped, or embedded with niobium.

In an example, an EEG electrode can be made from silicone material which has been impregnated, doped, or embedded with tungsten particles or pieces. In another example, an EEG electrode can be made from hydrogel material which has been impregnated, doped, or embedded with graphite. In another example, an EEG electrode can be made from polypropylene glycol material which has been impregnated, doped, or embedded with tungsten particles or pieces. In another example, an EEG electrode can be made from polytetrafluoroethylene (PTFE) which has been impregnated, doped, or embedded with gallium. In another example, an EEG electrode can be made from thermoplastic elastomer (TPE) which has been impregnated, doped, or embedded with nickel or nickel alloy particles or pieces. In another example, an EEG electrode can be made from cellulose which has been impregnated, doped, or embedded with silver or sliver alloy particles or pieces.

In an example, an EEG electrode can be made from polyethylene glycol (PEG) which has been impregnated, doped, or embedded with graphite. In another example, electrodes can be made polytetrafluoroethylene (PTFE) which has been impregnated, doped, or embedded with graphene. In another example, an EEG electrode can be made from polyvinyl alcohol (PVOH) which has been impregnated, doped, or embedded with graphite. In another example, an EEG electrode can be made from hydrogel material which has been impregnated, doped, or embedded with steel particles or pieces. In another example, an EEG electrode can be made from hydroxypropyl methylcellulose (HPMC) which has been impregnated, doped, or embedded with steel particles or pieces. In another example, an EEG electrode can be made from HPMC which has been impregnated, doped, or embedded with gallium. In another example, an EEG electrode can be made from rubber which has been impregnated, doped, or embedded with gallium.

In an example, an EEG electrode can be made from polystyrenesulfonate (PEDOT/PSS) which has been impregnated, doped, or embedded with carbon particles or microstructures. In another example, an EEG electrode can be made from thermoplastic elastomer (TPE) which has been impregnated, doped, or embedded with carbon nanotubes. In another example, an EEG electrode can be made from thermoplastic polyurethane (TPU) material which has been impregnated, doped, or embedded with carbon nanotubes. In another example, an EEG electrode can be made from polydimethylsiloxane (PDMS) which has been impregnated, doped, or embedded with graphite. In another example, an EEG electrode can be made from PDMS which has been impregnated, doped, or embedded with aluminum or aluminum alloy particles or pieces. In another example, an EEG electrode can be made from cellulose which has been impregnated, doped, or embedded with nickel or nickel alloy particles or pieces.

In an example, an EEG electrode can be made from hydroxypropyl methylcellulose (HPMC) which has been impregnated, doped, or embedded with gold or gold alloy particles or pieces. In another example, an EEG electrode can be made from rubber which has been impregnated, doped, or embedded with steel particles or pieces. In another example, an EEG electrode can be made from styrene ethylene butylene streyene (SEBS) which has been impregnated, doped, or embedded with niobium. In another example, an EEG electrode can be made from polystyrenesulfonate (PEDOT/PSS) which has been impregnated, doped, or embedded with carbon nanotubes. In another example, an EEG electrode can be made from polytetrafluoroethylene (PTFE) which has been impregnated, doped, or embedded with graphite. In another example, an EEG electrode can be made from thermoplastic polyurethane (TPU) material which has been impregnated, doped, or embedded with carbon particles or microstructures. In another example, an EEG electrode can be made from TPU which has been impregnated, doped, or embedded with aluminum or aluminum alloy particles or pieces.

In an example, an EEG electrode can be made from thermoplastic vulcanizate (TPV) material which has been impregnated, doped, or embedded with aluminum or aluminum alloy particles or pieces. In another example, an EEG electrode can be made from elastomeric polymer material which has been impregnated, doped, or embedded with copper or copper alloy particles or pieces. In another example, an EEG electrode can be made from hydrogel material which has been impregnated, doped, or embedded with silver chloride. In another example, an EEG electrode can be made from hydroxypropyl cellulose which has been impregnated, doped, or embedded with tungsten particles or pieces.

In an example, an EEG electrode can be made from hydroxypropyl methylcellulose which has been impregnated, doped, or embedded with steel particles or pieces. In another example, electrodes can be made styrene ethylene butylene streyene (SEBS) which has been impregnated, doped, or embedded with graphene. In another example, an EEG electrode can be made from polypropylene glycol material which has been impregnated, doped, or embedded with niobium. In another example, an EEG electrode can be made from polytetrafluoroethylene (PTFE) which has been impregnated, doped, or embedded with niobium. In another example, an EEG electrode can be made from polyethylene terephthalate (PET) which has been impregnated, doped, or embedded with aluminum or aluminum alloy particles or pieces. In another example, an EEG electrode can be made from polyvinyl alcohol (PVOH) which has been impregnated, doped, or embedded with copper or copper alloy particles or pieces.

In an example, an EEG electrode can be made from thermoplastic elastomer (TPE) which has been impregnated, doped, or embedded with steel particles or pieces. In another example, electrodes can be made TPE which has been impregnated, doped, or embedded with tungsten particles or pieces. In another example, an EEG electrode can be made from silicone rubber which has been impregnated, doped, or embedded with tungsten particles or pieces. In another example, an EEG electrode can be made from polydimethylsiloxane (PDMS) which has been impregnated, doped, or embedded with silver chloride. In another example, an EEG electrode can be made from cellulose which has been impregnated, doped, or embedded with silver chloride. In another example, an EEG electrode can be made from hydroxypropyl methylcellulose which has been impregnated, doped, or embedded with carbon nanotubes. In another example, an EEG electrode can be made from polystyrenesulfonate (PEDOT/PSS) which has been impregnated, doped, or embedded with niobium.

In an example, an EEG electrode can be made from polytetrafluoroethylene (PTFE) which has been impregnated, doped, or embedded with aluminum or aluminum alloy particles or pieces. In another example, an EEG electrode can be made from polyethylene terephthalate (PET) which has been impregnated, doped, or embedded with graphene. In another example, an EEG electrode can be made from polyethylene terephthalate (PET) which has been impregnated, doped, or embedded with gold or gold alloy particles or pieces. In another example, an EEG electrode can be made from elastomeric polymer material which has been impregnated, doped, or embedded with gallium. In another example, an EEG electrode can be made from elastomeric polymer material which has been impregnated, doped, or embedded with gallium. In another example, an EEG electrode can be made from acetate thread, yarn, or fiber which has been coated or embedded with carbon particles or microstructures.

In an example, an EEG electrode can be made from cellulose which has been impregnated, doped, or embedded with niobium. In another example, an EEG electrode can be made from cellulose which has been impregnated, doped, or embedded with tungsten particles or pieces. In another example, an EEG electrode can be made from hydroxypropyl cellulose which has been impregnated, doped, or embedded with carbon particles or microstructures. In another example, an EEG electrode can be made from hydroxypropyl cellulose which has been impregnated, doped, or embedded with nickel or nickel alloy particles or pieces.

In an example, an EEG electrode can be made from polypropylene glycol material which has been impregnated, doped, or embedded with aluminum or aluminum alloy particles or pieces. In another example, an EEG electrode can be made from polystyrenesulfonate (PEDOT/PSS) which has been impregnated, doped, or embedded with silver or sliver alloy particles or pieces. In another example, an EEG electrode can be made from polystyrenesulfonate (PEDOT/PSS) which has been impregnated, doped, or embedded with nickel or nickel alloy particles or pieces. In another example, an EEG electrode can be made from polytetrafluoroethylene (PTFE) which has been impregnated, doped, or embedded with carbon nanotubes. In another example, an EEG electrode can be made from polyethylene terephthalate (PET) which has been impregnated, doped, or embedded with nickel or nickel alloy particles or pieces.

In an example, an EEG electrode can be made from thermoplastic elastomer (TPE) which has been impregnated, doped, or embedded with silver (or sliver alloy) particles or pieces. In another example, an EEG electrode can be made from thermoplastic polyurethane (TPU) material which has been impregnated, doped, or embedded with graphite. In another example, an EEG electrode can be made from thermoplastic polyurethane (TPU) material which has been impregnated, doped, or embedded with steel particles or pieces. In another example, an EEG electrode can be made from elastomeric polymer material which has been impregnated, doped, or embedded with nickel or nickel alloy particles or pieces.

In an example, an EEG electrode can be made from silicone rubber which has been impregnated, doped, or embedded with gold or gold alloy particles or pieces. In another example, an EEG electrode can be made from polydimethylsiloxane (PDMS) which has been impregnated, doped, or embedded with graphene. In another example, an EEG electrode can be made from hydrogel material which has been impregnated, doped, or embedded with gold or gold alloy particles or pieces. In another example, an EEG electrode can be made from hydroxypropyl methylcellulose (HPMC) which has been impregnated, doped, or embedded with carbon particles or microstructures. In another example, an EEG electrode can be made from HPMC which has been impregnated, doped, or embedded with nickel or nickel alloy particles or pieces.

In an example, an EEG electrode can be made from styrene ethylene butylene streyene (SEBS) which has been impregnated, doped, or embedded with carbon particles or microstructures. In another example, an EEG electrode can be made from polyethylene glycol (PEG) which has been impregnated, doped, or embedded with gold or gold alloy particles or pieces. In another example, an EEG electrode can be made from polyethylene terephthalate (PET) which has been impregnated, doped, or embedded with graphite. In another example, an EEG electrode can be made from PET which has been impregnated, doped, or embedded with steel particles or pieces. In another example, an EEG electrode can be made from thermoplastic elastomer (TPE) which has been impregnated, doped, or embedded with gold or gold alloy particles or pieces.

In an example, an EEG electrode can be made from thermoplastic polyurethane (TPU) material which has been impregnated, doped, or embedded with silver chloride. In another example, an EEG electrode can be made from thermoplastic vulcanizate (TPV) material which has been impregnated, doped, or embedded with nickel or nickel alloy particles or pieces. In another example, an EEG electrode can be made from hydroxypropyl cellulose which has been impregnated, doped, or embedded with silver or sliver alloy particles or pieces. In another example, an EEG electrode can be made from hydroxypropyl cellulose which has been impregnated, doped, or embedded with silver chloride. In another example, an EEG electrode can be made from hydroxypropyl cellulose which has been impregnated, doped, or embedded with gold or gold alloy particles or pieces.

In an example, an EEG electrode can be made from hydroxypropyl cellulose which has been impregnated, doped, or embedded with steel particles or pieces. In another example, an EEG electrode can be made from hydroxypropyl methylcellulose (HPMC) which has been impregnated, doped, or embedded with copper or copper alloy particles or pieces. In another example, an EEG electrode can be made from HPMC which has been impregnated, doped, or embedded with tungsten particles or pieces. In another example, an EEG electrode can be made from hydroxypropyl methylcellulose which has been impregnated, doped, or embedded with tungsten particles or pieces.

In an example, an EEG electrode can be made from rubber which has been impregnated, doped, or embedded with niobium. In another example, an EEG electrode can be made from polypropylene glycol material which has been impregnated, doped, or embedded with gold or gold alloy particles or pieces. In another example, an EEG electrode can be made from polystyrene (PST) which has been impregnated, doped, or embedded with carbon nanotubes. In another example, an EEG electrode can be made from polystyrenesulfonate (PEDOT/PSS) which has been impregnated, doped, or embedded with steel particles or pieces. In another example, an EEG electrode can be made from polyethylene terephthalate (PET) which has been impregnated, doped, or embedded with copper or copper alloy particles or pieces. In another example, an EEG electrode can be made from polyethylene terephthalate (PET) which has been impregnated, doped, or embedded with tungsten particles or pieces.

In an example, an EEG electrode can be made from polyvinyl alcohol (PVOH) which has been impregnated, doped, or embedded with carbon particles or microstructures. In another example, an EEG electrode can be made from PVOH which has been impregnated, doped, or embedded with silver or sliver alloy particles or pieces. In another example, an EEG electrode can be made from polyvinyl alcohol (PVOH) which has been impregnated, doped, or embedded with silver chloride. In another example, an EEG electrode can be made from thermoplastic elastomer (TPE) which has been impregnated, doped, or embedded with carbon particles or microstructures. In another example, an EEG electrode can be made from TPE which has been impregnated, doped, or embedded with graphite.

In an example, an EEG electrode can be made from TPE which has been impregnated, doped, or embedded with aluminum or aluminum alloy particles or pieces. In another example, an EEG electrode can be made from thermoplastic polyurethane (TPU) material which has been impregnated, doped, or embedded with graphene. In another example, an EEG electrode can be made from elastomeric polymer material which has been impregnated, doped, or embedded with steel particles or pieces. In another example, an EEG electrode can be made from silicone material which has been impregnated, doped, or embedded with gallium. In another example, an EEG electrode can be made from hydrogel material which has been impregnated, doped, or embedded with copper or copper alloy particles or pieces.

In an example, an EEG electrode can be made from hydroxypropyl cellulose which has been impregnated, doped, or embedded with aluminum or aluminum alloy particles or pieces. In another example, an EEG electrode can be made from hydroxypropyl cellulose which has been impregnated, doped, or embedded with gallium. In another example, an EEG electrode can be made from rubber which has been impregnated, doped, or embedded with aluminum or aluminum alloy particles or pieces. In another example, an EEG electrode can be made from rubber which has been impregnated, doped, or embedded with tungsten particles or pieces.

In an example, an EEG electrode can be made from polystyrene (PST) which has been impregnated, doped, or embedded with graphene. In another example, an EEG electrode can be made from polystyrene (PST) which has been impregnated, doped, or embedded with aluminum or aluminum alloy particles or pieces. In another example, an EEG electrode can be made from polystyrenesulfonate (PEDOT/PSS) which has been impregnated, doped, or embedded with gold or gold alloy particles or pieces. In another example, an EEG electrode can be made from polystyrenesulfonate (PEDOT/PSS) which has been impregnated, doped, or embedded with tungsten particles or pieces.

In an example, an EEG electrode can be made from polytetrafluoroethylene (PTFE) which has been impregnated, doped, or embedded with steel particles or pieces. In another example, an EEG electrode can be made from polyethylene terephthalate (PET) which has been impregnated, doped, or embedded with carbon particles or microstructures. In another example, an EEG electrode can be made from polyethylene terephthalate (PET) which has been impregnated, doped, or embedded with niobium. In another example, an EEG electrode can be made from polyvinyl alcohol (PVOH) which has been impregnated, doped, or embedded with gallium.

In an example, an EEG electrode can be made from hydrogel material which has been impregnated, doped, or embedded with aluminum or aluminum alloy particles or pieces. In another example, an EEG electrode can be made from hydroxypropyl methylcellulose (HPMC) which has been impregnated, doped, or embedded with graphite. In another example, an EEG electrode can be made from HPMC which has been impregnated, doped, or embedded with silver or sliver alloy particles or pieces. In another example, an EEG electrode can be made from hydroxypropyl methylcellulose which has been impregnated, doped, or embedded with gallium. In another example, an EEG electrode can be made from rubber which has been impregnated, doped, or embedded with copper or copper alloy particles or pieces.

In an example, an EEG electrode can be made from polyethylene glycol (PEG) which has been impregnated, doped, or embedded with silver chloride. In another example, an EEG electrode can be made from polystyrenesulfonate (PEDOT/PSS) which has been impregnated, doped, or embedded with silver chloride. In another example, an EEG electrode can be made from polytetrafluoroethylene (PTFE) which has been impregnated, doped, or embedded with carbon particles or microstructures. In another example, an EEG electrode can be made from polytetrafluoroethylene (PTFE) which has been impregnated, doped, or embedded with silver chloride. In another example, an EEG electrode can be made from polytetrafluoroethylene (PTFE) which has been impregnated, doped, or embedded with nickel or nickel alloy particles or pieces.

In an example, an EEG electrode can be made from polyethylene terephthalate (PET) which has been impregnated, doped, or embedded with gallium. In another example, an EEG electrode can be made from polyurethane which has been impregnated, doped, or embedded with nickel or nickel alloy particles or pieces. In another example, an EEG electrode can be made from polyurethane which has been impregnated, doped, or embedded with tungsten particles or pieces. In another example, an EEG electrode can be made from polyvinyl alcohol (PVOH) which has been impregnated, doped, or embedded with nickel or nickel alloy particles or pieces. In another example, an EEG electrode can be made from polyvinyl alcohol (PVOH) which has been impregnated, doped, or embedded with steel particles or pieces.

In an example, an EEG electrode can be made from thermoplastic elastomer (TPE) which has been impregnated, doped, or embedded with niobium. In another example, an EEG electrode can be made from hydroxypropyl methylcellulose (HPMC) which has been impregnated, doped, or embedded with niobium. In another example, an EEG electrode can be made from thermoplastic elastomer (TPE) which has been impregnated, doped, or embedded with copper or copper alloy particles or pieces. In another example, an EEG electrode can be made from thermoplastic polyurethane (TPU) material which has been impregnated, doped, or embedded with gallium. In another example, an EEG electrode can be made from thermoplastic vulcanizate (TPV) material which has been impregnated, doped, or embedded with steel particles or pieces.

In an example, an EEG electrode can be made from elastomeric polymer material which has been impregnated, doped, or embedded with graphite. In another example, an EEG electrode can be made from rubber which has been impregnated, doped, or embedded with carbon particles or microstructures. In another example, an EEG electrode can be made from styrene ethylene butylene streyene (SEBS) which has been impregnated, doped, or embedded with copper or copper alloy particles or pieces. In another example, an EEG electrode can be made from polyurethane which has been impregnated, doped, or embedded with silver chloride.

In an example, an EEG electrode can be made from elastomeric polymer material which has been impregnated, doped, or embedded with carbon nanotubes. In another example, an EEG electrode can be made from acetate thread, yarn, or fiber coated or embedded with copper or copper alloy particles or pieces. In another example, an EEG electrode can be made from silicone rubber which has been impregnated, doped, or embedded with aluminum or aluminum alloy particles or pieces. In another example, an EEG electrode can be made from hydrogel material which has been impregnated, doped, or embedded with silver or sliver alloy particles or pieces. In another example, an EEG electrode can be made from hydrogel material which has been impregnated, doped, or embedded with niobium. In another example, an EEG electrode can be made from hydrogel material which has been impregnated, doped, or embedded with niobium; and a data processor.

In an example, an EEG electrode can be made from polyethylene glycol (PEG) which has been impregnated, doped, or embedded with graphene. In another example, an EEG electrode can be made from thermoplastic polyurethane (TPU) material which has been impregnated, doped, or embedded with silver or sliver alloy particles or pieces. In another example, an EEG electrode can be made from thermoplastic vulcanizate (TPV) material which has been impregnated, doped, or embedded with carbon nanotubes. In another example, an EEG electrode can be made from thermoplastic vulcanizate (TPV) material which has been impregnated, doped, or embedded with gold or gold alloy particles or pieces. In another example, an EEG electrode can be made from polydimethylsiloxane (PDMS) which has been impregnated, doped, or embedded with copper or copper alloy particles or pieces.

In an example, an EEG electrode can be made from hydrogel material which has been impregnated, doped, or embedded with carbon particles or microstructures. In another example, an EEG electrode can be made from hydrogel material which has been impregnated, doped, or embedded with tungsten particles or pieces. In another example, an EEG electrode can be made from cellulose which has been impregnated, doped, or embedded with graphite. In another example, an EEG electrode can be made from rubber which has been impregnated, doped, or embedded with carbon nanotubes.

In an example, an EEG electrode can be made from styrene ethylene butylene streyene (SEBS) which has been impregnated, doped, or embedded with aluminum or aluminum alloy particles or pieces. In another example, an EEG electrode can be made from polyethylene glycol (PEG) which has been impregnated, doped, or embedded with gallium. In another example, an EEG electrode can be made from polystyrene (PST) which has been impregnated, doped, or embedded with graphite. In another example, an EEG electrode can be made from polyvinyl alcohol (PVOH) which has been impregnated, doped, or embedded with aluminum or aluminum alloy particles or pieces.

In an example, an EEG electrode can be made from silicone material which has been impregnated, doped, or embedded with carbon nanotubes. In another example, an EEG electrode can be made from silicone rubber which has been impregnated, doped, or embedded with graphene. In another example, an EEG electrode can be made from silicone rubber which has been impregnated, doped, or embedded with niobium. In another example, an EEG electrode can be made from polydimethylsiloxane (PDMS) which has been impregnated, doped, or embedded with steel particles or pieces.

In an example, an EEG electrode can be made from hydroxypropyl methylcellulose which has been impregnated, doped, or embedded with graphite. In another example, an EEG electrode can be made from hydroxypropyl methylcellulose which has been impregnated, doped, or embedded with silver chloride. In another example, an EEG electrode can be made from hydroxypropyl methylcellulose which has been impregnated, doped, or embedded with nickel or nickel alloy particles or pieces. In another example, an EEG electrode can be made from styrene ethylene butylene streyene (SEBS) which has been impregnated, doped, or embedded with gold or gold alloy particles or pieces.

In an example, an EEG electrode can be made from polypropylene glycol material which has been impregnated, doped, or embedded with copper or copper alloy particles or pieces. In another example, an EEG electrode can be made from polystyrene (PST) which has been impregnated, doped, or embedded with silver chloride. In another example, an EEG electrode can be made from polystyrenesulfonate (PEDOT/PSS) which has been impregnated, doped, or embedded with graphene. In another example, an EEG electrode can be made from polyurethane which has been impregnated, doped, or embedded with gold or gold alloy particles or pieces.

In an example, an EEG electrode can be made from polyurethane which has been impregnated, doped, or embedded with steel particles or pieces. In another example, an EEG electrode can be made from thermoplastic polyurethane (TPU) material which has been impregnated, doped, or embedded with gold or gold alloy particles or pieces. In another example, an EEG electrode can be made from thermoplastic polyurethane (TPU) material which has been impregnated, doped, or embedded with copper or copper alloy particles or pieces. In another example, an EEG electrode can be made from thermoplastic vulcanizate (TPV) material which has been impregnated, doped, or embedded with graphite.

In an example, an EEG electrode can be made from elastomeric polymer material which has been impregnated, doped, or embedded with aluminum or aluminum alloy particles or pieces. In another example, an EEG electrode can be made from silicone material which has been impregnated, doped, or embedded with silver chloride. In another example, an EEG electrode can be made from silicone rubber which has been impregnated, doped, or embedded with carbon nanotubes. In another example, an EEG electrode can be made from silicone rubber which has been impregnated, doped, or embedded with nickel or nickel alloy particles or pieces.

In an example, an EEG electrode can be made from hydrogel material which has been impregnated, doped, or embedded with graphene. In another example, an EEG electrode can be made from hydroxypropyl cellulose which has been impregnated, doped, or embedded with graphite. In another example, an EEG electrode can be made from polypropylene glycol material which has been impregnated, doped, or embedded with silver or sliver alloy particles or pieces. In another example, an EEG electrode can be made from polystyrene (PST) which has been impregnated, doped, or embedded with steel particles or pieces.

In an example, an EEG electrode can be made from polystyrenesulfonate (PEDOT/PSS) which has been impregnated, doped, or embedded with copper or copper alloy particles or pieces. In another example, an EEG electrode can be made from thermoplastic polyurethane (TPU) material which has been impregnated, doped, or embedded with niobium. In another example, an EEG electrode can be made from thermoplastic vulcanizate (TPV) material which has been impregnated, doped, or embedded with graphene. In another example, an EEG electrode can be made from thermoplastic vulcanizate (TPV) material which has been impregnated, doped, or embedded with copper or copper alloy particles or pieces.

In an example, an EEG electrode can be made from elastomeric polymer material which has been impregnated, doped, or embedded with graphene. In another example, an EEG electrode can be made from silicone material which has been impregnated, doped, or embedded with niobium. In another example, an EEG electrode can be made from polydimethylsiloxane (PDMS) which has been impregnated, doped, or embedded with carbon particles or microstructures. In another example, an EEG electrode can be made from polydimethylsiloxane (PDMS) which has been impregnated, doped, or embedded with silver or sliver alloy particles or pieces.

In an example, an EEG electrode can be made from polydimethylsiloxane (PDMS) which has been impregnated, doped, or embedded with gold or gold alloy particles or pieces. In another example, an EEG electrode can be made from polydimethylsiloxane (PDMS) which has been impregnated, doped, or embedded with tungsten particles or pieces. In another example, an EEG electrode can be made from hydroxypropyl cellulose which has been impregnated, doped, or embedded with niobium. In another example, an EEG electrode can be made from hydroxypropyl methylcellulose which has been impregnated, doped, or embedded with graphene.

In an example, an EEG electrode can be made from rubber which has been impregnated, doped, or embedded with graphite. In another example, an EEG electrode can be made from rubber which has been impregnated, doped, or embedded with silver or sliver alloy particles or pieces. In another example, an EEG electrode can be made from styrene ethylene butylene streyene (SEBS) which has been impregnated, doped, or embedded with gallium. In another example, an EEG electrode can be made from polyurethane which has been impregnated, doped, or embedded with aluminum or aluminum alloy particles or pieces.

In an example, an EEG electrode can be made from polyurethane which has been impregnated, doped, or embedded with gallium. In another example, an EEG electrode can be made from elastomeric polymer material which has been impregnated, doped, or embedded with niobium. In another example, an EEG electrode can be made from elastomeric polymer material which has been impregnated, doped, or embedded with tungsten particles or pieces. In another example, an EEG electrode can be made from silicone material which has been impregnated, doped, or embedded with gold or gold alloy particles or pieces.

In an example, an EEG electrode can be made from silicone rubber which has been impregnated, doped, or embedded with silver (or sliver alloy) particles or pieces. In another example, an EEG electrode can be made from silicone rubber which has been impregnated, doped, or embedded with copper or copper alloy particles or pieces. In another example, an EEG electrode can be made from hydroxypropyl cellulose which has been impregnated, doped, or embedded with carbon nanotubes. In another example, an EEG electrode can be made from hydroxypropyl cellulose which has been impregnated, doped, or embedded with graphene.

In an example, an EEG electrode can be made from polypropylene glycol material which has been impregnated, doped, or embedded with graphite. In another example, an EEG electrode can be made from polypropylene glycol material which has been impregnated, doped, or embedded with steel particles or pieces. In another example, an EEG electrode can be made from polyethylene terephthalate (PET) which has been impregnated, doped, or embedded with silver chloride. In another example, an EEG electrode can be made from polyurethane which has been impregnated, doped, or embedded with carbon particles or microstructures.

In an example, an EEG electrode can be made from polyurethane which has been impregnated, doped, or embedded with carbon nanotubes. In another example, an EEG electrode can be made from polyurethane which has been impregnated, doped, or embedded with copper or copper alloy particles or pieces. In another example, an EEG electrode can be made from thermoplastic vulcanizate (TPV) material which has been impregnated, doped, or embedded with silver chloride. In another example, an EEG electrode can be made from thermoplastic vulcanizate (TPV) material which has been impregnated, doped, or embedded with tungsten particles or pieces.

In an example, an EEG electrode can be made from elastomeric polymer material which has been impregnated, doped, or embedded with silver chloride. In another example, an EEG electrode can be made from elastomeric polymer material which has been impregnated, doped, or embedded with conductive metal particles or pieces. In another example, an EEG electrode can be made from silicone material which has been impregnated, doped, or embedded with copper or copper alloy particles or pieces. In another example, an EEG electrode can be made from silicone rubber which has been impregnated, doped, or embedded with graphite.

In an example, an EEG electrode can be made from silicone rubber which has been impregnated, doped, or embedded with silver chloride. In another example, an EEG electrode can be made from polydimethylsiloxane (PDMS) which has been impregnated, doped, or embedded with gallium. In another example, an EEG electrode can be made from hydrogel material which has been impregnated, doped, or embedded with carbon nanotubes. In another example, an EEG electrode can be made from hydrogel material which has been impregnated, doped, or embedded with nickel or nickel alloy particles or pieces.

In an example, an EEG electrode can be made from cellulose which has been impregnated, doped, or embedded with copper or copper alloy particles or pieces. In another example, an EEG electrode can be made from cellulose which has been impregnated, doped, or embedded with gallium. In another example, an EEG electrode can be made from hydroxypropyl methylcellulose (HPMC) which has been impregnated, doped, or embedded with graphene. In another example, an EEG electrode can be made from hydroxypropyl methylcellulose which has been impregnated, doped, or embedded with silver or sliver alloy particles or pieces.

In an example, an EEG electrode can be made from hydroxypropyl methylcellulose which has been impregnated, doped, or embedded with copper or copper alloy particles or pieces. In another example, an EEG electrode can be made from styrene ethylene butylene streyene (SEBS) which has been impregnated, doped, or embedded with silver chloride. In another example, an EEG electrode can be made from polypropylene glycol material which has been impregnated, doped, or embedded with graphene. In another example, an EEG electrode can be made from polyethylene terephthalate (PET) which has been impregnated, doped, or embedded with silver or sliver alloy particles or pieces.

In an example, an EEG electrode can be made from thermoplastic polyurethane (TPU) material which has been impregnated, doped, or embedded with nickel or nickel alloy particles or pieces. In another example, an EEG electrode can be made from thermoplastic vulcanizate (TPV) material which has been impregnated, doped, or embedded with carbon particles or microstructures. In another example, an EEG electrode can be made from elastomeric polymer material which has been impregnated, doped, or embedded with carbon particles or microstructures. In another example, an EEG electrode can be made from elastomeric polymer material which has been impregnated, doped, or embedded with silver or sliver alloy particles or pieces.

In an example, an EEG electrode can be made from silicone material which has been impregnated, doped, or embedded with graphene. In another example, an EEG electrode can be made from silicone material which has been impregnated, doped, or embedded with aluminum or aluminum alloy particles or pieces. In another example, an EEG electrode can be made from silicone material which has been impregnated, doped, or embedded with nickel or nickel alloy particles or pieces. In another example, an EEG electrode can be made from polydimethylsiloxane (PDMS) which has been impregnated, doped, or embedded with nickel or nickel alloy particles or pieces.

In an example, an EEG electrode can be made from hydrogel material which has been impregnated, doped, or embedded with gallium. In another example, an EEG electrode can be made from cellulose which has been impregnated, doped, or embedded with steel particles or pieces. In another example, an EEG electrode can be made from hydroxypropyl cellulose which has been impregnated, doped, or embedded with copper or copper alloy particles or pieces. In another example, an EEG electrode can be made from hydroxypropyl methylcellulose which has been impregnated, doped, or embedded with aluminum or aluminum alloy particles or pieces.

In an example, an EEG electrode can be made from hydroxypropyl methylcellulose which has been impregnated, doped, or embedded with niobium. In another example, an EEG electrode can be made from rubber which has been impregnated, doped, or embedded with graphene. In another example, an EEG electrode can be made from styrene ethylene butylene streyene (SEBS) which has been impregnated, doped, or embedded with graphite. In another example, an EEG electrode can be made from styrene ethylene butylene streyene (SEBS) which has been impregnated, doped, or embedded with steel particles or pieces.

In an example, an EEG electrode can be made from polyethylene glycol (PEG) which has been impregnated, doped, or embedded with carbon particles or microstructures. In another example, an EEG electrode can be made from polyethylene glycol (PEG) which has been impregnated, doped, or embedded with carbon nanotubes. In another example, an EEG electrode can be made from polyethylene glycol (PEG) which has been impregnated, doped, or embedded with copper or copper alloy particles or pieces. In another example, an EEG electrode can be made from polyethylene glycol (PEG) which has been impregnated, doped, or embedded with niobium.

In an example, an EEG electrode can be made from polyethylene glycol (PEG) which has been impregnated, doped, or embedded with tungsten particles or pieces. In another example, an EEG electrode can be made from polypropylene glycol material which has been impregnated, doped, or embedded with carbon particles or microstructures. In another example, an EEG electrode can be made from polypropylene glycol material which has been impregnated, doped, or embedded with carbon nanotubes. In another example, an EEG electrode can be made from polystyrene (PST) which has been impregnated, doped, or embedded with gold or gold alloy particles or pieces.

In an example, an EEG electrode can be made from polystyrene (PST) which has been impregnated, doped, or embedded with copper or copper alloy particles or pieces. In another example, an EEG electrode can be made from polystyrene (PST) which has been impregnated, doped, or embedded with gallium. In another example, an EEG electrode can be made from polystyrene (PST) which has been impregnated, doped, or embedded with niobium. In another example, an EEG electrode can be made from polystyrene (PST) which has been impregnated, doped, or embedded with tungsten particles or pieces.

In an example, an EEG electrode can be made from polytetrafluoroethylene (PTFE) which has been impregnated, doped, or embedded with silver (or sliver alloy) particles or pieces. In another example, an EEG electrode can be made from polytetrafluoroethylene (PTFE) which has been impregnated, doped, or embedded with gold or gold alloy particles or pieces. In another example, an EEG electrode can be made from polytetrafluoroethylene (PTFE) which has been impregnated, doped, or embedded with tungsten particles or pieces. In another example, an EEG electrode can be made from polyethylene terephthalate (PET) which has been impregnated, doped, or embedded with carbon nanotubes.

In an example, an EEG electrode can be made from polyurethane which has been impregnated, doped, or embedded with graphene. In another example, an EEG electrode can be made from polyvinyl alcohol (PVOH) which has been impregnated, doped, or embedded with tungsten particles or pieces. In another example, an EEG electrode can be made from thermoplastic elastomer (TPE) which has been impregnated, doped, or embedded with gallium. In another example, an EEG electrode can be made with polydimethylsiloxane (PDMS) which has been impregnated, doped, or coated with carbon or silver particles or structures.

In an example, an EEG electrode can be made from polyethylene terephthalate (PET) which has been impregnated, doped, embedded, or coated with graphene. In another example, an EEG electrode can be made from polydimethylsiloxane (PDMS) which has been impregnated, doped, embedded, or coated with aluminum or aluminum alloy particles or pieces. In another example, an EEG electrode can include one or more protrusions, prongs, springs, pistons, electromagnetic actuators, compressible foam components, and inflatable chambers. In another example, an EEG sensing hairband, tiara, or headband. In another example, a hairband, tiara, or headband can have a sinusoidal shape.

In an example, a headband or eyewear can have with soft prongs and/or teeth which protrude into and/or under a person's hair. The prongs and/or teeth can be made from a silicone material (such as polydimethylsiloxane) which has been impregnated, doped, coated, or embedded with conductive material (such as a metal and/or carbon) in order to provide consistent but comfortable contact with the person's head. In another example, an EEG electrode can be made from a polymer which has been impregnated, doped, coated, or embedded with conductive material and have prongs and/or teeth which protrude into and/or under a person's hair. In another example, EEG electrodes can be made from a silicone material which has been impregnated, doped, coated, or embedded with silver or carbon and have prongs and/or teeth which protrude into and/or under a person's hair.

In an example, EEG electrodes can be located at placement sites of Modified Combinatorial Nomenclature (MCN) electrode placement system which are selected from the group consisting of F3, F4, F7, F8, Fz, T3, T4, T5, T6, P3, P4, Pz, O1, O2, C3, C4, and Cz. The electrodes can be made from a silicone material (such as PDMS) which has been impregnated, doped, coated, or embedded with conductive material (such as metal and/or carbon) in order to provide consistent but comfortable contact with the person's head. In another example, the prongs and/or teeth can be made from a silicone material (such as PDMS) which has been impregnated, doped, coated, or embedded with conductive material (such as metal and/or carbon) in order to provide consistent but comfortable contact with the person's head.

In an example, a device can comprise prongs and/or teeth which protrude into and/or under the person's hair. This can enable good electromagnetic communication with the person's head at locations on the person's head which are covered by hair. In another example, prongs and/or teeth can be made from a silicone material (such as PDMS) which has been impregnated, doped, coated, or embedded with conductive material (such as a metal and/or carbon) in order to provide consistent but comfortable contact with the person's head. In another example, conductive metal can be silver or aluminum. In another example, carbon material can be in the form of nanotubes or graphene. In another example, electrodes can be made from a silicone material which has been impregnated, doped, coated, or embedded with silver or carbon and have prongs and/or teeth which protrude into and/or under a person's hair. In another example, an electrode can be a capacitive electrode. In another example, an electrode can be a dry electrode.

In an example, an EEG electrode can be made from low-conductivity material which has been doped, impregnated, or coated with a high-conductivity material. In another example, an electrode can comprise a dielectric layer of low-conductivity material between two layers of high-conductivity material. In another example, an electrode can comprise a layer of high-conductivity material between two layers of low-conductivity material. In another example, electrode prongs and/or teeth can be made from an elastomeric polymer which is doped, embedded, impregnated, or coated with conductive material. In another example, portions of electrodes can be made from an elastomeric polymer which is doped, embedded, impregnated, or coated with conductive material. In another example, the polymer can be a silicone material. In another example, the polymer can be PDMS. In another example, the conductive material can be silver. In another example, the conductive material can be carbon. In another example, the conductive material can be carbon nanotubes or graphene.

In an example, a mobile wearable device can include one or more springs which hold one or more electrodes gently against a person's head. In another example, the tensions and/or lengths of these one or more springs can be manually (and individually) adjusted by the person to adjust fit and/or comfort. In another example, the tensions and/or lengths of these one or more springs can be automatically adjusted by the device to optimize electromagnetic communication between the one or more electrodes and the person's brain. In another example, a mobile wearable device can include one or more electromagnetic solenoids which hold one or more electrodes gently against a person's head. In another example, the lengths or pressures of these one or more solenoids can be manually adjusted by the person to adjust fit and/or comfort. In another example, the lengths or pressures of these solenoids can be automatically adjusted by the device to optimize electromagnetic communication between the one or more electrodes and the person's brain.

In an example, an EEG electrode can be made by printing, coating, and/or spraying a layer of elastic conductive material onto a layer of elastic non-conductive material. In another example, an EEG electrode can be formed by printing, coating, and/or spraying conductive material onto a non-conductive hair-penetrating protrusion. In another example, an EEG electrode can be made by printing, coating, and/or spraying conductive material onto a plurality of non-conductive flexible hair-penetrating protrusions. In another example, an EEG electrode can be made by printing, coating, painting, or spraying carbon-based ink or particles onto low-conductivity material. In another example, an EEG electrode can be made by printing, coating, painting, or spraying silver chloride onto low-conductivity material.

In an example, an electrode can be a capacitor which is made by bonding together alternating layers of conductive and non-conductive elastomeric material. In another example, an EEG electrode can be made by 3D printing, wherein conductive ink is printed onto a layer of non-conductive material. In another example, an EEG electrode can be made by coating a hair comb or hair band with conductive ink or paint. In another embodiment, an electrode can be formed by dipping a hair comb into conductive ink or paint. In another example, an EEG electrode can be made by embroidering or stitching an orthogonal mesh of conductive threads or yarns. In another example, an EEG electrode can be made by embroidering or stitching onto a hat or cap using conductive threads or yarns. In another example, an electrode can be made by injection molding with a silicone-based polymer.

In an example, an EEG electrode can be made by printing, coating, and/or spraying a layer of flexible conductive material onto a layer of flexible non-conductive material. In another example, an electrode can be made by printing, coating, and/or spraying conductive material onto a non-conductive polymer hair-penetrating protrusion. In another example, an EEG electrode can be made by printing, coating, and/or spraying conductive material onto a plurality of non-conductive hair-penetrating prongs, teeth, or combs. In another example, an electrode can be formed by printing, coating, painting, or spraying conductive ink onto low-conductivity material. In another example, an EEG electrode can be made by printing, coating, painting, or spraying silver-based ink or particles onto low-conductivity material.

In an example, an EEG electrode can be made by printing, spraying, or adhering a layer of conductive material onto a layer of non-conductive material. In another embodiment, an EEG electrode can be made by printing, spraying, or adhering a layer of conductive hydrogel onto the inner (e.g. body-facing) surface of a headband. In another example, an EEG electrode can be made by screen printing onto a layer of non-conductive material with conductive ink. In another example, an electrode can be formed by spraying a plurality of flexible hair-penetrating protrusions with conductive ink or paint. In another example, an electrode can be made by stitching conductive threads or yarns onto fabric in an orthogonal mesh. In another example, an EEG electrode can be made by weaving or knitting electrodes in an orthogonal pattern using conductive threads or yarns.

In an example, an electrode can be a dielectric structure which is made by bonding together alternating layers of conductive and non-conductive polymers. In another embodiment, an EEG electrode can be made by 3D printing, wherein conductive ink is printed onto an article of clothing. In another example, an electrode can be formed by adhering (or otherwise bonding) an elastomeric conductive polymer to the inner (e.g. body-facing) surface of a semicircular band; wherein the band curves around the posterior half of a person's head. In another example, an EEG electrode can be made by adhering (or otherwise bonding) an elastomeric conductive polymer to the inner (e.g. body-facing) surface of a semicircular band; wherein the band curves around the anterior half of a person's head from one ear to the other ear. In another example, an electrode can be formed by adhering and/or bonding conductive PDMS electrodes onto the inner (e.g. body-facing) surface of a headband.

In an example, an EEG electrode can be made by bonding together alternating layers of conductive and non-conductive polymers. In another example, an EEG electrode can be made by dipping a plurality of flexible hair-penetrating protrusions into conductive material. In another example, an EEG electrode can be made by embroidering or stitching a sinusoidal or zigzag pattern with conductive threads or yarns. In another example, an electrode can be made by embroidering or stitching an orthogonal mesh with conductive threads or yarns onto fabric. In another example, an EEG electrode can be formed by extruding and curing alternating layers of conductive and non-conductive material. In another example, an EEG electrode can be made by pouring and curing alternating layers of conductive and non-conductive elastic polymers.

In an example, an electrode can be made by printing, coating, and/or spraying carbon-based conductive ink onto a non-conductive hair-penetrating protrusion. In another example, an EEG electrode can be made by printing, coating, and/or spraying conductive material onto the non-conductive core of a flexible hair-penetrating protrusion. In another example, an EEG electrode can be made by printing, coating, and/or spraying non-conductive material onto conductive flexible hair-penetrating protrusions. In another example, an EEG electrode can be formed by printing, coating, painting, or spraying copper-based ink or particles onto low-conductivity material.

In an example, an EEG electrode can be made by printing, coating, painting, or spraying steel particles onto low-conductivity material. In another example, an EEG electrode can be made by printing, spraying, or adhering a layer of conductive material onto a non-conductive core of a hair-penetrating protrusion. In another example, an electrode can be made by printing, spraying, or adhering a layer of elastomeric conductive polymer material onto the inner (e.g. body-facing) surface of a headband. In another example, an EEG electrode can be made by bonding together alternating layers of conductive and non-conductive elastomeric material. In another example, an electrode can be formed by dipping a plurality of flexible hair-penetrating protrusions into conductive ink or paint. In another embodiment, an electrode can be made by embroidering or stitching a sinusoidal or zigzag pattern with conductive threads or yarns onto fabric. In another example, an electrode can be made by embroidering or stitching an orthogonal mesh with conductive threads or yarns onto an article of clothing. In another example, an EEG electrode can be made by filling a non-conductive lumen with a conductive liquid.

In an example, an EEG electrode can be made by pouring and curing alternating layers of conductive and non-conductive low modulus polymers. In another example, an electrode can be formed by printing conductive carbon-based ink onto a layer of non-conductive material in a sinusoidal or zigzag pattern. In another example, an EEG electrode can be made by printing with conductive carbon-based ink. In another example, an electrode can be formed by printing conductive graphene-containing ink onto fabric in a sinusoidal or zigzag pattern. In another example, an electrode can be made by printing conductive ink onto non-conductive material. In another example, an EEG electrode can be made by printing conductive silver-based ink onto a layer of non-conductive material in a sinusoidal or zigzag pattern. In another example, an EEG electrode can be made by printing conductive silver-based ink.

In an example, an EEG electrode can be made by printing, coating, and/or spraying a layer of conductive material onto a non-conductive longitudinal hair-penetrating protrusion. In another example, an EEG electrode can be made by printing, coating, and/or spraying conductive material onto a longitudinal non-conductive core of a hair-penetrating protrusion. In another embodiment, an electrode can be made by printing, coating, and/or spraying conductive material onto a non-conductive hair-penetrating protrusion. In another example, an electrode can be formed by printing, coating, and/or spraying silver-based conductive ink onto a non-conductive hair-penetrating protrusion. In another example, an EEG electrode can be made by printing, coating, painting, or spraying gold particles onto low-conductivity material.

In an example, a deformable, flexible, conductive electrode can comprise one or more protrusions, prongs, teeth, combs, pins, and/or petals which slide between strands of a person's hair so that the electrode is in electromagnetic communication with a person's brain despite being on a portion of the person's head which is covered by hair. In another example, a deformable, flexible, conductive electrode can comprise one or more protrusions, prongs, teeth, combs, pins, and/or petals which engage with a person's hair so that the electrode is in electromagnetic communication with a person's brain despite being on a portion of the person's head which is covered by hair. In another example, a deformable, flexible, conductive electrode can comprise one or more protrusions, prongs, teeth, combs, pins, and/or petals which intermesh and/or interdigitate with a person's hair so that the electrode is in electromagnetic communication with a person's brain despite being on a portion of the person's head which is covered by hair.

In an example, a deformable, flexible, conductive electrode can be configured to be in electromagnetic communication with a person's brain despite the person's hair. In another example, a electrode can comprise one or more deformable, flexible, and conductive prongs which protrude between strands of a person's hair so that the electrode is in electromagnetic communication with a person's brain despite being on a portion of the person's head which is covered by hair. In another example, an electrode can be peanut shaped. In another example, an electrode can comprise a hair-penetrating protrusion which is tapered with the smaller section being closer to a person's head. In another example, an electrode can have a dumbbell shape. In another example, an electrode can have a linear shape. In another example, an electrode can have a parabolic shape whose convex surface protrudes between strands of a person's hair. In another example, an electrode can have an arcuate or round shape. In another example, an electrode can have a sawtooth shape whose peaks protrude into a person's hair. In another example, an electrode can have a helical shape. In another example, an electrode can comprise a plurality of helical hair-penetrating conductive protrusions.

In an example, an electrode can include a hair-penetrating protrusion with a circular cross-sectional shape in a plane which is orthogonal to the surface of a person's head. In another example, an electrode can include a hair-penetrating protrusion with a linear cross-sectional shape in a plane which is parallel to the surface of a person's head. In another example, an electrode can comprise a hair-penetrating protrusion with a square cross-sectional shape in a plane which is orthogonal to the surface of a person's head. In another example, an electrode can include a hair-penetrating protrusion with a tapered cross-sectional shape in a plane which is parallel to the surface of a person's head. In another example, an electrode can include a hair-penetrating protrusion with an arcuate cross-sectional shape in a plane which is parallel to the surface of a person's head.

In an example, an electrode can comprise a plurality of hair-penetrating conductive protrusions which extend toward the surface of a person's head in a perpendicular (or orthogonal) manner. In another example, an electrode can comprise a plurality of hair-penetrating conductive protrusions which extend toward the surface of a person's head at an acute angle. In another example, an electrode can comprise a plurality of hair-penetrating conductive protrusions which are inserted between layers of a person's hair at an acute angle relative to the surface of the person's head. In another example, an electrode can have a polygonal shape. In another example, an electrode can have a rounded-rectangular shape. In another example, an electrode can have a sinusoidal shape whose peaks protrude into a person's hair. In another example, an electrode can have an hour-glass shape. In another example, an electrode can be circular.

In an example, an electrode can include a hair-penetrating protrusion with a circular cross-sectional shape in a plane which is parallel to the surface of a person's head. In another example, an electrode can include a hair-penetrating protrusion with a hexagonal cross-sectional shape in a plane which is orthogonal to the surface of a person's head. In another example, an electrode can comprise a hair-penetrating protrusion with a polygonal cross-sectional shape in a plane which is orthogonal to the surface of a person's head. In another example, an electrode can include a hair-penetrating protrusion with a square cross-sectional shape in a plane which is parallel to the surface of a person's head. In another example, an electrode can include a hair-penetrating protrusion with an annular cross-sectional shape in a plane which is orthogonal to the surface of a person's head. In another example, an electrode can comprise a hair-penetrating protrusion with an oval or elliptical cross-sectional shape in a plane which is orthogonal to the surface of a person's head.

In an example, a deformable, flexible, conductive electrode can comprise one or more protrusions, prongs, teeth, combs, pins, and/or petals which protrude, penetrate, and/or extend between strands of a person's hair so that the electrode is in electromagnetic communication with a person's brain despite being on a portion of the person's head which is covered by hair. In another example, a deformable, flexible, conductive electrode can comprise one or more protrusions, prongs, teeth, combs, pins, and/or petals which slide upward under a layer of a person's hair so that the electrode is in electromagnetic communication with a person's brain despite being on a portion of the person's head which is covered by hair. In another example, a deformable, flexible, conductive electrode can comprise one or more protrusions, prongs, teeth, combs, pins, and/or petals which clamp onto a person's hair so that the electrode is in electromagnetic communication with a person's brain despite being on a portion of the person's head which is covered by hair.

In an example, an electrode can comprise concentric conductive rings. In another example, an electrode can comprise nested conductive rings. In another example, an electrode can have a polyhedral shape. In another example, an electrode can have a square shape. In another example, an electrode can have a zigzag shape whose peaks protrude into a person's hair. In another example, an electrode can have an oval or elliptical shape. In another example, an electrode can include a hair-penetrating protrusion with a conic-section-shaped cross-sectional shape in a plane which is parallel to the surface of a person's head. In another example, an electrode can include a hair-penetrating protrusion with a hexagonal cross-sectional shape in a plane which is parallel to the surface of a person's head. In another example, an electrode can include a hair-penetrating protrusion with a polygonal cross-sectional shape in a plane which is parallel to the surface of a person's head. In another example, an electrode can comprise a hair-penetrating protrusion with a square cross-sectional shape in a plane which is parallel to the surface of a person's head.

In an example, an electrode can include a hair-penetrating protrusion with an annular cross-sectional shape in a plane which is parallel to the surface of a person's head. In another example, an electrode can comprise a hair-penetrating protrusion with an oval or elliptical cross-sectional shape in a plane which is parallel to the surface of a person's head. In another example, a deformable, flexible, conductive electrode can comprise one or more protrusions, prongs, teeth, combs, pins, and/or petals which are inserted between strands of a person's hair so that the electrode is in electromagnetic communication with a person's brain despite being on a portion of the person's head which is covered by hair.

In an example, an electrode can comprise one or more deformable, flexible, and conductive pins which protrude between strands of a person's hair so that the electrode is in electromagnetic communication with a person's brain despite being on a portion of the person's head which is covered by hair. In another example, an electrode can comprise one or more deformable, flexible, and conductive teeth which protrude between strands of a person's hair so that the electrode is in electromagnetic communication with a person's brain despite being on a portion of the person's head which is covered by hair. In another example, an electrode can comprise a hair-penetrating protrusion which is tapered so that the cross-sectional perimeter of a first portion which is closer to the surface of a person's head is smaller than the cross-sectional perimeter of second portion which is farther from the surface of the person's head.

In an example, an electrode can have a conic-section shape. In another example, an electrode can have a hexagonal shape. In another example, an electrode can have a parabolic shape whose peak penetrates into a person's hair. In another example, an electrode can have a rectangular shape. In another example, an electrode can have an annular and/or ring shape. In another example, an electrode can have an undulating and/or sinusoidal shape. In another example, an electrode can include a hair-penetrating protrusion with a conic-section-shaped cross-sectional shape in a plane which is orthogonal to the surface of a person's head. In another example, an electrode can include a hair-penetrating protrusion with a linear cross-sectional shape in a plane which is orthogonal to the surface of a person's head. In another example, an electrode can comprise a hair-penetrating protrusion with a square cross-sectional shape in a plane which is orthogonal to the surface of a person's head. In another example, an electrode can include a hair-penetrating protrusion with a tapered cross-sectional shape in a plane which is orthogonal to the surface of a person's head. In another example, an electrode can include a hair-penetrating protrusion with an arcuate cross-sectional shape in a plane which is orthogonal to the surface of a person's head.

In an example, a wearable mobile device for monitoring electromagnetic brain activity can include an array of hair-penetrating conductive protrusions with a two-dimensional cross-sectional area in a plane which is substantially parallel to the surface of a person's head when the device is worn. In another example, protrusions toward the center of this cross-sectional area can be closer together than protrusions toward the periphery of this cross-sectional area. In another example, protrusions toward the center of this cross-sectional area can be longer than protrusions toward the periphery of this cross-sectional area. In another example, protrusions toward the center of this cross-sectional area can have a higher Shore A value than protrusions toward the periphery of this cross-sectional area. In another example, protrusions toward the center of this cross-sectional area can be more conductive than protrusions toward the periphery of this cross-sectional area.

In an example, an electrode can comprise 2 dielectric protrusions. In another example, an electrode can comprise 4 dielectric protrusions. In another example, an electrode can comprise 6 dielectric protrusions. In another example, an electrode can comprise 8 dielectric protrusions. In another example, an EEG electrode can be made from a low-conductivity polymer which has been doped, impregnated, coated, dipped, sprayed, or printed with high-conductivity material. In another example, a hair-penetrating protrusion can be made with a low-conductivity flexible material which has been doped, impregnated, coated, dipped, sprayed, or printed with a high-conductivity material. In another example, an EEG electrode can be made from conductive silicone-based material. In another example, an EEG electrode can be made from silicone polymer. In another example, an EEG electrode can be made with polydimethylsiloxane (PDMS).

In an example, an EEG electrode can be made from silicone-based material (such as PDMS) which has been doped, impregnated, and/or embedded with activated carbon particles. In another example, an EEG electrode can be made from silicone-based material (such as PDMS) which has been doped, impregnated, and/or embedded with graphene nanoplatelets. In another example, an EEG electrode can be made from silicone-based material (such as PDMS) which has been doped, impregnated, and/or embedded with carbon nanotubes with a length between 1 and 5 microns. In another example, an EEG electrode can be made from silicone-based material (such as PDMS) which has been doped, impregnated, and/or embedded with metal powder. In another example, an EEG electrode can be made from silicone-based material (such as PDMS) which has been doped, impregnated, and/or embedded with metal particles. In another example, an EEG electrode can be made from silicone-based material (such as PDMS) which has been doped, impregnated, and/or embedded with silver fibers.

In an example, an EEG electrode can be made from silicone-based material (such as PDMS) which has been doped, impregnated, and/or embedded with copper. In another example, an EEG electrode can be made from silicone-based material (such as PDMS) which has been doped, impregnated, and/or embedded with PEDOT. In another example, an EEG electrode can be made from silicone-based material (such as PDMS) which is coated with aluminum. In another example, an EEG electrode can be made from silicone-based material (such as PDMS) which is coated with carbon nanotubes. In another example, an EEG electrode can be made from silicone-based material (such as PDMS) which is coated with conductive particles. In another example, an EEG electrode can be made from silicone-based material (such as PDMS) which is coated with graphite. In another example, an EEG electrode can be made from silicone-based material (such as PDMS) which is coated with multiwall carbon nanotubes.

In an example, an EEG electrode can be made from silicone-based material (such as PDMS) which is coated with silver fibers. In another example, an EEG electrode can be made from silicone-based material (such as PDMS) which is coated with stainless steel. In another example, an electrode can be made with a hydrogel material. In another example, an EEG electrode can be made from hydrogel in an osmotically-permeable membrane. In another example, an EEG electrode can be made with poly(3,4-ethylenedioxythiophene):poly(styrene sulfonate) (PEDOT:PSS). In another example, an EEG electrode can be made with small filaments of PEDOT:PSS.

In an example, an EEG electrode can be made from silicon-based hydrogel. In another example, an EEG electrode can be made from hydrogel material which has been doped, impregnated, and/or embedded with carbon. In another example, an EEG electrode can be made from hydrogel material which has been doped, impregnated, and/or embedded with carbon nanotubes with a length between 1 and 5 microns. In another example, an EEG electrode can be made from hydrogel material which has been doped, impregnated, and/or embedded with copper. In another example, an EEG electrode can be made from hydrogel material which has been doped, impregnated, and/or embedded with metal particles. In another example, an EEG electrode can be made from hydrogel material which has been doped, impregnated, and/or embedded with silver. In another example, an EEG electrode can be made from hydrogel material which has been printed, doped, impregnated, and/or embedded with silver-based ink.

In an example, an EEG electrode can be made from hydrogel material which is coated with activated carbon particles. In another example, an electrode can be made with a hydrogel material which is coated with carbon black. In another example, an EEG electrode can be made from hydrogel material which is coated with carbon particles. In another example, an EEG electrode can be made from hydrogel material which is coated with graphene nanoplatelets. In another example, an EEG electrode can be made from hydrogel material which is coated with metal powder. In another example, an electrode can be made with a hydrogel material which is coated with silver fibers.

In an example, an EEG electrode can be made from hydrogel material which is coated with stainless steel. In another example, an EEG electrode can be made with PEDOT and/or PEDOT:PSS which has been doped, impregnated, and/or embedded with carbon. In another example, an EEG electrode can be made with PEDOT and/or PEDOT:PSS which has been doped, impregnated, and/or embedded with carbon nanotubes with lengths between 1 and 5 microns. In another example, an EEG electrode can be made with PEDOT and/or PEDOT:PSS which has been doped, impregnated, and/or embedded with copper. In another example, an EEG electrode can be made with PEDOT and/or PEDOT:PSS which has been doped, impregnated, and/or embedded with metal particles. In another example, an EEG electrode can be made with PEDOT and/or PEDOT:PSS which has been doped, impregnated, and/or embedded with silver. In another example, an EEG electrode can be made with PEDOT and/or PEDOT:PSS which has been printed, doped, impregnated, and/or embedded with silver-based ink.

In an example, an EEG electrode can be made with PEDOT and/or PEDOT:PSS which is coated with activated carbon particles. In another example, an EEG electrode can be made with PEDOT and/or PEDOT:PSS which is coated with carbon black. In another example, an electrode can be made with PEDOT and/or PEDOT:PSS which is coated with carbon particles. In another example, an EEG electrode can be made with PEDOT and/or PEDOT:PSS which is coated with graphene nanoplatelets. In another example, an electrode can be made with PEDOT and/or PEDOT:PSS which is coated with metal powder. In another example, an EEG electrode can be made with PEDOT and/or PEDOT:PSS which is coated with silver fibers. In another example, an EEG electrode can be made with PEDOT and/or PEDOT:PSS which is coated with stainless steel.

In an example, an EEG electrode can be made with thermoplastic polyurethane (TPU) which has been doped, impregnated, and/or embedded with carbon. In another example, an EEG electrode can be made with thermoplastic polyurethane (TPU) which has been doped, impregnated, and/or embedded with carbon nanotubes with a length between 1 and 5 microns. In another example, an EEG electrode can be made with thermoplastic polyurethane (TPU) which has been doped, impregnated, and/or embedded with copper. In another example, an EEG electrode can be made with thermoplastic polyurethane (TPU) which has been doped, impregnated, and/or embedded with metal particles. In another example, an EEG electrode can be made with thermoplastic polyurethane (TPU) which has been doped, impregnated, and/or embedded with PEDOT. In another example, an EEG electrode can be made with thermoplastic polyurethane (TPU) which has been doped, impregnated, and/or embedded with silver chloride.

In an example, an EEG electrode can be made with thermoplastic polyurethane (TPU) which has been doped, impregnated, and/or embedded with single wall carbon nanotubes. In another example, an electrode can be made with thermoplastic polyurethane (TPU) which is coated with aluminum. In another example, an EEG electrode can be made with thermoplastic polyurethane (TPU) which is coated with carbon nanotubes. In another example, an electrode can be made with thermoplastic polyurethane (TPU) which is coated with conductive particles. In another example, an EEG electrode can be made with thermoplastic polyurethane (TPU) which is coated with graphite. In another example, an EEG electrode can be made with thermoplastic polyurethane (TPU) which is coated with multiwall carbon nanotubes.

In an example, an EEG electrode can be made with thermoplastic polyurethane (TPU) which is coated with silver. In another example, an EEG electrode can be made with thermoplastic polyurethane (TPU) which is coated with silver ink. In another example, an EEG electrode can be made with cellulose. In another example, an EEG electrode can be made with hydroxypropyl methylcellulose (HPMC). In another example, an EEG electrode can be made from cellulose material (such as HPMC) which has been doped, impregnated, and/or embedded with carbon. In another example, an EEG electrode can be made from cellulose material (such as HPMC) which has been doped, impregnated, and/or embedded with carbon nanotubes with a length between 1 and 5 microns.

In an example, an EEG electrode can be made from cellulose material (such as HPMC) which has been doped, impregnated, and/or embedded with copper. In another example, an electrode can be made with a cellulose material (such as HPMC) which has been doped, impregnated, and/or embedded with metal particles. In another example, an EEG electrode can be made from cellulose material (such as HPMC) which has been doped, impregnated, and/or embedded with silver. In another example, an EEG electrode can be made from cellulose material (such as HPMC) which has been printed, doped, impregnated, and/or embedded with silver ink.

In an example, an EEG electrode can be made from cellulose material (such as HPMC) which is coated with activated carbon particles. In another example, an electrode can be made with a cellulose material (such as HPMC) which is coated with carbon black. In another example, an EEG electrode can be made from cellulose material (such as HPMC) which is coated with carbon particles. In another example, an EEG electrode can be made from cellulose material (such as HPMC) which is coated with graphene nanoplatelets. In another example, an EEG electrode can be made from cellulose material (such as HPMC) which is coated with metal powder. In another example, an EEG electrode can be made from cellulose material (such as HPMC) which is coated with silver chloride. In another example, an EEG electrode can be made from cellulose material (such as HPMC) which is coated with single wall carbon nanotubes. In another example, an EEG electrode can be made by coating open-cell foam with a conductive layer. In another example, an EEG electrode can be made by hydrating a hydrogel in a conductive solution. In another example, an EEG electrode can be made by coating neoprene with PEDOT:PSS.

In an example, an EEG electrode can be made by adding carbon nanotubes to IPN-based PEDOT:PSS. In another example, an EEG electrode can be made by adding plasticizers to PEDOT:PSS. In another example, an electrode can be made by adding adsorbents to a polymer matrix. In another example, an EEG electrode can be made with two or more polymers with different conductivity levels. In another example, an EEG electrode can be made by coating and/or plating copper onto a polyimide. In another example, an electrode can be made by adding adhesives to conductive rubber. In another example, an EEG electrode can be made by adding PEDOT:PSS to a PDMS core.

In an example, an EEG electrode can be made from conductive rubber. In another example, an EEG electrode can be made with an interpenetrating polymer network (IPN). In another example, an EEG electrode can be made with polyimide (PI). In another example, an EEG electrode can be made with polyurethane. In another example, an EEG electrode can be made with styrene ethylene butylene streyene (SEBS). In another example, an electrode can include activated carbon particles. In another example, an EEG electrode can include carbon black. In another example, an electrode can include carbon particles. In another example, an electrode can include graphene nanoplatelets. In another example, an electrode can include metal powder.

In an example, an electrode can include PEDOT:PSS. In another example, an EEG electrode can include silver fibers. In another example, an electrode can include stainless steel. In another example, material for an electrode can be made by adding electroconductive material to a base material. In another example, material for an electrode can be made by adding adsorbent material to a base material. In another example, an electrode can measure electromagnetic conductivity. In another example, an EEG electrode can measure electromagnetic impedance. In another example, an electrode can measure electromagnetic capacitance. In another example, one or more portions of an electrode can be made with low-durometer material. In another example, an EEG electrode can be made with material with a Shore A value between 40 and 80.

In an example, an electrode can be made with amorphous material. In another example, an EEG electrode can be made with elastomeric material. In another example, an EEG electrode can be made with ion-permeable material. In another example, an EEG electrode can be made from polymer which has been doped, impregnated, coated, dipped, sprayed, or printed with metal particles, microstructures, or powder. In another example, a hair-penetrating protrusion can comprise a low-conductivity flexible core which has been coated, dipped, sprayed, or printed with a high-conductivity material.

In an example, an EEG electrode can be made from high-consistency silicone material. In another example, an EEG electrode can be made with polydimethylsiloxane (PDMS). In another example, an EEG electrode can be made from silicone-based material (such as PDMS) which has been doped, impregnated, and/or embedded with conductive particles. In another example, an EEG electrode can be made from silicone-based material (such as PDMS) which has been doped, impregnated, and/or embedded with carbon. In another example, an EEG electrode can be made from silicone-based material (such as PDMS) which has been doped, impregnated, and/or embedded with carbon black. In another example, an EEG electrode can be made from silicone-based material (such as PDMS) which has been doped, impregnated, and/or embedded with multiwall carbon nanotubes.

In an example, an electrode can be made with a silicone-based material (such as PDMS) which has been doped, impregnated, and/or embedded with silver. In another example, an EEG electrode can be made from silicone-based material (such as PDMS) which has been printed, doped, impregnated, and/or embedded with silver-based ink. In another example, an EEG electrode can be made from silicone-based material (such as PDMS) which has been doped, impregnated, and/or embedded with stainless steel. In another example, an EEG electrode can be made from silicone-based material (such as PDMS) which has been doped, impregnated, and/or embedded with PEDOT:PSS. In another example, an EEG electrode can be made from silicone-based material (such as PDMS) which is coated with carbon. In another example, an EEG electrode can be made from silicone-based material (such as PDMS) which is coated with carbon nanotubes with lengths between 1 and 5 microns.

In an example, an EEG electrode can be made from silicone-based material (such as PDMS) which is coated with copper. In another example, an EEG electrode can be made from silicone-based material (such as PDMS) which is coated with metal particles. In another example, an EEG electrode can be made from silicone-based material (such as PDMS) which is coated with silver. In another example, an EEG electrode can be made from silicone-based material (such as PDMS) which is coated with silver ink. In another example, an EEG electrode can be made from silicone-based material (such as PDMS) which is coated with PEDOT.

In an example, an EEG electrode can be made from saline hydrogel. In another example, an electrode can be made with a conductive interpenetrating network hydrogel. In another example, an EEG electrode can be made with an aqueous suspension of PEDOT:PSS. In another example, an EEG electrode can be made from hydrogel material which has been doped, impregnated, and/or embedded with activated carbon particles. In another example, an EEG electrode can be made from hydrogel material which has been doped, impregnated, and/or embedded with carbon black. In another example, an EEG electrode can be made from hydrogel material which has been doped, impregnated, and/or embedded with carbon particles. In another example, an EEG electrode can be made from hydrogel material which has been doped, impregnated, and/or embedded with graphene nanoplatelets. In another example, an EEG electrode can be made from hydroxyethyl methacrylate hydrogel.

In an example, an EEG electrode can be made from hydrogel material which has been doped, impregnated, and/or embedded with metal powder. In another example, an EEG electrode can be made from hydrogel material which has been doped, impregnated, and/or embedded with silver chloride. In another example, an EEG electrode can be made from hydrogel material which has been doped, impregnated, and/or embedded with single wall carbon nanotubes. In another example, an EEG electrode can be made from hydrogel which has been doped, impregnated, or coated with conductive material.

In an example, an EEG electrode can be made from hydrogel material which is coated with aluminum. In another example, an EEG electrode can be made from hydrogel material which is coated with carbon nanotubes. In another example, an EEG electrode can be made from hydrogel material which is coated with conductive particles. In another example, an electrode can be made with a hydrogel material which is coated with graphite. In another example, an EEG electrode can be made from hydrogel material which is coated with silver. In another example, an EEG electrode can be made from hydrogel material which is coated with silver ink. In another example, an EEG electrode can be made from polyvinyl alcohol hydrogel.

In an example, an EEG electrode can be made with PEDOT and/or PEDOT:PSS which has been doped, impregnated, and/or embedded with activated carbon particles. In another example, an EEG electrode can be made with PEDOT and/or PEDOT:PSS which has been doped, impregnated, and/or embedded with carbon black. In another example, an EEG electrode can be made with PEDOT and/or PEDOT:PSS which has been doped, impregnated, and/or embedded with carbon particles. In another example, an EEG electrode can be made with PEDOT and/or PEDOT:PSS which has been doped, impregnated, and/or embedded with graphene nanoplatelets. In another example, an EEG electrode can be made with PEDOT and/or PEDOT:PSS which has been doped, impregnated, and/or embedded with metal powder.

In an example, an EEG electrode can be made with PEDOT and/or PEDOT:PSS which has been doped, impregnated, and/or embedded with silver chloride. In another example, an EEG electrode can be made with PEDOT and/or PEDOT:PSS which has been doped, impregnated, and/or embedded with single wall carbon nanotubes. In another example, an EEG electrode can be made with PEDOT and/or PEDOT:PSS which is coated with aluminum. In another example, an EEG electrode can be made with PEDOT and/or PEDOT:PSS which is coated with carbon nanotubes. In another example, an EEG electrode can be made with PEDOT and/or PEDOT:PSS which is coated with conductive particles. In another example, an EEG electrode can be made with PEDOT and/or PEDOT:PSS which is coated with graphite. In another example, an EEG electrode can be made with PEDOT and/or PEDOT:PSS which is coated with silver. In another example, an electrode can be made with PEDOT and/or PEDOT:PSS which is coated with silver-based ink.

In an example, an EEG electrode can be made with thermoplastic polyurethane (TPU) which has been doped, impregnated, and/or embedded with activated carbon particles. In another example, an EEG electrode can be made with thermoplastic polyurethane (TPU) which has been doped, impregnated, and/or embedded with carbon black. In another example, an EEG electrode can be made with thermoplastic polyurethane (TPU) which has been doped, impregnated, and/or embedded with carbon particles. In another example, an EEG electrode can be made with thermoplastic polyurethane (TPU) which has been doped, impregnated, and/or embedded with graphene nanoplatelets. In another example, an EEG electrode can be made with thermoplastic polyurethane (TPU) which has been doped, impregnated, and/or embedded with metal powder.

In an example, an EEG electrode can be made with thermoplastic polyurethane (TPU) which has been doped, impregnated, and/or embedded with PEDOT:PSS. In another example, an EEG electrode can be made with thermoplastic polyurethane (TPU) which has been doped, impregnated, and/or embedded with silver fibers. In another example, an EEG electrode can be made with thermoplastic polyurethane (TPU) which has been doped, impregnated, and/or embedded with stainless steel. In another example, an EEG electrode can be made with thermoplastic polyurethane (TPU) which is coated with carbon. In another example, an EEG electrode can be made with thermoplastic polyurethane (TPU) which is coated with carbon nanotubes with a length between 1 and 5 microns. In another example, an EEG electrode can be made with thermoplastic polyurethane (TPU) which is coated with copper. In another example, an EEG electrode can be made with thermoplastic polyurethane (TPU) which is coated with metal particles. In another example, an EEG electrode can be made with thermoplastic polyurethane (TPU) which is coated with PEDOT. In another example, an EEG electrode can be made with thermoplastic polyurethane (TPU) which is coated with silver chloride. In another example, an EEG electrode can be made with thermoplastic polyurethane (TPU) which is coated with single wall carbon nanotubes.

In an example, an EEG electrode can be made from cellulose derivative. In another example, an electrode can be made with cellulose material (such as HPMC) which has been doped, impregnated, and/or embedded with activated carbon particles. In another example, an EEG electrode can be made from cellulose material (such as HPMC) which has been doped, impregnated, and/or embedded with carbon black. In another example, an EEG electrode can be made from cellulose material (such as HPMC) which has been doped, impregnated, and/or embedded with carbon particles. In another example, an EEG electrode can be made from cellulose material (such as HPMC) which has been doped, impregnated, and/or embedded with graphene nanoplatelets. In another example, an EEG electrode can be made from cellulose material (such as HPMC) which has been doped, impregnated, and/or embedded with metal powder.

In an example, an EEG electrode can be made from cellulose material (such as HPMC) which has been doped, impregnated, and/or embedded with silver chloride. In another example, an EEG electrode can be made from cellulose material (such as HPMC) which has been doped, impregnated, and/or embedded with single wall carbon nanotubes. In another example, an EEG electrode can be made from cellulose material (such as HPMC) which is coated with aluminum. In another example, an EEG electrode can be made from cellulose material (such as HPMC) which is coated with carbon nanotubes. In another example, an EEG electrode can be made from cellulose material (such as HPMC) which is coated with conductive particles. In another example, an EEG electrode can be made from cellulose material (such as HPMC) which is coated with graphite. In another example, an EEG electrode can be made from cellulose material (such as HPMC) which is coated with multiwall carbon nanotubes.

In an example, an EEG electrode can be made from cellulose material (such as HPMC) which is coated with silver fibers. In another example, an EEG electrode can be made from cellulose material (such as HPMC) which is coated with stainless steel. In another example, an electrode can be made by coating open-cell foam with PEDOT:PSS. In another example, an EEG electrode can be made by hydrating a hydrogel in a saline solution. In another example, an EEG electrode can be made from combination of PDMS and PEDOT:PSS. In another example, an EEG electrode can be made by adding graphene to Interpenetrating polymer Network (IPN) based PEDOT:PSS. In another example, an EEG electrode can be made by adding solvents to PEDOT:PSS.

In an example, an EEG electrode can be made by adding carbon nanotubes to a polymer matrix. In another example, an EEG electrode can be made by infusing carbon into a thermoplastic elastomer. In another example, an EEG electrode can be made with two or more polymers with different durometer levels. In another example, an electrode can be made printing, spraying, coating, and/or painting conductive ink onto a polyamide. In another example, an EEG electrode can be made by infusing or coating copper into a silicon material. In another example, an EEG electrode can be made by adding a mixture of carbon nanotubes and carbon black to a styrene polymer by coating, spraying, or printing silver onto vinyl. In another example, an EEG electrode can be made with polyacetylene.

In an example, an EEG electrode can be made from thermoplastic elastomer (TPE). In another example, an EEG electrode can be made with poly(oxyethylene) (PEG). In another example, an electrode can be made with polypropylene glycol. In another example, an EEG electrode can be made with polyvinyl alcohol (PVA). In another example, an EEG electrode can be made with thermoplastic polyurethane (TPU). In another example, an electrode can include aluminum. In another example, an electrode can include carbon nanotubes. In another example, an electrode can include conductive particles. In another example, an EEG electrode can include graphite.

In an example, an electrode can include multiwall carbon nanotubes. In another example, an electrode can include silver. In another example, an electrode can include silver ink. In another example, material for an electrode can be made by adding activated carbon particles to a base material. In another example, material for an EEG electrode can be made by adding stretchable material to a base material. In another example, an electrode can measure electromagnetic resistance between two locations on a person's head. In another example, an electrode can measure voltage differences between two locations on a person's head. In another example, an electrode can be a capacitive EEG electrode. In another example, an EEG electrode can be made with material which has a low Shore A value. In another example, an electrode can be made with material with a Shore A value between 5 and 50.

In an example, an EEG electrode can be made with deformable material. In another example, an electrode can be made with flexible material. In another example, an EEG electrode can be made from low-conductivity material (such as a low-conductivity polymer) which has been doped, impregnated, coated, dipped, sprayed, or printed with high-conductivity material (such as a high-conductivity metal). In another example, an electrode can include a plurality of flexible hair-penetrating protrusions.

In an example, an EEG electrode can be made from silicone-based material. In another example, an EEG electrode can be made from silicone rubber. In another example, an EEG electrode can be made with dimethicone. In another example, an EEG electrode can be made from silicone-based material (such as PDMS) which has been doped, impregnated, and/or embedded with carbon particles. In another example, an EEG electrode can be made from silicone-based material (such as PDMS) which has been doped, impregnated, and/or embedded with graphite. In another example, an EEG electrode can be made from silicone-based material (such as PDMS) which has been doped, impregnated, and/or embedded with carbon nanotubes. In another example, an EEG electrode can be made from silicone-based material (such as PDMS) which has been doped, impregnated, and/or embedded with single wall carbon nanotubes.

In an example, an electrode can be made with a silicone-based material (such as PDMS) which has been doped, impregnated, and/or embedded with silver chloride. In another example, an EEG electrode can be made from silicone-based material (such as PDMS) which has been doped, impregnated, and/or embedded with aluminum. In another example, an EEG electrode can be made from silicone-based material (such as PDMS) which is coated with activated carbon particles. In another example, an electrode can be made with a silicone-based material (such as PDMS) which is coated with carbon black. In another example, an EEG electrode can be made from silicone-based material (such as PDMS) which is coated with carbon particles. In another example, an EEG electrode can be made from silicone-based material (such as PDMS) which is coated with graphene nanoplatelets.

In an example, an EEG electrode can be made from silicone-based material (such as PDMS) which is coated with metal powder. In another example, an EEG electrode can be made from silicone-based material (such as PDMS) which is coated with silver chloride. In another example, an EEG electrode can be made from silicone-based material (such as PDMS) which is coated with single wall carbon nanotubes. In another example, an EEG electrode can be made from silicone-based material (such as PDMS) which is coated with PEDOT:PSS. In another example, an electrode can be made with a hydrogel which is cured via ultraviolet light. In another example, an EEG electrode can be made with poly(3,4-ethylenedioxythiophene (PEDOT). In another example, an EEG electrode can be made from linear biopolymer of PEDOT:PSS. In another example, an EEG electrode can be made from hydrogel material which has been doped, impregnated, and/or embedded with aluminum. In another example, an EEG electrode can be made from hydrogel material which has been doped, impregnated, and/or embedded with carbon nanotubes. In another example, an EEG electrode can be made from hydrogel material which has been doped, impregnated, and/or embedded with conductive particles. In another example, an EEG electrode can be made from hydrogel material which has been doped, impregnated, and/or embedded with graphite.

In an example, an EEG electrode can be made from hydrogel material which has been doped, impregnated, and/or embedded with multiwall carbon nanotubes. In another example, an EEG electrode can be made from hydrogel material which has been doped, impregnated, and/or embedded with silver fibers. In another example, an EEG electrode can be made from hydrogel material which has been doped, impregnated, and/or embedded with stainless steel. In another example, an electrode can be made with a hydrogel material which is coated with carbon. In another example, an EEG electrode can be made from hydrogel material which is coated with carbon nanotubes with a length between 1 and 5 microns.

In an example, an EEG electrode can be made from hydrogel material which is coated with copper. In another example, an electrode can be made with a hydrogel material which is coated with metal particles. In another example, an EEG electrode can be made from hydrogel material which is coated with silver chloride. In another example, an EEG electrode can be made from hydrogel material which is coated with single wall carbon nanotubes. In another example, an EEG electrode can be made with PEDOT and/or PEDOT:PSS which has been doped, impregnated, and/or embedded with aluminum. In another example, an EEG electrode can be made with PEDOT and/or PEDOT:PSS which has been doped, impregnated, and/or embedded with carbon nanotubes. In another example, an EEG electrode can be made with PEDOT and/or PEDOT:PSS which has been doped, impregnated, and/or embedded with conductive particles. In another example, an EEG electrode can be made with PEDOT and/or PEDOT:PSS which has been doped, impregnated, and/or embedded with graphite.

In an example, an electrode can be made with PEDOT and/or PEDOT:PSS which has been doped, impregnated, and/or embedded with multiwall carbon nanotubes. In another example, an EEG electrode can be made with PEDOT and/or PEDOT:PSS which has been doped, impregnated, and/or embedded with silver fibers. In another example, an EEG electrode can be made with PEDOT and/or PEDOT:PSS which has been doped, impregnated, and/or embedded with stainless steel. In another example, an EEG electrode can be made with PEDOT and/or PEDOT:PSS which is coated with carbon. In another example, an electrode can be made with PEDOT and/or PEDOT:PSS which is coated with carbon nanotubes with lengths between 1 and 5 microns. In another example, an EEG electrode can be made with PEDOT and/or PEDOT:PSS which is coated with copper.

In an example, an EEG electrode can be made with PEDOT and/or PEDOT:PSS which is coated with metal particles. In another example, an EEG electrode can be made with PEDOT and/or PEDOT:PSS which is coated with silver chloride. In another example, an EEG electrode can be made with PEDOT and/or PEDOT:PSS which is coated with single wall carbon nanotubes. In another example, an EEG electrode can be made with thermoplastic polyurethane (TPU) which has been doped, impregnated, and/or embedded with aluminum. In another example, an EEG electrode can be made with thermoplastic polyurethane (TPU) which has been doped, impregnated, and/or embedded with carbon nanotubes. In another example, an EEG electrode can be made with thermoplastic polyurethane (TPU) which has been doped, impregnated, and/or embedded with conductive particles. In another example, an EEG electrode can be made with polyphenylene vinylene.

In an example, an electrode can be made with thermoplastic polyurethane (TPU) which has been doped, impregnated, and/or embedded with graphite. In another example, an EEG electrode can be made with thermoplastic polyurethane (TPU) which has been doped, impregnated, and/or embedded with multiwall carbon nanotubes. In another example, an electrode can be made with thermoplastic polyurethane (TPU) which has been doped, impregnated, and/or embedded with silver. In another example, an EEG electrode can be made with thermoplastic polyurethane (TPU) which has been printed, doped, impregnated, and/or embedded with silver ink. In another example, an EEG electrode can be made with thermoplastic polyurethane (TPU) which is coated with activated carbon particles. In another example, an EEG electrode can be made with thermoplastic polyurethane (TPU) which is coated with carbon black. In another example, an EEG electrode can be made with thermoplastic polyurethane (TPU) which is coated with carbon particles.

In an example, an EEG electrode can be made with thermoplastic polyurethane (TPU) which is coated with graphene nanoplatelets. In another example, an electrode can be made with thermoplastic polyurethane (TPU) which is coated with metal powder. In another example, an EEG electrode can be made with thermoplastic polyurethane (TPU) which is coated with PEDOT:PSS. In another example, an EEG electrode can be made with thermoplastic polyurethane (TPU) which is coated with silver fibers. In another example, an electrode can be made with thermoplastic polyurethane (TPU) which is coated with stainless steel.

In an example, an EEG electrode can be made from hydroxypropyl cellulose. In another example, an EEG electrode can be made from cellulose material (such as HPMC) which has been doped, impregnated, and/or embedded with aluminum. In another example, an EEG electrode can be made from cellulose material (such as HPMC) which has been doped, impregnated, and/or embedded with carbon nanotubes. In another example, an EEG electrode can be made from cellulose material (such as HPMC) which has been doped, impregnated, and/or embedded with conductive particles. In another example, an EEG electrode can be made from cellulose material (such as HPMC) which has been doped, impregnated, and/or embedded with graphite.

In an example, an EEG electrode can be made from cellulose material (such as HPMC) which has been doped, impregnated, and/or embedded with multiwall carbon nanotubes. In another example, an EEG electrode can be made from cellulose material (such as HPMC) which has been doped, impregnated, and/or embedded with silver fibers. In another example, an electrode can be made with a cellulose material (such as HPMC) which has been doped, impregnated, and/or embedded with stainless steel. In another example, an EEG electrode can be made from cellulose material (such as HPMC) which is coated with carbon. In another example, an EEG electrode can be made from cellulose material (such as HPMC) which is coated with carbon nanotubes with a length between 1 and 5 microns.

In an example, an EEG electrode can be made from cellulose material (such as HPMC) which is coated with copper. In another example, an electrode can be made with a cellulose material (such as HPMC) which is coated with metal particles. In another example, an EEG electrode can be made from cellulose material (such as HPMC) which is coated with silver. In another example, an EEG electrode can be made from cellulose material (such as HPMC) which is coated with silver-based ink. In another example, an EEG electrode can be made by printing conductive silver ink on fabric. In another example, an EEG electrode can be made by impregnating foam with PEDOT. In another example, an EEG electrode can be made adding metal particles to IPN-based PEDOT:PSS. In another example, an EEG electrode can be made from combination of PDMS and PEDOT. In another example, an EEG electrode can be made by adding surfactants to PEDOT:PSS.

In an example, an EEG electrode can be made by adding carbon to a plastic material. In another example, an EEG electrode can be made with mixture of different polymers. In another example, an electrode can be made with a matrix of silicones and hydrogels. In another example, an EEG electrode can be made by printing, spraying, coating, or plating metal material onto a polymer core. In another example, an electrode can be made by adding PEDOT:PSS to a layer of PDMS. In another example, an EEG electrode can be made from conductive polymer. In another example, an EEG electrode can be made with an electroactive polymer. In another example, an EEG electrode can be made with polyethylene glycol. In another example, an EEG electrode can be made with polypropylene oxide. In another example, an EEG electrode can be made with rubber. In another example, an EEG electrode can be made with thermoplastic vulcanizate (TPV).

In an example, an electrode can include carbon. In another example, an electrode can include carbon nanotubes with lengths between 1 and 5 microns. In another example, an EEG electrode can include copper. In another example, an electrode can include metal particles. In another example, an electrode can include PEDOT. In another example, an electrode can include silver chloride. In another example, an electrode can include single wall carbon nanotubes. In another example, material for an electrode can be made by adding adhesive material to a base material. In another example, material for an electrode can be made by adding surfactant material to a base material. In another example, a wearable EEG device can have hair-penetrating protrusions and a vibrating member which vibrates the protrusions to help the protrusions move through the person's hair.

In an example, an electrode can comprise 2 pairs of conductive polymer electrodes. In another example, an electrode can comprise 4 pairs of conductive polymer electrodes. In another example, an electrode can comprise 6 pairs of conductive polymer electrodes. In another example, an electrode can comprise 8 pairs of conductive polymer electrodes. In another example, an electrode can comprise a conductive layer and a non-conductive layer. In another example, an electrode can comprise a first layer with a first conductivity layer and a second layer with a second conductivity layer, wherein the second conductivity level is less than the first conductivity level. In another example, an electrode can comprise a flexible electroconductive layer and a flexible non-electroconductive layer. In another example, these two layers can be substantially parallel. In another example, an electrode can include a high-conductivity layer which is worn closer to the surface of a person's head and a low-conductivity layer which is worn farther from the surface of the person's head. In another example, an electrode can include two flexible conductive layers separated by a flexible non-conductive layer. In another example, these three layers can be substantially parallel.

In an example, an electrode can comprise alternating layers of low-conductivity material and high-conductivity material. In another example, an electrode can comprise two conductive layers separated by an insulating layer. In another example, an electrode can include two flexible layers of high-conductivity material separated by a flexible layer of low-conductivity material. In another example, an electrode can include two flexible layers of high-conductivity material separated by a space or gap. In another example, an electrode can include a dielectric layer. In another example, an electrode can comprise an adhesive layer which is adhered to a conductive layer. In another example, an electrode can include a capacitive layer. In another example, an electrode can include a capacitive electrode. In another example, an electrode can comprise an inner low-conductivity layer and an outer high-conductivity layer.

In an example, an electrode can comprise an inner high-conductivity layer and an outer low-conductivity layer. In another example, an electrode can include one or more hair-penetrating protrusions with inner low-conductivity cores and outer high-conductivity coatings or layers. In another example, an electrode can include one or more hair-penetrating protrusions with inner high-conductivity cores and outer low-conductivity coatings or layers. In another example, an electrode can comprise high-conductivity and low-conductivity layers with different thicknesses. In another example, a non-conductive layer can be thinner than a conductive layer. In another example, a non-conductive layer can be thicker than a conductive layer. In another example, an electrode can comprise high-conductivity and low-conductivity layers with different orientations. In another example, conductive strands with selected orientations can be embedded in non-conductive material. In another example, longitudinal conductive strands with a plurality of orientations can be embedded in non-conductive material. In another example, conductive rings can be embedded in non-conductive material.

In an example, an electrode can comprise two conductive layers separated by a dielectric elastomer. In another example, an electrode can comprise conductive layers with a dielectric coating. In another example, an electrode can comprise a dielectric coating between conductive layers. In another example, an electrode can comprise a dielectric layer between conductive layers. In another example, an electrode can comprise a flexible dielectric coating between conductive layers. In another example, an electrode can comprise a flexible dielectric layer between conductive layers. In another example, an electrode can comprise a flexible dielectric elastomer between conductive layers. In another example, an electrode can comprise high-conductivity and low-conductivity layers with different elasticity levels.

In an example, an electrode can include a low-conductivity layer which is worn closer to the surface of a person's head and a high-conductivity layer which is worn farther from the surface of the person's head. In another example, an electrode can include a low-conductivity layer which is configured to be worn a first average distance from the surface of a person's head and a high-conductivity layer which is configured to be worn a second average distance from the surface of the person's head, wherein the second average distance is greater than the first average distance.

In an example, an electrode which is worn on a portion of a person's head which is covered with hair can comprise a base which is configured to have an orientation which is generally parallel to the surface of a person's head and 2 to 4 hair-penetrating and/or hair-engaging protrusions which extend inward from the base toward the surface of the person's head. In another example, the protrusions can extend between strands (and/or under layers) of the person's hair and achieve better electromagnetic communication with the person's brain. In another example, an electrode which is worn on a portion of a person's head which is covered with hair can comprise a base with an orientation which is generally parallel to the surface of a person's head and 2 to 4 hair-penetrating and/or hair-engaging protrusions with longitudinal axes which are generally orthogonal to the surface of the person's head. In another example, an electrode can comprise 2 pairs of conductive hair-penetrating protrusions.

In an example, an electrode which is worn on a portion of a person's head which is covered with hair can comprise a base which is configured to have an orientation which is generally parallel to the surface of a person's head and 5 to 8 hair-penetrating and/or hair-engaging protrusions which extend inward from the base toward the surface of the person's head. In another example, the protrusions can extend between strands (and/or under layers) of the person's hair and achieve better electromagnetic communication with the person's brain. In another example, an electrode which is worn on a portion of a person's head which is covered with hair can comprise a base with an orientation which is generally parallel to the surface of a person's head and 5 to 8 hair-penetrating and/or hair-engaging protrusions with longitudinal axes which are generally orthogonal to the surface of the person's head. In another example, an electrode can comprise 4 pairs of conductive hair-penetrating protrusions.

In an example, an electrode can comprise a base which is a first distance from a person's head and a plurality of conductive protrusions, prongs, teeth, combs, pins, and/or petals which extend inward to a second distance from the person's head, wherein the second distance is between 50% and 90% of the first distance. In another example, an electrode can comprise a base which is a first distance from a person's head and a plurality of conductive protrusions, prongs, teeth, combs, pins, and/or petals which extend inward to a second distance from the person's head, wherein the second distance is between 10% and 50% of the first distance.

In an example, an electrode can comprise a plurality of hair-penetrating protrusions which are in electromagnetic communication with a person's brain. In another example, an electrode can comprise a base which is worn a first distance from the surface of a person's head and a plurality of protrusions which extend inward from the base through the person's hair to a second distance from the surface of the person's head, wherein the second distance is less than the first distance. In another example, an electrode can comprise a base which is worn a first distance from the surface of a person's head and two protrusions which extend inward from the base through the person's hair to a second distance from the surface of the person's head, wherein the second distance is less than the first distance.

In an example, an electrode can comprise one or more protrusions, prongs, teeth, combs, pins, and/or petals with longitudinal axes which have generally-vertical orientations when they are worn on a person's head. In another example, an electrode can comprise one or more protrusions, prongs, teeth, combs, pins, and/or petals with longitudinal cross-sectional perimeters which have generally-vertical orientations when worn on a person's head. In another example, a conductive hair-penetrating protrusion can have a flexible conductive core which is covered with non-conductive material. In another example, a flexible conductive core of a hair-penetrating protrusion can be made from PDMS, TPU, or PEDOT:PSS. In another example, a flexible conductive core of a hair-penetrating protrusion can be made from a hydrogel. In another example, a wearable EEG device can have at least 10 hair-penetrating conductive protrusions.

In an example, a wearable mobile device for monitoring electromagnetic brain activity can include an array of conductive hair-penetrating conductive protrusions. In another example, these protrusions can protrude inward from a base toward the surface of a person's head at an acute angle relative to the base, instead of a conventional perpendicular orientation. In another example, these protrusions can protrude inward from a base toward the surface of a person's head at different angles. In another example, protrusions in such an array can protrude toward a person's head can be tilted toward the periphery of the array. In another example, protrusions can be tilted in a partially-radial manner, away from the center of the array and toward the perimeter of the array. In this manner, the protrusions can better penetrate through layers of hair without creating uncomfortable points of high-pressure contact with the person's head. In another example, protrusions can be angled toward the periphery of the array in a windmill, whorl, or whorl-windmill pattern.

In an example, an electrode can comprise one or more protrusions, prongs, teeth, combs, pins, and/or petals which are upwardly inserted into a person's hair. In another example, an electrode can comprise one or more protrusions, prongs, teeth, combs, pins, and/or petals which are inserted into a person's hair with an upward motion. In another example, an electrode can comprise one or more protrusions, prongs, teeth, combs, pins, and/or petals which face upward when worn on a person's head. In another example, an electrode can comprise one or more protrusions, prongs, teeth, combs, pins, and/or petals which face inward and upward when worn on a person's head. In another example, a wearable EEG device can have a plurality of hair-penetrating protrusions which are inserted under the outer layer of a person's hair so that they are generally not visible. In another example, an electrode can comprise a base which is worn outside a layer of a person's hair and one or more protrusions, prongs, teeth, combs, pins, and/or petals which are worn interior to (or within) the layer so that they are not visible.

In an example, an electrode can comprise 6 pairs of conductive hair-penetrating protrusions. In another example, an electrode can comprise 8 pairs of conductive hair-penetrating protrusions. In another example, protrusions, prongs, teeth, combs, pins, and/or petals can face inward toward a person's head from a base which is worn on the person's head. In another example, an electrode can comprise one or more protrusions, prongs, teeth, combs, pins, and/or petals with longitudinal axes which have generally-horizontal orientations when they are worn on a person's head.

In an example, an electrode can comprise a base which is generally parallel to the surface of a person's head and one or more protrusions, prongs, teeth, combs, pins, and/or petals which are generally orthogonal to the surface of the person's head. In another example, an electrode can include: a base; a first hair-penetrating protrusion which extends at a first angle from the base toward the surface of a person's head; and a second hair-penetrating protrusion which extends at a second angle from the base toward the surface of a person's head, wherein the second angle differs from the first angle by at least 10 degrees. In another example, an electrode can include: a base; a first hair-penetrating protrusion which extends at a first angle from the base toward the surface of a person's head; and a second hair-penetrating protrusion which extends at a second angle from the base toward the surface of a person's head, wherein the second angle differs from the first angle by 10 to 45 degrees. In another example, each electrode can have 4 to 6 hair-penetrating or hair-engaging conductive protrusions. In another example, an electrode can comprise 3 pairs of conductive hair-penetrating protrusions.

In an example, an electrode can comprise: a base which is worn outside a layer of a person's hair; and one or more conductive protrusions which extend inward from the base through the layer to be in electromagnetic communication with the person's brain. In another example, an electrode can comprise: a base which is worn outside a layer of a person's hair; and one or more conductive strips which extend inward from the base through the layer to be in electromagnetic communication with the person's brain. In another example, an electrode can comprise: a base which is worn outside a layer of a person's hair; and one or more conductive protrusions which extend inward from the base through the layer at different angles. In another example, an electrode can comprise: a base which is worn outside a layer of a person's hair; and one or more pairs of conductive protrusions which extend inward from the base through the layer at different angles. In another example, an electrode can comprise: a base which is worn outside a layer of a person's hair; and one or more pairs of tapered conductive protrusions which extend inward from the base through the layer at different angles.

In an example, an electrode can comprise: a base which is worn outside a layer of a person's hair; and one or more pairs of generally-parallel conductive protrusions which extend inward from the base through the layer at different angles. In another example, an electrode can comprise: a base which is worn outside a layer of a person's hair; and one or more pairs of generally-parallel linear conductive protrusions which extend inward from the base through the layer at different angles. In another example, an electrode can comprise: a base which is worn outside a layer of a person's hair; and one or more pairs of conductive protrusions with hydrogel tips which extend inward from the base through the layer at different angles.

In an example, an electrode can comprise a base which is worn a first distance from the surface of a person's head and at least two protrusions which extend inward from the base through the person's hair to a second distance from the surface of the person's head, wherein the second distance is less than the first distance. In another example, an electrode can comprise a base which is worn a first distance from the surface of a person's head and 2 to 4 protrusions which extend inward from the base through the person's hair to a second distance from the surface of the person's head, wherein the second distance is less than the first distance.

In an example, an electrode can comprise a base which is worn a first distance from the surface of a person's head and 4 to 8 protrusions which extend inward from the base through the person's hair to a second distance from the surface of the person's head, wherein the second distance is less than the first distance. In another example, an electrode can comprise a base which is worn a first distance from the surface of a person's head and 2 to 4 pairs of conductive protrusions which extend inward from the base through the person's hair to a second distance from the surface of the person's head, wherein the second distance is less than the first distance. In another example, an electrode can comprise a base which is worn a first distance from the surface of a person's head and 4 to 8 pairs of conductive protrusions which extend inward from the base through the person's hair to a second distance from the surface of the person's head, wherein the second distance is less than the first distance.

In an example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 10 mm to 30 mm apart from each other. In another example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 5 mm to 20 mm apart from each other.

In an example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 20 mm to 100 mm apart from each other. In another example, an electrode can comprise a base which is worn a first distance from the surface of a person's head and a plurality of conductive protrusions which extend inward from the base through the person's hair to a second distance from the surface of the person's head, wherein the second distance is 5 mm to 20 mm less than the first distance.

In an example, an electrode can comprise a base which is worn a first distance from the surface of a person's head and a plurality of conductive protrusions which extend inward from the base through the person's hair to a second distance from the surface of the person's head, wherein the second distance is 20 mm to 50 mm less than the first distance. In another example, an electrode can comprise a base which is worn a first distance from the surface of a person's head and a plurality of conductive protrusions which extend inward from the base through the person's hair to a second distance from the surface of the person's head, wherein the second distance is 1 mm to 10 mm less than the first distance.

In an example, an electrode can comprise a base which is worn a first distance from the surface of a person's head and a plurality of tapered conductive protrusions which extend inward from the base through the person's hair to a second distance from the surface of the person's head, wherein the second distance is less than the first distance, and wherein portions of the tapered conductive protrusions which are closest to the surface of the person's head have a smaller cross-sectional perimeter than portions of the tapered conductive protrusions which are farthest from the surface of the person's head.

In an example, an electrode can include a first hair-penetrating protrusion made from a first material and a second hair-penetrating protrusion made from a second material. In another example, an electrode can include a first hair-penetrating protrusion with a first conductivity level and a second hair-penetrating protrusion with a second conductivity level, wherein the second level is greater than the first level. In another example, an electrode can include a first hair-penetrating protrusion with a first resistance level and a second hair-penetrating protrusion with a second resistance level, wherein the second level is greater than the first level.

In an example, an electrode can include a first hair-penetrating protrusion with a first durometer level and a second hair-penetrating protrusion with a second durometer level, wherein the second level is greater than the first level. In another example, an electrode can include a first hair-penetrating protrusion made from a first mixture of a non-conductive polymer and a conductive material and a second hair-penetrating protrusion made from a second mixture of a non-conductive polymer and a conductive material, wherein the second mixture is different than the first material. In another example, an electrode can include a first hair-penetrating protrusion made with a first proportion of a non-conductive polymer and conductive material and a second hair-penetrating protrusion made with a second proportion of the non-conductive polymer and the conductive material, wherein the second proportion is different than the first proportion.

In an example, an electrode can include a first hair-penetrating protrusion with a first shape and a second hair-penetrating protrusion with a second shape. In another example, an electrode can include a first hair-penetrating protrusion with a first cross-sectional shape and a second hair-penetrating protrusion with a second cross-sectional shape, wherein the second cross-sectional shape is different than the first cross-sectional shape. In another example, an electrode can include a first hair-penetrating protrusion with a first shape and a second hair-penetrating protrusion with a second shape, wherein the second protrusion is more arcuate than the first protrusion.

In an example, an electrode can include a first hair-penetrating protrusion with a first shape and a second hair-penetrating protrusion with a second shape, wherein the second protrusion is larger than the first protrusion. In another example, an electrode can include a first hair-penetrating protrusion with a first shape and a second hair-penetrating protrusion with a second shape, wherein the second protrusion is longer than the first protrusion. In another example, an electrode can include a first hair-penetrating protrusion with a first cross-sectional size and a second hair-penetrating protrusion with a second cross-sectional size, wherein the second size is greater than the first size.

In an example, a mobile wearable device with electrodes can include a plurality of conductive protrusions which extend inward from a base toward the surface of a person's head. In another example, these conductive protrusions can be combs, teeth, prongs, protuberances, or undulations. In example, these conductive protrusions are sufficiently resilient and rigid to penetrate through layers of a person's hair, but not so resilient and rigid that they cause discomfort as they contact the person's head. In another example, these conductive protrusions are sufficiently soft and deformable that they do not cause discomfort as they contact the surface of a person's head, but not so soft and deformable that they do not penetrate through layers of the person's hair. In example, these conductive protrusions are sufficiently resilient and rigid to penetrate through layers of a person's hair, but also sufficiently soft and deformable that they do not cause discomfort as they contact the person's head.

In an example, a plurality of conductive hair-penetrating protrusions can be configured in a single ring. In another example, a plurality of conductive hair-penetrating protrusions can be configured in nested rings. In another example, a plurality of conductive hair-penetrating protrusions can be configured in nested (e.g. concentric) rings, wherein each protrusion is ring-shaped and wherein the ring-shaped protrusions are nested (e.g. concentric) within each other. In another example, a plurality of conductive hair-penetrating protrusions can be configured in nested (e.g. concentric) rings, wherein each ring comprises multiple protrusions and wherein the rings of protrusions are nested (e.g. concentric) within each other.

In an example, a plurality of conductive hair-penetrating protrusions can be configured in a single circle. In another example, a plurality of conductive hair-penetrating protrusions can be configured in nested circles. In another example, a plurality of conductive hair-penetrating protrusions can be configured in nested (e.g. concentric) circles, wherein each protrusion is ring-shaped and wherein the ring-shaped protrusions are nested (e.g. concentric) within each other. In another example, a plurality of conductive hair-penetrating protrusions can be configured in nested (e.g. concentric) circles, wherein each ring comprises multiple protrusions and wherein the circles of protrusions are nested (e.g. concentric) within each other.

In an example, a plurality of conductive hair-penetrating protrusions can be configured in a single polygon. In another example, a plurality of conductive hair-penetrating protrusions can be configured in nested polygons. In another example, a plurality of conductive hair-penetrating protrusions can be configured in nested (e.g. concentric) polygons, wherein each protrusion is ring-shaped and wherein the ring-shaped protrusions are nested (e.g. concentric) within each other. In another example, a plurality of conductive hair-penetrating protrusions can be configured in nested (e.g. concentric) polygons, wherein each ring comprises multiple protrusions and wherein the polygons of protrusions are nested (e.g. concentric) within each other.

In an example, a plurality of conductive hair-penetrating protrusions can be configured in a square or rectangular grid. In another example, a plurality of conductive hair-penetrating protrusions can be configured in an orthogonal array. In another example, a plurality of conductive hair-penetrating protrusions can be configured in an orthogonal array, wherein a first set of protrusions in the array have a first orientation, wherein a second set of protrusions in the array have a second orientation, and wherein the second orientation is orthogonal (e.g. perpendicular) to the first orentation. In another example, a plurality of conductive hair-penetrating protrusions can be configured in an orthogonal array, wherein a first row of protrusions in the array has a first orientation, wherein a second row of protrusions in the array has a second orientation, and wherein the second orientation is orthogonal (e.g. perpendicular) to the first orientation. In another example, a plurality of conductive hair-penetrating protrusions can be configured in an orthogonal matrix, wherein a row of protrusions in the array has a first orientation, wherein a column of protrusions in the array has a second orientation, and wherein the second orientation is orthogonal (e.g. perpendicular) to the first orientation.

In an example, a plurality of hair-penetrating protrusions in an electrode can have different lengths. In another example, protrusions toward the center of the electrode can be longer than protrusions toward the periphery of the electrode. In another example, protrusions in the middle of an array of protrusions can be longer than protrusions toward the edges of the array. In another example, protrusions at one end of a linear array of protrusions can be longer than protrusions at the other end. In another example, a plurality of hair-penetrating protrusions in an electrode can have different diameters. In another example, protrusions toward the center of the electrode can be wider than protrusions toward the periphery of the electrode. In another example, protrusions in the middle of an array of protrusions can be wider than protrusions toward the edges of the array. In another example, protrusions at one end of a linear array of protrusions can be wider than protrusions at the other end.

In an example, a plurality of conductive hair-penetrating protrusions can be configured in a linear manner. In another example, a plurality of conductive hair-penetrating protrusions can be configured in a linear manner, wherein each protrusion has a linear shape and wherein the linear protrusions are generally parallel to each other. In another example, a plurality of conductive hair-penetrating protrusions can be configured in a linear manner, wherein each line comprises multiple protrusions and wherein the lines of protrusions are generally parallel.

In an example, a plurality of hair-penetrating protrusions in an electrode can have different tapers. In another example, protrusions toward the center of the electrode can be more tapered than protrusions toward the periphery of the electrode. In another example, protrusions in the middle of an array of protrusions can be more tapered than protrusions toward the edges of the array. In another example, protrusions at one end of a linear array of protrusions can be more tapered than protrusions at the other end. In another example, a plurality of hair-penetrating protrusions in an electrode can have different lengths. In another example, protrusions toward the center of the electrode can be shorter than protrusions toward the periphery of the electrode. In another example, protrusions in the middle of an array of protrusions can be shorter than protrusions toward the edges of the array. In another example, protrusions at one end of a linear array of protrusions can be shorter than protrusions at the other end.

In an example, an electrode can comprise an array of hair-penetrating conductive protrusions, wherein each protrusion in the array has a longitudinal axis (extending toward the person's head) and a longitudinal cross-sectional shape which is shaped like a conic section. In another example, an electrode can comprise an array of hair-penetrating conductive protrusions, wherein each protrusion in the array has a longitudinal axis (extending toward the person's head) and a longitudinal cross-sectional shape which is parabolic. In another example, an electrode can comprise an array of hair-penetrating conductive protrusions, wherein each protrusion in the array has a longitudinal axis (extending toward the person's head) and a longitudinal cross-sectional shape which is shaped like a golf tee.

In an example, a plurality of hair-penetrating protrusions in an electrode can have different diameters. In another example, protrusions toward the center of the electrode can be narrower than protrusions toward the periphery of the electrode. In another example, protrusions in the middle of an array of protrusions can be narrower than protrusions toward the edges of the array. In another example, protrusions at one end of a linear array of protrusions can be narrower than protrusions at the other end. In another example, a plurality of hair-penetrating protrusions in an electrode can have different tapers. In another example, protrusions toward the center of the electrode can be less tapered than protrusions toward the periphery of the electrode. In another example, protrusions in the middle of an array of protrusions can be less tapered than protrusions toward the edges of the array. In another example, protrusions at one end of a linear array of protrusions can be less tapered than protrusions at the other end.

In an example, the distance between an electrode and the surface of a person's head can be adjusted. In another example, the distance between an electrode and the surface of a person's head can be automatically adjusted. In another example, the distance between an electrode and the surface of a person's head can be manually adjusted. In another example, the distance between an electrode and the surface of a person's head can be adjusted by movement of an electromagnetic actuator. In another example, the distance between an electrode and the surface of a person's head can be adjusted by a hydraulic mechanism. In another example, the distances between a plurality of electrodes and the surface of a person's head can be individually adjusted. In another example, the distances between a plurality of electrodes and the surface of a person's head can be individually and automatically adjusted. In another example, the distance between an electrode and the surface of a person's head can be adjusted by inflation of a gas-filled chamber. In another example, the distance between an electrode and the surface of a person's head can be adjusted by adjusting the tension in a spring, coil, other tensile member, or elastic member.

In an example, the distance between an electrode and the surface of a person's head can be adjusted by changing the tension of a spring and/or coil. In another example, the distance between an electrode and the surface of a person's head can be adjusted by changing the tension of an elastic strap and/or band. In another example, an electromagnetic energy can be moved closer to the surface of a person's head by a compressible material. In another example, an electromagnetic energy can be moved closer to the surface of a person's head by compressible foam. In another example, an electromagnetic energy can be moved closer to the surface of a person's head by a hydraulic mechanism. In another example, an electromagnetic energy can be moved closer to the surface of a person's head by a pneumatic mechanism. In another example, an electromagnetic energy can be moved closer to the surface of a person's head by a telescoping mechanism. In another example, an electromagnetic energy can be moved closer to the surface of a person's head by a piston mechanism.

In an example, an electromagnetic energy can be moved closer to the surface of a person's head by a metal spring. In another example, an electromagnetic energy can be moved closer to the surface of a person's head by a plastic spring. In another example, an electromagnetic energy can be moved closer to the surface of a person's head by a leaf spring. In another example, an electromagnetic energy can be moved closer to the surface of a person's head by a helical or spiral spring. In another example, an electromagnetic energy can be moved closer to the surface of a person's head by an adjustable strap or band. In another example, an electromagnetic energy can be moved closer to the surface of a person's head by an electromagnetic mechanism. In another example, an electromagnetic energy can be moved closer to the surface of a person's head by a solenoid mechanism.

In an example, the force with which an electrode is pressed against the surface of a person's head can be adjusted. In another example, the force with which an electrode is pressed against the surface of a person's head can be automatically adjusted. In another example, the force with which an electrode is pressed against the surface of a person's head can be manually adjusted. In another example, the force with which an electrode is pressed against the surface of a person's head can be adjusted by movement of an electromagnetic actuator. In another example, the force with which an electrode is pressed against the surface of a person's head can be adjusted by a hydraulic mechanism. In another example, the forces with which a plurality of electrodes are pressed against the surface of a person's head can be individually adjusted. In another example, the forces with which a plurality of electrodes are pressed against the surface of a person's head can be individually and automatically adjusted.

In an example, the force with which an electrode is pressed against the surface of a person's head can be adjusted by inflation of a gas-filled chamber. In another example, the force with which an electrode is pressed against the surface of a person's head can be adjusted by adjusting the tension in a spring, coil, other tensile member, or elastic member. In another example, the force with which an electrode is pressed against the surface of a person's head can be adjusted by changing the tension of a spring and/or coil. In another example, the force with which an electrode is pressed against the surface of a person's head can be adjusted by changing the tension of an elastic strap and/or band. In another example, an electrode can be pressed against the surface of a person's head by a compressible material. In another example, an electrode can be pressed against the surface of a person's head by compressible foam.

In an example, an electrode can be pressed against the surface of a person's head by a hydraulic mechanism. In another example, an electrode can be pressed against the surface of a person's head by a pneumatic mechanism. In another example, an electrode can be pressed against the surface of a person's head by a telescoping mechanism. In another example, an electrode can be pressed against the surface of a person's head by a piston mechanism. In another example, an electrode can be pressed against the surface of a person's head by a metal spring. In another example, an electrode can be pressed against the surface of a person's head by a plastic spring. In another example, an electrode can be pressed against the surface of a person's head by a leaf spring. In another example, an electrode can be pressed against the surface of a person's head by a helical or spiral spring. In another example, an electrode can be pressed against the surface of a person's head by an adjustable strap or band. In another example, an electrode can be pressed against the surface of a person's head by an electromagnetic mechanism. In another example, an electrode can be pressed against the surface of a person's head by a solenoid mechanism.

In an example, an electrode can be vibrated and/or oscillated in order to penetrate a layer of a person's hair and achieve better electromagnetic communication with a person's brain. In another example, an electrode can be vibrated and/or oscillated until it penetrates a layer of a person's hair and achieves a desired level of electromagnetic communication with a person's brain. In another example, a mobile wearable device can include an electromagnetic vibrator which moves hair-penetrating protrusions back and forth to help the protrusions penetrate layers of the person's hair.

In an example, a mobile wearable device can include an electromagnetic vibrator which moves hair-penetrating protrusions back and forth to help the protrusions slide between strands of the person's hair. In another example, when a person first puts on the device, the device can automatically vibrate until good electromagnetic communication is established between the hair-penetrating protrusions and the person's brain. In another example, when a person first puts on the device, the device can automatically vibrate until improvement of electromagnetic communication between the hair-penetrating protrusions and the person's brain stops improving due to vibration. In another example, when a person first puts on the device, the device can automatically vibrate until a selected level of electromagnetic communication between the hair-penetrating protrusions and the person's brain is achieved.

In an example, an electrode can have a plurality of protrusions which movably extend toward the surface of a person's head or retract away from the surface of the person's head. In another example, an electrode can have a plurality of protrusions which are automatically extended toward the surface of a person's head or retracted away from the surface of the person's head. In another example, an electrode can have a plurality of protrusions which are automatically extended toward the surface of a person's head or retracted away from the surface of the person's head so as to automatically adjust the pressure with which the protrusions contact the surface of person's head. In another example, an electrode can have a plurality of protrusions which are automatically extended toward the surface of a person's head or retracted away from the surface of the person's head so as to automatically adjust the distance between the protrusions and the surface of person's head.

In an example, an electrode can include a gimbal mechanism which maintains a desired angle of contact between the electrode and the surface of a person's head, even if the electrode is moved. In another example, an electrode can include a gimbal mechanism which maintains a desired angle of contact between the electrode and the surface of a person's head, even when the person moves. In another example, an electrode can be rotated so as to penetrate a layer of a person's hair and achieve better electromagnetic communication with the person's brain. In another example, an electrode can be rotated around an axis which is substantially orthogonal to the surface of a person's head so as to penetrate a layer of a person's hair and achieve better electromagnetic communication with the person's brain. In another example, an electrode can be rotated, in an oscillating manner, around an axis which is substantially orthogonal to the surface of a person's head so as to penetrate a layer of a person's hair and achieve better electromagnetic communication with the person's brain.

In an example, a mobile wearable device can include a plurality of electromagnetic actuators which rotate hair-penetrating protrusions back and forth (e.g. clockwise and counter-clockwise) to help the protrusions slide between strands of the person's hair. In another example, when a person first puts on the device, the device can automatically rotate the protrusions back and forth until good electromagnetic communication is established between the hair-penetrating protrusions and the person's brain. In another example, when a person first puts on the device, the device can automatically rotate the protrusions back and forth until improvement of electromagnetic communication between the hair-penetrating protrusions and the person's brain stops improving due to vibration. In another example, when a person first puts on the device, the device can automatically rotate the protrusions back and forth until a selected level of electromagnetic communication between the hair-penetrating protrusions and the person's brain is achieved.

In an example, an electrode can be extended toward and retracted away from the surface of a person's head in an oscillating manner so as to penetrate a layer of a person's hair and achieve better electromagnetic communication with the person's brain. In another example, an electrode can be vibrated so as to penetrate a layer of a person's hair and achieve better electromagnetic communication with the person's brain. In another example, an electrode can be oscillated so as to penetrate a layer of a person's hair and achieve better electromagnetic communication with the person's brain.

In an example, an EEG electrode can be made from soft (e.g. elastomeric) conductive polymer-based material. In another example, a conductive polymer-based material can be made by impregnating or coating polydimethylsiloxane with carbon or sliver. In another example, a conductive polymer-based material can be made from a polymer (e.g. polydimethylsiloxane, polybutylene terephthalate, or polyurethane) which has been impregnated, doped, filled, and/or coated with electro-conductive material (e.g. silver, carbon nanotubes or other forms of carbon, copper, aluminum, nickel, platinum, or gold). In another example, an EEG electrode can be made with hydrogel. In another example, this device can further comprise a battery, a data processor, a wireless data transmitter, and a wireless data receiver. In another example, electrodes can be EEG (electroencephalographic) electrodes and/or electrodes which detect, measure, and/or record the electromagnetic activity of a person's brain.

In an example, an EEG electrode can comprise a linear array of protrusions which extend between strands of hair to contact a person's scalp. In another example, an EEG electrode can comprise a two-dimensional array (e.g. matrix) of protrusions. In another example, an electrode can comprise two or more concentric rings of protrusions. In another example, protrusions can be tapered in a proximal to distal manner, wherein distal means closer to the person's head. In another example, a distal portion of a protrusion can be more conductive (e.g. have a higher concentration of conductive material) than a proximal portion of a protrusion. In another example, hair-penetrating protrusions on an EEG electrode can be made with a soft (e.g. elastomeric) conductive polymer-based material.

In an example, an EEG electrode can be made from elastic, stretchable, and/or deformable conductive material. In another example, an EEG electrode can be made from elastic, stretchable, and/or deformable conductive material with a Shore A value which is less than 80. In another example, a first set of electrodes (which are configured to be worn on a portion of a person's head which is not covered by hair) can have a lower average Shore value than a second set of electrodes (which is configured to be worn on a portion of the person's head which is covered with hair). In another example, electrodes which are configured to be worn on portions of a person's head which are covered with hair can comprise a plurality of hair-penetrating and/or hair-engaging protrusions, combs, teeth, or prongs which penetrate and/or engage layers of the person's hair.

In an example, electrodes which are configured to be worn on the posterior portion of a person's head can have a plurality of hair-penetrating and/or hair-engaging protrusions, combs, teeth, or prongs for good electromagnetic communication with the person's occipital lobe. These protrusions, combs, teeth, or prongs can protrude between strands of hair to contact the person's skin. In another example, electrodes which are worn on the posterior a person's head can have a plurality of hair-engaging protrusions, combs, teeth, or prongs which hold the electrodes in place by engaging the person's hair.

In an example, a wearable mobile device for measuring brain activity can have a plurality of combs, prongs, teeth which extend under layers of a person's hair. In another example, a wearable mobile device for measuring brain activity can have a plurality of combs, prongs, teeth which extend downward into layers of a person's hair. In another example, an electrode can comprise a capacitor which is made by bonding together alternating layers of conductive and non-conductive polymers. In another example, an EEG electrode can be made by adhering (or otherwise bonding) together a first flexible non-conductive layer, a flexible conductive layer, and a second flexible non-conductive layer; wherein the flexible conductive layer is between the first flexible non-conductive layer and the second flexible non-conductive layer.

In another embodiment, an electrode can be made by printing, spraying, or adhering a layer of conductive material onto a non-conductive core of a flexible hair-penetrating protrusion. In another example, an electrode can be formed by printing, spraying, or adhering a layer of conductive TPU (e.g. TPU which has been doped with conductive material) onto the inner (e.g. body-facing) surface of a headband. In another example, an EEG electrode can be made by screen printing with conductive ink onto an article of clothing. In another example, an electrode can be formed by spraying a plurality of flexible hair-penetrating protrusions with conductive material. In another example, an EEG electrode can be made by stitching conductive threads or yarns onto fabric in a sinusoidal and/or zigzag pattern. In another example, an electrode can be formed by weaving or knitting electrodes in a sinusoidal pattern using conductive threads or yarns. In another example, an electrode can be made by weaving an orthogonal mesh with conductive and non-conductive threads or yarns.

In an example, an EEG electrode can comprise one or more deformable, flexible, and conductive micro-columns which protrude between strands of a person's hair so that the electrode is in electromagnetic communication with a person's brain despite being on a portion of the person's head which is covered by hair. In another example, an electrode can comprise a sinusoidal hair-penetrating protrusion which is tapered with the smaller section being closer to a person's head.

In an example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 10 mm to 30 mm apart from each other. In another example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 5 mm to 20 mm apart from each other.

In an example, an electrode can comprise a base which is worn a first distance from the surface of a person's head and a plurality of conductive protrusions which extend inward from the base through the person's hair to a second distance from the surface of the person's head, wherein the second distance is less than the first distance, and wherein the conductive protrusions are 20 mm to 100 mm apart from each other. In another example, an electrode can comprise a base which is worn a first distance from the surface of a person's head and a plurality of conductive protrusions which extend inward from the base through the person's hair to a second distance from the surface of the person's head, wherein the second distance is 5 mm to 20 mm less than the first distance.

In an example, an electrode can comprise a base which is worn a first distance from the surface of a person's head and a plurality of conductive protrusions which extend inward from the base through the person's hair to a second distance from the surface of the person's head, wherein the second distance is 20 mm to 50 mm less than the first distance. In another example, an electrode can comprise a base which is worn a first distance from the surface of a person's head and a plurality of conductive protrusions which extend inward from the base through the person's hair to a second distance from the surface of the person's head, wherein the second distance is 1 mm to 10 mm less than the first distance.

Having discussed several general embodiment variations which can apply to different dry electrode designs, we now discuss specific examples which are shown in FIGS. 3 through 69. The example variations which have discussed thus far can be applied to the specific examples shown in these figures where relevant.

Figure 1:
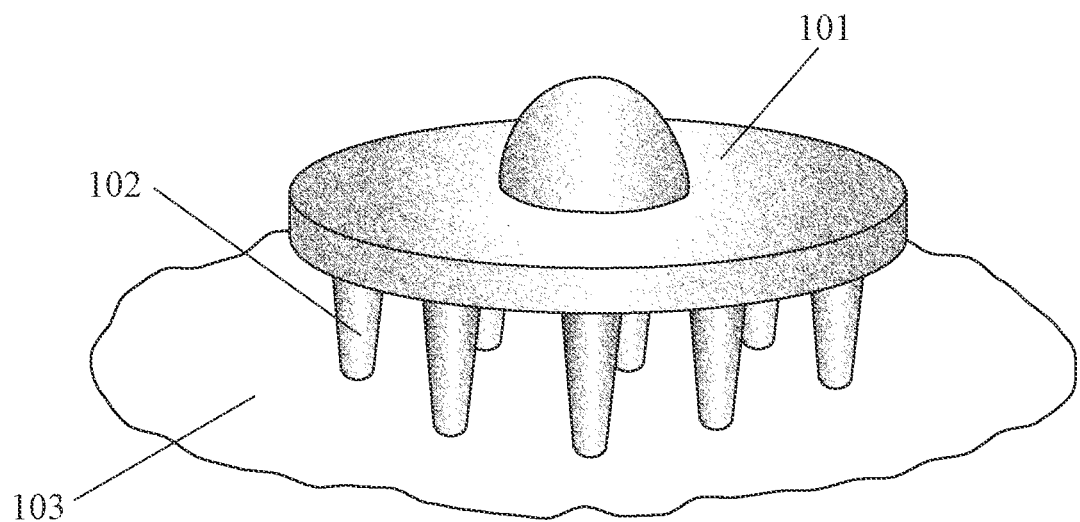
FIGS. 1 and 2 show two views of an EEG electrode with homogenous parallel protrusions such as those that can be found in the prior art.
Figure 2:
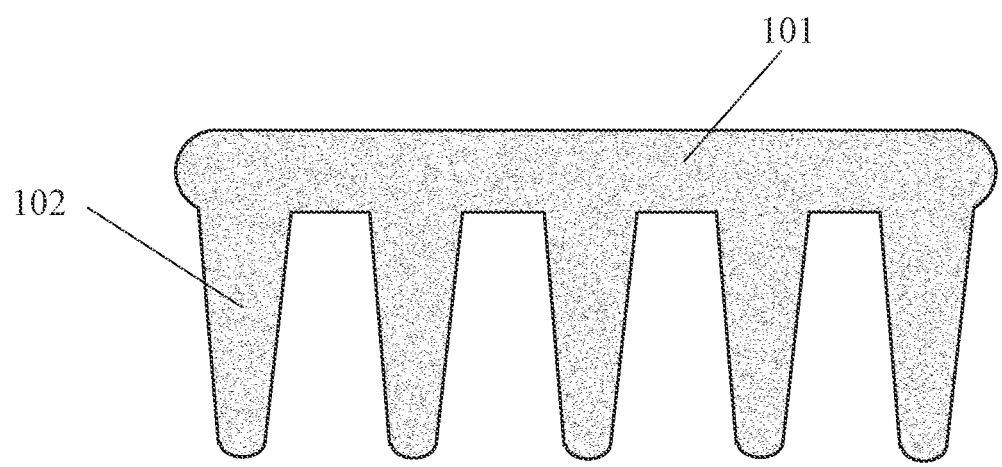

FIGS. 1 and 2 show an oblique top-side view and a cross-sectional side view, respectively, of a dry EEG electrode of a type in the prior art for use on a hair-covered portion of a person's head. This electrode comprises: a disk-shaped portion 101; and a plurality of conductive protrusions (e.g. pins, prongs, teeth, spikes, and/or protrusions) including protrusion 102 which extend outward perpendicularly from the disk portion toward the surface of the person's head 103 in order to penetrate between hairs and come into contact with the surface of the person's head. Subsequent figures in this disclosure, starting with FIG. 3, are not prior art.

FIG. 3 shows a side cross-sectional view of an EEG electrode for use on a hair-covered portion of a person's head comprising: (a) a (disk-shaped) distal portion 301 with a central cross-sectional plane 305 (which is substantially parallel to the surface of a person's head); and (b) a plurality of electroconductive proximal protrusions (e.g. pins, prongs, teeth, spikes, fingers, and/or protrusions), including protrusions 302, 303, and 304, which extend out from the distal portion toward the person's head in order to penetrate between hairs and come into contact with the surface of the person's head; wherein each protrusion in the plurality of electroconductive proximal protrusions has a central longitudinal axis, including axes 306, 307, and 308; wherein a linear extension of a first central longitudinal axis 307 of a first protrusion 303 in the plurality of conductive proximal protrusions intersects the central cross-sectional plane of the distal portion at a first distance (which can be zero) from a center of the distal portion; wherein a linear extension of a second central longitudinal axis 306 of a second protrusion 302 in the plurality of conductive proximal protrusions intersects the central cross-sectional plane of the distal portion at a second distance from the center of the distal portion; wherein the second distance is greater than the first distance; wherein a protrusion angle is the angle of intersection between a linear extension of a central longitudinal axis of a protrusion and the cross-sectional plane of the distal portion which faces toward, or aligns with, the center of the cross-sectional plane of the distal portion; wherein a second protrusion angle 309 of the second protrusion 302 is greater than a first protrusion angle 310 of the first protrusion 303.

In an example, a distal portion of an electrode can have a circular and/or disk shape. In an example, the distal portion can have an oblong, oval, or elliptical shape. In an example, the distal portion can have a square or rectangular shape. In an example, the distal portion can have a rounded square or rounded rectangular shape. In an example, the distal portion can have a hexagonal shape. In an example, the distal portion of the electrode can have non-uniform thickness. In an example, the center of the distal portion can be thicker than the periphery of the distal portion. In an example, the center of the distal portion can be thinner than the periphery of the distal portion. In an example, the distal portion of the electrode can be electroconductive. In an example, a distal portion of an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, a plurality of electroconductive proximal protrusions (e.g. pins, prongs, teeth, spikes, fingers, and/or protrusions) can include a protrusion from the center of a distal portion of an electrode. In an example, the protrusion angle of a protrusion at the center of the distal portion can be 90 degrees. In an example, the protrusion angle of non-central protrusion can be in the range of 100 to 145 degrees. In an example, the protrusion angle of non-central protrusion can be in the range of 130 to 160 degrees. In an example, the protrusion angle of non-central protrusion can be at least 10 degrees greater than the protrusion angle of a protrusion at the center of the distal portion. In an example, the protrusion angle of non-central protrusion can be at least 30 degrees greater than the protrusion angle of a protrusion at the center of the distal portion. In an example, protrusions which are farther from the center of the electrode can tilt, point, bow, or curve away from the center of the electrode.

In an example, protrusions which are closer to the center of a distal portion of an electrode can be longer than protrusions which are farther from the center of the distal portion. In an example, protrusions which are farther from the center of a distal portion of an electrode can be longer than protrusions which are closer to the center of the distal portion. In an example, protrusions which are closer to the center of a distal portion of an electrode can be more flexible, be more elastic, have a higher Young's modulus, be more compressible, and/or have a lower durometer than protrusions which are farther from the center of the distal portion. In an example, protrusions which are farther from the center of a distal portion of an electrode can be more flexible, be more elastic, have a higher Young's modulus, be more compressible, and/or have a lower durometer than protrusions which are closer to the center of the distal portion.

In an example, a plurality of electroconductive proximal protrusions (e.g. pins, prongs, teeth, spikes, fingers, and/or protrusions) can comprise at least two nested (e.g. concentric) rings of protrusions. In an example, the protrusion angles of protrusions in an outer ring can be greater than the protrusion angles of protrusions in an inner ring. In an example, the protrusion angles of protrusions in an outer ring can be less than the protrusion angles of protrusions in an inner ring. In an example, there can be differences and/or variation in protrusion angles and/or protrusion directions of different protrusions around the circumference of a ring of protrusions. In an example, a plurality of electroconductive proximal protrusions (e.g. pins, prongs, teeth, spikes, fingers, and/or protrusions) can comprise a hub-and-spoke array of protrusions.

In an example, an EEG electrode can comprise a distal portion, a conductive protrusion which extends out from the center of the distal portion toward a person's head, and a ring of conductive protrusions around the central protrusion which also extend out from the distal portion toward the person's head. In an example, an EEG electrode can comprise a distal portion, a conductive protrusion which extends out from the center of the distal portion toward a person's head, and a ring of conductive protrusions around the periphery of the distal portion which also extend out from the distal portion toward the person's head. In an example, an EEG electrode can comprise a distal portion, a conductive protrusion which extends out from the center of the distal portion toward a person's head, and two rings of conductive protrusions around the central protrusion which also extend out from the distal portion toward the person's head. In an example, an EEG electrode can comprise a distal portion and two or more nested rings of conductive protrusions which extend out from the distal portion toward the person's head, wherein protrusions in an outer ring protrude from the distal portion at a greater center-facing angle than protrusions in an inner ring.

In an example, a plurality of electroconductive proximal protrusions (e.g. pins, prongs, teeth, spikes, fingers, and/or protrusions) can comprise an orthogonal grid (e.g. with at least two sets of orthogonal rows and columns) of protrusions. In an example, there can be differences and/or variation in protrusion angles and/or protrusion directions of different protrusions along a row or column of protrusions. In an example, a plurality of electroconductive proximal protrusions (e.g. pins, prongs, teeth, spikes, fingers, and/or protrusions) can comprise a hexagonal grid (e.g. a honey-comb-shaped array) of protrusions.

In an example, a protrusion can have a columnar shape. In an example, a protrusion can have a conic shape. In an example, a protrusion can have a conic section shape. In an example, a protrusion can have a frustal shape. In an example, a protrusion can have a parabolic shape. In an example, a protrusion can have an ellipsoidal shape. In an example, a protrusion can have a crescent and/or banana shape. In an example, a protrusion can have a pyramidic shape. In an example, a protrusion can have a hemispherical shape. In an example, a protrusion can have a distal (farther from head) hemispherical portion and a proximal (closer to head) frustum-shaped portion. In an example, a protrusion can have a distal hemispherical portion and a proximal paraboloid-shaped portion.

In an example, a hair-penetrating protrusion on an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 4:
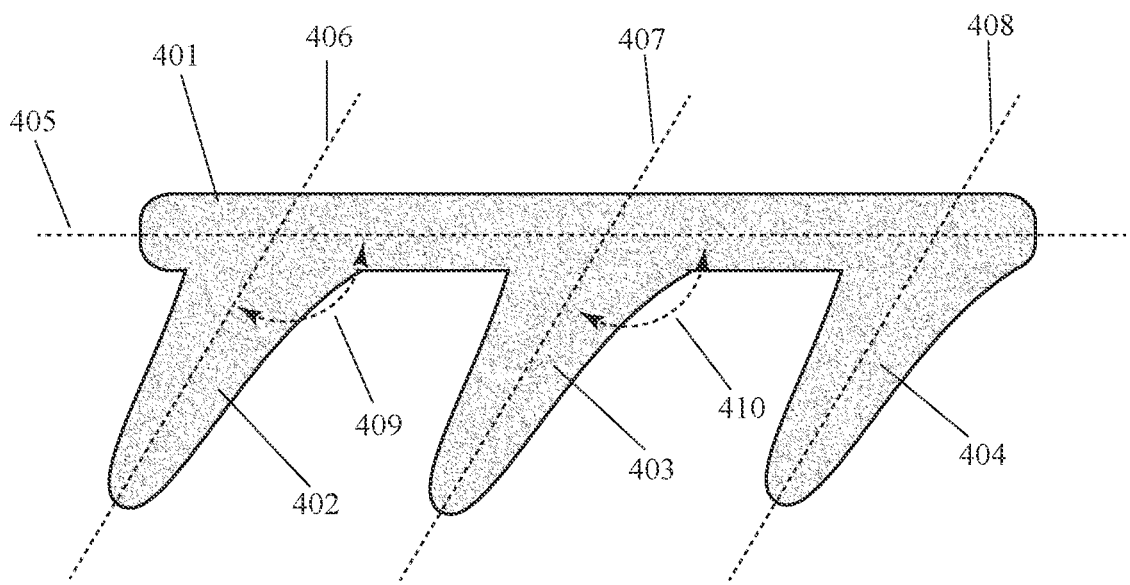
FIG. 4 shows an EEG electrode with protrusions which extend out from a base at the same angle and in the same direction.

FIG. 4 shows a side cross-sectional view of an EEG electrode for use on a hair-covered portion of a person's head comprising: (a) a (disk-shaped) distal portion 401 with a central cross-sectional plane 405 (which is substantially parallel to the surface of a person's head); and (b) a plurality of electroconductive proximal protrusions (e.g. pins, prongs, teeth, spikes, fingers, and/or protrusions), including protrusions 402, 403, and 404, which extend out from the distal portion toward the person's head in order to penetrate between hairs and come into contact with the surface of the person's head; wherein each protrusion in the plurality of electroconductive proximal protrusions has a central longitudinal axis, including axes 406, 407, and 408; wherein a linear extension of a first central longitudinal axis 407 of a first protrusion 403 in the plurality of conductive proximal protrusions intersects the central cross-sectional plane of the distal portion at a first distance (which can be zero) from a center of the distal portion; wherein a linear extension of a second central longitudinal axis 406 of a second protrusion 402 in the plurality of conductive proximal protrusions intersects the central cross-sectional plane of the distal portion at a second distance from the center of the distal portion; wherein the second distance is greater than the first distance; wherein a protrusion angle is the angle of intersection between a linear extension of a central longitudinal axis of a protrusion and the cross-sectional plane of the distal portion which faces toward, or aligns with, the center of the cross-sectional plane of the distal portion; wherein a second protrusion angle 409 of the second protrusion 402 is equal to a first protrusion angle 410 of the first protrusion 403; and wherein the first protrusion angle is within the range of 95 to 160 degrees.

In an example, a distal portion of an electrode can have a circular and/or disk shape. In an example, the distal portion can have an oblong, oval, or elliptical shape. In an example, the distal portion can have a square or rectangular shape. In an example, the distal portion can have a rounded square or rounded rectangular shape. In an example, the distal portion can have a hexagonal shape. In an example, the distal portion of the electrode can have non-uniform thickness. In an example, the center of the distal portion can be thicker than the periphery of the distal portion. In an example, the center of the distal portion can be thinner than the periphery of the distal portion. In an example, the distal portion of the electrode can be electroconductive. In an example, a distal portion of an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, a plurality of electroconductive proximal protrusions (e.g. pins, prongs, teeth, spikes, fingers, and/or protrusions) can include a protrusion from the center of a distal portion of an electrode. In an example, protrusions which are closer to the center of a distal portion of an electrode can be longer than protrusions which are farther from the center of the distal portion. In an example, protrusions which are farther from the center of a distal portion of an electrode can be longer than protrusions which are closer to the center of the distal portion. In an example, protrusions which are closer to the center of a distal portion of an electrode can be more flexible, be more elastic, have a higher Young's modulus, be more compressible, and/or have a lower durometer than protrusions which are farther from the center of the distal portion. In an example, protrusions which are farther from the center of a distal portion of an electrode can be more flexible, be more elastic, have a higher Young's modulus, be more compressible, and/or have a lower durometer than protrusions which are closer to the center of the distal portion.

In an example, a plurality of electroconductive proximal protrusions (e.g. pins, prongs, teeth, spikes, fingers, and/or protrusions) can comprise at least two nested (e.g. concentric) rings of protrusions. In an example, a plurality of electroconductive proximal protrusions (e.g. pins, prongs, teeth, spikes, fingers, and/or protrusions) can comprise a hub-and-spoke array of protrusions. In an example, a plurality of electroconductive proximal protrusions (e.g. pins, prongs, teeth, spikes, fingers, and/or protrusions) can comprise an orthogonal grid (e.g. with at least two sets of orthogonal rows and columns) of protrusions. In an example, a plurality of electroconductive proximal protrusions (e.g. pins, prongs, teeth, spikes, fingers, and/or protrusions) can comprise a hexagonal grid (e.g. honeycomb-shaped array) of protrusions.

In an example, an electrode can comprise: a circular distal portion; and an array of conductive protrusions which extend out from the distal portion toward the surface of a person's head, wherein all of the protrusions are angled, tilted, and/or bent toward the same half of the circumference of distal portion. In an example, an electrode can comprise: a circular distal portion; and an array of conductive protrusions which extend out from the distal portion toward the surface of a person's head, wherein all of the protrusions are angled, tilted, and/or bent toward the same quadrant of the circumference of distal portion. In an example, an electrode can comprise: a quadrilateral distal portion; and an array of conductive protrusions which extend out from the distal portion toward the surface of a person's head, wherein all of the protrusions are angled, tilted, and/or bent toward the same side of the quadrilateral distal portion.

In an example, a protrusion can have a columnar shape. In an example, a protrusion can have a conic shape. In an example, a protrusion can have a conic section shape. In an example, a protrusion can have a frustal shape. In an example, a protrusion can have a parabolic shape. In an example, a protrusion can have an ellipsoidal shape. In an example, a protrusion can have a crescent and/or banana shape. In an example, a protrusion can have a pyramidic shape. In an example, a protrusion can have a hemispherical shape. In an example, a protrusion can have a distal (farther from head) hemispherical portion and a proximal (closer to head) frustum-shaped portion. In an example, a protrusion can have a distal hemispherical portion and a proximal paraboloid-shaped portion.

In an example, a hair-penetrating protrusion on an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 5:
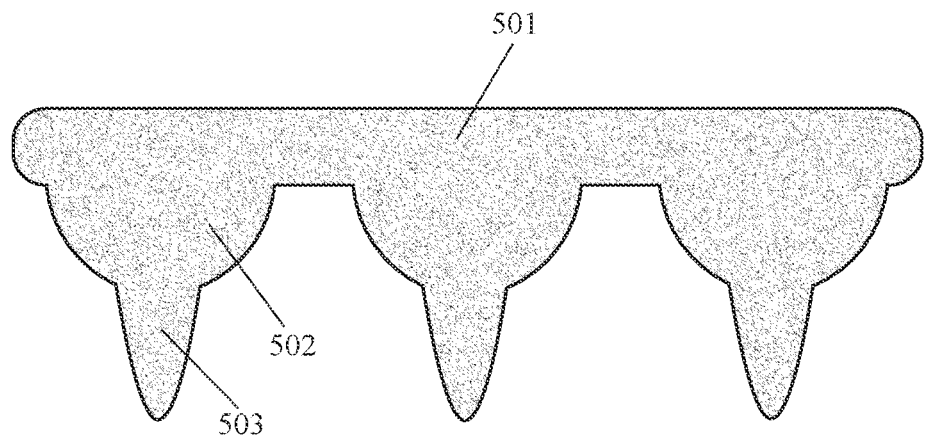
FIG. 5 shows an EEG electrode with protrusions having hemispherical distal portions and paraboloid-shaped proximal portions.

FIG. 5 shows a side cross-sectional view of an EEG electrode for use on a hair-covered portion of a person's head comprising: a (disk-shaped) distal portion 501; and a plurality of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein a protrusion in the plurality of electroconductive proximal protrusions further comprises a hemispherical distal portion 502 (which is farther from the surface of the person's head) and a paraboloid-shaped proximal portion 503 (which is closer to the surface of the person's head). In an example, a protrusion can have a shape like an ice cream cone with a scoop of ice cream on it. In an example, a protrusion can have a shape like a champagne glass without a base on the stem.

In an example, a distal portion of an electrode can have a circular and/or disk shape. In an example, the distal portion can have an oblong, oval, or elliptical shape. In an example, the distal portion can have a square or rectangular shape. In an example, the distal portion can have a rounded square or rounded rectangular shape. In an example, the distal portion can have a hexagonal shape. In an example, the distal portion of the electrode can have non-uniform thickness. In an example, the center of the distal portion can be thicker than the periphery of the distal portion. In an example, the center of the distal portion can be thinner than the periphery of the distal portion. In an example, the distal portion of the electrode can be electroconductive. In an example, a distal portion of an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, a plurality of electroconductive proximal protrusions (e.g. pins, prongs, teeth, spikes, fingers, and/or protrusions) can comprise at least two nested (e.g. concentric) rings of protrusions. In an example, a plurality of electroconductive proximal protrusions (e.g. pins, prongs, teeth, spikes, fingers, and/or protrusions) can comprise a hub-and-spoke array of protrusions. In an example, a plurality of electroconductive proximal protrusions (e.g. pins, prongs, teeth, spikes, fingers, and/or protrusions) can comprise an orthogonal grid (e.g. with at least two sets of orthogonal rows and columns) of protrusions. In an example, a plurality of electroconductive proximal protrusions (e.g. pins, prongs, teeth, spikes, fingers, and/or protrusions) can comprise a hexagonal grid (e.g. honeycomb-shaped array) of protrusions.

In an example, a hair-penetrating protrusion on an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 6:
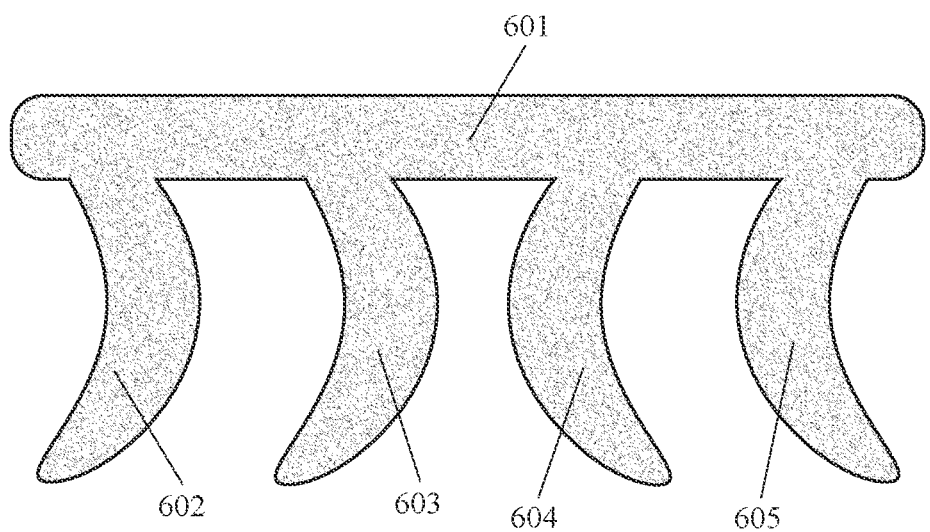
FIG. 6 shows an EEG electrode with crescent-shaped protrusions which bow in toward the electrode center.

FIG. 6 shows a side cross-sectional view of an EEG electrode for use on a hair-covered portion of a person's head comprising: a (disk-shaped) distal portion 601; and a plurality of crescent and/or banana-shaped electroconductive proximal protrusions (e.g. pins, prongs, teeth, spikes, fingers, and/or protrusions), including protrusions 602, 603, 604, and 605, which extend out from the distal portion toward the person's head in order to penetrate between hairs and come into contact with the surface of the person's head; wherein protrusions in the plurality of crescent and/or banana-shaped electroconductive proximal protrusions have curved sides which bow inward toward the center of the distal portion.

In an example, a distal portion of an electrode can have a circular and/or disk shape. In an example, a distal portion of an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

In an example, a plurality of electroconductive proximal protrusions (e.g. pins, prongs, teeth, spikes, fingers, and/or protrusions) can comprise at least two nested (e.g. concentric) rings of protrusions. In an example, a plurality of electroconductive proximal protrusions (e.g. pins, prongs, teeth, spikes, fingers, and/or protrusions) can comprise a hub-and-spoke array of protrusions.

In an example, a protrusion can have a concave side which faces away from the center of the distal portion and a convex side which faces toward the center of the distal portion. In an example, a protrusion can have a shape like a hanging banana. In an example, protrusions on one side of a cross-section of an electrode can curve in a first direction and protrusions on the other side of the cross-section of the electrode can curve in the opposite direction. In an example, the proximal ends of crescent or banana-shaped protrusions can all point away from the central proximal-to-distal axis of the electrode. In an example, the proximal ends of arcuate protrusions can all point away from the central proximal-to-distal axis of the electrode. In an example, protrusions which are farther from the center of the electrode can tilt, point, bow, or curve away from the center of the electrode.

In an example, a hair-penetrating protrusion on an electrode can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 7:
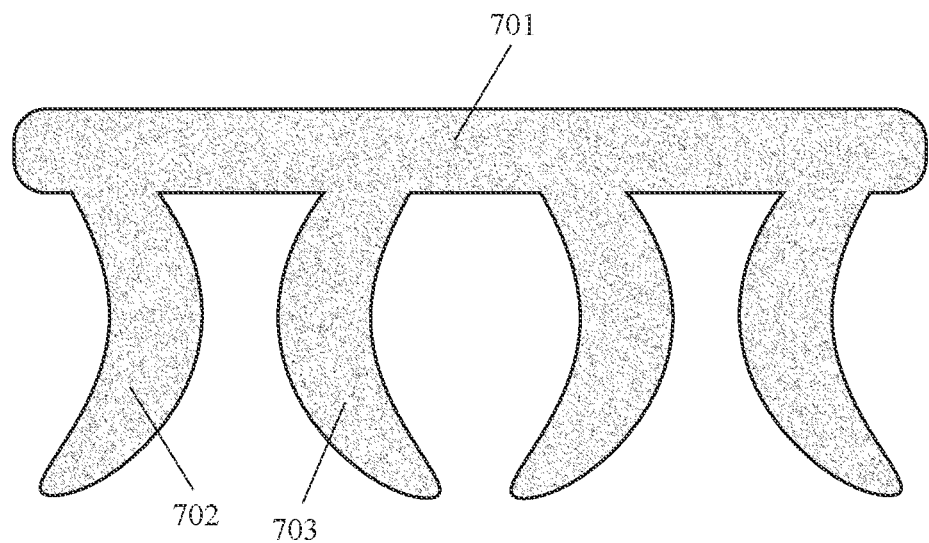
FIG. 7 shows an EEG electrode with crescent-shaped protrusions which bow in toward and out from the electrode center.

FIG. 7 shows a side cross-sectional view of an EEG electrode for use on a hair-covered portion of a person's head comprising: a (disk-shaped) distal portion 701; and at least two nested rings of crescent and/or banana-shaped electroconductive proximal protrusions (e.g. pins, prongs, teeth, spikes, fingers, and/or protrusions) which extend out from the distal portion toward the person's head in order to penetrate between hairs and come into contact with the surface of the person's head; wherein protrusions in a first (e.g. inner) ring, including protrusion 703, have curved sides which bow outward away from the center of the distal portion; and wherein protrusions in a second (outer) ring, including protrusion 702, have curved sides which bow inward toward the center of the distal portion.

In an example, a distal portion of an electrode can have a circular and/or disk shape. In an example, a hair-penetrating protrusion can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 8:
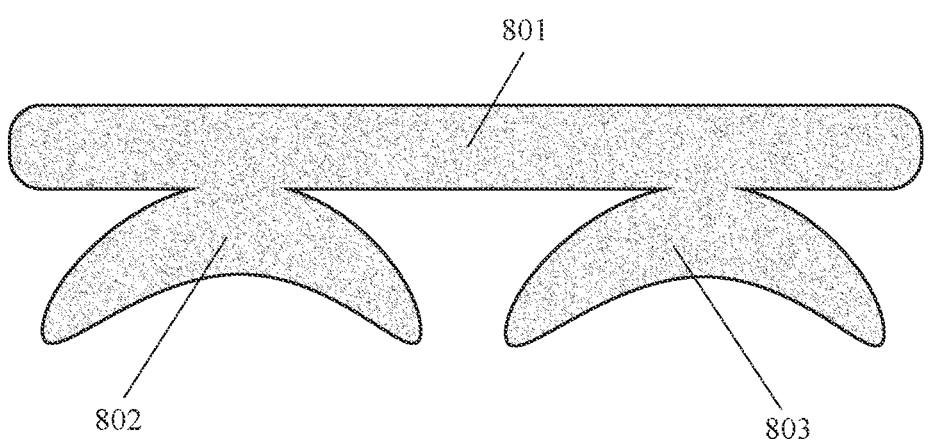
FIG. 8 shows an EEG electrode with crescent-shaped protrusions which bow away from a person's head.

FIG. 8 shows a side cross-sectional view of an EEG electrode for use on a hair-covered portion of a person's head comprising: a (disk-shaped) distal portion 801; and a plurality of crescent and/or banana-shaped electroconductive proximal protrusions (e.g. pins, prongs, teeth, spikes, fingers, and/or protrusions) which extend out from the distal portion toward the person's head in order to penetrate between hairs and come into contact with the surface of the person's head; wherein the protrusions, including protrusions 802 and 803, have curved sides which bow (upward) away from the surface of the person's head. In an example, the longitudinal axes of crescent or banana shaped protrusions can be substantially parallel to the plane of the distal portion of the electrode.

In an example, a distal portion of an electrode can have a circular and/or disk shape. In an example, a hair-penetrating protrusion can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 9:
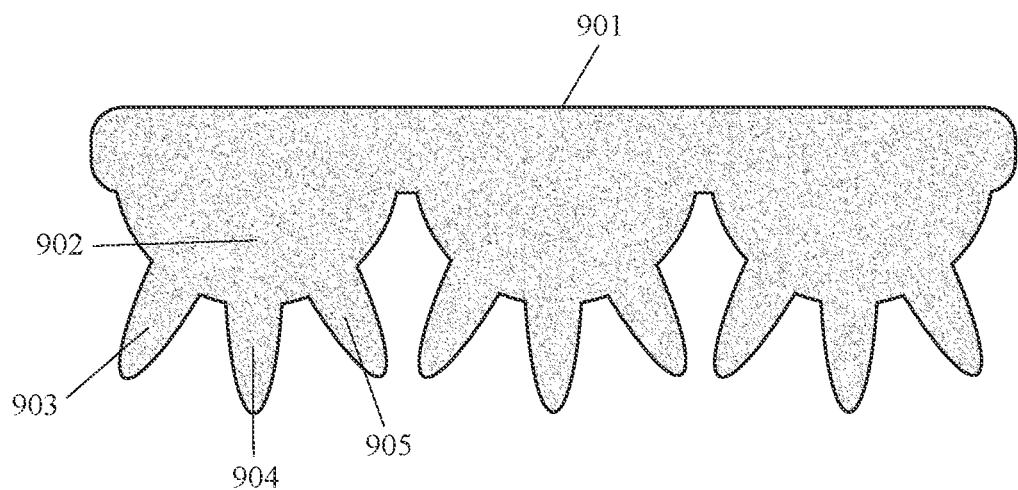
FIG. 9 shows an EEG electrode with protrusions having hemispherical distal portions and pluralities of paraboloid-shaped proximal portions.

FIG. 9 shows a side cross-sectional view of an EEG electrode for use on a hair-covered portion of a person's head comprising: a (disk-shaped) distal portion 901; and a plurality of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein a protrusion in the plurality of electroconductive proximal protrusions further comprises a hemispherical distal (farther from the person's head) portion 902 and a plurality of paraboloidal proximal (closer to the person's head) portions 903, 904, and 905. In other words, this example is an EEG electrode with a bovinely inspired topography which is udderly conductive.

In an example, a distal portion of an electrode can have a circular and/or disk shape. In an example, a hair-penetrating protrusion can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 10:
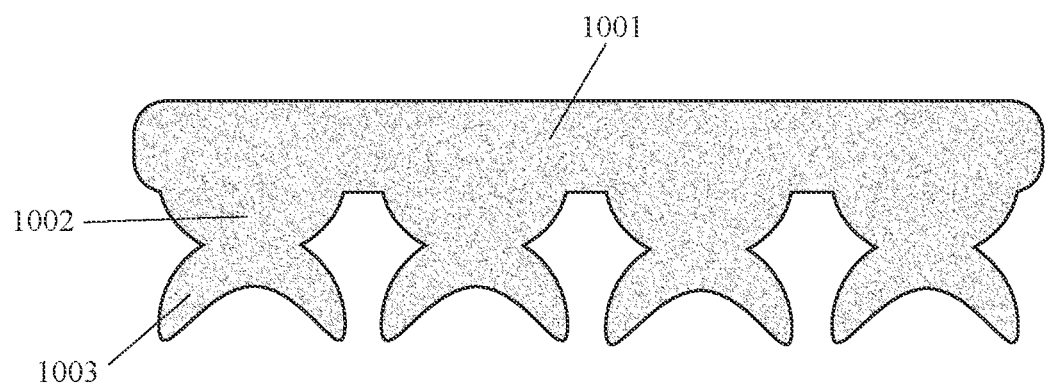
FIG. 10 shows an EEG electrode with protrusions having hemispherical distal portions and crescent-shaped proximal portions.

FIG. 10 shows a side cross-sectional view of an EEG electrode for use on a hair-covered portion of a person's head comprising: a (disk-shaped) distal portion 1001; and a plurality of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein a protrusion in the plurality of electroconductive proximal protrusions further comprises a hemispherical distal (farther from the person's head) portion 1002 and a crescent or banana-shaped proximal (closer to the person's head) portion 1003.

In an example, a distal portion of an electrode can have a circular and/or disk shape. In an example, a hair-penetrating protrusion can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 11:
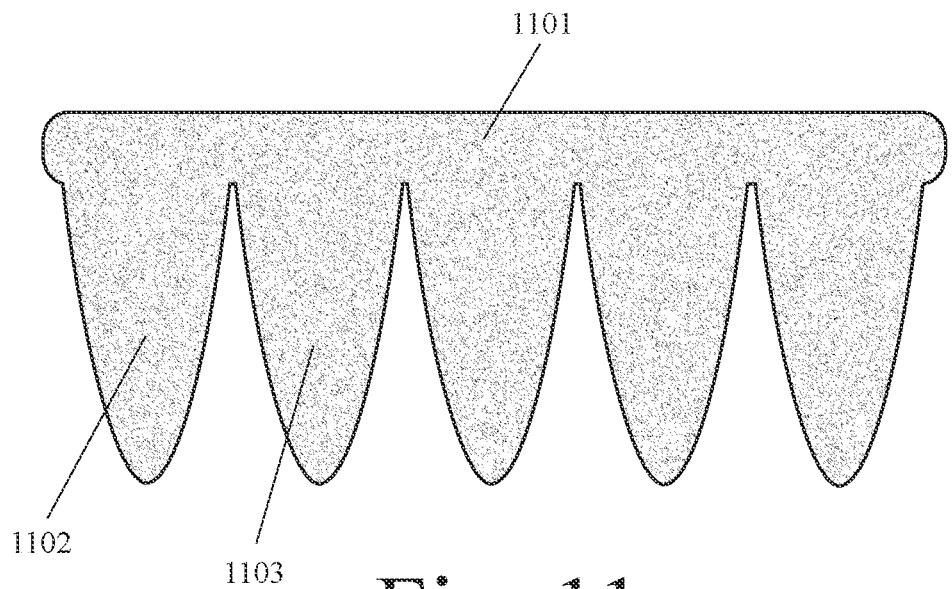
FIG. 11 shows an EEG electrode with first number of paraboloid-shaped protrusions.

FIG. 11 shows a side cross-sectional view of an EEG electrode for use on a hair-covered portion of a person's head comprising: a (disk-shaped) distal portion 1101; and a plurality of paraboloid-shaped proximal protrusions, including 1102 and 1103, which extend out from the distal portion toward the person's head in order to penetrate between hairs and come into contact with the surface of the person's head. In this example, there are six protrusions in a side cross-section of the electrode. Relevant variations discussed elsewhere in this disclosure or in priority-linked disclosures can also be applied to the example in this figure.

Figure 12:
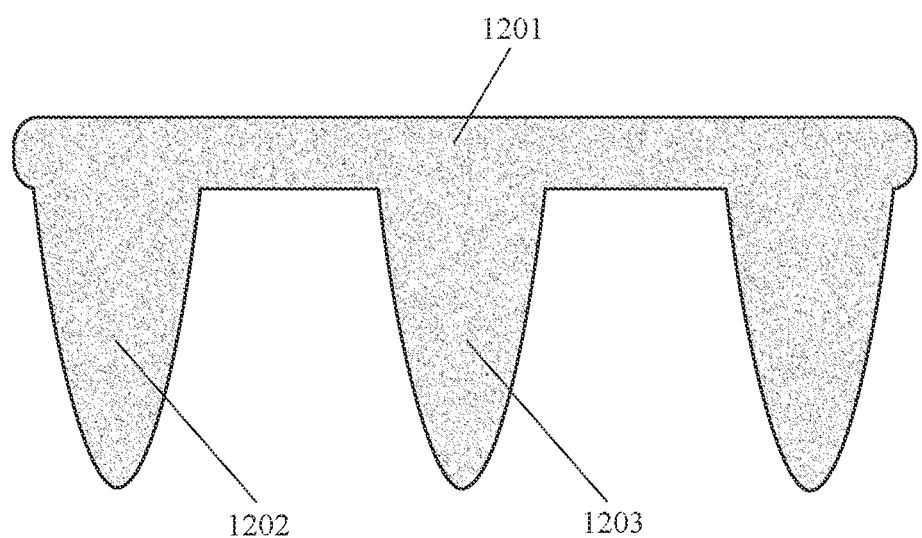
FIG. 12 shows an EEG electrode with second number of paraboloid-shaped protrusions.

FIG. 12 shows a side cross-sectional view of an EEG electrode for use on a hair-covered portion of a person's head comprising: a (disk-shaped) distal portion 1201; and a plurality of paraboloid-shaped proximal protrusions, including 1202 and 1203, which extend out from the distal portion toward the person's head in order to penetrate between hairs and come into contact with the surface of the person's head. In this example, there are three protrusions in a side cross-section of the electrode. Relevant variations discussed elsewhere in this disclosure or in priority-linked disclosures can also be applied to the example in this figure.

Figure 13:
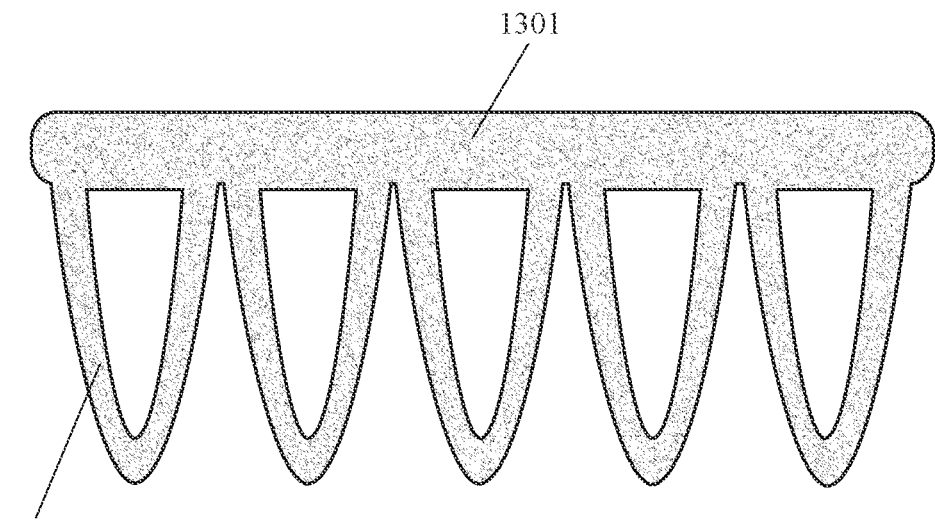
FIG. 13 shows an EEG electrode with arch-shaped protrusions.

FIG. 13 shows a side cross-sectional view of an EEG electrode for use on a hair-covered portion of a person's head comprising: a (disk-shaped) distal portion 1301; and a plurality of arch-shaped proximal protrusions including 1302 and 1303 which extend out from the distal portion toward the person's head in order to penetrate between hairs and come into contact with the surface of the person's head.

In an example, an arch-shaped protrusion can have a parabolic, conic section, catenary, and/or carlavian curve shape. In an example, an electrode can comprise a distal portion and a plurality of proximal loops which extend out from the distal portion toward the person's head in order to penetrate between hairs and come into contact with the surface of the person's head. In an example, protruding arches and/or loops can be oriented along spokes which radiate from the center of the distal portion. In an example, protruding arches and/or loops can be parallel to each other. In an example, protruding arches and/or loops can be configured in a hexagonal grid. Relevant variations discussed elsewhere in this disclosure or in priority-linked disclosures can also be applied to the example in this figure.

Figure 14:
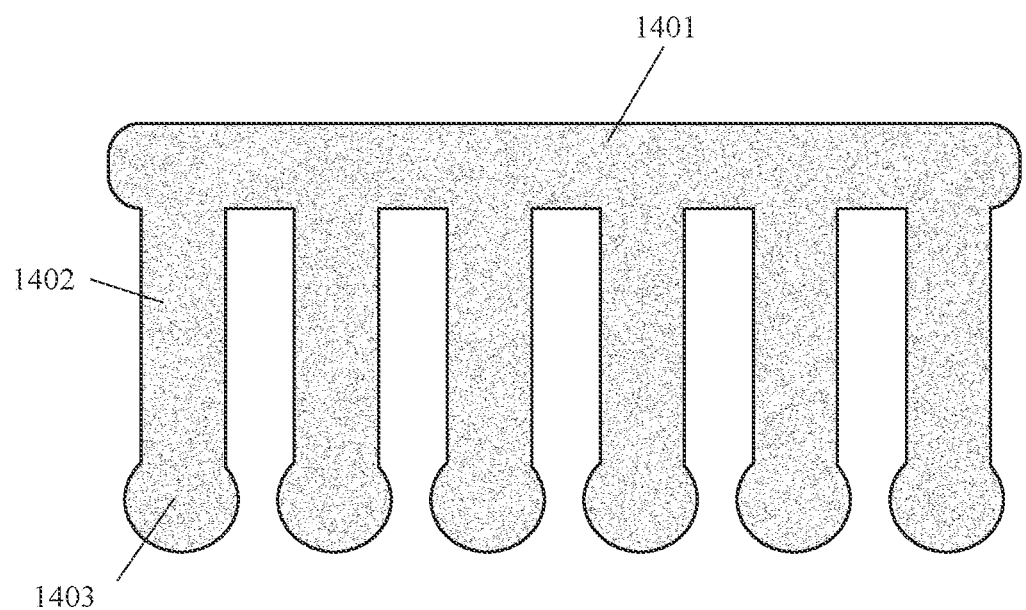
FIG. 14 shows an EEG electrode with column-and-ball protrusions.

FIG. 14 shows a side cross-sectional view of an EEG electrode for use on a hair-covered portion of a person's head comprising: a distal portion 1401; and a plurality of column-and-ball protrusions which extend out from the distal portion toward the person's head in order to penetrate between hairs and come into contact with the surface of the person's head, wherein a column-and-ball protrusion further comprises a distal (farther from the surface of a person's head) column 1402 and a proximal (closer to the surface of the person's head) ball 1403.

In an example, a protrusion can comprise a column with a ball attached to its proximal end, wherein the ball has a diameter which is greater than the diameter of the column. In an example, a column can be a circular column. In an example, the column and ball can comprise a single piece made from the same material. In an example, the column and ball can be different pieces which are attached together and/or made from different materials. In an example, the diameter of a ball portion of a protrusion which is closer to the center of the electrode can be greater than the diameter of a ball portion of a protrusion which is farther from the center of the electrode. In an example, the diameter of a ball portion of a protrusion which is closer to the center of the electrode can be less than the diameter of a ball portion of a protrusion which is farther from the center of the electrode.

In an example, a plurality of column-and-ball protrusions can be configured in two or more nested (e.g. concentric) rings. In an example, a plurality of column-and-ball protrusions can be configured in an orthogonal grid. In an example, column-and-ball protrusions can extend out perpendicularly from a distal portion of an electrode toward the surface of a person's head. Relevant variations discussed elsewhere in this disclosure or in priority-linked disclosures can also be applied to the example in this figure.

Figure 15:
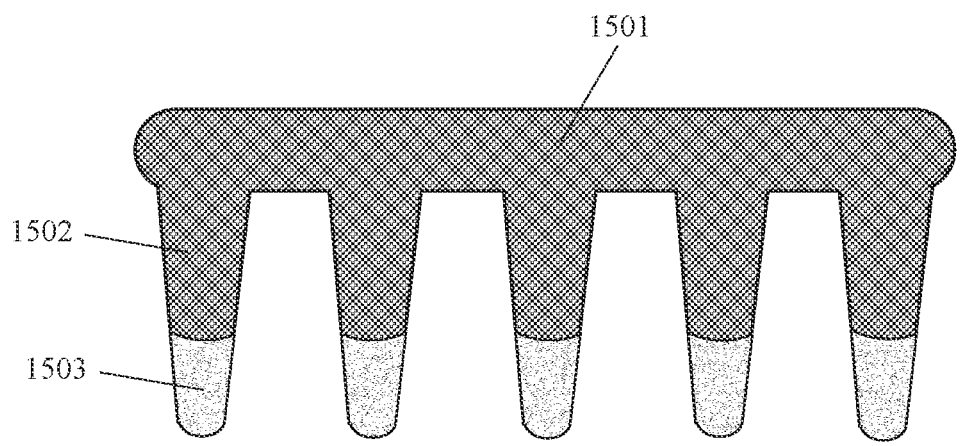
FIG. 15 shows an EEG electrode with protrusions having distal portions made from a first material and proximal portions made from a second material.

FIG. 15 shows a side cross-sectional view of an EEG electrode for use on a hair-covered portion of a person's head comprising: a distal portion 1501; and a plurality of protrusions which extend out from the distal portion toward the person's head in order to penetrate between hairs and come into contact with the surface of the person's head, wherein a protrusion further comprises a distal (farther from the surface of a person's head) portion 1502 made from a first material and a proximal (closer to the surface of the person's head) portion 1503 made from a second material.

In an example, the distal half of a protrusion is made from a first material and the proximal half of the protrusion is made from a second material. In an example, between half and three-quarters of a protrusion is made from a first material and the rest of the protrusion is made from a second material. In an example, the 50% to 75% of a protrusion which is closest to the distal portion of the electrode is made from a first material and the rest of the protrusion is made from a second material. In an example, a protrusion is made from a first material except for a proximal (closest to the surface of a person's head) tip, peak, vertex, or cap which is made from a second material. In an example, a protrusion is made from a first material except for a coating on the tip, peak, vertex, or cap of the protrusion which is made from a second material.

In an example, the conductivity of the first material is greater than that of the second material. In an example, the durometer of the first material is greater than that of the second material. In an example, the Young's modulus of the first material is greater than that of the second material. In an example, the elasticity of the first material is greater than that of the second material. In an example, the flexibility of the first material is greater than that of the second material. In an example, the conductivity of the first material is less than that of the second material. In an example, the durometer of the first material is less than that of the second material. In an example, the Young's modulus of the first material is less than that of the second material. In an example, the elasticity of the first material is less than that of the second material. In an example, the flexibility of the first material is less than that of the second material.

In an example, the first material is a metal (e.g. silver). In an example, the first material is an inherently-conductive polymer. In an example, the first material is an inherently-nonconductive polymer. In an example, the first material is an inherently-nonconductive polymer (e.g. PDMS) which has been made conductive by doping, impregnation, and/or coating with carbon structures (e.g. carbon nanotubes). In an example, the first material is an inherently-nonconductive polymer (e.g. PDMS) which has been made conductive by doping, impregnation, and/or coating with metal. In an example a first material can have a higher amount of doping or impregnation with metal and/or carbon structures than a second material.

In an example, the second material is a metal (e.g. silver). In an example, the second material is an inherently-conductive polymer. In an example, the second material is an inherently-nonconductive polymer. In an example, the second material is an inherently-nonconductive polymer (e.g. PDMS) which has been made conductive by doping, impregnation, and/or coating with carbon structures (e.g. carbon nanotubes). In an example, the second material is an inherently-nonconductive polymer (e.g. PDMS) which has been made conductive by doping, impregnation, and/or coating with metal. In an example a second material can have a higher amount of doping or impregnation with metal and/or carbon structures than a first material.

In an example, the proportion of the first material vs. the second material in a protrusion can vary with distance from the center of the electrode. In an example, a protrusion which is closer to the center of the electrode can have a greater percentage of a first material than a protrusion which is farther from the center. In an example, a protrusion which is closer to the center of the electrode can have a lower percentage of a first material than a protrusion which is farther from the center. Relevant variations discussed elsewhere in this disclosure or in priority-linked disclosures can also be applied to the example in this figure.

Figure 16:
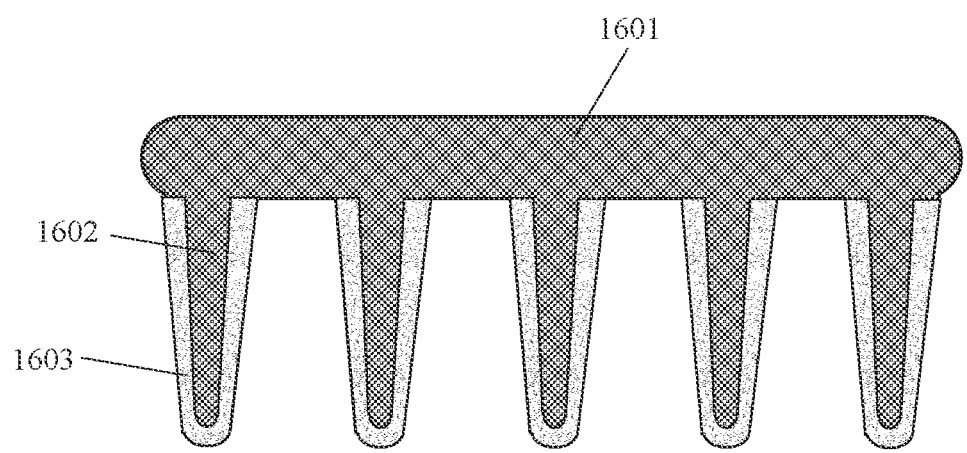
FIG. 16 shows an EEG electrode with protrusions having inner cores made from a first material and outer layers made from a second material.

FIG. 16 shows a side cross-sectional view of an EEG electrode for use on a hair-covered portion of a person's head comprising: a distal portion 1601; and a plurality of protrusions which extend out from the distal portion toward the person's head in order to penetrate between hairs and come into contact with the surface of the person's head, wherein a protrusion further comprises a inner core 1602 made from a first material and an outer layer 1603 made from a second material.

In an example, an inner core of a protrusion spans between 20% and 60% of a cross-sectional area of a protrusion. In an example, an inner core of a protrusion spans between 40% and 80% of a cross-sectional area of the protrusion. In an example an inner core extends all the way from the distal portion an electrode to the proximal tip, peak, vertex, or cap of a protrusion. In an example an inner core spans between 50% and 95% of the longitudinal axis of a protrusion. In an example, an inner core can be a cylindrical core within a frustum-shape protrusion. In an example, an inner core can be a frustum-shaped core within a frustum-shape protrusion. In an example, an inner core can be a cylindrical core within a cylindrical protrusion.

In an example, the conductivity of the first material is greater than that of the second material. In an example, the durometer of the first material is greater than that of the second material. In an example, the Young's modulus of the first material is greater than that of the second material. In an example, the elasticity of the first material is greater than that of the second material. In an example, the flexibility of the first material is greater than that of the second material. In an example an inner core is fluid. In an example an inner core is a conductive fluid. In an example, the conductivity of the first material is less than that of the second material. In an example, the durometer of the first material is less than that of the second material. In an example, the Young's modulus of the first material is less than that of the second material. In an example, the elasticity of the first material is less than that of the second material. In an example, the flexibility of the first material is less than that of the second material.

In an example, an inner core of a protrusion can be stiffer and/or more resilient than an outer layer of a protrusion. In an example, an outer layer of a protrusion can more compliant or compressible than an inner core of a protrusion. In an example, an inner core can be made with metal and an outer layer can be made with a conductive polymer. In an example, an inner core can be made with metal and an outer layer can be made with an inherently-nonconductive polymer (e.g. PDMS) which has been made conductive by doping, impregnation, and/or coating with carbon structures (e.g. carbon nanotubes) and/or metal.

In an example, the first material is a metal (e.g. silver). In an example, the first material is an inherently-conductive polymer. In an example, the first material is an inherently-nonconductive polymer. In an example, the first material is an inherently-nonconductive polymer (e.g. PDMS) which has been made conductive by doping, impregnation, and/or coating with carbon structures (e.g. carbon nanotubes). In an example, the first material is an inherently-nonconductive polymer (e.g. PDMS) which has been made conductive by doping, impregnation, and/or coating with metal. In an example a first material can have a higher amount of doping or impregnation with metal and/or carbon structures than a second material.

In an example, the second material is a metal (e.g. silver). In an example, the second material is an inherently-conductive polymer. In an example, the second material is an inherently-nonconductive polymer. In an example, the second material is an inherently-nonconductive polymer (e.g. PDMS) which has been made conductive by doping, impregnation, and/or coating with carbon structures (e.g. carbon nanotubes). In an example, the second material is an inherently-nonconductive polymer (e.g. PDMS) which has been made conductive by doping, impregnation, and/or coating with metal. In an example a second material can have a higher amount of doping or impregnation with metal and/or carbon structures than a first material.

In an example, the size and/or shape of an inner core can vary with distance from the center of the electrode. In an example, a protrusion which is closer to the center of the electrode can have a larger inner core than a protrusion which is farther from the center. In an example, a protrusion which is closer to the center of the electrode can have a smaller inner core than a protrusion which is farther from the center. Relevant variations discussed elsewhere in this disclosure or in priority-linked disclosures can also be applied to the example in this figure.

Figure 17:
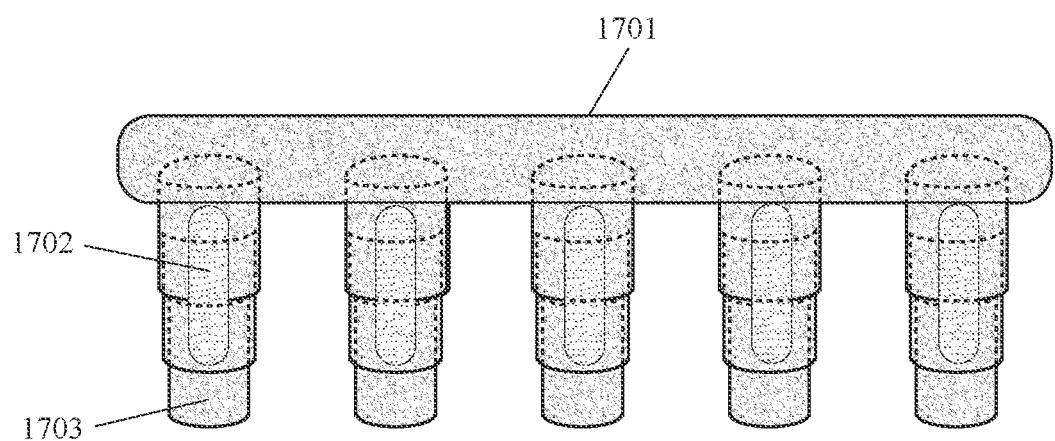
FIG. 17 shows an EEG electrode with parallel telescoping protrusions.

FIG. 17 shows a side cross-sectional view of an EEG electrode for use on a hair-covered portion of a person's head comprising: a distal portion 1701; and a plurality of telescoping conductive protrusions which extend out from the distal portion toward the person's head in order to penetrate between hairs and come into contact with the surface of the person's head, wherein a telescoping conductive protrusion further comprises a inner compressible portion 1702 and an outer sequence of telescoping segments 1703. In this example, the protrusions extend out from the distal portion in a perpendicular manner.

In an example, the outer sequence of telescoping segments can be nested (e.g. concentric) cylinders. In an example, the outer sequence of telescoping segments can be nested (e.g. concentric) segments with different diameters. In an example, the outer sequence of telescoping segments can comprise two telescoping segments with different diameters. In an example, the outer sequence of telescoping segments can comprise three or more telescoping segments with different diameters. In an example, telescoping segments can have equal lengths. In an example, proximal (closer to the surface of a person's head) telescoping segments can be shorter than distal (farther from the surface of a person's head) telescoping segments.

In an example, an inner compressible portion can be a chamber which contains a gas. In an example, the amount of contact and/or pressure between protrusions and the surface of a person's head can be adjusted by changing the pressure of a gas inside such a chamber. In an example, an inner compressible portion can be a spring and/or coil. In an example, the amount of contact and/or pressure between protrusions and the surface of a person's head can be adjusted by rotating such a spring and/or coil. In an example, an inner compressible portion can be made from compressible (e.g. low durometer) foam. Relevant variations discussed elsewhere in this disclosure or in priority-linked disclosures can also be applied to the example in this figure.

Figure 18:
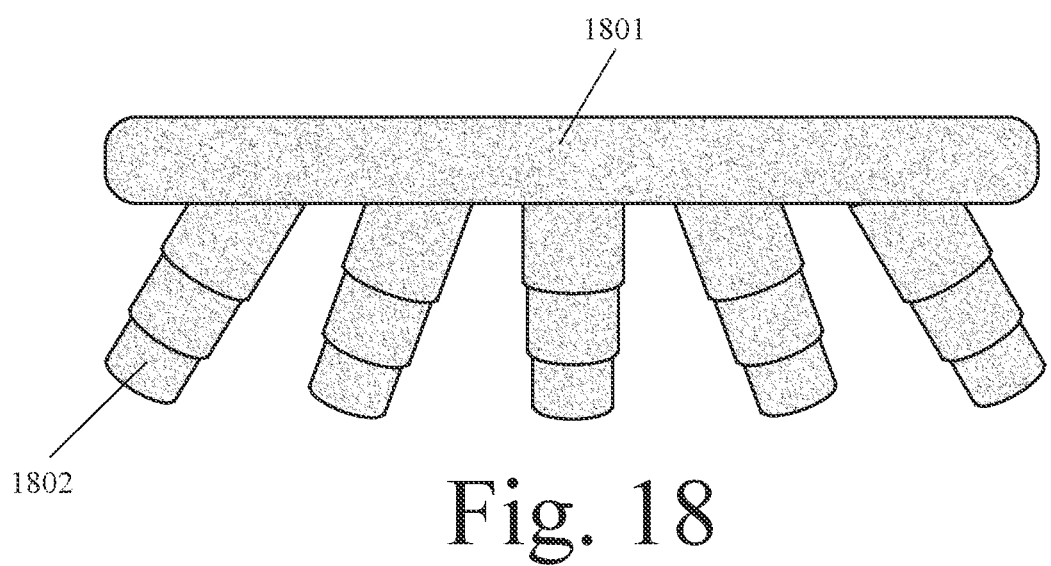
FIG. 18 shows an EEG electrode with non-parallel telescoping protrusions.

FIG. 18 shows a side cross-sectional view of an EEG electrode for use on a hair-covered portion of a person's head comprising: a distal portion 1801; and a plurality of conductive protrusions which extend out from the distal portion toward the person's head in order to penetrate between hairs and come into contact with the surface of the person's head, wherein a conductive protrusion further comprises a inner compressible portion 1802 and an outer sequence of telescoping segments 1803. In this example, protrusions extend out from the distal portion at different angles. In this example, the angles at which protrusions extend out from the distal portion vary with the distance of a protrusion from the center of the electrode. In an example, protrusions which are closer to the center of the electrode can be more perpendicular than protrusions which are farther from the center of the electrode. In an example, protrusions which are farther from the center of the electrode can tilt, point, bow, or curve away from the center of the electrode.

In an example, the outer sequence of telescoping segments can be nested (e.g. concentric) cylinders. In an example, the outer sequence of telescoping segments can be nested (e.g. concentric) segments with different diameters. In an example, the outer sequence of telescoping segments can comprise two telescoping segments with different diameters. In an example, the outer sequence of telescoping segments can comprise three or more telescoping segments with different diameters. In an example, telescoping segments can have equal lengths. In an example, proximal (closer to the surface of a person's head) telescoping segments can be shorter than distal (farther from the surface of a person's head) telescoping segments.

In an example, an inner compressible portion can be a chamber which contains a gas. In an example, the amount of contact and/or pressure between protrusions and the surface of a person's head can be adjusted by changing the pressure of a gas inside such a chamber. In an example, an inner compressible portion can be a spring and/or coil. In an example, the amount of contact and/or pressure between protrusions and the surface of a person's head can be adjusted by rotating such a spring and/or coil. In an example, an inner compressible portion can be made from compressible (e.g. low durometer) foam. Relevant variations discussed elsewhere in this disclosure or in priority-linked disclosures can also be applied to the example in this figure.

Figure 19:
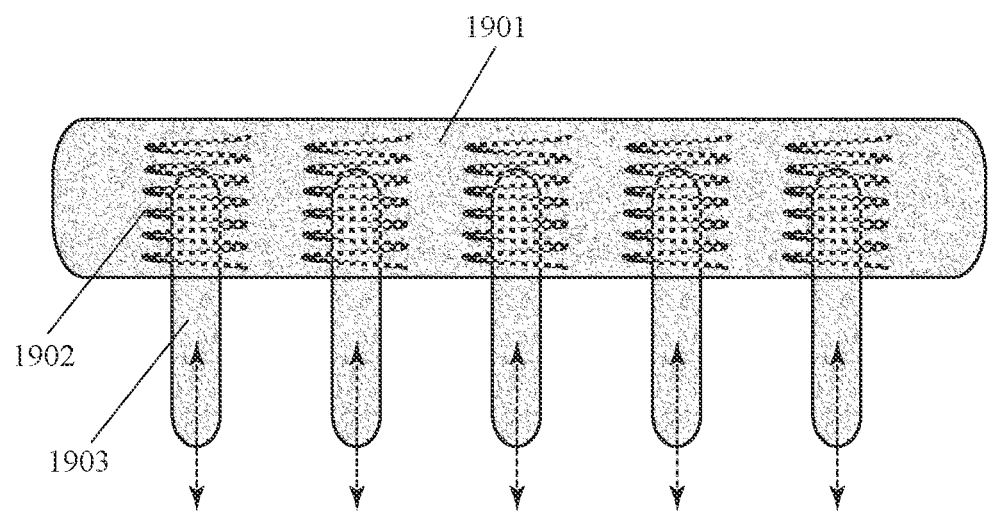
FIG. 19 shows an EEG electrode with protrusions connected to springs.

FIG. 19 shows a side cross-sectional view of an EEG electrode for use on a hair-covered portion of a person's head comprising: a distal portion 1901; a plurality of movable conductive protrusions, including 1903, which extend out from the distal portion toward the person's head in order to penetrate between hairs and come into contact with the surface of the person's head; and a plurality of springs (or coils), including 1902, which compel protrusions in the plurality of movable conductive protrusions toward the surface of the person's head.

In this example, there is a spring (or coil) for each protrusion. This enables independent movement of different protrusions. In this example, springs (or coils) are within the distal portion of the electrode. Alternatively, springs (or coils) can be external to the distal portion of the electrode. In this example, protrusions extend out in a perpendicular manner from the distal portion. In another example, the angles at which protrusions extend out from the distal portion can vary with the distance of protrusions from the center of the electrode. In an example, a spring (or coil) can encircle a distal portion of a protrusion. In an example, a spring (or coil) can press against the distal end of a protrusion.

In an example, the size and shape of springs (or coils) can vary with distance from the center of the electrode. In an example, a spring (or coil) which is connected to a protrusion which is closer to the center of the electrode can be larger (e.g. larger, stronger, and/or more resilient) than a spring which is connected to a protrusion which is farther from the center of the electrode. In an example, a spring (or coil) which is connected to a protrusion which is father from the center of the electrode can be larger (e.g. larger, stronger, and/or more resilient) than a spring which is connected to a protrusion which is closer to the center of the electrode. Relevant variations discussed elsewhere in this disclosure or in priority-linked disclosures can also be applied to the example in this figure.

Figure 20:
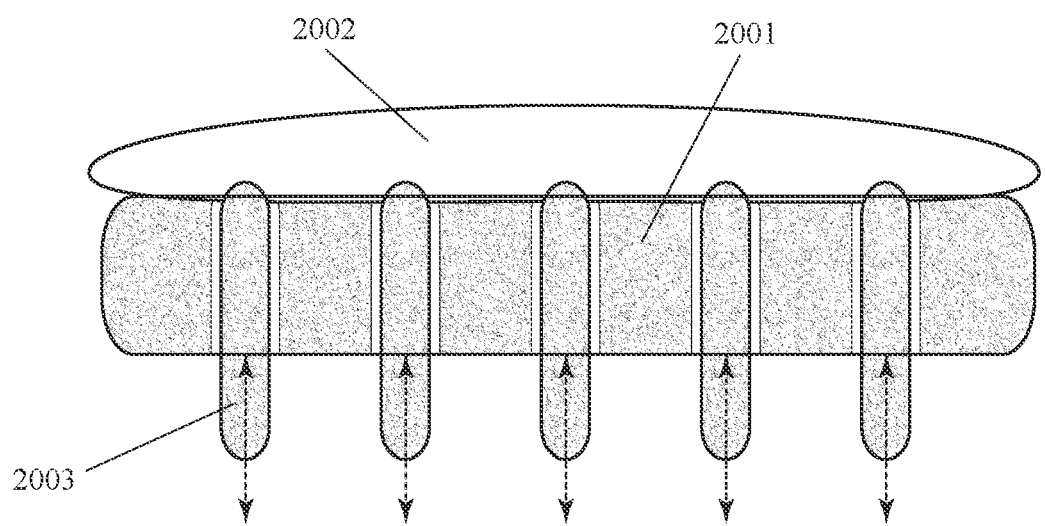
FIG. 20 shows an EEG electrode with protrusions connected to an expandable chamber.

FIG. 20 shows a side cross-sectional view of an EEG electrode for use on a hair-covered portion of a person's head comprising: a distal portion 2001; a plurality of movable conductive protrusions, including 2003, which extend out from the distal portion toward the person's head in order to penetrate between hairs and come into contact with the surface of the person's head; and an expandable gas-filled or fluid-filled chamber 2002 which compels protrusions in the plurality of movable conductive protrusions toward the surface of the person's head as the chamber is expanded.

In an example, the amount of pressure exerted by protrusions on the surface of a person's head can be adjusted by changing the degree to which the expandable chamber is filled with a gas or liquid. In an example, the amount of pressure exerted by protrusions on the surface of a person's head can be adjusted by changing the pressure of a gas or liquid within the expandable chamber. In this example, an expandable chamber is on the distal side of the distal portion and protrusions extend through the distal portion in order to contact the expandable chamber. In an alternative example, an expandable chamber can be on the proximal side of the distal portion and protrusions need not extend through the distal portion.

In an example, an expandable chamber can be inflated by being filled with a gas (such as air). In an example, the expandable chamber can be a balloon. In an example, a chamber can be expanded by being filled with a liquid. In this example, an expandable chamber is in contact with all of the protrusions and moves all of the protrusions when it is expanded. In an alternative example, there can be a plurality of expandable chambers, wherein each chamber is in contact with one protrusion; this would enable independent movement of different protrusions.

In an example, expansion of a chamber with a gas of liquid can be done manually by the person wearing the device by using a manual air or liquid pump. In an example, this device can further comprise an electromagnetic motor and pump which automatically pumps air or liquid into a chamber. In an example, this device can further comprise an electromagnetic motor and pump which automatically pumps air or liquid into a chamber until a desired pressure level is reached. In an example, this device can further comprise one or more pressure sensors on one or more protrusions, wherein an automatic pump adjusts the pressure inside one or more expandable chambers in order to adjust the pressure levels between protrusions and the surface of a person's head. Pressure levels can also be automatically adjusted in order to achieve desired levels of conductivity between protrusions and the surface of a person's head. In an example, there can be a separate pneumatic or hydraulic mechanism for each protrusion which selectively and independently adjusts the degree of pressure between each protrusion and the surface of a person's head. Relevant variations discussed elsewhere in this disclosure or in priority-linked disclosures can also be applied to the example in this figure.

Figure 21:
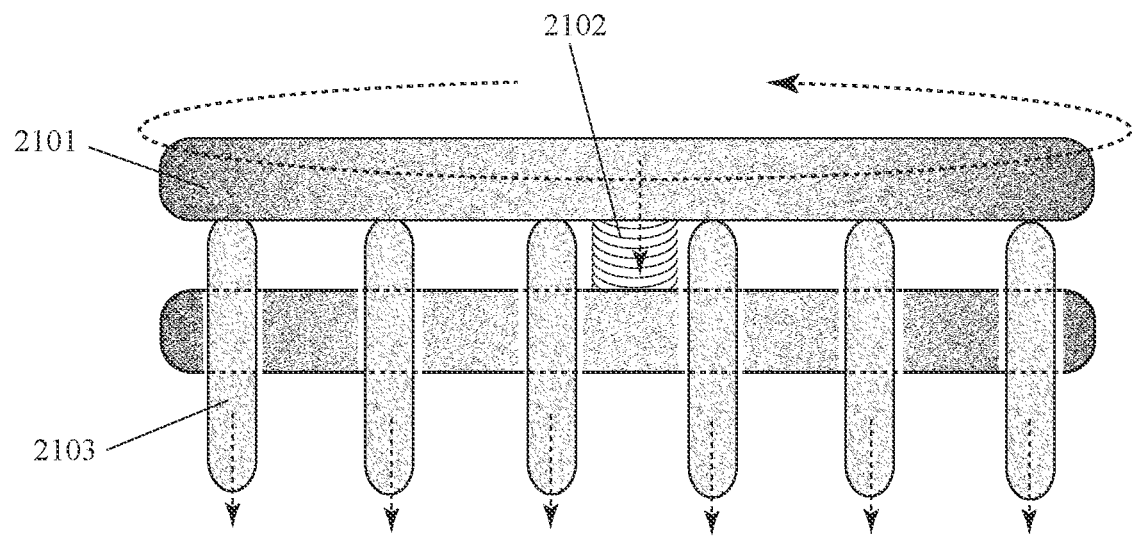
FIGS. 21 and 22 show two views of an EEG electrode with a rotatable threaded mechanism which changes the length of protrusions.
Figure 22:
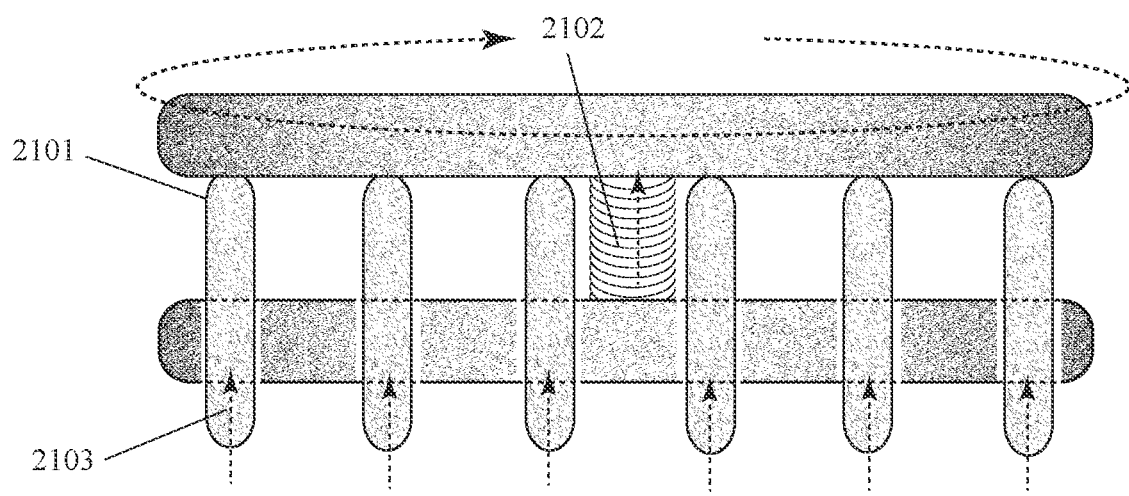

FIGS. 21 and 22 show two side cross-sectional views, at two different times, of an EEG electrode for use on a hair-covered portion of a person's head comprising: a distal portion 2101; a plurality of movable conductive protrusions, including 2103, which extend toward the person's head in order to penetrate between hairs and come into contact with the surface of the person's head; and a (helical) threaded mechanism 2102 which is connected to the distal portion, wherein rotation of the distal portion rotates the threaded mechanism, rotation of the thread mechanism moves the distal portion toward the surface of the person's head, and movement of the distal portion toward the surface of the person's head increases the pressure exerted by protrusions (in plurality of movable conductive protrusions) against the surface of the person's head.

FIG. 21 shows this electrode at a first time wherein rotation of the distal portion in a first direction (e.g. counterclockwise) moves the distal portion closer toward the surface of the person's head and increases contact and/or pressure between the protrusions and the surface of the person's head. FIG. 22 shows this electrode at a second time wherein rotation of the distal portion in a second direction (e.g. clockwise) moves the distal portion farther from the surface of the person's head and decreases contact and/or pressure between the protrusions and the surface of the person's head.

In an example, rotation of the distal portion can be done manually. In an example, this device can further comprise an actuator which automatically rotates the distal portion. In an example, the device can further comprise one or more pressure sensors on one or more protrusions, wherein these pressure sensors measure pressure levels between protrusions and the surface of a person's head. In an example, an actuator can automatically rotate the distal portion in order to achieve desired levels of contact, pressure, and/or conductivity between protrusions and the surface of a person's head. Relevant variations discussed elsewhere in this disclosure or in priority-linked disclosures can also be applied to the example in this figure.

Figure 23:
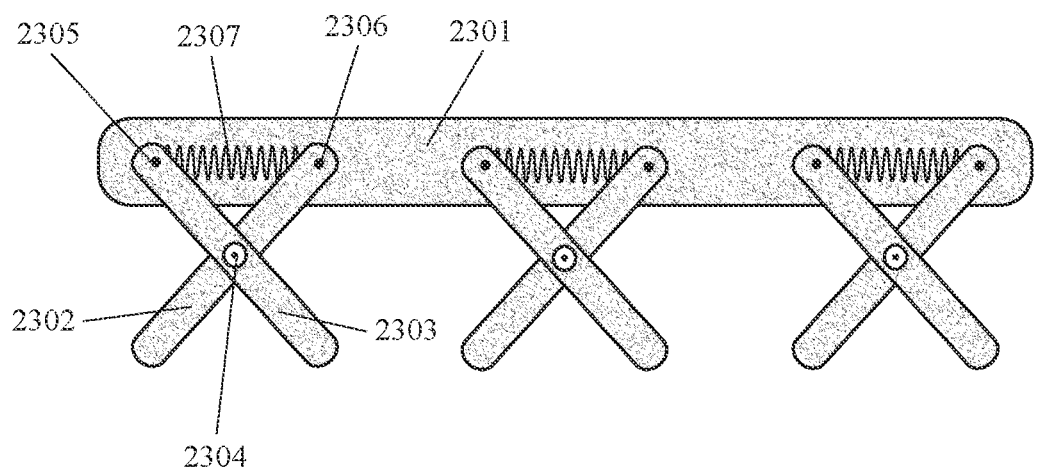
FIG. 23 shows an EEG electrode with straight scissor-like articulated protrusions.

FIG. 23 shows a cross-sectional view of an EEG electrode for use on a hair-covered portion of a person's head comprising: (a) a distal portion 2301; and (b) a plurality of articulated conductive protrusions which extend out from the distal portion toward the person's head in order to penetrate between hairs and come into contact with the surface of the person's head; wherein each protrusion further comprises a first longitudinal segment 2302 (e.g. segment, section, bar, prong, or arm) which is movably attached to the distal portion by a first connection, joint, or axle 2306; wherein each protrusion further comprises a second longitudinal segment 2303 (e.g. segment, section, bar, prong, or arm) which is movably attached to the distal portion by a second connection, joint, or axle 2305; and wherein the first and second longitudinal segments are movably connected to each other by a third connection, joint, or axle 2304. In an example, a protrusion can further comprise a spring or elastic band 2307 between the first and second longitudinal segments.

In an example, movement of a second longitudinal segment (e.g. segment, section, bar, prong, or arm) relative to a first longitudinal segment (e.g. segment, section, bar, prong, or arm), or vice versa, changes the distance by which a protrusion extends out from the distal portion, thereby changing the degree of contact and/or pressure between the protrusion and the surface of the person's head. In an example, rotation, tilting, or pivoting of a second longitudinal segment relative to a first longitudinal segment, or vice versa, around the third connection, joint, or axle changes the extension distance of a protrusion, thereby changing the degree of contact and/or pressure between the protrusion and the surface of the person's head. In an example, scissor movement of the second longitudinal segment relative to the first longitudinal segment, or vice versa, around the third connection, joint, or axle changes the extension distance of the protrusion, thereby changing the degree of contact and/or pressure between the protrusion and the surface of the person's head.

In this example, longitudinal axes of first and second longitudinal segments (e.g. segments, sections, bars, prongs, or arms) are straight. In another example, longitudinal axes of the first and second longitudinal segments (e.g. segments, sections, bars, prongs, or arms) can be arcuate. In another example, longitudinal axes of the first and second longitudinal segments (e.g. segments, sections, bars, prongs, or arms) can bow outward, away from each other. In another example, longitudinal axes of the first and second longitudinal segments (e.g. segments, sections, bars, prongs, or arms) can bow inward, toward each other. In an example, first and second longitudinal segments can move relative to each other like the two articulated segments of a pair of scissors.

In an example, the distal ends of first and second longitudinal segments can be connected to each other by a spring, elastic band, or other tensile member which draws the ends together and/or pushes the ends apart. In an example, portions of first and second longitudinal segments which are distal (farther from the surface of a person's head) relative to a third connection can be connected to each other by a spring, elastic band, or other tensile member which draws the ends together and/or pushes the ends apart. In an example, portions of first and second longitudinal segments which are proximal (closer to the surface of a person's head) relative to a third connection can be connected to each other by a spring, elastic band, or other tensile member which draws the ends together and/or pushes the ends apart. In an example, contact and/or pressure between the proximal ends of longitudinal segments and the surface of a person's head can cause contraction (or expansion) of the spring, elastic band, or other tensile member. Relevant variations discussed elsewhere in this disclosure or in priority-linked disclosures can also be applied to the example in this figure.

Figure 24:
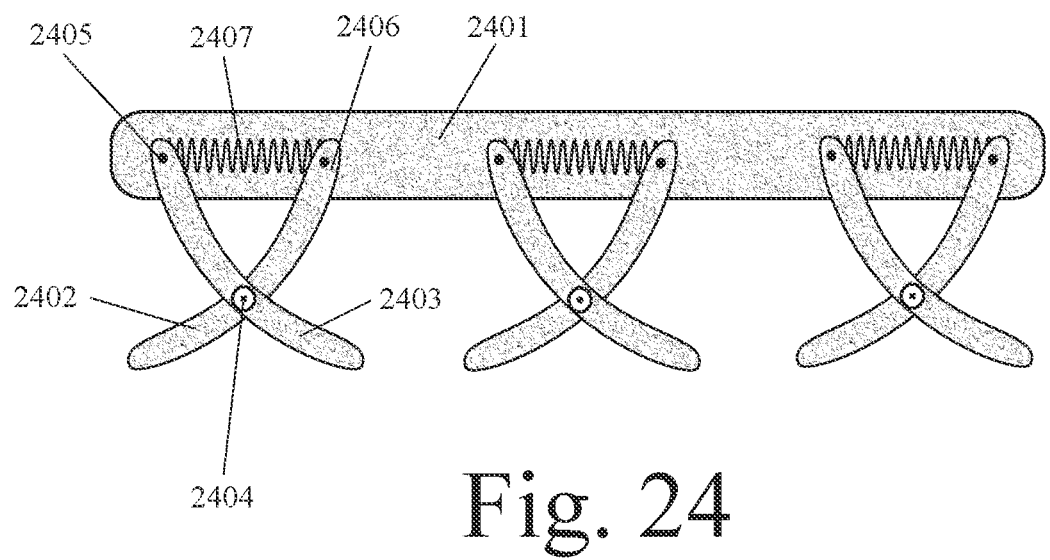
FIG. 24 shows an EEG electrode with arcuate scissor-like articulated protrusions.

FIG. 24 shows a cross-sectional view of an EEG electrode for use on a hair-covered portion of a person's head comprising: (a) a distal portion 2401; and (b) a plurality of articulated conductive protrusions which extend out from the distal portion toward the person's head in order to penetrate between hairs and come into contact with the surface of the person's head; wherein each protrusion further comprises a first longitudinal segment 2402 (e.g. segment, section, bar, prong, or arm) which is movably attached to the distal portion by a first connection, joint, or axle 2406; wherein each protrusion further comprises a second longitudinal segment 2403 (e.g. segment, section, bar, prong, or arm) which is movably attached to the distal portion by a second connection, joint, or axle 2405; and wherein the first and second longitudinal segments are movably connected to each other by a third connection, joint, or axle 2404. In an example, a protrusion can further comprise a spring or elastic band 2407 between the first and second longitudinal segments.

In an example, movement of a second longitudinal segment (e.g. segment, section, bar, prong, or arm) relative to a first longitudinal segment (e.g. segment, section, bar, prong, or arm), or vice versa, changes the distance by which a protrusion extends out from the distal portion, thereby changing the degree of contact and/or pressure between the protrusion and the surface of the person's head. In an example, rotation, tilting, or pivoting of a second longitudinal segment relative to a first longitudinal segment, or vice versa, around the third connection, joint, or axle changes the extension distance of a protrusion, thereby changing the degree of contact and/or pressure between the protrusion and the surface of the person's head. In an example, scissor movement of the second longitudinal segment relative to the first longitudinal segment, or vice versa, around the third connection, joint, or axle changes the extension distance of the protrusion, thereby changing the degree of contact and/or pressure between the protrusion and the surface of the person's head.

In this example, longitudinal axes of first and second longitudinal segments (e.g. segments, sections, bars, prongs, or arms) are arcuate. In this example, longitudinal axes of the first and second longitudinal segments (e.g. segments, sections, bars, prongs, or arms) can bow inward, toward each other. In an example, first and second longitudinal segments can move relative to each other like the two articulated segments of a pair of scissors.

In an example, the distal ends of first and second longitudinal segments can be connected to each other by a spring, elastic band, or other tensile member which draws the ends together and/or pushes the ends apart. In an example, portions of first and second longitudinal segments which are distal (farther from the surface of a person's head) relative to a third connection can be connected to each other by a spring, elastic band, or other tensile member which draws the ends together and/or pushes the ends apart. In an example, portions of first and second longitudinal segments which are proximal (closer to the surface of a person's head) relative to a third connection can be connected to each other by a spring, elastic band, or other tensile member which draws the ends together and/or pushes the ends apart. In an example, contact and/or pressure between the proximal ends of longitudinal segments and the surface of a person's head can cause contraction (or expansion) of the spring, elastic band, or other tensile member. Relevant variations discussed elsewhere in this disclosure or in priority-linked disclosures can also be applied to the example in this figure.

Figure 25:
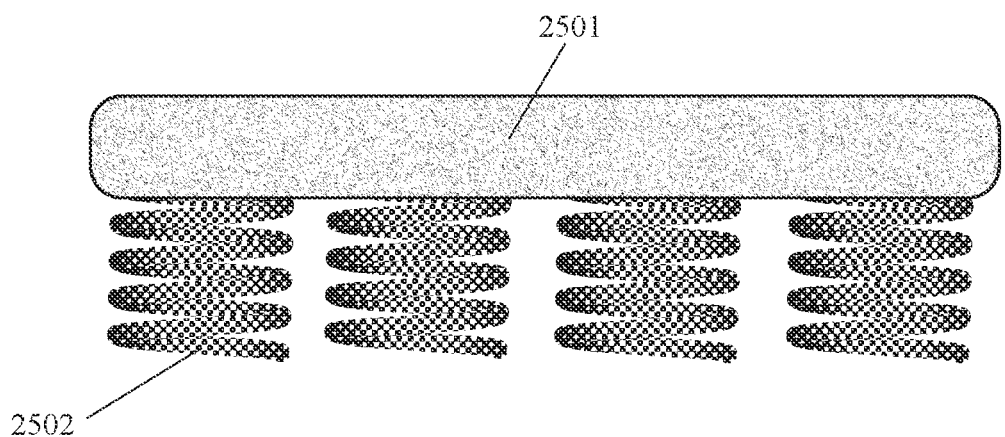
FIG. 25 shows an EEG electrode with helical protrusions.

FIG. 25 shows a cross-sectional view of an EEG electrode for use on a hair-covered portion of a person's head comprising: a distal portion 2501; and a plurality of helical conductive protrusions, including 2502, which extend out from the distal portion toward the person's head in order to penetrate between hairs and come into contact with the surface of the person's head. In an example, there can also be a soft sphere (e.g. ball) at the end of a helical conductive protrusion.

In an example, a distal portion of an electrode can have a circular and/or disk shape. In an example, a distal portion can have an oblong, oval, or elliptical shape. In an example, a distal portion can have a square or rectangular shape. In an example, a distal portion can have a rounded square or rounded rectangular shape. In an example, a distal portion can have a hexagonal shape. In an example, the distal portion of the electrode can have non-uniform thickness. In an example, the center of a distal portion can be thicker than the periphery of the distal portion. In an example, the center of a distal portion can be thinner than the periphery of the distal portion.

In an example, a helical conductive protrusion can be a spring or coil. In an example, an electrode can comprise two or more nested (e.g. concentric) rings of helical conductive protrusions. In an example, an electrode can comprise two or more rows and columns of helical conductive protrusions. In an example, the longitudinal axis of a helical conductive protrusion can be substantially perpendicular to the best-fitting plane of the distal portion of an electrode. In an example, the diameter of a helical conductive protrusion can vary with distance from the distal portion. In an example, the diameter of a helical conductive protrusion can decrease with distance from the distal portion. In an example, the diameter of a helical conductive protrusion can increase with distance from the distal portion.

In an example, the angle between a longitudinal axis of a helical conductive protrusion and the best-fitting plan of a distal portion can vary with the distance of the protrusion from the center of the distal portion. In an example, the angle between a longitudinal axis of a helical conductive protrusion and the best-fitting plan of a distal portion can increase with the distance of the protrusion from the center of the distal portion. In an example, the angle between a longitudinal axis of a helical conductive protrusion and the best-fitting plan of a distal portion can decrease with the distance of the protrusion from the center of the distal portion.

In an example, a helical conductive protrusion can be a metal spring or coil. In an example, a helical conductive protrusion can be a conductive-polymer spring or coil. In an example, a helical conductive protrusion can be made from an inherently-nonconductive polymer (e.g. PDMS) which has been made conductive by doping, impregnation, and/or coating with carbon structures (e.g. carbon nanotubes). In an example, a helical conductive protrusion can be made from metal and an inherently-conductive polymer.

In an example, a helical conductive protrusion can be made from metal and an inherently-nonconductive polymer. In an example, a helical conductive protrusion can be made from metal and an inherently-nonconductive polymer (e.g. PDMS) which has been made conductive by doping, impregnation, and/or coating with carbon structures (e.g. carbon nanotubes). In an example, a helical conductive protrusion can have a metal core and a conductive-polymer outer layer (or coating). Relevant variations discussed elsewhere in this disclosure or in priority-linked disclosures can also be applied to the example in this figure.

Figure 26:
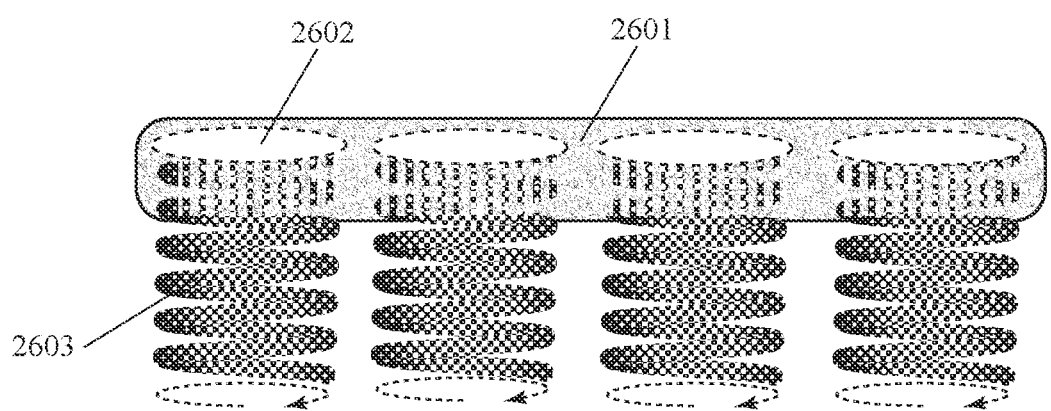
FIG. 26 shows an EEG electrode with rotatable helical protrusions.

FIG. 26 shows a cross-sectional view of an EEG electrode for use on a hair-covered portion of a person's head comprising: a distal portion 2601; a plurality of helical conductive protrusions, including protrusion 2603, which extend out from the distal portion toward the person's head in order to penetrate between hairs and come into contact with the surface of the person's head; and a plurality of actuators, including actuator 2602, which rotate helical conductive protrusions in the plurality of helical conductive protrusions. In an example, there can also be a soft sphere (e.g. ball) at the end of a helical conductive protrusion. In an example, rotation of a helical conductive protrusion enhances the ability of the protrusion to penetrate between hairs and come into contact with the surface of the person's head, but not penetrate or abrade the person's skin.

In an example, a distal portion of an electrode can have a circular and/or disk shape. In an example, a distal portion can have an oblong, oval, or elliptical shape. In an example, a distal portion can have a square or rectangular shape. In an example, a distal portion can have a rounded square or rounded rectangular shape. In an example, a distal portion can have a hexagonal shape. In an example, the distal portion of the electrode can have non-uniform thickness. In an example, the center of a distal portion can be thicker than the periphery of the distal portion. In an example, the center of a distal portion can be thinner than the periphery of the distal portion.

In an example, a helical conductive protrusion can be a spring or coil. In an example, an electrode can comprise two or more nested (e.g. concentric) rings of helical conductive protrusions. In an example, an electrode can comprise two or more rows and columns of helical conductive protrusions. In an example, the longitudinal axis of a helical conductive protrusion can be substantially perpendicular to the best-fitting plane of the distal portion of an electrode. In an example, the diameter of a helical conductive protrusion can vary with distance from the distal portion. In an example, the diameter of a helical conductive protrusion can decrease with distance from the distal portion. In an example, the diameter of a helical conductive protrusion can increase with distance from the distal portion.

In an example, the angle between a longitudinal axis of a helical conductive protrusion and the best-fitting plan of a distal portion can vary with the distance of the protrusion from the center of the distal portion. In an example, the angle between a longitudinal axis of a helical conductive protrusion and the best-fitting plan of a distal portion can increase with the distance of the protrusion from the center of the distal portion. In an example, the angle between a longitudinal axis of a helical conductive protrusion and the best-fitting plan of a distal portion can decrease with the distance of the protrusion from the center of the distal portion.

In an example, a helical conductive protrusion can be a metal spring or coil. In an example, a helical conductive protrusion can be a conductive-polymer spring or coil. In an example, a helical conductive protrusion can be made from an inherently-nonconductive polymer (e.g. PDMS) which has been made conductive by doping, impregnation, and/or coating with carbon structures (e.g. carbon nanotubes). In an example, a helical conductive protrusion can be made from metal and an inherently-conductive polymer. In an example, a helical conductive protrusion can be made from metal and an inherently-nonconductive polymer. In an example, a helical conductive protrusion can be made from metal and an inherently-nonconductive polymer (e.g. PDMS) which has been made conductive by doping, impregnation, and/or coating with carbon structures (e.g. carbon nanotubes). In an example, a helical conductive protrusion can have a metal core and a conductive-polymer outer layer (or coating).

In an example, an actuator can be a small electromagnetic motor. In an example, an actuator can be within the distal portion of the electrode. In an example, an actuator can be between the distal portion of the electrode and a helical conductive protrusion which extends out from the electrode. In an example, an actuator can rotate a helical conductive protrusion in a clockwise (or counter-clockwise) direction around the central longitudinal axis of the protrusion. In an example, there can be one actuator for each protrusion. Relevant variations discussed elsewhere in this disclosure or in priority-linked disclosures can also be applied to the example in this figure.

Figure 27:
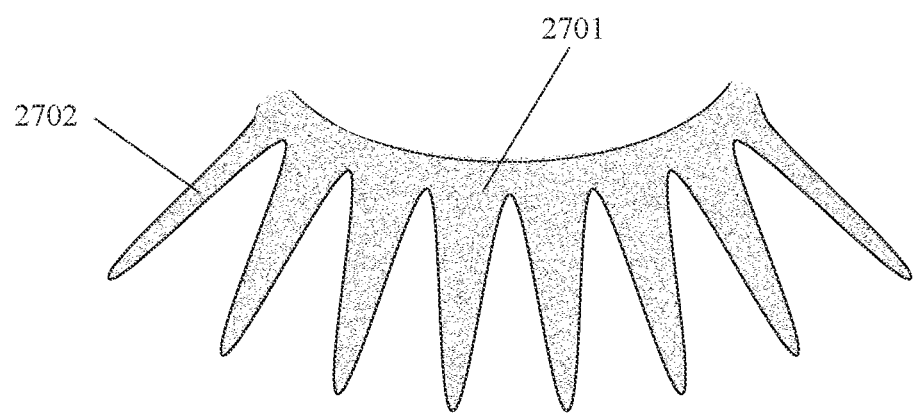
FIG. 27 shows an EEG electrode with a convex distal portion and protrusions.

FIG. 27 shows a cross-sectional view of an EEG electrode for use on a hair-covered portion of a person's head comprising: a convex distal portion 2701 whose center curves toward the surface of a person's head and whose perimeter curves away from the surface of the person's head; a plurality of protrusions (e.g. prongs, teeth, spikes, fingers, and/or protrusions), including protrusion 2702, which extend out from the distal portion toward the person's head in order to penetrate between hairs and come into contact with the surface of the person's head.

In an example, a protrusion can have a sinusoidal shape. In an example, a protrusion can be shaped like three or four phases of a four-phase sine wave. In an example, a plurality of protrusions can be shaped like a sine wave. In an example, a plurality of protrusions have the shape of a sine wave along a curved line. In an example, a plurality of protrusions have the shape of a sine wave along an arc. In an example, a plurality of protrusions have the shape of a sine wave along a conic section. In an example, a plurality of protrusions have the shape of a sine wave along a section of a sphere or ellipse. In an example, an electrode with protrusions can be "shaped like eyelashes", wherein "shaped like eyelashes" means having a downward convex shape and longitudinal protrusions which extend out radially and downward from the convex shape.

In an example, the angle between a longitudinal axis of a protrusion and the best-fitting plane of the distal portion can vary with the distance of the protrusion from the center of the distal portion. In an example, the angle between a longitudinal axis of a protrusion and the best-fitting plane of the distal portion can increase with the distance of the protrusion from the center of the distal portion. In an example, the angle between a longitudinal axis of a protrusion and the surface of a person's head can vary with the distance of the protrusion from the center of the distal portion. In an example, the angle between a longitudinal axis of a protrusion and the surface of a person's head can increase with the distance of the protrusion from the center of the distal portion. Relevant variations discussed elsewhere in this disclosure or in priority-linked disclosures can also be applied to the example in this figure.

Figure 28:
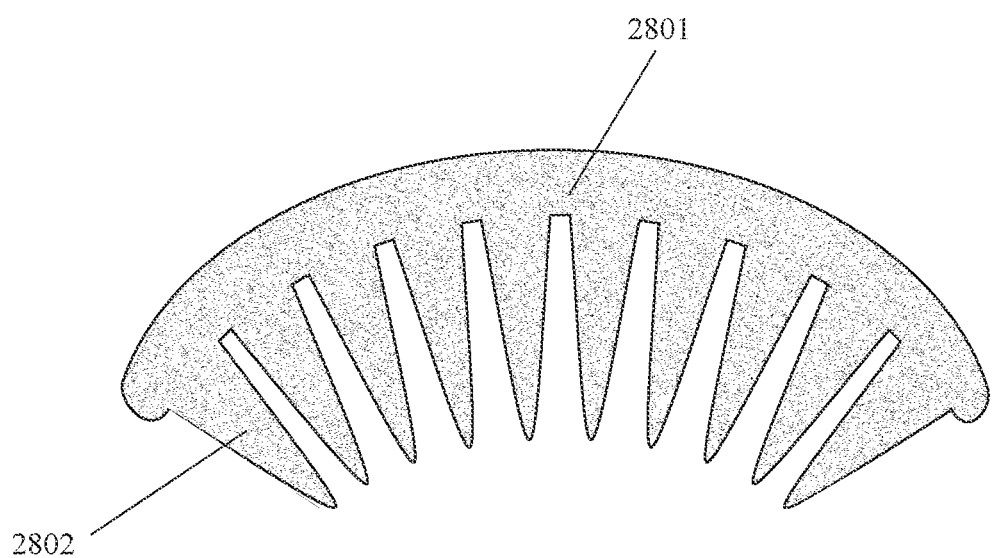
FIG. 28 shows an EEG electrode with a concave distal portion and protrusions.

FIG. 28 shows a cross-sectional view of an EEG electrode for use on a hair-covered portion of a person's head comprising: a concave distal portion 2801 whose center curves away from the surface of a person's head and whose perimeter curves toward the surface of the person's head; a plurality of protrusions (e.g. prongs, teeth, spikes, fingers, and/or protrusions), including protrusion 2802, which extend out from the distal portion toward the person's head in order to penetrate between hairs and come into contact with the surface of the person's head.

In an example, a protrusion can have a sinusoidal shape. In an example, a protrusion can have a parabolic-shaped cross-section. In an example, a protrusion can have a paraboloidal shape. In an example, a protrusion can be shaped like three or four phases of a four-phase sine wave. In an example, a plurality of protrusions can be shaped like a sine wave. In an example, a plurality of protrusions have the shape of a sine wave along a curved line. In an example, a plurality of protrusions have the shape of a sine wave along an arc. In an example, a plurality of protrusions have the shape of a sine wave along a conic section. In an example, a plurality of protrusions have the shape of a sine wave along a section of a sphere or ellipse. In an example, virtual extensions (in a proximal direction) of the longitudinal axes of a plurality of protrusions can intersect virtually in space. In an example, virtual extensions in a proximal direction of the longitudinal axes of a plurality of protrusions can intersect virtually on or in a person's head.

In an example, the angle between a longitudinal axis of a protrusion and the best-fitting plane of the distal portion can vary with the distance of the protrusion from the center of the distal portion. In an example, the angle between a longitudinal axis of a protrusion and the best-fitting plane of the distal portion can decrease with the distance of the protrusion from the center of the distal portion. In an example, the angle between a longitudinal axis of a protrusion and the best-fitting plane of the distal portion can increase with the distance of the protrusion from the center of the distal portion. In an example, the angle between a longitudinal axis of a protrusion and the surface of a person's head can vary with the distance of the protrusion from the center of the distal portion. In an example, the angle between a longitudinal axis of a protrusion and the surface of a person's head can decrease with the distance of the protrusion from the center of the distal portion. Relevant variations discussed elsewhere in this disclosure or in priority-linked disclosures can also be applied to the example in this figure.

Figure 29:
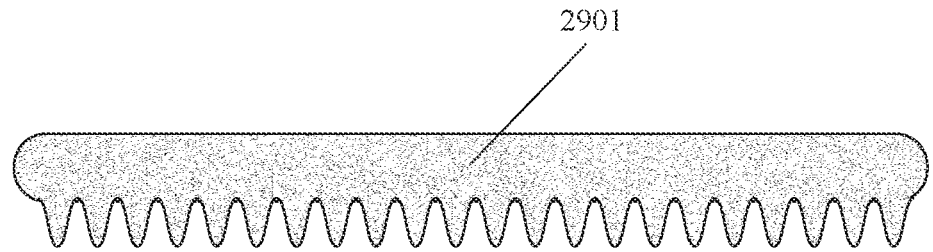
FIG. 29 shows an EEG electrode with a flat sinusoidal side.

FIG. 29 shows a cross-sectional view of an EEG electrode for use on a hair-covered portion of a person's head comprising: a conductive electrode 2901, wherein the electrode has a lateral cross-sectional shape with a flat distal side and a sinusoidal proximal side, wherein the distal side faces away from the surface of a person's head, wherein the proximal side faces toward the surface of the person's head, and wherein sinusoidal protrusions on the proximal side penetrate between hairs and come into contact with the surface of the person's head. In an example, a longitudinal axis of the sinusoidal proximal side can be substantially parallel to the flat distal side.

In an example, sinusoidal protrusions can be sinusoidal ridges. In an example, a proximal side can comprise a series of sinusoidal ridges which span an electrode laterally. In an example, sinusoidal protrusions can be sinusoidal rings. In an example, a proximal side can comprise a series of nested sinusoidal rings around the center of an electrode. In an example, sinusoidal protrusions can be sinusoidal peaks. In an example, a proximal side of an electrode can have a two-directional sinusoidal surface (e.g. similar to interior of an egg carton).

In an example, a longitudinal axis of the sinusoidal proximal side of an electrode can be substantially parallel to the flat distal side of the electrode. In an example, there can be between 2 and 8 sinusoidal ridges, rings, or peaks on the proximal side of the electrode. In an example, there can be between 5 and 15 sinusoidal ridges, rings, or peaks on the proximal side of the electrode. In an example, there can be between 10 and 30 sinusoidal ridges, rings, or peaks on the proximal side of the electrode. In an example, the amplitude of a sinusoidal wave of ridges, rings, or peaks on the proximal side can be between 50% and 80% of the average distance between the proximal and distal sides of the electrode. In an example, the amplitude of a sinusoidal wave of ridges, rings, or peaks on the proximal side can between 100% and 150% of the average distance between the proximal and distal sides of the electrode.

In an example, sinusoidal protrusions on the proximal side of an electrode can all have the same amplitude. In an example, the amplitudes of sinusoidal protrusions on an electrode can vary with distance of protrusions from the center of the electrode. In an example, the amplitudes of sinusoidal protrusions on an electrode can increase with increased distance of the protrusions from the center of the electrode. In an example, the amplitudes of sinusoidal protrusions which are farther from the center of an electrode can be greater than the amplitudes of sinusoidal protrusions which are closer to the center of the electrode. In an example, the amplitudes of sinusoidal protrusions on an electrode can decrease with increased distance of the protrusions from the center of the electrode. In an example, the amplitudes of sinusoidal protrusions which are farther from the center of an electrode can be less than the amplitudes of sinusoidal protrusions which are closer to the center of the electrode.

In an example, sinusoidal protrusions on the proximal side of an electrode can all have the same wavelength. In an example, the wavelengths of sinusoidal protrusions on an electrode can vary with distance of protrusions from the center of the electrode. In an example, the wavelengths of sinusoidal protrusions on an electrode can increase with increased distance of the protrusions from the center of the electrode. In an example, the wavelengths of sinusoidal protrusions which are farther from the center of an electrode can be greater than the wavelengths of sinusoidal protrusions which are closer to the center of the electrode. In an example, the wavelengths of sinusoidal protrusions on an electrode can decrease with increased distance of the protrusions from the center of the electrode. In an example, the wavelengths of sinusoidal protrusions which are farther from the center of an electrode can be less than the wavelengths of sinusoidal protrusions which are closer to the center of the electrode.

In an example, sinusoidal ridges, rings, or peaks can be made from an inherently-nonconductive polymer (e.g. PDMS) which has been made conductive by doping, impregnation, and/or coating with carbon structures (e.g. carbon nanotubes). In an example, sinusoidal ridges, rings, or peaks can be made from an inherently-nonconductive polymer (e.g. PDMS) which has been made conductive by doping, impregnation, and/or coating with metal (e.g. silver). In an alternative example, a proximal side of an electrode can have sawtooth wave shape instead of a sinusoidal wave shape. Relevant variations discussed elsewhere in this disclosure or in priority-linked disclosures can also be applied to the example in this figure.

Figure 30:
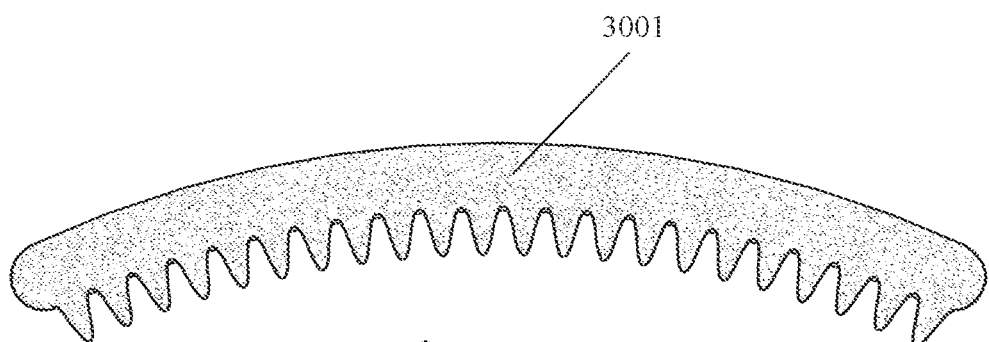
FIG. 30 shows an EEG electrode with a concave sinusoidal side.

FIG. 30 shows a cross-sectional view of an EEG electrode for use on a hair-covered portion of a person's head comprising: a conductive electrode 3001, wherein the electrode has a lateral cross-sectional shape with a curved distal side whose center bows outward in a distal direction; and a sinusoidal proximal side, wherein the distal side faces away from the surface of a person's head, wherein the proximal side faces toward the surface of the person's head, and wherein sinusoidal protrusions on the proximal side penetrate between hairs and come into contact with the surface of the person's head. In an example, a longitudinal axis of the sinusoidal proximal side can be substantially parallel to the curved distal side. In an example, the center of the electrode can be farther from the surface of the person's head than the periphery (or perimeter) of the electrode.

In an example, sinusoidal protrusions can be sinusoidal ridges. In an example, a proximal side can comprise a series of sinusoidal ridges which span an electrode laterally. In an example, sinusoidal protrusions can be sinusoidal rings. In an example, a proximal side can comprise a series of nested sinusoidal rings around the center of an electrode. In an example, sinusoidal protrusions can be sinusoidal peaks. In an example, a proximal side of an electrode can have a two-directional sinusoidal surface (e.g. similar to interior of an egg carton).

In an example, there can be between 2 and 8 sinusoidal ridges, rings, or peaks on the proximal side of the electrode. In an example, there can be between 5 and 15 sinusoidal ridges, rings, or peaks on the proximal side of the electrode. In an example, there can be between 10 and 30 sinusoidal ridges, rings, or peaks on the proximal side of the electrode. In an example, the amplitude of a sinusoidal wave of ridges, rings, or peaks on the proximal side can between 50% and 80% of the average distance between the proximal and distal sides of the electrode. In an example, the amplitude of a sinusoidal wave of ridges, rings, or peaks on the proximal side can between 100% and 150% of the average distance between the proximal and distal sides of the electrode.

In an example, sinusoidal protrusions on the proximal side of an electrode can all have the same amplitude. In an example, the amplitudes of sinusoidal protrusions on an electrode can vary with distance of protrusions from the center of the electrode. In an example, the amplitudes of sinusoidal protrusions on an electrode can increase with increased distance of the protrusions from the center of the electrode. In an example, the amplitudes of sinusoidal protrusions which are farther from the center of an electrode can be greater than the amplitudes of sinusoidal protrusions which are closer to the center of the electrode. In an example, the amplitudes of sinusoidal protrusions on an electrode can decrease with increased distance of the protrusions from the center of the electrode. In an example, the amplitudes of sinusoidal protrusions which are farther from the center of an electrode can be less than the amplitudes of sinusoidal protrusions which are closer to the center of the electrode.

In an example, sinusoidal protrusions on the proximal side of an electrode can all have the same wavelength. In an example, the wavelengths of sinusoidal protrusions on an electrode can vary with distance of protrusions from the center of the electrode. In an example, the wavelengths of sinusoidal protrusions on an electrode can increase with increased distance of the protrusions from the center of the electrode. In an example, the wavelengths of sinusoidal protrusions which are farther from the center of an electrode can be greater than the wavelengths of sinusoidal protrusions which are closer to the center of the electrode. In an example, the wavelengths of sinusoidal protrusions on an electrode can decrease with increased distance of the protrusions from the center of the electrode. In an example, the wavelengths of sinusoidal protrusions which are farther from the center of an electrode can be less than the wavelengths of sinusoidal protrusions which are closer to the center of the electrode.

In an example, sinusoidal ridges, rings, or peaks can be made from an inherently-nonconductive polymer (e.g. PDMS) which has been made conductive by doping, impregnation, and/or coating with carbon structures (e.g. carbon nanotubes). In an example, sinusoidal ridges, rings, or peaks can be made from an inherently-nonconductive polymer (e.g. PDMS) which has been made conductive by doping, impregnation, and/or coating with metal (e.g. silver). In an alternative example, a proximal side of an electrode can have sawtooth wave shape instead of a sinusoidal wave shape. Relevant variations discussed elsewhere in this disclosure or in priority-linked disclosures can also be applied to the example in this figure.

Figure 31:
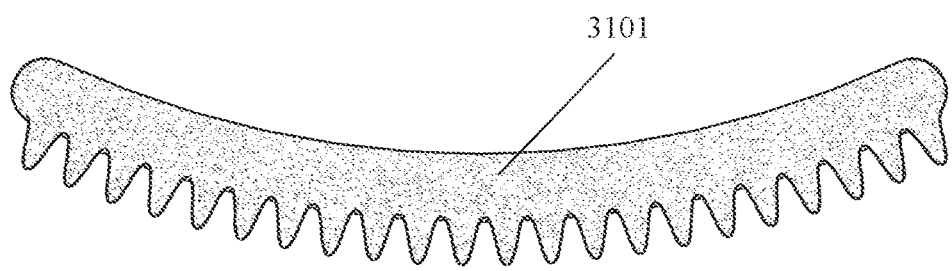
FIG. 31 shows an EEG electrode with a convex sinusoidal side.

FIG. 31 shows a cross-sectional view of an EEG electrode for use on a hair-covered portion of a person's head comprising: a conductive electrode 3101, wherein the electrode has a lateral cross-sectional shape with a curved distal side whose center bows inward in a proximal direction; and a sinusoidal proximal side, wherein the distal side faces away from the surface of a person's head, wherein the proximal side faces toward the surface of the person's head, and wherein sinusoidal protrusions on the proximal side penetrate between hairs and come into contact with the surface of the person's head. In an example, a longitudinal axis of the sinusoidal proximal side can be substantially parallel to the curved distal side. In an example, the center of the electrode can be closer to the surface of the person's head than the periphery (or perimeter) of the electrode.

In an example, sinusoidal protrusions can be sinusoidal ridges. In an example, a proximal side can comprise a series of sinusoidal ridges which span an electrode laterally. In an example, sinusoidal protrusions can be sinusoidal rings. In an example, a proximal side can comprise a series of nested sinusoidal rings around the center of an electrode. In an example, sinusoidal protrusions can be sinusoidal peaks. In an example, a proximal side of an electrode can have a two-directional sinusoidal surface (e.g. similar to interior of an egg carton).

In an example, there can be between 2 and 8 sinusoidal ridges, rings, or peaks on the proximal side of the electrode. In an example, there can be between 5 and 15 sinusoidal ridges, rings, or peaks on the proximal side of the electrode. In an example, there can be between 10 and 30 sinusoidal ridges, rings, or peaks on the proximal side of the electrode. In an example, the amplitude of a sinusoidal wave of ridges, rings, or peaks on the proximal side can between 50% and 80% of the average distance between the proximal and distal sides of the electrode. In an example, the amplitude of a sinusoidal wave of ridges, rings, or peaks on the proximal side can between 100% and 150% of the average distance between the proximal and distal sides of the electrode.

In an example, sinusoidal protrusions on the proximal side of an electrode can all have the same amplitude. In an example, the amplitudes of sinusoidal protrusions on an electrode can vary with distance of protrusions from the center of the electrode. In an example, the amplitudes of sinusoidal protrusions on an electrode can increase with increased distance of the protrusions from the center of the electrode. In an example, the amplitudes of sinusoidal protrusions which are farther from the center of an electrode can be greater than the amplitudes of sinusoidal protrusions which are closer to the center of the electrode. In an example, the amplitudes of sinusoidal protrusions on an electrode can decrease with increased distance of the protrusions from the center of the electrode. In an example, the amplitudes of sinusoidal protrusions which are farther from the center of an electrode can be less than the amplitudes of sinusoidal protrusions which are closer to the center of the electrode.

In an example, sinusoidal protrusions on the proximal side of an electrode can all have the same wavelength. In an example, the wavelengths of sinusoidal protrusions on an electrode can vary with distance of protrusions from the center of the electrode. In an example, the wavelengths of sinusoidal protrusions on an electrode can increase with increased distance of the protrusions from the center of the electrode. In an example, the wavelengths of sinusoidal protrusions which are farther from the center of an electrode can be greater than the wavelengths of sinusoidal protrusions which are closer to the center of the electrode. In an example, the wavelengths of sinusoidal protrusions on an electrode can decrease with increased distance of the protrusions from the center of the electrode. In an example, the wavelengths of sinusoidal protrusions which are farther from the center of an electrode can be less than the wavelengths of sinusoidal protrusions which are closer to the center of the electrode.

In an example, sinusoidal ridges, rings, or peaks can be made from an inherently-nonconductive polymer (e.g. PDMS) which has been made conductive by doping, impregnation, and/or coating with carbon structures (e.g. carbon nanotubes). In an example, sinusoidal ridges, rings, or peaks can be made from an inherently-nonconductive polymer (e.g. PDMS) which has been made conductive by doping, impregnation, and/or coating with metal (e.g. silver). In an alternative example, a proximal side of an electrode can have sawtooth wave shape instead of a sinusoidal wave shape. Relevant variations discussed elsewhere in this disclosure or in priority-linked disclosures can also be applied to the example in this figure.

Figure 32:
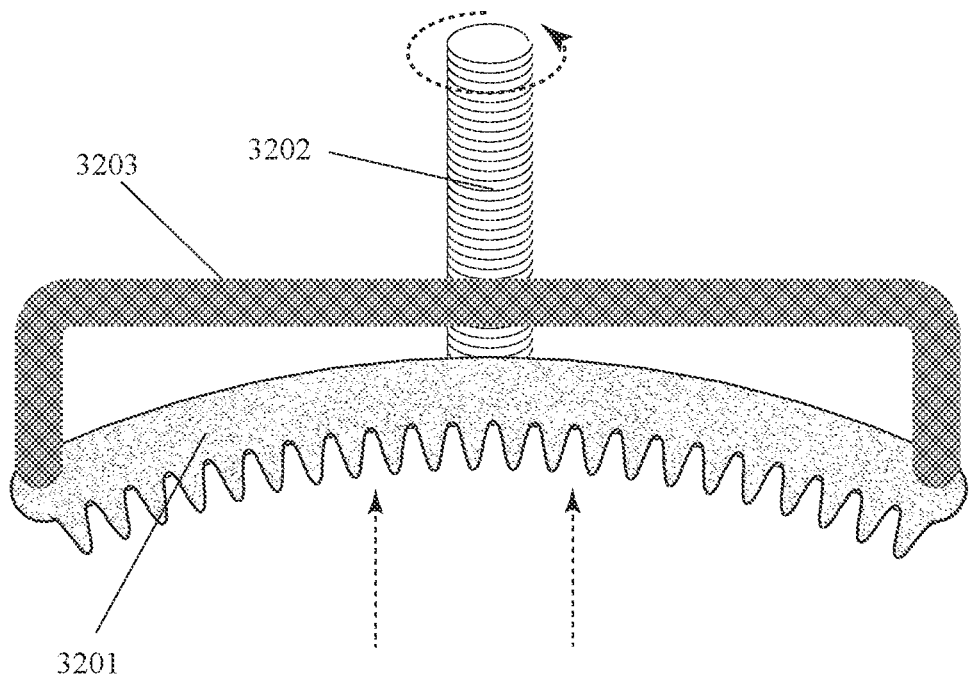
FIGS. 32 and 33 show two views of an EEG electrode wherein rotation of a threaded connector changes the concavity or convexity of the electrode.
Figure 33:
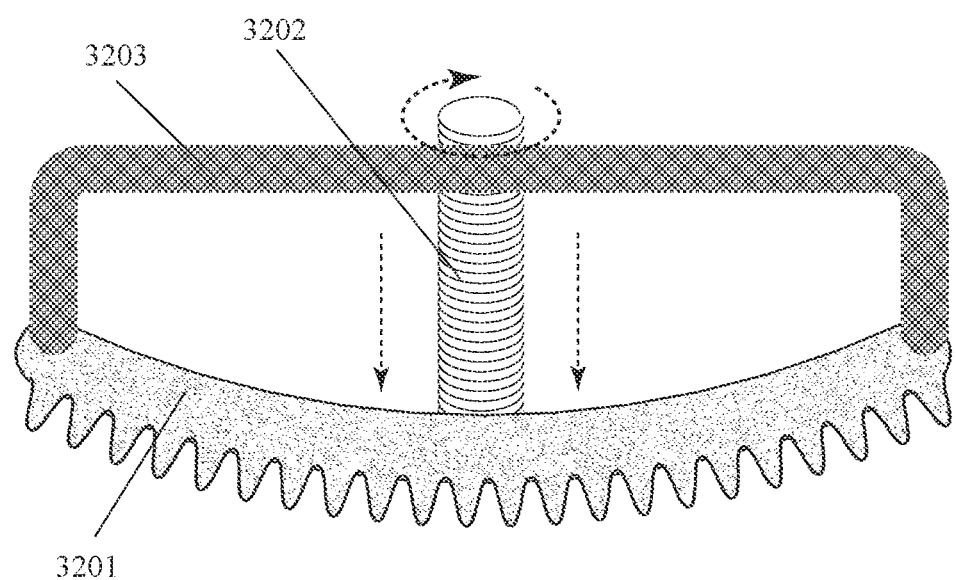

FIGS. 32 and 33 show two cross-sectional views, at two different times, of an EEG electrode for use on a hair-covered portion of a person's head comprising: a distal portion 3203, a proximal portion 3201, wherein the proximal portion is attached to the distal portion, wherein protrusions extend out from the proximal portion to penetrate between hairs and come into contact with the surface of the person's head, and wherein distal means farther from the surface of a person's head and proximal means closer to the surface of the person's head; and a threaded connector 3202 between the distal portion and the proximal portion, wherein rotation of the threaded connector or rotation of the distal portion around the threaded connector changes the concavity or convexity of the proximal portion and changes the level of contact and/or pressure between the protrusions and the surface of the person's head. In an example, the distal portion can be stiffer and/or less flexible than the proximal portion.

FIG. 32 shows this electrode at a first time wherein rotation of the threaded connector in a first direction (e.g. counter-clockwise) has pulled the center of the proximal portion closer toward the distal portion, thereby making the proximal portion more convex relative to the surface of the person's head. FIG. 33 shows this electrode at a second time wherein rotation of the threaded connector in a second direction (e.g. clockwise) has pushed the center of the proximal portion farther from the distal portion, thereby making the proximal portion more concave relative to the surface of the person's head. Relevant variations discussed elsewhere in this disclosure or in priority-linked disclosures can also be applied to the example in this figure.

Figure 34:
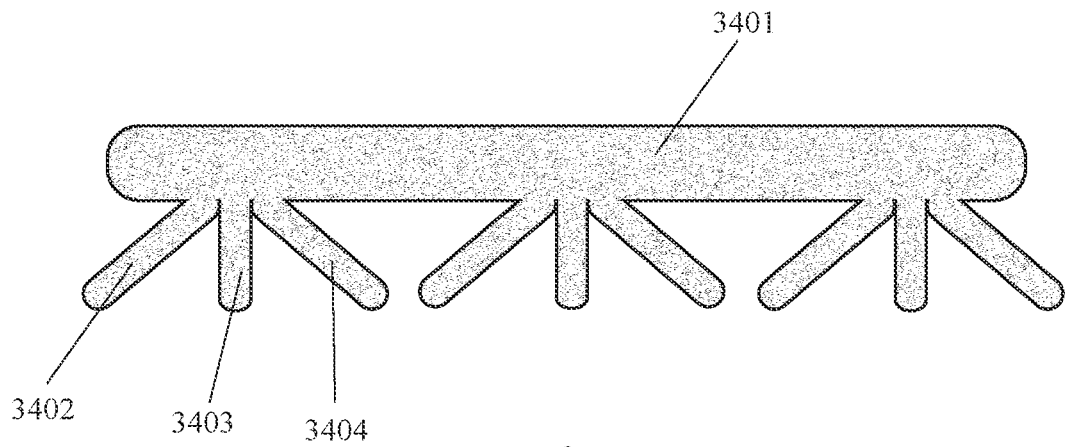
FIG. 34 shows an EEG electrode with sets of protrusions wherein one protrusion tilts away from the electrode central axis, one protrusion is perpendicular to this axis, and one protrusion tilts toward this axis.

FIG. 34 shows a cross-sectional view of an EEG electrode for use on a hair-covered portion of a person's head comprising: a distal portion 3401; and a plurality of sets of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein (with the possible exception of a set of electroconductive proximal protrusions at the center of the electrode) a set of electroconductive proximal protrusions further comprises: at least one proximal protrusion 3402 whose proximal end tilts (e.g. is angled) away from a central proximal-to-distal axis of the electrode; at least one proximal protrusion 3403 which is perpendicular to the (lateral plane of the) distal portion; and at least one proximal protrusion 3404 whose proximal end tilts (e.g. is angled) toward the central proximal-to-distal axis of the electrode.

In an example, there can be three protrusions in a set. In an example, a set of electroconductive proximal protrusions comprise three protrusions whose proximal ends are at the vertexes of a virtual equilateral triangle. In an example, there can be four protrusions in a set. In an example, a set of electroconductive proximal protrusions comprise four protrusions whose proximal ends are at the vertexes of a virtual square. In an example, there can be six protrusions in a set. In an example, a set of electroconductive proximal protrusions comprise six protrusions whose proximal ends are at the vertexes of a virtual hexagon. In an example, there can be eight protrusions in a set. In an example, a set of electroconductive proximal protrusions comprise eight protrusions whose proximal ends are at the vertexes of a virtual octagon.

In an example, a set of electroconductive proximal protrusions can comprise at least three protrusions, including: at least one protrusion which tilts (e.g. is angled) away from a central proximal-to-distal axis of the electrode, at least one protrusion which is parallel to the central proximal-to-distal axis of the electrode, and at least one protrusion which tilts (e.g. is angled) toward the central proximal-to-distal axis of the electrode. In an example, a set of electroconductive proximal protrusions can comprise at least three protrusions, including: at least one protrusion which extends out from the distal portion at an obtuse angle; at least one protrusion which extends out from the distal portion at a right angle; and at least one protrusion which extends out from the distal portion at an acute angle.

In an example, a set of electroconductive proximal protrusions can comprise at least three protrusions, including: at least one protrusion which extends out from the distal portion at a 135 degree angle; at least one protrusion which extends out from the distal portion at a 90 degree angle; and at least one protrusion which extends out from the distal portion at a 45 degree angle. In an example, a set of electroconductive proximal protrusions can comprise at least three protrusions, including: at least one protrusion which extends out from the distal portion at a 120 degree angle; at least one protrusion which extends out from the distal portion at a 90 degree angle; and at least one protrusion which extends out from the distal portion at a 60 degree angle.

In an example, a set of electroconductive proximal protrusions can comprise at least three protrusions which extend out different polar angles relative to a central point, wherein the polar angles are evenly distributed around a 360-degree circle. In an example, a set of electroconductive proximal protrusions can comprise three protrusions which extend out at different polar angles relative to a central point and wherein the polar angles of neighboring protrusions differ by 120 degrees. In an example, a set of electroconductive proximal protrusions can comprise four protrusions which extend out at different polar angles relative to a central point and wherein the polar angles of neighboring protrusions differ by 90 degrees.

In an example, a set of electroconductive proximal protrusions can comprise six protrusions which extend out at different polar angles relative to a central point and wherein the polar angles of neighboring protrusions differ by 60 degrees. In an example, a set of electroconductive proximal protrusions can comprise eight protrusions which extend out at different polar angles relative to a central point and wherein the polar angles of neighboring protrusions differ by 45 degrees.

In an example, a set of electroconductive proximal protrusions, wherein neighboring pairs of protrusions have longitudinal axial vectors which differ from each other by 120 degrees. In an example, a set of electroconductive proximal protrusions, wherein neighboring pairs of protrusions have longitudinal axial vectors which differ from each other by 90 degrees. In an example, a set of electroconductive proximal protrusions, wherein neighboring pairs of protrusions have longitudinal axial vectors which differ from each other by 60 degrees. In an example, a set of electroconductive proximal protrusions, wherein neighboring pairs of protrusions have longitudinal axial vectors which differ from each other by 45 degrees. In an example, sets of proximal protrusions from an EEG electrode look (technically speaking) "like a bunch of chicken feet." Relevant variations discussed elsewhere in this disclosure or in priority-linked disclosures can also be applied to the example in this figure.

Figure 35:
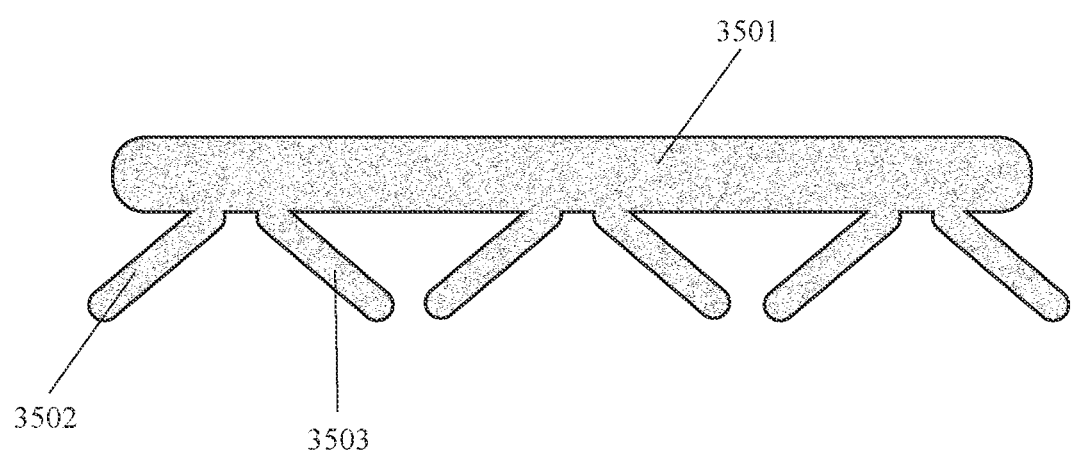
FIG. 35 shows an EEG electrode with sets of protrusions wherein one protrusion tilts away from the electrode central axis and one protrusion tilts toward this axis.

FIG. 35 shows a cross-sectional view of an EEG electrode for use on a hair-covered portion of a person's head comprising: a distal portion 3501; and a plurality of sets of electroconductive proximal protrusions (e.g. pins, prongs, teeth, spikes, fingers, and/or protrusions) which extend out from the distal portion toward the person's head in order to penetrate between hairs and come into contact with the surface of the person's head; wherein (with the possible exception of a set of electroconductive proximal protrusions at the center of the electrode) a set of electroconductive proximal protrusions further comprises: at least one proximal protrusion 3502 whose proximal end tilts (e.g. is angled) away from a central proximal-to-distal axis of the electrode; and at least one proximal protrusion 3503 whose proximal end tilts (e.g. is angled) toward the central proximal-to-distal axis of the electrode.

In an example, an EEG can have a plurality of sets of protrusions which extend outward toward the surface of a person's head. In an example, two protrusions in a set have longitudinal axes whose (shadow) projections onto the same virtual two-dimensional plane differ by 90 degrees. In an example, two protrusions in a set have longitudinal axes whose (shadow) projections onto the same virtual two-dimensional plane intersect at a 90-degree angle. In an example, two protrusions in a set have longitudinal axes whose (shadow) projections onto the same virtual two-dimensional plane differ by between 55 and 95 degrees. In an example, two protrusions in a set have longitudinal axes whose (shadow) projections onto the same virtual two-dimensional plane intersect at an angle between 55 and 95 degrees. Relevant variations discussed elsewhere in this disclosure or in priority-linked disclosures can also be applied to the example in this figure.

Figure 36:
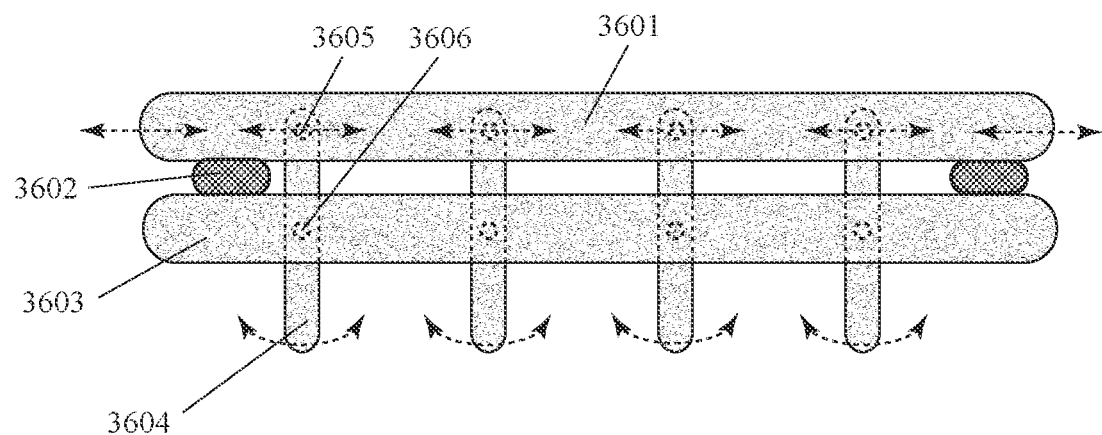
FIG. 36 shows an EEG electrode with protrusions which are moveably connected to distal and proximal portions of the electrode and actuators which move the protrusions.

FIG. 36 shows a cross-sectional view of an EEG electrode for use on a hair-covered portion of a person's head comprising: a distal portion 3601; a proximal portion 3603; one or more actuators, including actuator 3602, which move (e.g. shift) the distal portion relative to the proximal portion, or vice versa; and a plurality of electroconductive proximal protrusions (e.g. pins, prongs, teeth, spikes, fingers, and/or protrusions), including protrusion 3604, which extend out toward the person's head in order to penetrate between hairs and come into contact with the surface of the person's head, wherein the proximal protrusions are moveably connected to the distal portion and to the proximal portion, and wherein movement of the distal portion relative to the proximal portion, or vice versa, causes the proximal protrusions to move (e.g. shift) relative to the surface of the person's head, thereby enhancing the ability of the protrusions to penetrate between hairs. In this example, the proximal protrusions are moveably connected to the distal and proximal portions by joints (e.g. joints or axles), including joints 3605 and 3606. In an example, an actuator can be an electromagnetic motor.

In an example, distal and proximal portions can be substantially parallel to each other. In an example, distal and proximal portions can be substantially-parallel disks, squares, or rounded squares. In an example, movement of a distal portion of an electrode relative to a proximal portion of the electrode, or vice versa, can be lateral shifting (or sliding) of one portion relative to the other. In an example, movement of one a distal portion of the electrode relative to a proximal portion of the electrode, or vice versa, can be lateral or vertical vibration. In an example, lateral shifting (or sliding) of a distal portion relative to a proximal portion, or vice versa, can cause lateral movement of protrusions relative to the surface of a person's head, thereby enhancing the ability of the protrusions to penetrate between hairs and contact the surface of the person's head.

In an example, protrusions can contact the surface of a person's head in a perpendicular manner (e.g. at a perpendicular angle). In an example, the angles at which protrusions contact the surface of a person's head can vary as actuators move the distal portion relative to the proximal portion, or vice versa. In an example, one of the angles at which protrusions can contact the surface of the person's head is 90 degrees. In an example, one of the ways in which protrusions can contact the surface of the person's head in a perpendicular manner. In an example, protrusions are not restricted to contacting the surface of the person's head in a non-perpendicular manner.

In an example, angles at which protrusions contact a person's head can vary within a range of 45 to 135 degrees as actuators move the distal and/or proximal portions of the electrode. In an example, angles at which protrusions contact a person's head can vary within a range of 60 to 120 degrees as actuators move the distal and/or proximal portions of the electrode. In an example, angles at which protrusions contact a person's head can vary within a range of 75 to 105 degrees as actuators move the distal and/or proximal portions of the electrode.

In an example, protrusions can extend out from the main body of the electrode in a perpendicular manner (e.g. at a perpendicular angle). In an example, angles at which protrusions extend out proximally from the proximal portion of the electrode can vary as actuators move the distal portion relative to the proximal portion, or vice versa. In an example, one of the angles by which protrusions can extend out proximally from the proximal portion of the electrode is 90 degrees. In an example, one of the ways in which protrusions can extend out from the proximal portion of the electrode is perpendicularly. Protrusions are not restricted to extending out from the proximal portion only a non-perpendicular manner.

In an example, angles at which protrusions extend out from the proximal portion can vary within a range of 45 to 135 degrees as actuators move the distal and/or proximal portions of the electrode. In an example, angles at which protrusions extend out from the proximal portion can vary within a range of 60 to 120 degrees as actuators move the distal and/or proximal portions of the electrode. In an example, angles at which protrusions extend out from the proximal portion can vary within a range of 75 to 105 degrees as actuators move the distal and/or proximal portions of the electrode. Relevant variations discussed elsewhere in this disclosure or in priority-linked disclosures can also be applied to the example in this figure.

Figure 37:
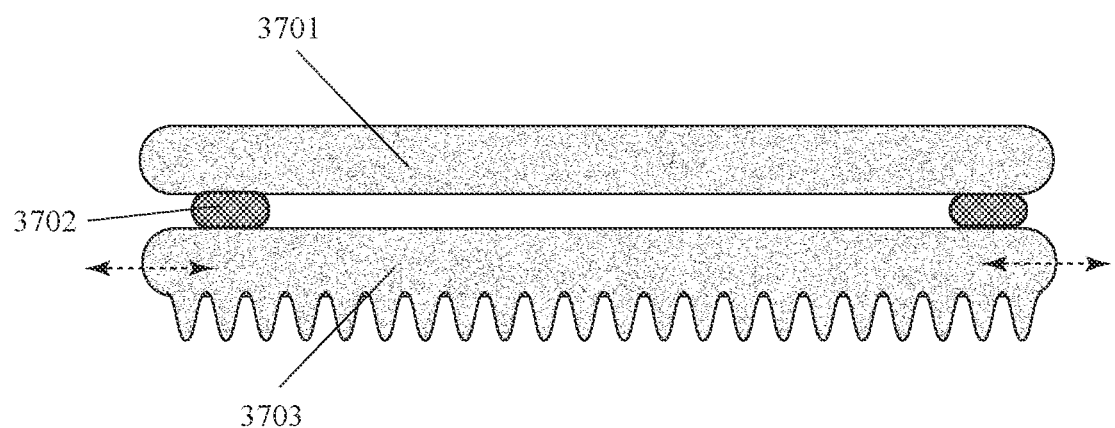
FIG. 37 shows an EEG electrode with protrusions on a proximal portion of the electrode which is shifted by one or more actuators.

FIG. 37 shows a cross-sectional view of an EEG electrode for use on a hair-covered portion of a person's head comprising: a distal portion 3701; a proximal portion 3703, wherein the proximal side of the proximal portion has a sinusoidal shape which enables it to penetrate between hairs and come into contact with the surface of a person's head; and one or more actuators, including actuator 3702, which move (e.g. shift) the proximal portion relative to the distal portion. Distal means farther from the surface of a person's head and proximal means closer to the surface of the person's head. In an example, an actuator can be an electromagnetic motor.

In an example, distal and proximal portions can be substantially parallel to each other. In an example, distal and proximal portions can be substantially-parallel disks, squares, or rounded squares. In an example, movement of a proximal portion of an electrode can be lateral shifting or sliding. In an example, movement of a proximal portion of an electrode can be vibration. In an example, shifting, sliding, or vibration of a proximal portion can enable sinusoidal protrusions to penetrate between hairs and contact the surface of the person's head. In an example, sinusoidal protrusions can extend out from the main body of an electrode in a perpendicular manner.

In an example, sinusoidal protrusions on a proximal portion of an electrode can be sinusoidal ridges. In an example, a proximal side can comprise a series of sinusoidal ridges which span an electrode laterally. In an example, sinusoidal protrusions can be sinusoidal rings. In an example, a proximal side can comprise a series of nested sinusoidal rings around the center of an electrode. In an example, sinusoidal protrusions can be sinusoidal peaks. In an example, a proximal side of an electrode can have a two-directional sinusoidal surface (e.g. similar to interior of an egg carton). In an example, there can be between 2 and 8 sinusoidal ridges, rings, or peaks on an electrode. In an example, there can be between 5 and 15 sinusoidal ridges, rings, or peaks on an electrode. In an example, there can be between 10 and 30 sinusoidal ridges, rings, or peaks on an electrode.

In an example, sinusoidal protrusions on the proximal side of an electrode can all have the same amplitude. In an example, the amplitudes of sinusoidal protrusions on an electrode can vary with distance of protrusions from the center of the electrode. In an example, the amplitudes of sinusoidal protrusions on an electrode can increase with increased distance of the protrusions from the center of the electrode. In an example, the amplitudes of sinusoidal protrusions which are farther from the center of an electrode can be greater than the amplitudes of sinusoidal protrusions which are closer to the center of the electrode. In an example, the amplitudes of sinusoidal protrusions on an electrode can decrease with increased distance of the protrusions from the center of the electrode. In an example, the amplitudes of sinusoidal protrusions which are farther from the center of an electrode can be less than the amplitudes of sinusoidal protrusions which are closer to the center of the electrode.

In an example, sinusoidal protrusions on the proximal side of an electrode can all have the same wavelength. In an example, the wavelengths of sinusoidal protrusions on an electrode can vary with distance of protrusions from the center of the electrode. In an example, the wavelengths of sinusoidal protrusions on an electrode can increase with increased distance of the protrusions from the center of the electrode. In an example, the wavelengths of sinusoidal protrusions which are farther from the center of an electrode can be greater than the wavelengths of sinusoidal protrusions which are closer to the center of the electrode. In an example, the wavelengths of sinusoidal protrusions on an electrode can decrease with increased distance of the protrusions from the center of the electrode. In an example, the wavelengths of sinusoidal protrusions which are farther from the center of an electrode can be less than the wavelengths of sinusoidal protrusions which are closer to the center of the electrode.

In an example, sinusoidal ridges, rings, or peaks can be made from an inherently-nonconductive polymer (e.g. PDMS) which has been made conductive by doping, impregnation, and/or coating with carbon structures (e.g. carbon nanotubes). In an example, sinusoidal ridges, rings, or peaks can be made from an inherently-nonconductive polymer (e.g. PDMS) which has been made conductive by doping, impregnation, and/or coating with metal (e.g. silver). In an alternative example, a proximal side of an electrode can have sawtooth wave shape instead of a sinusoidal wave shape. Relevant variations discussed elsewhere in this disclosure or in priority-linked disclosures can also be applied to the example in this figure.

Figure 38:
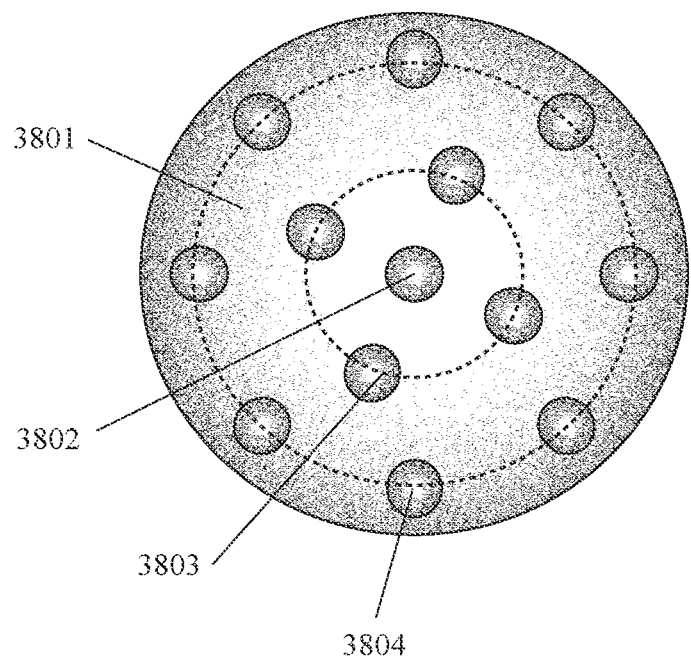
FIG. 38 shows an EEG electrode with at least two nested rings of protrusions.

FIG. 38 shows a proximal side view of an EEG electrode for use on a hair-covered portion of a person's head, wherein the proximal side is the side which faces toward the surface of a person's head. This EEG electrode comprises: an electrode base 3801; and a plurality of electroconductive proximal protrusions (e.g. pins, prongs, teeth, spikes, fingers, and/or protrusions), including protrusions 3802, 3803, and 3804, which extend out from the electrode base toward the person's head in order to penetrate between hairs and come into contact with the surface of the person's head; wherein the plurality of electroconductive proximal protrusions further comprises at least two nested (e.g. concentric) rings of protrusions. In this example, protrusion 3803 is part of a first (inner) ring of protrusions and protrusion 3804 is part of a second (outer) ring of protrusions. In this example, the plurality of electroconductive proximal protrusions also includes a central protrusion 3802 which is not part of a ring.

In an example, an electrode base can have a circular and/or disk shape. In an example, an electrode base can have an elliptical, oval, and/or oblong shape. In an example, an electrode base can have a (rounded) square or (rounded) rectangular shape. In an example, a protrusion can have a columnar shape. In an example, a protrusion can have a conic, conic section, and/or frustal shape. In an example, a protrusion can have a parabolic and/or paraboloidal shape. In an example, a protrusion can have a hemispherical shape. In an example, a protrusion can extend out from an electrode base in a perpendicular manner.

In an example, an electrode can have two nested (e.g. concentric) rings of protrusions extending from a base toward the surface of a person's head. In an example, an electrode can have two nested (e.g. concentric) rings of protrusions extending from a base toward the surface of a person's head, plus a central protrusion extending from axial center of the base. In an example, an electrode can have three or more nested (e.g. concentric) rings of protrusions extending from a base toward the surface of a person's head. In an example, an electrode can have three or more nested (e.g. concentric) rings of protrusions extending from a base toward the surface of a person's head, plus a central protrusion extending from the center of the base.

In an example, the number of protrusions in a ring can be greater for outer rings (which are farther from the center of the electrode) than for inner rings (which are closer to the center of the electrode). In an example, an inner ring can have four protrusions and an outer ring can have six protrusions. In an example, an inner ring can have four protrusions and an outer ring can have eight protrusions. In an example, an inner ring can have six protrusions and an outer ring can have nine protrusions. In an example, an inner ring can have six protrusions and an outer ring can have twelve protrusions.

In an example, protrusions in an outer ring (farther from the center of the electrode) can be longer than protrusions in an inner ring (closer to the center of the electrode). In an example, protrusions in an outer ring (farther from the center of the electrode) can be more flexible, more compressible, and/or have a lower durometer than protrusions in an inner ring (closer to the center of the electrode). In an example, protrusions in an outer ring (farther from the center of the electrode) can be tilted and/or angled toward the center of the electrode more than protrusions in an inner ring (closer to the center of the electrode).

In an example, protrusions in an outer ring (farther from the center of the electrode) can be tilted and/or angled away from center of the electrode more than protrusions in an inner ring (closer to the center of the electrode). In an example, protrusions in an outer ring (farther from the center of the electrode) can be shorter than protrusions in an inner ring (closer to the center of the electrode). In an example, protrusions in an outer ring (farther from the center of the electrode) can be less flexible, less compressible, and/or have a higher durometer than protrusions in an inner ring (closer to the center of the electrode). Relevant variations discussed elsewhere in this disclosure or in priority-linked disclosures can also be applied to the example in this figure.

Figure 39:
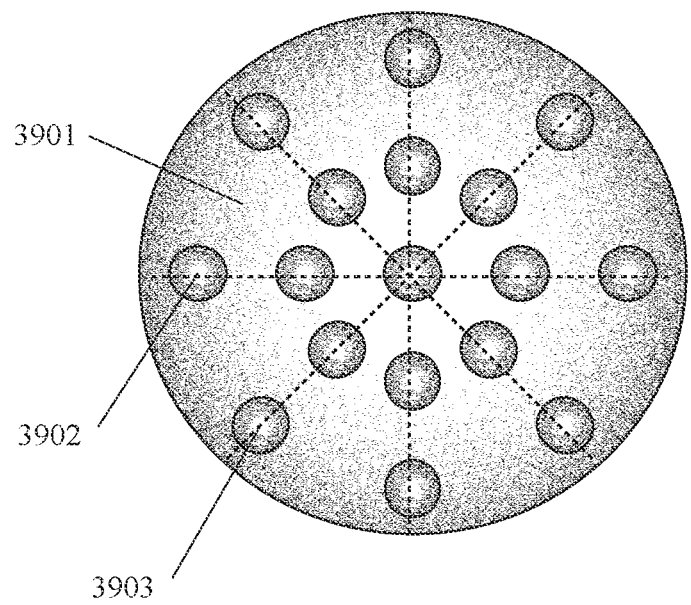
FIG. 39 shows an EEG electrode with a radial spoke array of protrusions.

FIG. 39 shows a proximal side view of an EEG electrode for use on a hair-covered portion of a person's head, wherein the proximal side is the side which faces toward the surface of a person's head. This EEG electrode comprises: an electrode base 3901; and a plurality of electroconductive proximal protrusions (e.g. pins, prongs, teeth, spikes, fingers, and/or protrusions), including protrusions 3902 and 3903, which extend out from the electrode base toward the person's head in order to penetrate between hairs and come into contact with the surface of the person's head; wherein the plurality of electroconductive proximal protrusions has a radial spoke (e.g. hub and spoke) configuration. In this example, protrusion 3902 is part of a first radial line (e.g. spoke) of protrusions and protrusion 3903 is part of a second radial line (e.g. spoke) of protrusions.

In this example, an electrode base has a circular and/or disk shape. In an example, an electrode base can have an elliptical, oval, and/or oblong shape. In an example, an electrode base can have a (rounded) square or (rounded) rectangular shape. In an example, a protrusion can have a columnar shape. In an example, a protrusion can have a conic, conic section, and/or frustal shape. In an example, a protrusion can have a parabolic and/or paraboloidal shape. In an example, a protrusion can have a hemispherical shape. In an example, a protrusion can extend out from an electrode base in a perpendicular manner.

In this example, an electrode has eight radial lines, series, or spokes of protrusions. These radial lines extend out from the center of the electrode base. Alternatively, an electrode can have six radial lines, series, or spokes of protrusions. In an example, protrusions which are farther from the center of the base can be longer than protrusions which are closer to the center of the base. In an example, protrusions which are farther from the center of the base can be more flexible, more compressible, and/or have a lower durometer than protrusions which are closer to the center of the base. In an example, protrusions which are farther from the center of the base can be tilted and/or angled toward the center of the base more than protrusions which are closer to the center of the base.

In an example, protrusions which are farther from the center of the base can be shorter than protrusions which are closer to the center of the base. In an example, protrusions which are farther from the center of the base can be less flexible, less compressible, and/or have a higher durometer than protrusions which are closer to the center of the base. In an example, protrusions which are farther from the center of the base can be tilted and/or angled away from the center of the base more than protrusions which are closer to the center of the base. Relevant variations discussed elsewhere in this disclosure or in priority-linked disclosures can also be applied to the example in this figure.

Figure 40:
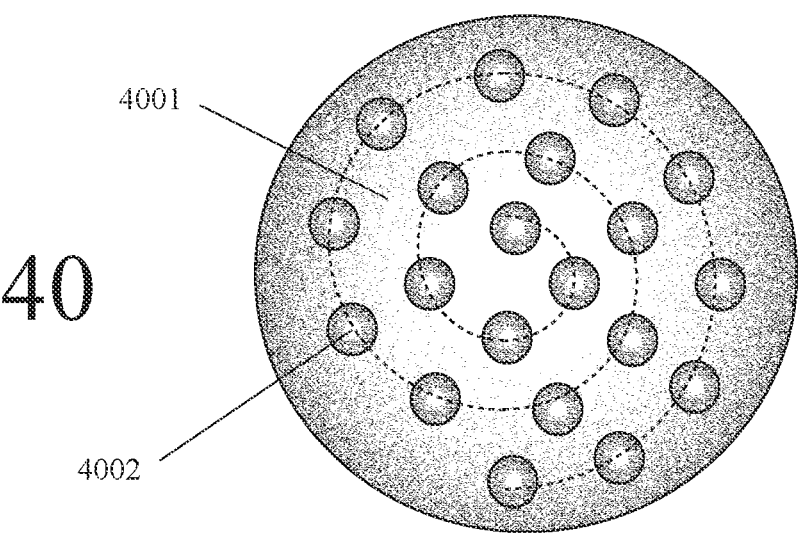
FIG. 40 shows an EEG electrode with a spiral array of protrusions.

FIG. 40 shows a proximal side view of an EEG electrode for use on a hair-covered portion of a person's head, wherein the proximal side is the side which faces toward the surface of a person's head. This EEG electrode comprises: an electrode base 4001; and a plurality of electroconductive proximal protrusions (e.g. pins, prongs, teeth, spikes, fingers, and/or protrusions), including protrusion 4002, which extend out from the electrode base toward the person's head in order to penetrate between hairs and come into contact with the surface of the person's head; wherein the plurality of electroconductive proximal protrusions has a spiral configuration. Relevant variations discussed elsewhere in this disclosure or in priority-linked disclosures can also be applied to the example in this figure.

Figure 41:
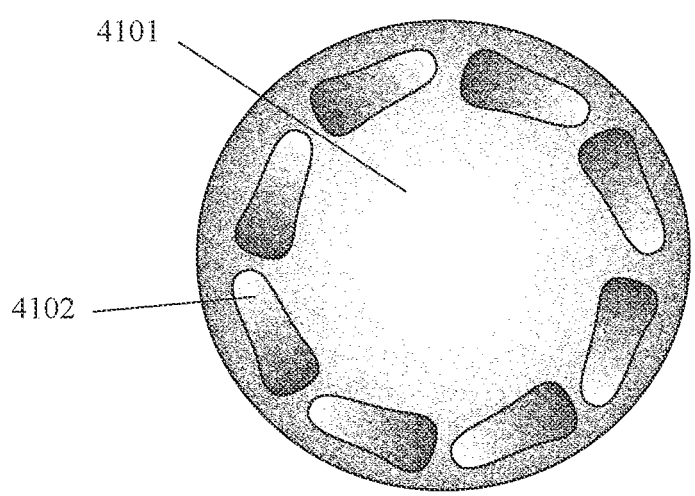
FIG. 41 shows an EEG electrode with a ring of protrusions which extend out in a non-perpendicular manner.

The upper portion of FIG. 41 shows a proximal side view and the lower portion of FIG. 41 shows a lateral side view of an EEG electrode for use on a hair-covered portion of a person's head, wherein the proximal side is the side which faces toward the surface of a person's head. This EEG electrode comprises: an electrode base 4101; and a ring of electroconductive proximal protrusions (e.g. pins, prongs, teeth, spikes, fingers, and/or protrusions), including protrusion 4102, which extend out in a non-perpendicular manner from the electrode base toward the person's head in order to penetrate between hairs and come into contact with the surface of the person's head.

In this example, the proximal end of each protrusion is tilted toward the neighboring protrusion, forming a "head-to-toe" ring of protrusions in the proximal side view. In this example, all of the protrusions extend out from the electrode base at the same, non-perpendicular angle, but they extend in different directions. In this example, all of the protrusions in the ring extend out from the electrode base at the same, non-perpendicular angle, but the directions in which they extend vary and are substantially-aligned with the circle of the ring. Relevant variations discussed elsewhere in this disclosure or in priority-linked disclosures can also be applied to the example in this figure.

The upper portion of FIG. 42 shows a proximal side view and the lower portion of FIG. 42 shows a lateral side view of an EEG electrode for use on a hair-covered portion of a person's head, wherein the proximal side is the side which faces toward the surface of a person's head. This EEG electrode comprises: an electrode base 4201; a ring of electroconductive proximal protrusions (e.g. pins, prongs, teeth, spikes, fingers, and/or protrusions), including protrusion 4202, which extend out in a non-perpendicular manner from the electrode base toward the person's head in order to penetrate between hairs and come into contact with the surface of the person's head; and an actuator 4203 which rotates the electrode base.

In this example, the proximal end of each protrusion is tilted toward the neighboring protrusion, forming a "head-to-toe" ring of protrusions in the proximal side view. In this example, all of the protrusions extend out from the electrode base at the same, non-perpendicular angle, but they extend in different directions. In this example, all of the protrusions in the ring extend out from the electrode base at the same, non-perpendicular angle, but the directions in which they extend vary and are substantially-aligned with the circle of the ring. Relevant variations discussed elsewhere in this disclosure or in priority-linked disclosures can also be applied to the example in this figure.

The upper portion of FIG. 42 shows a proximal side view and the lower portion of FIG. 42 shows a lateral side view of an EEG electrode for use on a hair-covered portion of a person's head, wherein the proximal side is the side which faces toward the surface of a person's head. This EEG electrode comprises: an electrode base 4201; a ring of electroconductive proximal protrusions (e.g. pins, prongs, teeth, spikes, fingers, and/or protrusions), including protrusion 4202, which extend out in a non-perpendicular manner from the electrode base toward the person's head in order to penetrate between hairs and come into contact with the surface of the person's head; and an actuator 4203 which rotates the electrode base. Relevant variations discussed elsewhere in this disclosure or in priority-linked disclosures can also be applied to the example in this figure.

Figure 43:
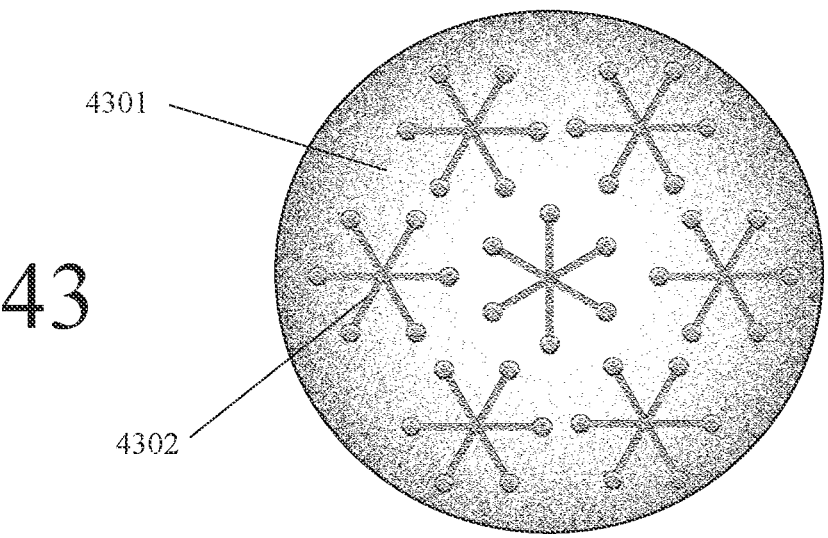
FIG. 43 shows an EEG electrode with sets of six protrusions which extend out radially from the center of a set.

FIG. 43 shows a proximal side view of an EEG electrode for use on a hair-covered portion of a person's head, wherein the proximal side is the side which faces toward the surface of a person's head. This EEG electrode comprises: an electrode base 4301; a plurality of sets of electroconductive proximal protrusions (e.g. pins, prongs, teeth, spikes, fingers, and/or protrusions), including set 4302, which extend out in a non-perpendicular manner from the electrode base toward the person's head in order to penetrate between hairs and come into contact with the surface of the person's head; wherein each set further comprises six protrusions which extend out radially from the center of the set.

In an example, from a proximal side perspective, a set of six protrusions can look like an asterisk. In an example, a set of protrusions can comprise six equidistant spokes. In an example, a set of protrusions can comprise six spokes which are evenly distributed around the circumference of the set. In an example, the ends of the six protrusions can form the vertexes of a (virtual) equilateral hexagon. In an example, from a proximal side perspective, each protrusion in a set can intersect its neighboring protrusion at a 60-degree angle. In an example, each pair of neighboring protrusions (e.g. a pair of protrusions which are closest together) in a set can be separated by the same distance. In an example, a protrusion can be generally columnar, with a ball at its end. Relevant variations discussed elsewhere in this disclosure or in priority-linked disclosures can also be applied to the example in this figure.

Figure 44:
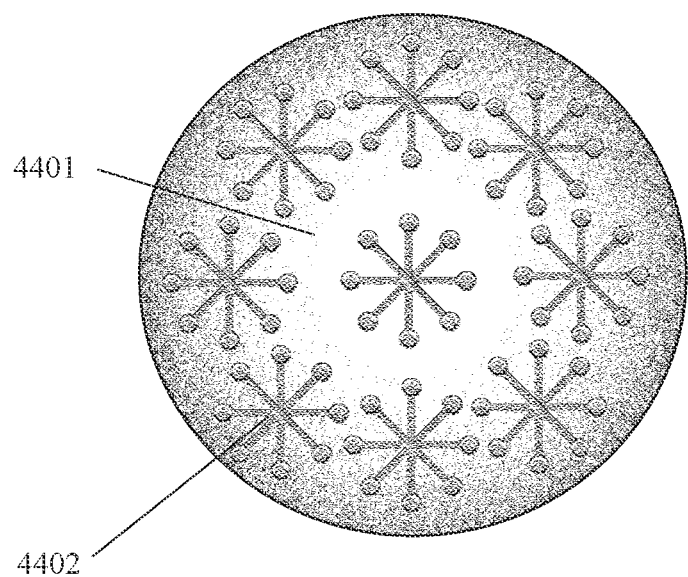
FIG. 44 shows an EEG electrode with sets of eight protrusions which extend out radially from the center of a set.

FIG. 44 shows a proximal side view of an EEG electrode for use on a hair-covered portion of a person's head, wherein the proximal side is the side which faces toward the surface of a person's head. This EEG electrode comprises: an electrode base 4401; a plurality of sets of electroconductive proximal protrusions (e.g. pins, prongs, teeth, spikes, fingers, and/or protrusions), including set 4402, which extend out in a non-perpendicular manner from the electrode base toward the person's head in order to penetrate between hairs and come into contact with the surface of the person's head; wherein each set further comprises eight protrusions which extend out radially from the center of the set.

In an example, a set of protrusions can comprise eight equidistant spokes. In an example, a set of protrusions can comprise eight spokes which are evenly distributed around the circumference of the set. In an example, the ends of the eight protrusions can form the vertexes of a (virtual) equilateral octagon. In an example, from a proximal side perspective, each protrusion in a set can intersect its neighboring protrusion at a 45-degree angle. In an example, each pair of neighboring protrusions (e.g. a pair of protrusions which are closest together) in a set can be separated by the same distance. In an example, a protrusion can be generally columnar, with a ball at its end. Relevant variations discussed elsewhere in this disclosure or in priority-linked disclosures can also be applied to the example in this figure.

Figure 45:
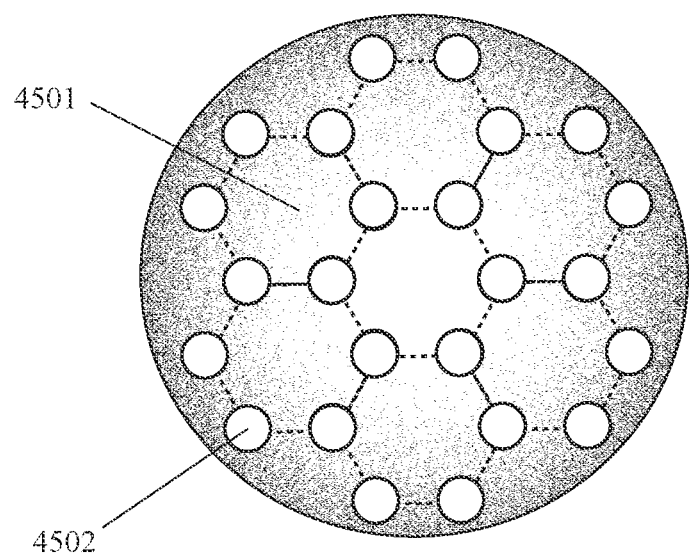
FIG. 45 shows an EEG electrode with a hexagonal grid of protrusions.

FIG. 45 shows a proximal side view of an EEG electrode for use on a hair-covered portion of a person's head, wherein the proximal side is the side which faces toward the surface of a person's head. This EEG electrode comprises: an electrode base 4501; a hexagonal grid (e.g. honeycomb grid) of electroconductive proximal protrusions (e.g. pins, prongs, teeth, spikes, fingers, and/or protrusions), including set 4502, which extend out in a non-perpendicular manner from the electrode base toward the person's head in order to penetrate between hairs and come into contact with the surface of the person's head, wherein there is a protrusion at each vertex of a hexagon in the hexagonal grid. Relevant variations discussed elsewhere in this disclosure or in priority-linked disclosures can also be applied to the example in this figure.

Figure 46:
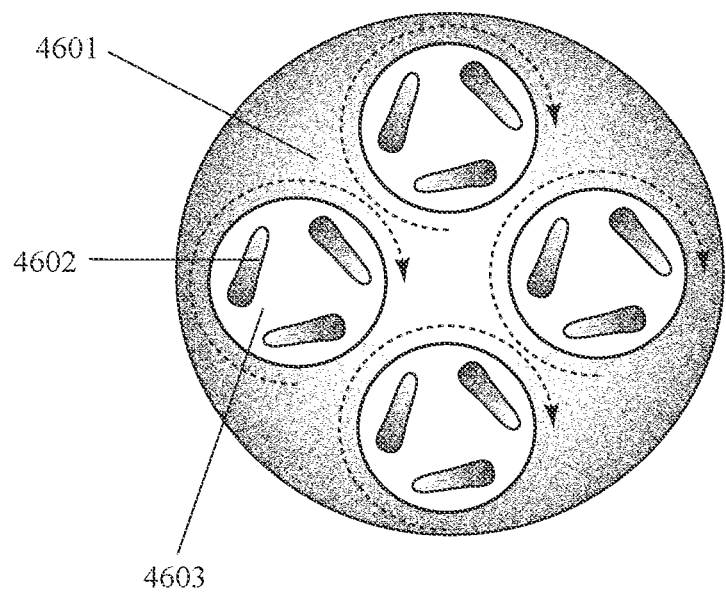
FIG. 46 shows an EEG electrode with at least two rotatable sets of protrusions.

FIG. 46 shows a proximal side view of an EEG electrode for use on a hair-covered portion of a person's head, wherein the proximal side is the side which faces toward the surface of a person's head. This EEG electrode comprises: a distal electrode base 4601; at least two rotatable sets (including set 4603) of electroconductive proximal protrusions (including protrusion 4602) which extend out from the electrode base toward the person's head in order to penetrate between hairs and come into contact with the surface of the person's head.

In an example, a set of protrusions can be a ring of protrusions. In an example, protrusions in a revolving set of protrusions can extend outward from an electrode base in a perpendicular manner (e.g. at 90-degree angles relative to the electrode base). In an example, protrusions in a revolving set of protrusions can extend outward from an electrode base in a non-perpendicular manner (e.g. at acute or obtuse angles relative to the electrode base). In an example, protrusions in a revolving set of protrusions can all extend outward from an electrode base at the same angle relative to the electrode base. In an example, protrusions in a set can be tilted or angled in the same direction that a set is rotated so that the tips of the protrusions tend to slide between stands of hair when the set is rotated.

In an example, an electrode can comprise at least two sets of proximal protrusions, wherein each set can be individually rotated (e.g. rotated and/or revolved) to enhance the ability of the protrusions to penetrate between hairs and come into contact with the surface of a person's head. In an example, an electrode can further comprise one or more actuators which automatically rotate one or more sets of protrusions. In an example, there can be at least three protrusions in each set. In an example, protrusions can extend outward from the electrode base in a non-perpendicular manner. In an example, protrusions in a set can all extend outward from the electrode base at the same angle, although in different directions.

In an example, an EEG electrode for use on a hair-covered portion of a person's head can comprise: a distal electrode base; at least two rotatable sets of electroconductive proximal protrusions which extend out from the electrode base toward the person's head in order to penetrate between hairs and come into contact with the surface of the person's head, wherein rotation of a set of protrusions enhances the ability of the protrusions to penetrate between hairs and come into contact with the surface of a person's head. In an example, the EEG electrode can further comprise one or more actuators (e.g. electromagnetic motors) which automatically rotate the sets of protrusions. Relevant variations discussed elsewhere in this disclosure or in priority-linked disclosures can also be applied to the example in this figure.

Figure 47:
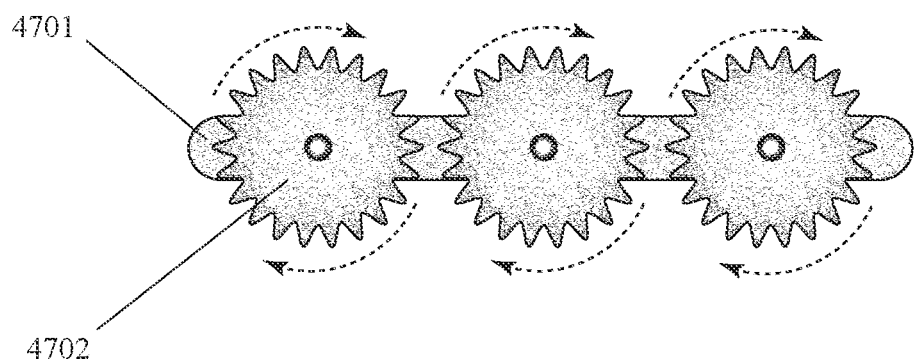
FIG. 47 shows an EEG electrode with rotatable wheels having protrusions.

FIG. 47 shows a side cross-sectional view of an EEG electrode for use on a hair-covered portion of a person's head comprising: an electrode base 4701; and a plurality of rotatable wheels (e.g. wheels, disks, or gears), including 4702; wherein a rotatable wheel has protrusions (e.g. protrusions, teeth, or cogs) around the wheel's perimeter which penetrate between hairs and come into contact with the surface of the person's head. In an example, an electrode can further comprise axles connected to the electrode base around which the wheels rotate. In an example, rotation of the wheels enhances the ability of protrusions on the wheels to penetrate between hairs and come into contact with the surface of a person's head.

In an example, an electrode base can be generally parallel to the surface of a person's head and rotatable wheels can be generally perpendicular to the surface of the person's head. In an example, an electrode can comprise at least three rotatable wheels with protrusions around their perimeters. In an example, an electrode can comprise six rotatable wheels with protrusions around their perimeters. In an example, protrusions on wheels can be rounded. In an example, the perimeter of a wheel can have a sinusoidal shape (e.g. a shape formed by applying a sine wave to a circle). In an example, protrusions on wheels can have vertexes. In an example, the perimeter of a wheel can have a sawtooth shape (e.g. a shape formed by applying a sawtooth wave to a circle).

In an example, rotatable wheels can be passively rotated by rolling contact with the person's head. In an example, the electrode can further comprise one or more actuators (e.g. electromagnetic motors) which actively rotate the one or more wheels. In an example, an actuator can rotate a wheel back and forth, in an iterative and/or oscillating manner, in clockwise and counterclockwise directions. In an example, an actuator can "wiggle" or vibrate a wheel back and forth.

In an example, protrusions on a wheel can be made with one or more materials selected from the group consisting of: metal; inherently-conductive polymer; inherently-nonconductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

Figure 48:
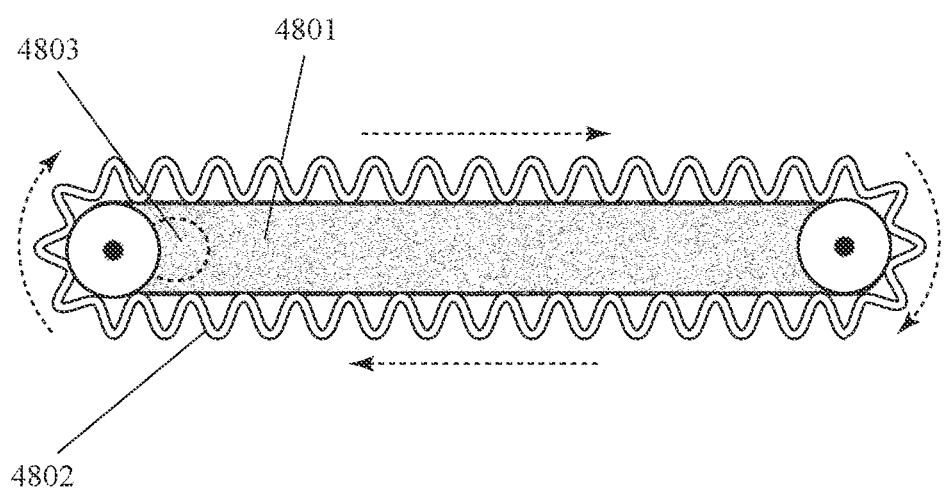
FIG. 48 shows an EEG electrode with a rotatable loop of protrusions.

FIG. 48 shows a side cross-sectional view of an EEG electrode for use on a hair-covered portion of a person's head comprising: an electrode base 4801; and a rotating loop 4802 of protrusions which penetrate between hairs and come into contact with the surface of the person's head; and one or more actuators (e.g. electromagnetic motors), such as 4803, which rotate the loop.

In an example, an electrode can comprise a loop of protrusions which rotates around an electrode base. In an example, an electrode can comprise a loop of protrusions which rotates around the perimeter of an electrode base. In an example, an electrode can comprise an oblong or circular loop of protrusions which rotates around an electrode base. In an example, an electrode can comprise a rotating chain-link loop of protrusions. In an example, an electrode can comprise a rotating trend, rotating track, and/or rotating chain-link loop of protrusions which penetrate between hairs and come into contact with the surface of the person's head. In an example, an electrode can comprise a rotating sinusoidal loop of protrusions. Relevant variations discussed elsewhere in this disclosure or in priority-linked disclosures can also be applied to the example in this figure.

Figure 49:
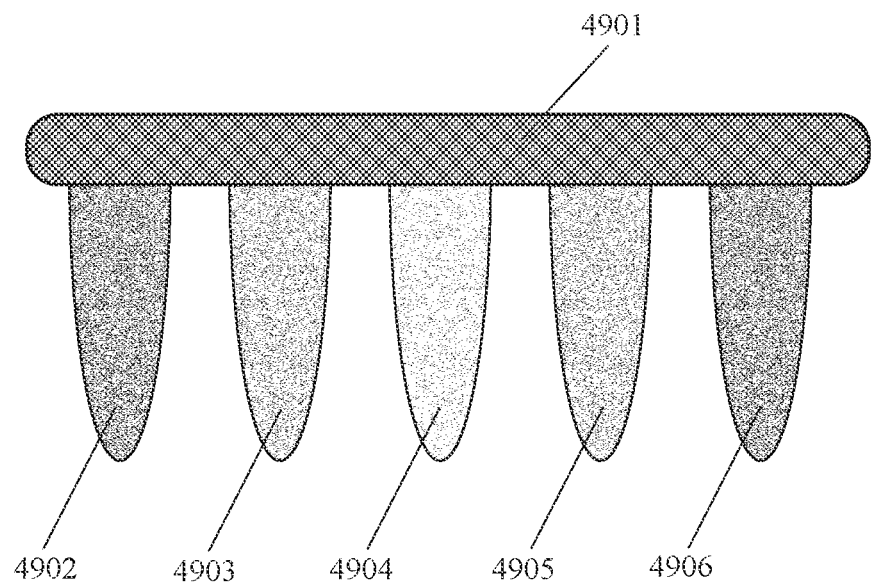
FIG. 49 shows an EEG electrode with radial variation in protrusion material.

FIG. 49 shows a side cross-sectional view of an EEG electrode for use on a hair-covered portion of a person's head comprising: a distal electrode base 4901; and a plurality of electroconductive proximal protrusions (e.g. pins, prongs, teeth, spikes, fingers, and/or protrusions), including protrusions 4902, 4903, 4904, 4905, and 4906, which extend out from the distal electrode base toward the person's head in order to penetrate between hairs and come into contact with the surface of the person's head; wherein a first protrusion which is a first distance from the center of the electrode base is made from a first material, wherein a second protrusion which is a second distance from the center of the electrode base is made from a second material, and wherein the second distance is greater than the first distance. In this example, protrusions 4903 and 4905 are made from a first material and protrusions 4902 and 4906 are made from a second material. In this example, protrusion 4904 is made from a third material.

In an example, the second material can be more elastic than the first material. In an example, the second material can be more flexible than the first material. In an example, the second material can be softer than the first material. In an example, the second material can be more compressible than the first material. In an example, the second material can have a lower durometer level than the first material. In an example, the second material can have a lower Young's modulus than the first material. In an example, the second material can be less electroconductive than the first material. In an example, the second material can be made with a lower percentage of metal than the first material.

In an example, the first material can be more elastic than the second material. In an example, the first material can be more flexible than the second material. In an example, the first material can be softer than the second material. In an example, the first material can be more compressible than the second material. In an example, the first material can have a lower durometer level than the second material. In an example, the first material can have a lower Young's modulus than the second material. In an example, the first material can be less electroconductive than the second material. In an example, the first material can be made with a lower percentage of metal than the second material.

FIG. 49 also shows an EEG electrode for use on a hair-covered portion of a person's head can comprise: a distal electrode base 4901; and a plurality of electroconductive proximal protrusions (e.g. pins, prongs, teeth, spikes, fingers, and/or protrusions) which extend out from the distal electrode base toward the person's head in order to penetrate between hairs and come into contact with the surface of the person's head; wherein a first protrusion 4904 which is a first distance from the center of the electrode base is made from a first material, wherein a second protrusion 4903 or 4905 which is a second distance from the center of the electrode base is made from a second material, wherein a third protrusion 4902 or 4906 which is a third distance from the center of the electrode base is made from a third material, wherein the second distance is greater than the first distance, and wherein the third distance is greater than the second distance.

In an example, the second material can be more elastic than the first material and the third material can be more elastic than the second material. In an example, the second material can be more flexible than the first material and the third material can be more flexible than the second material. In an example, the second material can be softer than the first material and the third material can be softer than the second material. In an example, the second material can be more compressible than the first material and the third material can be more compressible than the second material.

In an example, the second material can have a lower durometer level than the first material and the third material can have a lower durometer level than the second material. In an example, the second material can have a lower Young's modulus than the first material and the third material can have a lower Young's modulus than the second material. In an example, the second material can be less electroconductive than the first material and the third material can be less electroconductive than the second material. In an example, the second material can be made with a lower percentage of metal than the first material and the third material can be made with a lower percentage of metal than the second material.

In an example, the second material can be more elastic than the third material and the first material can be more elastic than the second material. In an example, the second material can be more flexible than the third material and the first material can be more flexible than the second material. In an example, the second material can be softer than the third material and the first material can be softer than the second material. In an example, the second material can be more compressible than the third material and the first material can be more compressible than the second material.

In an example, the second material can have a lower durometer level than the third material and the first material can have a lower durometer level than the second material. In an example, the second material can have a lower Young's modulus than the third material and the first material can have a lower Young's modulus than the second material. In an example, the second material can be less electroconductive than the third material and the first material can be less electroconductive than the second material. In an example, the second material can be made with a lower percentage of metal than the third material and the first material can be made with a lower percentage of metal than the second material.

In an example, a plurality of protrusions can comprise nested (e.g. concentric) rings of protrusions. In an example, an inner ring of protrusions can be made with a first material and an outer ring of protrusions can e made with a second material. In an example, the materials from which protrusions are made can have one or more attributes which differ with distance from the center of an electrode base. In an example, one of more protrusion material attributes which vary with distance from the center of an electrode base can be selected from the group consisting of: elasticity, flexibility, softness, compressibility, durometer level, Young's modulus, electroconductivity, and percentage of metal. In an example, one or more protrusion material attributes which vary with distance from the center of an electrode base can be selected from the group consisting of: hardness, stiffness, impedance, and percentage of non-conductive polymer.

In an example, a protrusion can have a parabolic and/or paraboloidal shape. In an example, a protrusion can have a sinusoidal shape. In an example, a protrusion can have a columnar shape. In an example, a protrusion can have a conic or conic-section shape. In an example, a protrusion can have a frustal shape. In an example, an electrode base can have a circular or disk shape. In an example, an electrode base can have an elliptical, oblong, or oval shape. In an example, an electrode base can have a (rounded) square or (rounded) rectangular shape. Relevant variations discussed elsewhere in this disclosure or in priority-linked disclosures can also be applied to the example in this figure.

Figure 50:
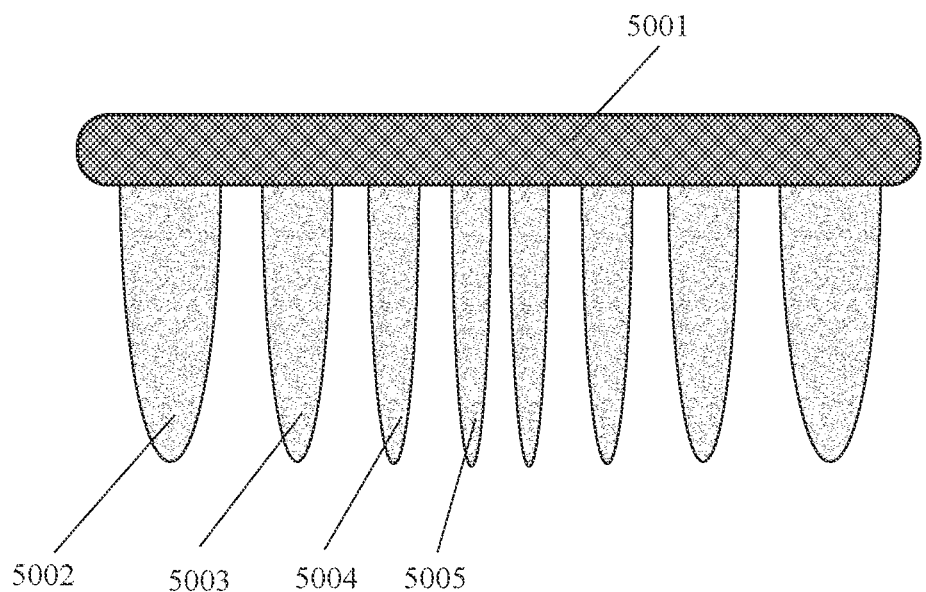
FIG. 50 shows an EEG electrode with radial variation in protrusion width.

FIG. 50 shows a side cross-sectional view of an EEG electrode for use on a hair-covered portion of a person's head comprising: a distal electrode base 5001; and a plurality of electroconductive proximal protrusions (e.g. pins, prongs, teeth, spikes, fingers, and/or protrusions), including protrusions 5002, 5003, 5004, and 5005, which extend out from the distal electrode base toward the person's head in order to penetrate between hairs and come into contact with the surface of the person's head; wherein a first protrusion 5005 which is a first distance from the center of the electrode base has a first width, wherein a second protrusion 5004 which is a second distance from the center of the electrode base has a second width, and wherein the second width is different than the first width. In this example, the second width is greater than the first width. In an alternative example, the second width can be less than the first width.

FIG. 50 also shows a side cross-sectional view of an EEG electrode for use on a hair-covered portion of a person's head comprising: a distal electrode base 5001; and a plurality of electroconductive proximal protrusions (e.g. pins, prongs, teeth, spikes, fingers, and/or protrusions), including protrusions 5002, 5003, 5004, and 5005, which extend out from the distal electrode base toward the person's head in order to penetrate between hairs and come into contact with the surface of the person's head; wherein a first protrusion 5005 which is a first distance from the center of the electrode base has a first width, wherein a second protrusion 5004 which is a second distance from the center of the electrode base has a second width, wherein a third protrusion 5003 which is a third distance from the center of the electrode base has a third width, wherein the second width is different than the first width, and wherein the third width is different than the second width. In this example, the second width is greater than the first width and the third width is greater than the second width. In an alternative example, the second width can be less than the first width and the third width can be less than the second width.

In an example, a plurality of protrusions can comprise nested (e.g. concentric) rings of protrusions. In an example, a protrusion can have a parabolic and/or paraboloidal shape. In an example, a protrusion can have a sinusoidal shape. In an example, a protrusion can have a columnar shape. In an example, a protrusion can have a conic or conic-section shape. In an example, a protrusion can have a frustal shape. In an example, an electrode base can have a circular or disk shape. In an example, an electrode base can have an elliptical, oblong, or oval shape. In an example, an electrode base can have a (rounded) square or (rounded) rectangular shape. Relevant variations discussed elsewhere in this disclosure or in priority-linked disclosures can also be applied to the example in this figure.

Figure 51:
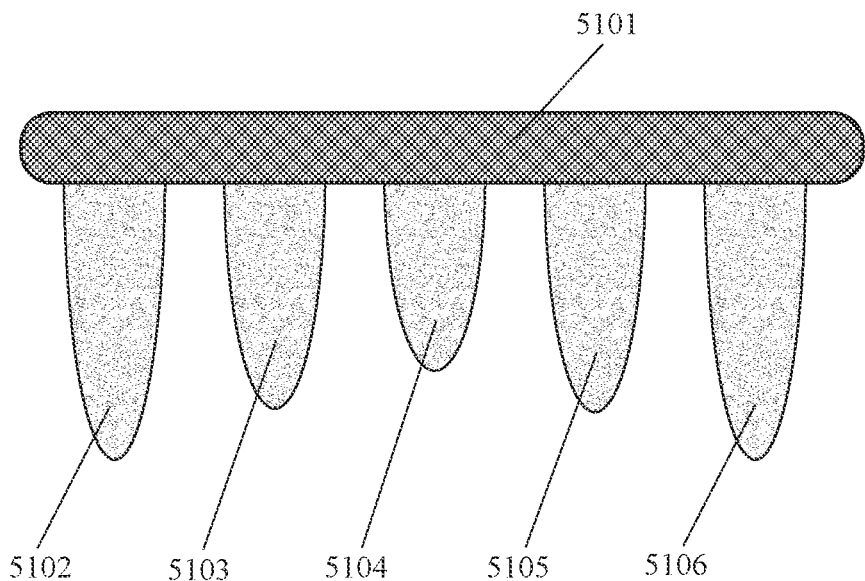
FIG. 51 shows an EEG electrode with radial variation in protrusion length.

FIG. 51 shows a side cross-sectional view of an EEG electrode for use on a hair-covered portion of a person's head comprising: a distal electrode base 5101; and a plurality of electroconductive proximal protrusions (e.g. pins, prongs, teeth, spikes, fingers, and/or protrusions), including protrusions 5102, 5103, 5104, 5105, and 5106, which extend out from the distal electrode base toward the person's head in order to penetrate between hairs and come into contact with the surface of the person's head; wherein a first protrusion which is a first distance from the center of the electrode base has a first length, wherein a second protrusion which is a second distance from the center of the electrode base has a second length, and wherein the second length is different than the first length. In this example, the second length is greater than the first length. In an alternative example, the second length can be less than the first length.

FIG. 51 also shows a side cross-sectional view of an EEG electrode for use on a hair-covered portion of a person's head comprising: a distal electrode base 5101; and a plurality of electroconductive proximal protrusions (e.g. pins, prongs, teeth, spikes, fingers, and/or protrusions), including protrusions 5102, 5103, 5104, 5105, and 5106, which extend out from the distal electrode base toward the person's head in order to penetrate between hairs and come into contact with the surface of the person's head; wherein a first protrusion 5104 which is a first distance from the center of the electrode base has a first length, wherein a second protrusion 5103 or 5105 which is a second distance from the center of the electrode base has a second length, wherein a third protrusion 5102 or 5106 which is a third distance from the center of the electrode base has a third length, wherein the second length is different than the first length, and wherein the third length is different than the second length. In this example, the second length is greater than the first length and the third length is greater than the second length. In an alternative example, the second length can be less than the first length and the third length can be less than the second length.

In an example, a plurality of protrusions can comprise nested (e.g. concentric) rings of protrusions. In an example, a protrusion can have a parabolic and/or paraboloidal shape. In an example, a protrusion can have a sinusoidal shape. In an example, a protrusion can have a columnar shape. In an example, a protrusion can have a conic or conic-section shape. In an example, a protrusion can have a frustal shape. In an example, an electrode base can have a circular or disk shape. In an example, an electrode base can have an elliptical, oblong, or oval shape. In an example, an electrode base can have a (rounded) square or (rounded) rectangular shape. Relevant variations discussed elsewhere in this disclosure or in priority-linked disclosures can also be applied to the example in this figure.

Figure 52:
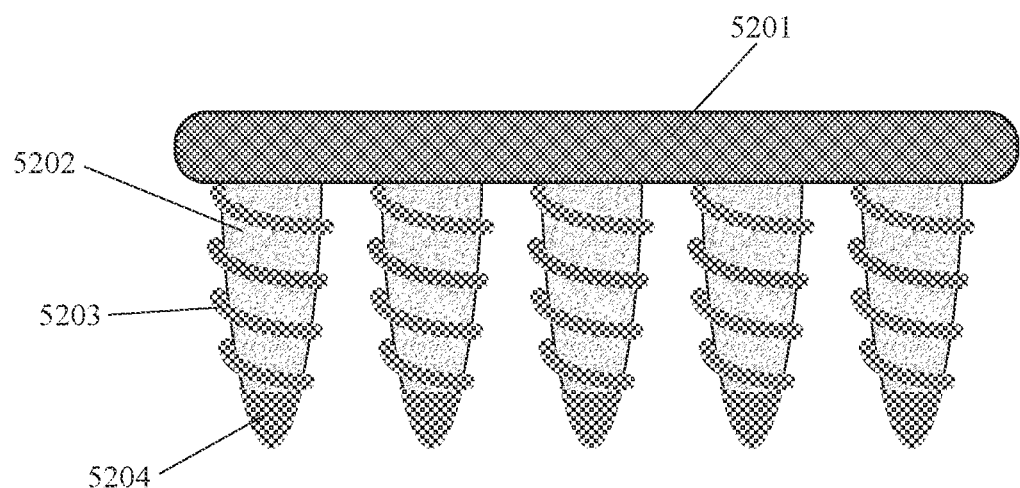
FIG. 52 shows an EEG electrode with protrusions encircled by a helical conductive springs.

FIG. 52 shows a side cross-sectional view of an EEG electrode for use on a hair-covered portion of a person's head comprising: a distal electrode base 5201; and a plurality of proximal protrusions (e.g. pins, prongs, teeth, spikes, fingers, and/or protrusions), including protrusion 5202, which extend out from the distal electrode base toward the person's head in order to penetrate between hairs and come into contact with the surface of the person's head; wherein a protrusion is encircled by a helical conductive spring (or coil) 5203; and wherein the tip of a protrusion has a conductive cap 5204 which is attached to the helical conductive spring (or coil). In an example a helical conductive spring (or coil) can be made from a conductive metal. In an example, a helical conductive spring (or coil) can be made from a conductive polymer.

In an example, a protrusion can have a parabolic and/or paraboloidal shape. In an example, a protrusion can have a sinusoidal shape. In an example, a protrusion can have a columnar shape. In an example, a protrusion can have a conic or conic-section shape. In an example, a protrusion can have a frustal shape. In an example, an electrode base can have a circular or disk shape. In an example, an electrode base can have an elliptical, oblong, or oval shape. In an example, an electrode base can have a (rounded) square or (rounded) rectangular shape. Relevant variations discussed elsewhere in this disclosure or in priority-linked disclosures can also be applied to the example in this figure.

Figure 53:
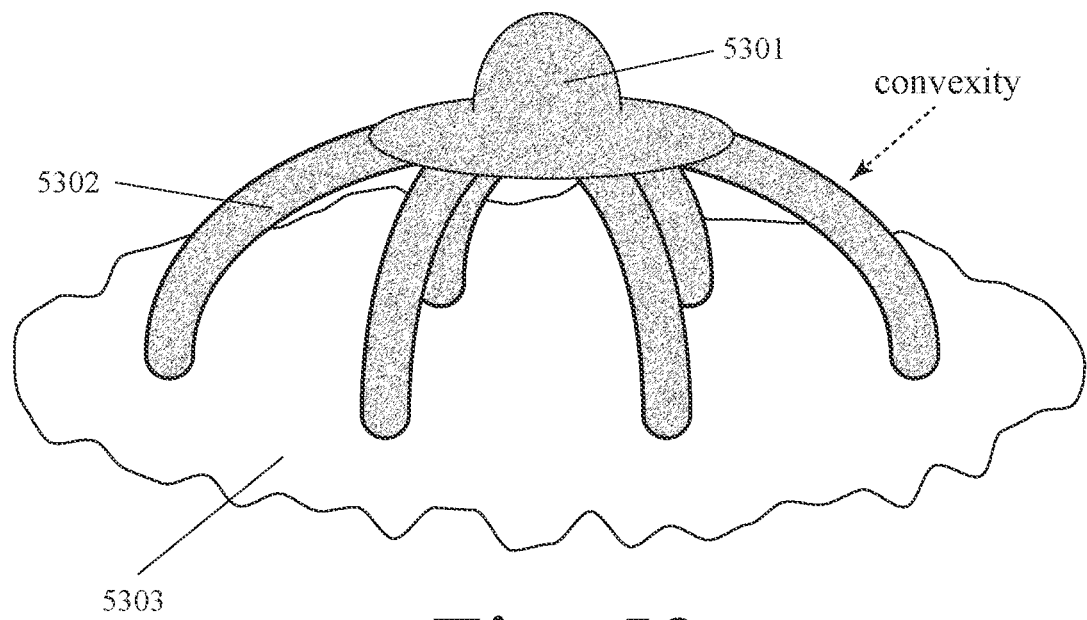
FIG. 53 shows an EEG electrode with convex legs which extend out radially.

FIG. 53 shows a side cross-sectional view of an EEG electrode for use on a hair-covered portion of a person's head comprising: an electrode hub 5301; and a plurality of arcuate conductive legs (e.g. legs, arms, fingers, branches, spokes, or protrusions), including leg 5302, which extend out radially from the electrode hub and also extend out toward the surface of a person's head 5303 in order to penetrate between hairs and come into contact with the surface of the person's head; wherein a middle portion of a leg bows away from the surface of the person's head. In an example, a conductive leg can be convex, wherein a middle portion of the leg bows away from the surface of a person's head.

In an example, an electrode with a hub and a plurality of radially-extending legs can be symmetric with respect to a central proximal-to-distal plane. In an example, radially-extending legs can be evenly distributed around the circumference of an electrode hub. In an example, an electrode can comprise a distal hub and six conductive legs which extend out radially from the hub and toward the surface of a person's head. In an example, six radially-extending legs can be pair-wise separated by 60-degree angles. In an example, neighboring legs (or virtual extensions thereof) can intersect at 60-degree angles. In an example, the proximal ends of six legs can form the vertexes of a virtual equilateral hexagon.

In an example, an electrode can comprise a distal hub and eight conductive legs which extend out radially from the hub and toward the surface of a person's head. In an example, eight radially-extending legs can be pair-wise separated by 45-degree angles. In an example, neighboring legs (or virtual extensions thereof) can intersect at 45-degree angles. In an example, the proximal ends of eight legs can form the vertexes of a virtual equilateral octagon. In an example, an electrode can comprise a distal hub and twelve conductive legs which extend out radially from the hub and toward the surface of a person's head. In an example, twelve radially-extending legs can be pair-wise separated by 30-degree angles. In an example, neighboring legs (or virtual extensions thereof), can intersect at 30-degree angles). In an example, the proximal ends of twelve legs can form the vertexes of a virtual equilateral dodecagon.

In an example, an arcuate conductive leg can be a single, continuous piece. In an example, an arcuate conductive leg can be a single, continuous piece which is made from a metal. In an example, an arcuate conductive leg can be a single, continuous piece which is made from a conductive polymer material. In an example, an arcuate conductive leg can be a single, continuous piece which is made from a polymer (e.g. PDMS) which has been doped, impregnated, and/or coated with carbon structures (e.g. carbon nanotubes) or a metal. In an example, an arcuate conductive leg can be flexible. In an example, an arcuate conductive leg can be articulated. In an example, an arcuate conductive leg can comprise two articulated and moveably-connected segments.

In an example, an arcuate conductive leg can have a shape which is a conic section. In an example, an arcuate conductive leg can have a shape which is a section (e.g. a quarter or half) of a circle or ellipse. In an example, a plurality of arcuate legs can comprise arcs of a section of a sphere or ellipsoid. In an example, the proximal end of an arcuate conductive leg can intersect the surface of a person's head in a perpendicular manner (e.g. at a 90-degree angle). In an example, the proximal end of an arcuate conductive leg can intersect the surface of a person's head at an acute angle. In an example, the proximal end of an arcuate conductive leg can be rounded. Relevant variations discussed elsewhere in this disclosure or in priority-linked disclosures can also be applied to the example in this figure.

Figure 54:
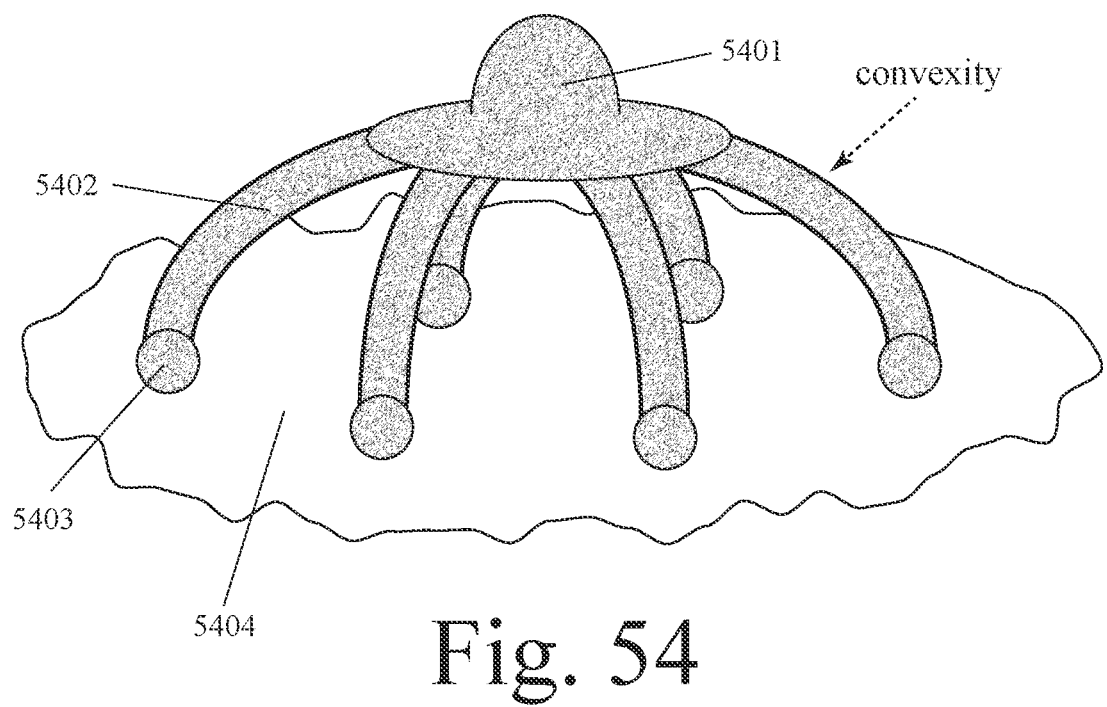
FIG. 54 shows an EEG electrode with convex legs with ball ends which extend out radially.

FIG. 54 shows a side cross-sectional view of an EEG electrode for use on a hair-covered portion of a person's head comprising: an electrode hub 5401; and a plurality of arcuate conductive legs (e.g. legs, arms, fingers, branches, spokes, or protrusions), including leg 5402, which extend out radially from the electrode hub and also extend out toward the surface of a person's head 5404 in order to penetrate between hairs and come into contact with the surface of the person's head; wherein a middle portion of a leg bows away from the surface of the person's head; and wherein there is a conductive ball 5403 on the proximal end of each leg. In an example, a conductive ball can be a separate piece which is attached to a leg. Alternatively, a conductive ball can be an integral portion of a continuous single-piece leg.

In an example, a conductive leg can be convex, wherein a middle portion of the leg bows away from the surface of a person's head. In an example, an electrode with a hub and a plurality of radially-extending legs can be symmetric with respect to a central proximal-to-distal plane. In an example, radially-extending legs can be evenly distributed around the circumference of an electrode hub. In an example, an electrode can comprise a distal hub and six conductive legs which extend out radially from the hub and toward the surface of a person's head. In an example, six radially-extending legs can be pair-wise separated by 60-degree angles. In an example, neighboring legs (or virtual extensions thereof) can intersect at 60-degree angles. In an example, the proximal ends of six legs can form the vertexes of a virtual equilateral hexagon.

In an example, an electrode can comprise a distal hub and eight conductive legs which extend out radially from the hub and toward the surface of a person's head. In an example, eight radially-extending legs can be pair-wise separated by 45-degree angles. In an example, neighboring legs (or virtual extensions thereof) can intersect at 45-degree angles. In an example, the proximal ends of eight legs can form the vertexes of a virtual equilateral octagon. In an example, an electrode with eight legs can be formed in an arthro podcast. In an example, an electrode can comprise a distal hub and twelve conductive legs which extend out radially from the hub and toward the surface of a person's head. In an example, twelve radially-extending legs can be pair-wise separated by 30-degree angles. In an example, neighboring legs (or virtual extensions thereof), can intersect at 30-degree angles). In an example, the proximal ends of twelve legs can form the vertexes of a virtual equilateral dodecagon.

In an example, an arcuate conductive leg can be a single, continuous piece. In an example, an arcuate conductive leg can be a single, continuous piece which is made from a metal. In an example, an arcuate conductive leg can be a single, continuous piece which is made from a conductive polymer material. In an example, an arcuate conductive leg can be a single, continuous piece which is made from a polymer (e.g. PDMS) which has been doped, impregnated, and/or coated with carbon structures (e.g. carbon nanotubes) or a metal. In an example, an arcuate conductive leg can be flexible. In an example, an arcuate conductive leg can be articulated. In an example, an arcuate conductive leg can comprise two articulated and moveably-connected segments.

In an example, an arcuate conductive leg can have a shape which is a conic section. In an example, an arcuate conductive leg can have a shape which is a section (e.g. a quarter or half) of a circle or ellipse. In an example, a plurality of arcuate legs can comprise arcs of a section of a sphere or ellipsoid. In an example, the proximal end of an arcuate conductive leg can intersect the surface of a person's head in a perpendicular manner (e.g. at a 90-degree angle). In an example, the proximal end of an arcuate conductive leg can intersect the surface of a person's head at an acute angle. Relevant variations discussed elsewhere in this disclosure or in priority-linked disclosures can also be applied to the example in this figure.

Figure 55:
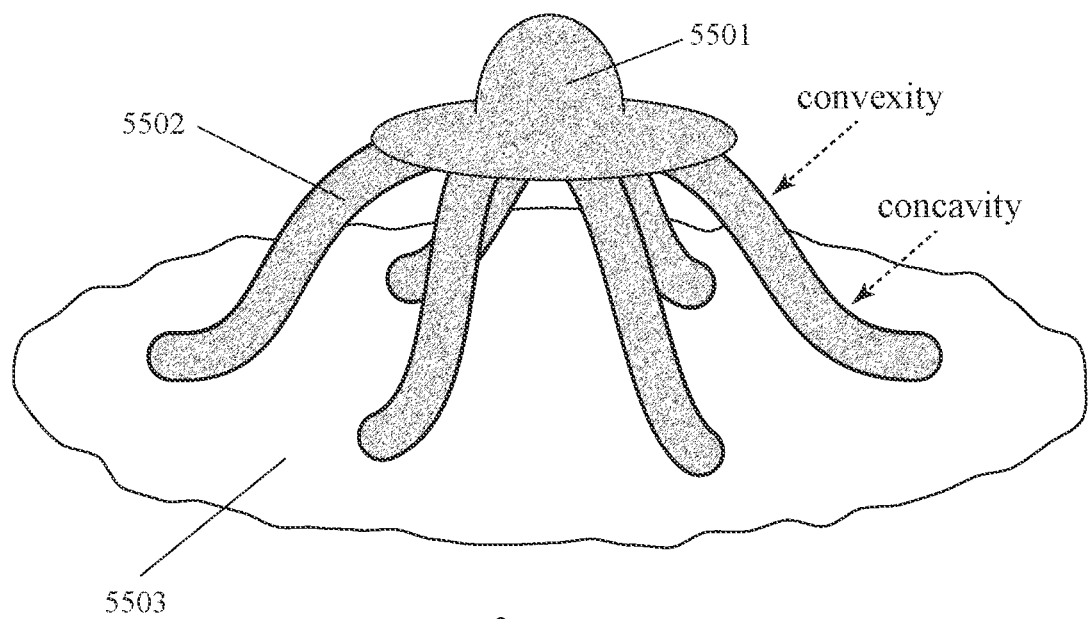
FIG. 55 shows an EEG electrode with convex-concave legs which extend out radially.

FIG. 55 shows a side cross-sectional view of an EEG electrode for use on a hair-covered portion of a person's head comprising: an electrode hub 5501; and a plurality of arcuate conductive legs (e.g. legs, arms, fingers, branches, spokes, or protrusions), including leg 5502, which extend out radially from the electrode hub and also extend out toward the surface of a person's head 5503 in order to penetrate between hairs and come into contact with the surface of the person's head; wherein a leg has a convex portion which bows away from the surface of the person's head and a concave portion which bows toward the surface of the person's head.

In an example, a convex portion of a leg can be closer to an electrode hub than a concave portion of the leg. In an example, the half of a leg which is closer to an electrode hub can bow (e.g. bow, bend, or curve) away from the surface of a person's head and the half of the leg which is farther from the hub can bow (e.g. bow, bend, or curve) toward the surface of the person's head. In another example, a convex portion of a leg can be farther from an electrode hub than a concave portion of the leg. In another example, the half of a leg which is farther from an electrode hub can bow (e.g. bow, bend, or curve) away from the surface of a person's head and the half of the leg which is closer to the hub can bow (e.g. bow, bend, or curve) toward the surface of the person's head.

In an example, an electrode with a hub and a plurality of radially-extending legs can be symmetric with respect to a central proximal-to-distal plane. In an example, radially-extending legs can be evenly distributed around the circumference of an electrode hub. In an example, an electrode can comprise a distal hub and six conductive legs which extend out radially from the hub and toward the surface of a person's head. In an example, six radially-extending legs can be pair-wise separated by 60-degree angles. In an example, neighboring legs (or virtual extensions thereof) can intersect at 60-degree angles. In an example, the proximal ends of six legs can form the vertexes of a virtual equilateral hexagon.

In an example, an electrode can comprise a distal hub and eight conductive legs which extend out radially from the hub and toward the surface of a person's head. In an example, eight radially-extending legs can be pair-wise separated by 45-degree angles. In an example, neighboring legs (or virtual extensions thereof) can intersect at 45-degree angles. In an example, the proximal ends of eight legs can form the vertexes of a virtual equilateral octagon. In an example, an electrode with eight legs can be formed in an arthro podcast. In an example, an electrode can comprise a distal hub and twelve conductive legs which extend out radially from the hub and toward the surface of a person's head. In an example, twelve radially-extending legs can be pair-wise separated by 30-degree angles. In an example, neighboring legs (or virtual extensions thereof), can intersect at 30-degree angles). In an example, the proximal ends of twelve legs can form the vertexes of a virtual equilateral dodecagon.

In an example, an arcuate conductive leg can be a single, continuous piece. In an example, an arcuate conductive leg can be a single, continuous piece which is made from a metal. In an example, an arcuate conductive leg can be a single, continuous piece which is made from a conductive polymer material. In an example, an arcuate conductive leg can be a single, continuous piece which is made from a polymer (e.g. PDMS) which has been doped, impregnated, and/or coated with carbon structures (e.g. carbon nanotubes) or a metal. In an example, an arcuate conductive leg can be flexible. In an example, an arcuate conductive leg can be articulated. In an example, an arcuate conductive leg can comprise two articulated and moveably-connected segments.

In an example, an arcuate conductive leg can have a shape which is a conic section. In an example, an arcuate conductive leg can have a shape which is a section (e.g. a quarter or half) of a circle or ellipse. In an example, a plurality of arcuate legs can comprise arcs of a section of a sphere or ellipsoid. Relevant variations discussed elsewhere in this disclosure or in priority-linked disclosures can also be applied to the example in this figure.

Figure 56:
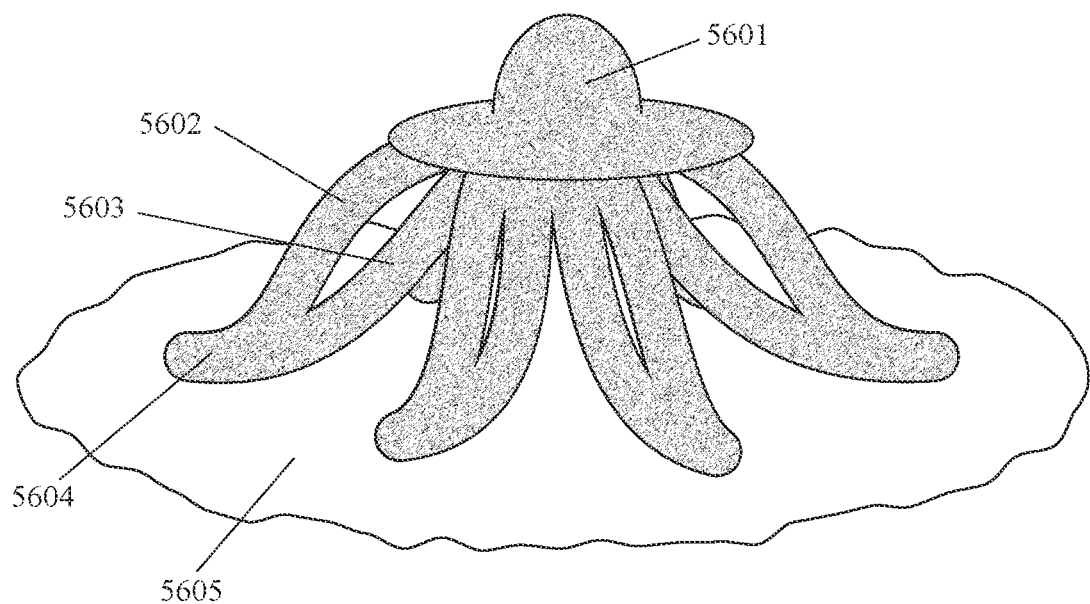
FIG. 56 shows an EEG electrode with bifurcated legs which extend out radially.

FIG. 56 shows a side cross-sectional view of an EEG electrode for use on a hair-covered portion of a person's head comprising: an electrode hub 5601; and a plurality of bifurcated conductive legs (e.g. legs, arms, fingers, branches, spokes, or protrusions), including leg 5602, which extend out radially from the electrode hub and also extend out toward the surface of a person's head 5603 in order to penetrate between hairs and come into contact with the surface of the person's head; wherein the middle portion of a leg is bifurcated, but distal and proximal ends of the leg are not bifurcated.

In an example, in the middle portion of a leg where the leg bifurcates, one branch can be convex and the other branch can be concave. In an example, an electrode with a hub and a plurality of radially-extending legs can be symmetric with respect to a central proximal-to-distal plane. In an example, radially-extending legs can be evenly distributed around the circumference of an electrode hub. In an example, an arcuate conductive leg can be flexible. Relevant variations discussed elsewhere in this disclosure or in priority-linked disclosures can also be applied to the example in this figure.

Figure 57:
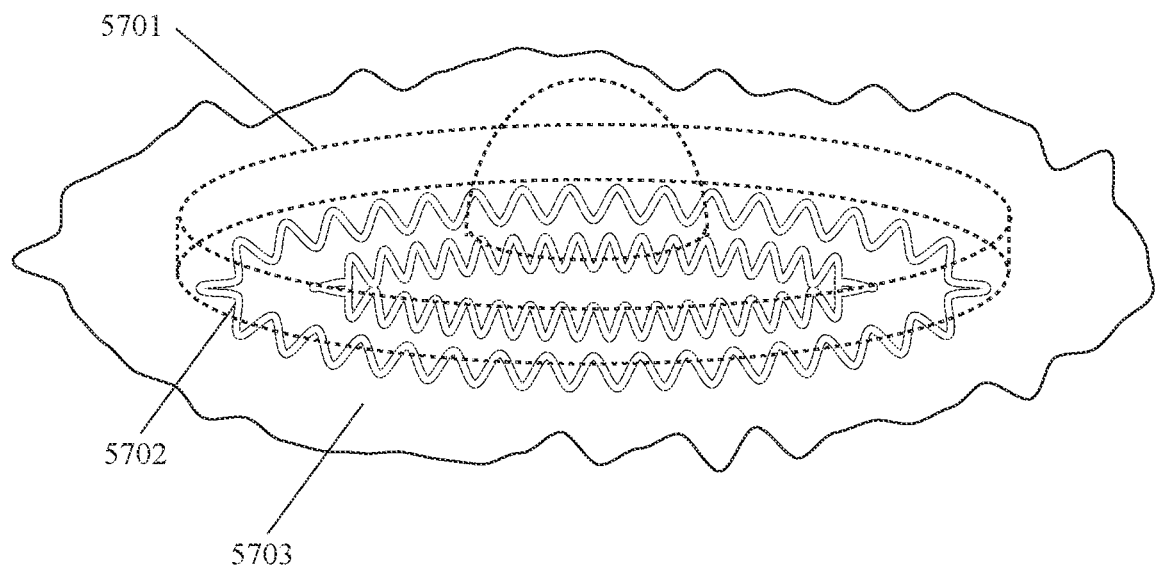
FIG. 57 shows an EEG electrode with nested sinusoidal conductive rings.

FIG. 57 shows a side cross-sectional view of an EEG electrode for use on a hair-covered portion of a person's head comprising: a distal electrode base 5701; and a plurality of nested (e.g. concentric) sinusoidal conductive rings, including 5702, on the proximal side of the base which penetrate between hairs and come into contact with the surface of the person's head 5703.

In an example, the amplitude of a sinusoidal curve of an outer nested sinusoidal ring can be different than the amplitude of a sinusoidal curve of an inner nested sinusoidal ring.

In an example, the amplitude of a sinusoidal curve of an outer nested sinusoidal ring can be greater than the amplitude of a sinusoidal curve of an inner nested sinusoidal ring. In an example, the wavelength of the sinusoidal curve of an outer nested sinusoidal ring can be different than the wavelength of the sinusoidal curve of an inner nested sinusoidal ring. In an example, the wavelength of the sinusoidal curve of an outer nested sinusoidal ring can be greater than the wavelength of the sinusoidal curve of an inner nested sinusoidal ring.

In another example, the amplitude of the sinusoidal curve of an outer nested sinusoidal ring can be less than the amplitude of the sinusoidal curve of an inner nested sinusoidal ring. In another example, the wavelength of the sinusoidal curve of an outer nested sinusoidal ring can be less than the wavelength of the sinusoidal curve of an inner nested sinusoidal ring. In another example, rings can have sawtooth-shaped protrusions instead of sinusoidal protrusions. Relevant variations discussed elsewhere in this disclosure or in priority-linked disclosures can also be applied to the example in this figure.

Figure 58:
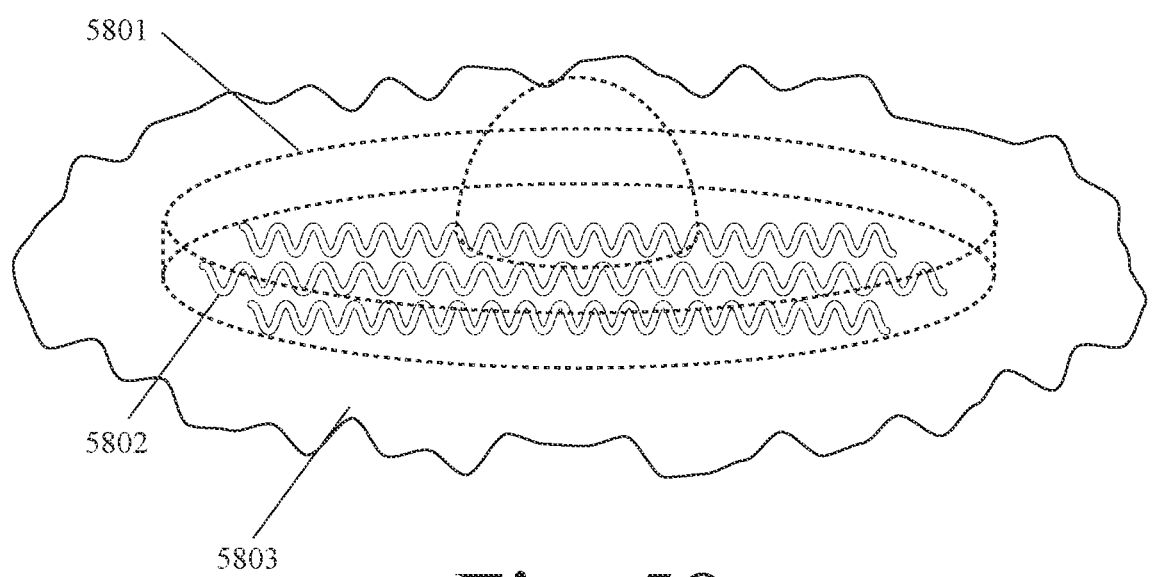
FIG. 58 shows an EEG electrode with parallel sinusoidal conductive ridges.

FIG. 58 shows a side cross-sectional view of an EEG electrode for use on a hair-covered portion of a person's head comprising: a distal electrode base 5801; and a plurality of parallel sinusoidal conductive ridges, including 5802, on the proximal side of the base which penetrate between hairs and come into contact with the surface of the person's head 5803. In another example, ridges can have a sawtooth shape instead of a sinusoidal shape. Relevant variations discussed elsewhere in this disclosure or in priority-linked disclosures can also be applied to the example in this figure.

Figure 59:
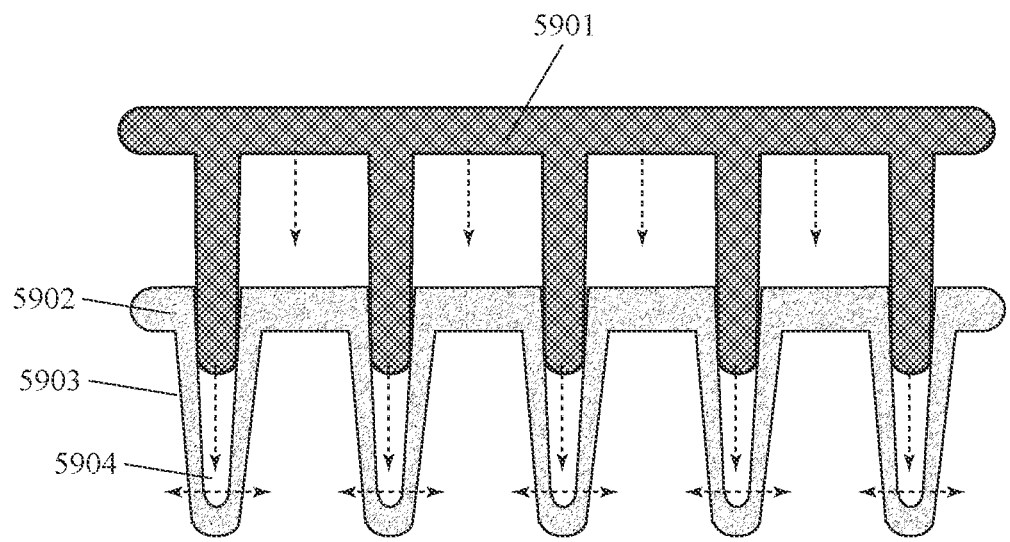
FIG. 59 shows an EEG electrode with a first set of protrusions which are inserted into the hollow cores of a second set of protrusions.

FIG. 59 shows a side cross-sectional view of an EEG electrode for use on a hair-covered portion of a person's head comprising: a first (distal) electrode portion 5901 which further comprises a plurality of first proximal protrusions extending out from the first electrode portion toward the surface of a person's head, and wherein a first proximal protrusion is made from a material with a first durometer level; and a second (proximal) electrode portion 5902 which further comprises a plurality of second protrusions (including protrusion 5903) extending out from the second electrode portion toward the surface of the person's head, wherein a second proximal protrusion is made from a material with a second durometer level, wherein the second durometer level is less than the first durometer level, wherein the second protrusion has a hollow core 5904 into which the first protrusion can be inserted, and wherein inserting the first protrusion into the hollow core of the second protrusion increases the stiffness, width, and/or length of the second protrusion, thereby enhancing the ability of the second protrusion to penetrate between hairs and contact the surface of a person's head. Relevant variations discussed elsewhere in this disclosure or in priority-linked disclosures can also be applied to the example in this figure.

Figure 60:
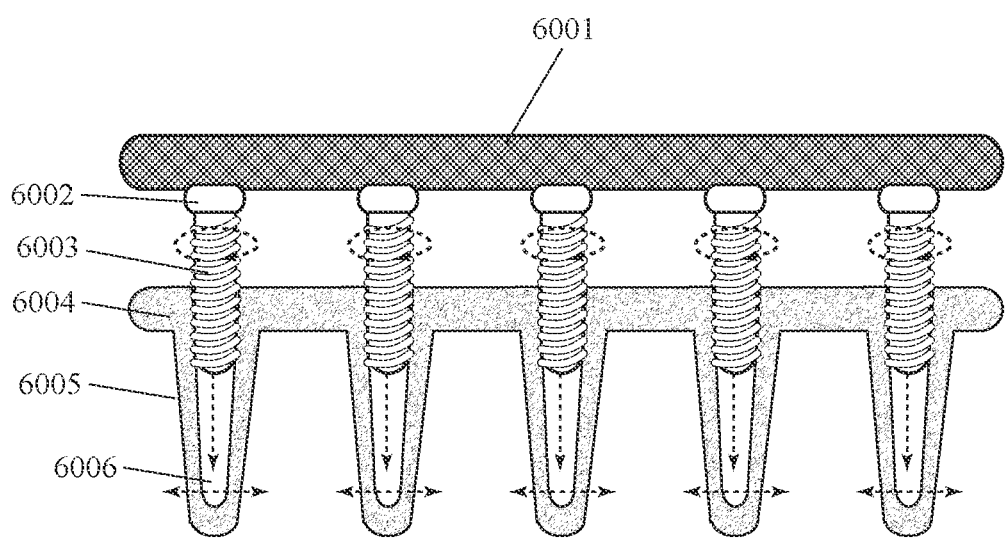
FIG. 60 shows an EEG electrode with threaded cylinders which are rotationally inserted into the hollow cores of protrusions.

FIG. 60 shows a side cross-sectional view of an EEG electrode for use on a hair-covered portion of a person's head comprising: a first (distal) electrode portion 6001; a second (proximal) electrode portion 6004 which further comprises a plurality of protrusions, including 6005, extending out from the second electrode portion toward the surface of the person's head; wherein a protrusion in the plurality of protrusions has a threaded hollow core 6006; a plurality of threaded cylinders, including 6003; and a plurality of actuators (e.g. electromagnetic motors), including 6002, which an actuator rotates a threaded cylinder; wherein rotational insertion of a threaded cylinder into a threaded hollow core of a protrusion increases the stiffness, width, and/or length of the protrusion, thereby enhancing the ability of the protrusion to penetrate between hairs and contact the surface of a person's head. Relevant variations discussed elsewhere in this disclosure or in priority-linked disclosures can also be applied to the example in this figure.

Figure 61:
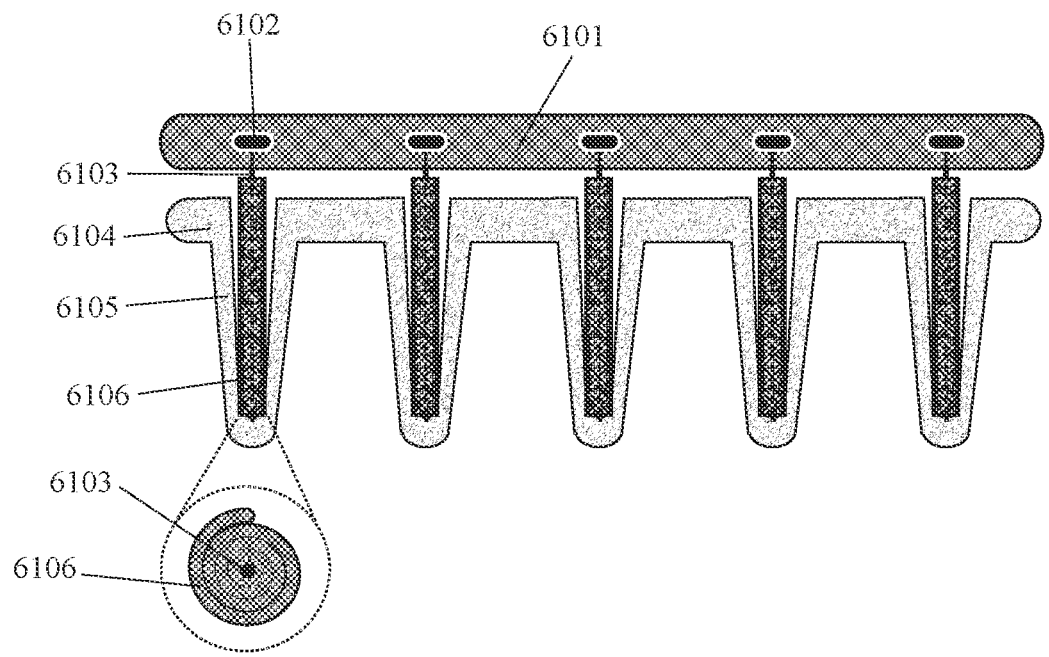
FIGS. 61 and 62 show two views of an EEG electrode with cylindrical coils in the hollow cores of protrusions.
Figure 62:
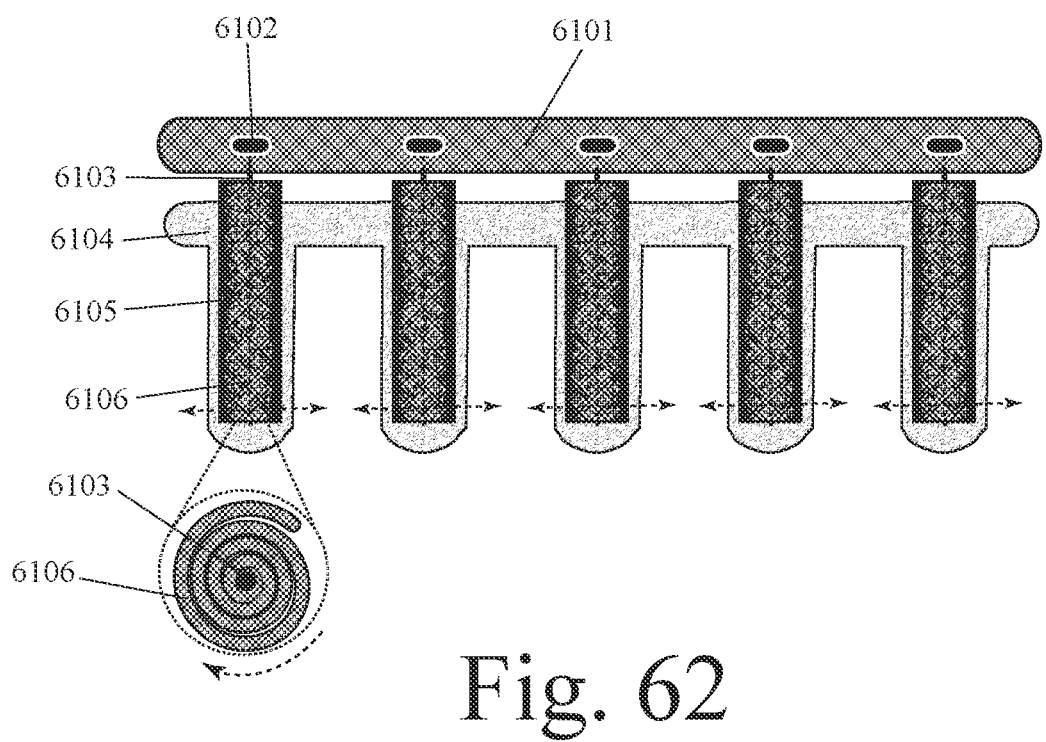

FIGS. 61 and 62 show two side cross-sectional views, at two different times, of an EEG electrode for use on a hair-covered portion of a person's head comprising: a distal electrode portion 6101; a proximal electrode portion 6104 which further comprises a plurality of protrusions, including 6105, extending out from the proximal electrode portion toward the surface of the person's head; wherein protrusions in the plurality of protrusions have hollow cores; a plurality of cylindrical coils, including 6106, which are coiled (e.g. rolled in a spiral manner) around central axles, including 6103, inside the hollow cores of the protrusions; and a plurality of actuators (e.g. electromagnetic motors), including 6102, which rotate the axles; wherein rotation of an axle in a first (e.g. clockwise) direction coils a cylindrical coil, which decreases the diameter of the cylindrical coil, which decreases the width (and/or stiffness) of the protrusion; and wherein rotation of an axle in a second (e.g. counter-clockwise) direction uncoils a cylindrical coil, which increases the diameter of the cylindrical coil, which increases the width (and/or stiffness) of the protrusion.

FIG. 61 shows this electrode at a first time wherein the cylindrical coils are tightly wound around their axles and the ends of the protrusions are relatively narrow and/or soft. FIG. 62 shows this electrode at a second time wherein the cylindrical coils are less rightly wound around their axles and the ends of the protrusions are relatively wide and/or stiff. The upper portions of FIGS. 61 and 62 shows side cross-sectional views of the entire electrode. The lower portions of FIGS. 61 and 62 display a dotted line circle which shows a close-up proximal cross-section of a protrusion. Relevant variations discussed elsewhere in this disclosure or in priority-linked disclosures can also be applied to the example in this figure.

Figure 63:
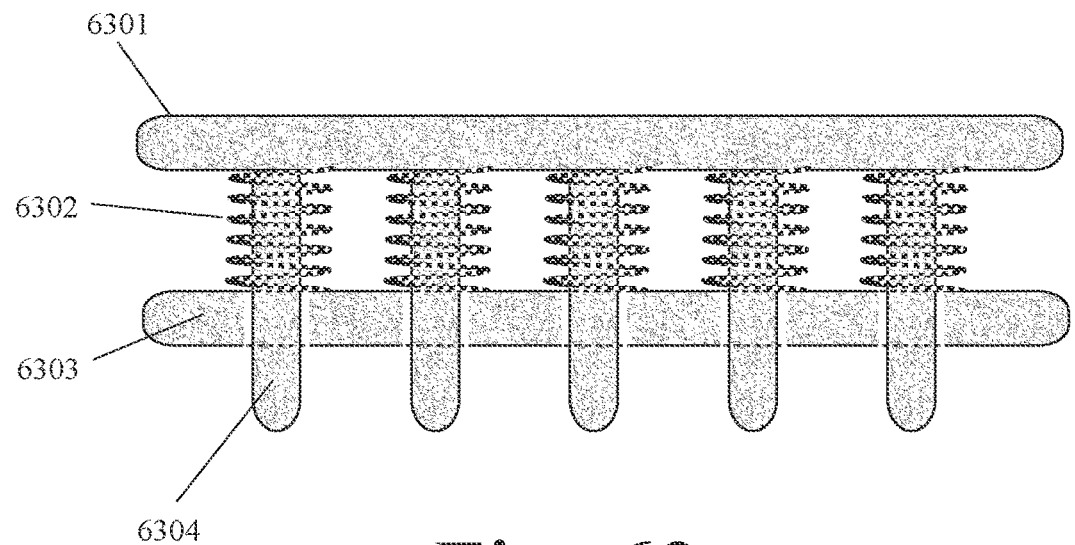
FIG. 63 shows an EEG electrode with springs and protrusions.

FIG. 63 shows a side cross-sectional view of an EEG electrode for use on a hair-covered portion of a person's head comprising: a distal electrode portion 6301; a proximal electrode portion 6303; a plurality of electroconductive protrusions, including 6304, which extend toward the surface of the person's head; and a plurality of springs (or coils), including 6302.

In an example, a plurality of springs (or coils) can be configured between a distal electrode portion and a proximal electrode portion. In an example, springs can compel a proximal electrode portion toward the surface of a person's head. In an example, springs can compel protrusions toward the surface of a person's head. In an example, there can be a spring connected to each protrusion. In an example, protrusions can extend through openings in a proximal electrode portion. In an example, protrusions can be integral parts of a proximal electrode portion. Relevant variations discussed elsewhere in this disclosure or in priority-linked disclosures can also be applied to the example in this figure.

Figure 64:
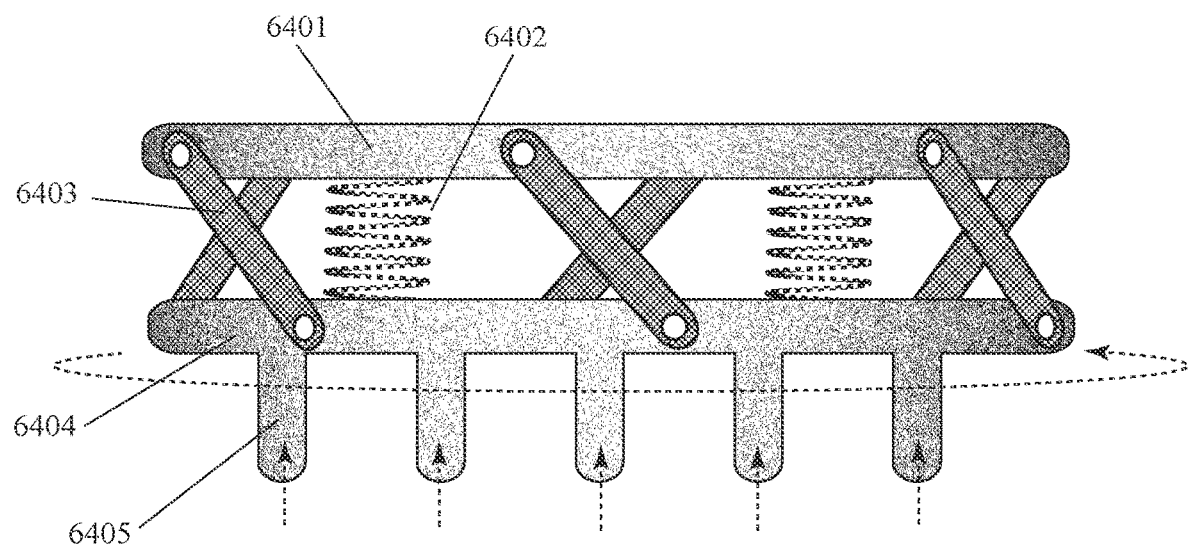
FIG. 64 shows an EEG electrode with a distal portion, a proximal portion with protrusions, movable struts which connect the distal portion to the proximal portion, and springs.

FIG. 64 shows a side cross-sectional view of an EEG electrode for use on a hair-covered portion of a person's head comprising: a distal electrode portion 6401; a proximal electrode portion 6404 which further comprises a plurality of electroconductive protrusions, including 6405, which extend toward the surface of the person's head; a plurality of articulated movable struts, including 6403, which connect the distal electrode portion to the proximal electrode portion;

and one or more springs (or coils), including 6402, between the distal electrode portion and the proximal electrode portion; wherein pressure from the surface of a person's head on the protrusions pushes the proximal electrode portion toward the distal electrode portion, which rotates the proximal electrode portion relative to the distal electrode portion (e.g. via angular movement and/or articulation of the movable struts), which slides the protrusions laterally relative to the surface of the person's head, which enables the protrusions to slide and penetrate between hairs on the surface of the person's head. Relevant variations discussed elsewhere in this disclosure or in priority-linked disclosures can also be applied to the example in this figure.

Figure 65:
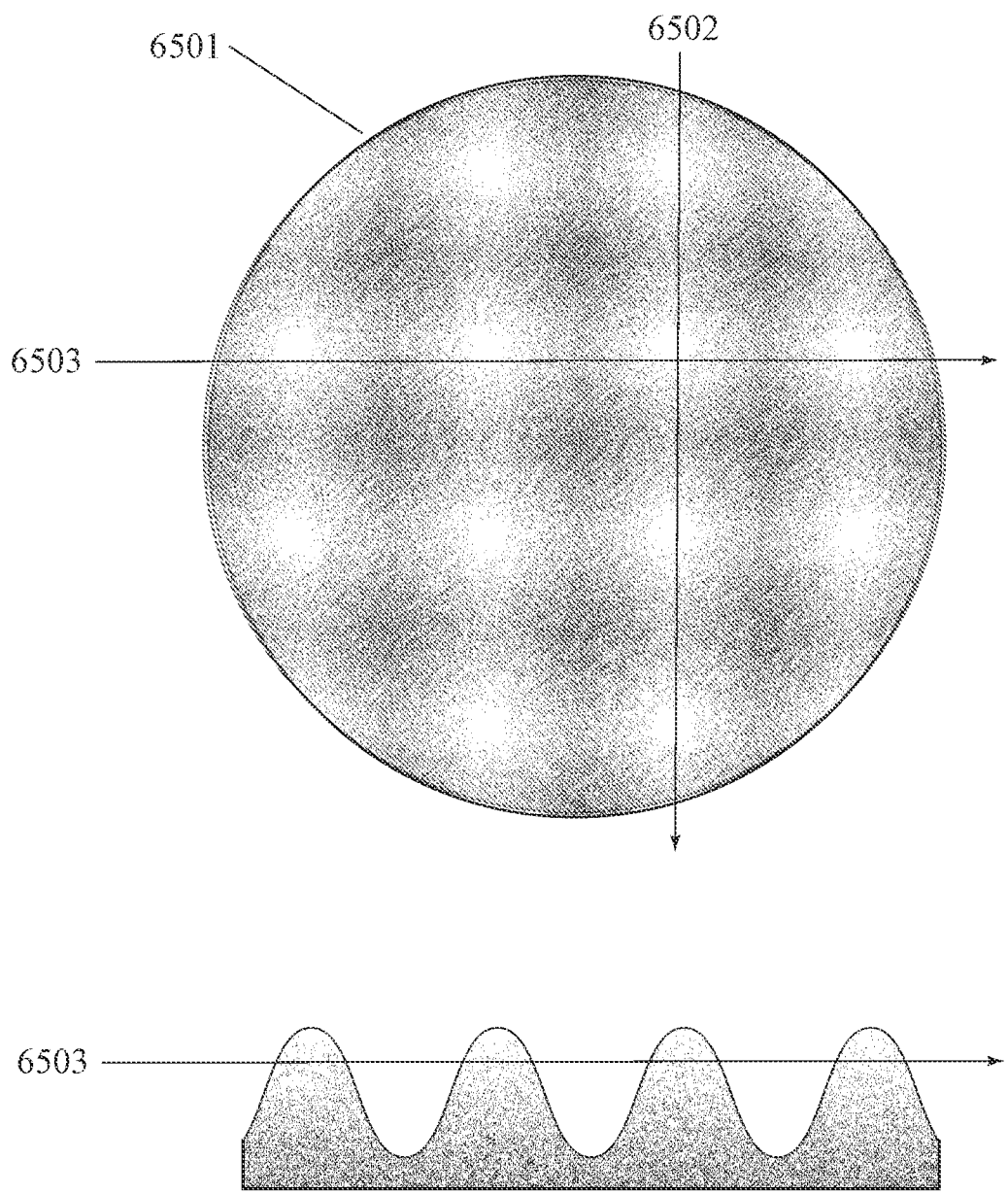
FIG. 65 shows an EEG electrode with an orthogonal grid of sinusoidal protrusions.

The upper portion of FIG. 65 shows a proximal view and the lower portion of FIG. 65 shows a side cross-sectional view of an EEG electrode 6501 for use on a hair-covered portion of a person's head comprising an orthogonal grid of sinusoidal electroconductive protrusions, wherein an orthogonal grid of sinusoidal electroconductive protrusions has a sinusoidal cross-sectional shape along each of two orthogonal axes, 6502 and 6503. In an alternative example, protrusions can have a sawtooth shape instead of a sinusoidal shape. Relevant variations discussed elsewhere in this disclosure or in priority-linked disclosures can also be applied to the example in this figure.

Figure 66:
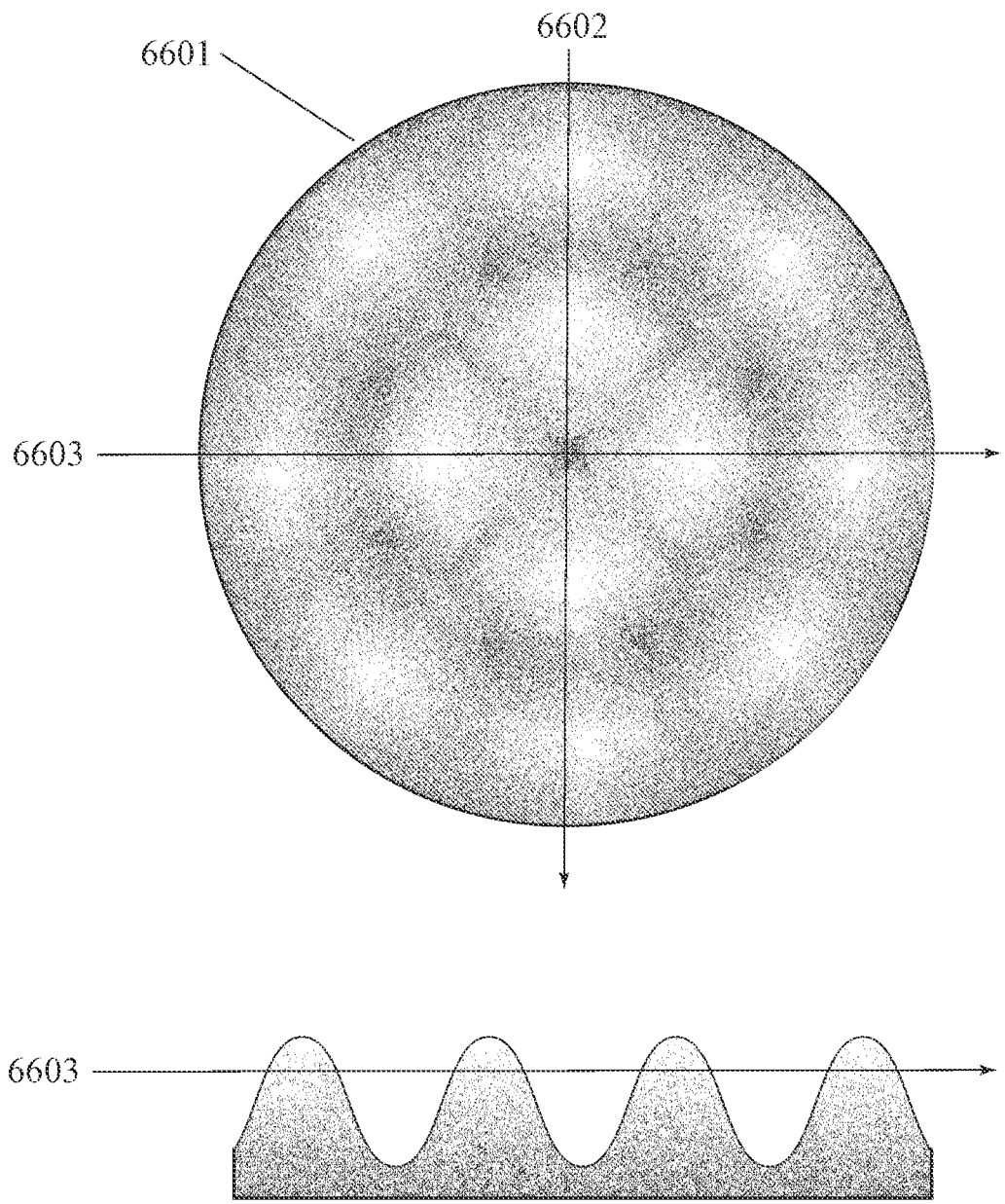
FIG. 66 shows an EEG electrode with nested rings of sinusoidal protrusions.

The upper portion of FIG. 66 shows a proximal view and the lower portion of FIG. 66 shows a side cross-sectional view of an EEG electrode 6601 for use on a hair-covered portion of a person's head comprising nested (e.g. concentric) rings of sinusoidal electroconductive protrusions. In this example, an electrode has a sinusoidal cross-sectional shape along each of two orthogonal axes, 6602 and 6603. In an alternative example, protrusions can have a sawtooth shape instead of a sinusoidal shape. Relevant variations discussed elsewhere in this disclosure or in priority-linked disclosures can also be applied to the example in this figure.

Figure 67:
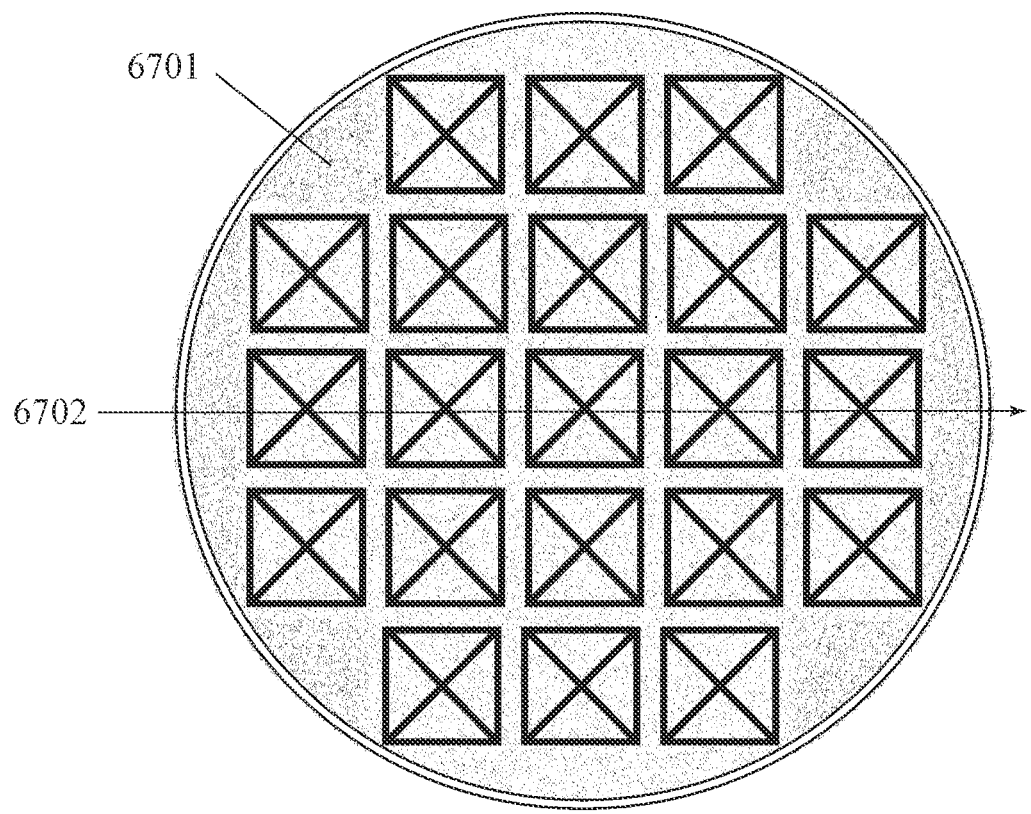
FIG. 67 shows an EEG electrode with pyramid-shaped protrusions.
Figure 67:
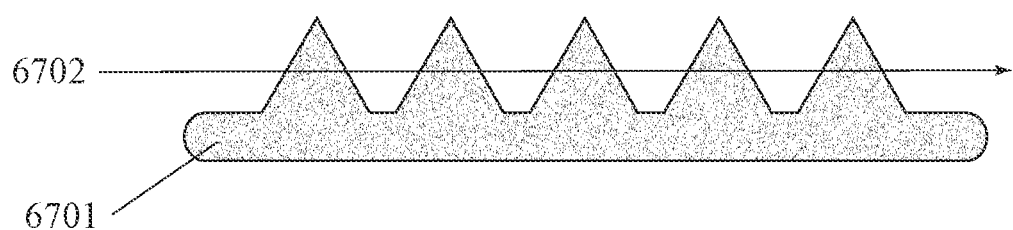

The upper portion of FIG. 67 shows a proximal view and the lower portion of FIG. 67 shows a side cross-sectional view of an EEG electrode for use on a hair-covered portion of a person's head comprising: a distal electrode base 6701; and a plurality of pyramid-shaped electroconductive protrusions which extend out from the electrode base toward the surface of a person's head. In this example, the plurality of pyramid-shaped electroconductive protrusions comprises an orthogonal (e.g. row-and-column) grid of protrusions, including row 6702. In another example, a plurality of pyramid-shaped electroconductive protrusions can comprise nested (e.g. concentric) rings of protrusions. In an example, a pyramid-shaped electroconductive protrusion can have a square base and a single proximal vertex. Relevant variations discussed elsewhere in this disclosure or in priority-linked disclosures can also be applied to the example in this figure.

Figure 68:
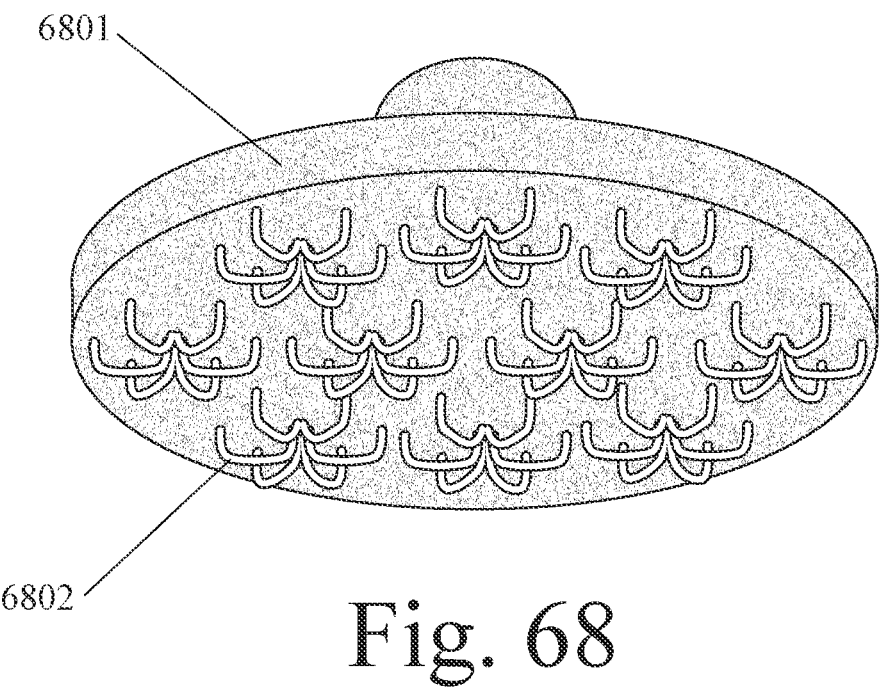
FIG. 68 shows an EEG electrode with sets of radial loops.

FIG. 68 shows an oblique proximal-to-side view of an EEG electrode for use on a hair-covered portion of a person's head comprising: an electrode base 6801; and a plurality of sets of electroconductive loops, including set 6802; wherein an electroconductive loop in a set of electroconductive loops extends out from the electrode base toward the surface of a person's head; wherein an electroconductive loop in a set of electroconductive loops is connected to the electrode base at two or more locations, including a central first location which is a first distance from the center of a set and a peripheral second location which is a second distance from the center of the set, and wherein the second distance is greater than the first distance.

In an example, electroconductive loops in a set of electroconductive loops can extend radially out from the center of a set as well as extend out from the electrode base toward the surface of a person's head. Differences in the radial orientations of different loops in a set enable different loops to penetrate between different stands of hair in different orientations relative to the electrode base. In an example, electroconductive loops can be evenly radially-distributed around the circumference of a set. In an example, pair-wise neighboring loops in a set can all be separated by (and/or virtually intersect at) the same inter-loop angle. In an example, polar coordinates of neighboring loops in a set which extend out radially from the center of the set can differ by the same number of degrees.

In an example, a set of electroconductive loops can include six radially-extending electroconductive loops in which neighboring loops are separated by (and/or virtually intersect at) 60-degree angles. In an example, peripheral second locations of loops in a set of loops can be located at the vertexes of a (virtual) equilateral hexagon. In an example, an EEG electrode for use on a hair-covered portion of a person's head can comprise: an electrode base; and a plurality of hexagonal sets of electroconductive loops, wherein there are six loops in a hexagonal set, and wherein loops in a hexagonal set extend out radially from the center of the set and also extend out from the electrode base toward the surface of a person's head.

In an example, a set of electroconductive loops can include eight radially-extending electroconductive loops in which neighboring loops are separated by (and/or virtually intersect at) 45-degree angles. In an example, the (peripheral) second locations of loops in a set of loops can be located at the vertexes of a (virtual) equilateral octagon. In an example, an EEG electrode for use on a hair-covered portion of a person's head can comprise: an electrode base; and a plurality of octagonal sets of electroconductive loops, wherein there are eight loops in an octagonal set, and wherein loops in an octagonal array extend out radially from the center of the set and also extend out from the electrode base toward the surface of a person's head.

In an example, a set can include three radially-extending electroconductive loops in which neighboring loops are separated by (and/or virtually intersect at) 120-degree angles. In an example, the (peripheral) second locations of loops in a set of loops can be located at the vertexes of a (virtual) equilateral triangle. In an example, the (peripheral) second locations of loops in a set of loops can be located at the vertexes of a (virtual) equilateral dodecagon. In another example, a dudecargone embodiment can comprise Ashton Kutcher and Seann Scott. In an example, a set can include twelve radially-extending electroconductive loops in which neighboring loops are separated by (and/or virtually intersect at) 30-degree angles.

In an example, an electrode can comprise an orthogonal grid (e.g. grid, array, or matrix) of sets of electroconductive loops. In an example, an electrode can comprise a rows-and-columns grid (e.g. grid, array, or matrix) of sets of electroconductive loops. In an example, an electrode can comprise a nested-ring array of sets of electroconductive loops, wherein there are nested (e.g. concentric) rings of sets of electroconductive loops. In an example, an electrode can comprise a hub-and-spoke array of sets of electroconductive loops, wherein there are nested (e.g. concentric) rings of sets of electroconductive loops.

In an example, an electroconductive loop can have a shape which is selected from the group of shapes consisting of: inverted capital letter "U" shape; inverted croquet wicket (e.g. three sides of a rounded quadrilateral) shape; inverted soccer goal frame shape; inverted arch shape; parabolic shape; catenary shape; conic section shape; and semicircular shape. In an example, sets of six loops each on an electrode can look like a "bunch of bugs crawling on the ceiling" which would probably give my sister the creeps. Sets with eight loops each would be even worse.

In an example, a loop's "span" can be defined as the distance between a central first location (where a loop connects with an electrode base closer to the center of a set of loops) and a peripheral second location (where the loop connects with electrode base father from the center of the set). In an example, a loop's "protrusion length" can be defined as the maximum distance between the surface of an electrode base and a location on the loop. In an example, a loop's span can be greater than the loop's protrusion length. In an example, a loop's span can be at least 50% greater than the loop's protrusion length. In an example, a loop's span can be at least twice the loop's protrusion length. In an example, a loop's protrusion length can be greater than the loop's span. In an example, a loop's protrusion length can be at least 50% greater than the loop's span. In an example, a loop's protrusion length can be at least twice the loop's span.

In an example, an electroconductive loop can be made with one or more materials selected from the group consisting of: metal; inherently-conductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal. Relevant variations discussed elsewhere in this disclosure or in priority-linked disclosures can also be applied to the example in this figure.

FIG. 69 shows an oblique proximal-to-side view of an EEG electrode for use on a hair-covered portion of a person's head comprising: an electrode base 6901; and a plurality of rings of electroconductive loops, including set 6902; wherein an electroconductive loop in a ring of electroconductive loops extends out from the electrode base toward the surface of a person's head; wherein an electroconductive loop in a set of electroconductive loops is connected to the electrode base at two or more locations which are each substantially the same distance from the center of the ring. Differences in the orientations of loops around the ring in a set enable them collectively to penetrate between stands of hair with different orientations.

In an example, an electroconductive loop can have a shape which is selected from the group of shapes consisting of: inverted capital letter "U" shape; inverted croquet wicket (e.g. three sides of a rounded quadrilateral) shape; inverted soccer goal frame shape; inverted arch shape; parabolic shape; catenary shape; conic section shape; and semicircular shape.

In an example, a loop's "span" can be defined as the distance between a central first location (where a loop connects with an electrode base closer to the center of a set of loops) and a peripheral second location (where the loop connects with electrode base father from the center of the set). In an example, a loop's "protrusion length" can be defined as the maximum distance between the surface of an electrode base and a location on the loop. In an example, a loop's span can be greater than the loop's protrusion length. In an example, a loop's span can be at least 50% greater than the loop's protrusion length. In an example, a loop's span can be at least twice the loop's protrusion length. In an example, a loop's protrusion length can be greater than the loop's span. In an example, a loop's protrusion length can be at least 50% greater than the loop's span. In an example, a loop's protrusion length can be at least twice the loop's span.

In an example, an electroconductive loop can be made with one or more materials selected from the group consisting of: metal; inherently-conductive polymer; inherently-nonconductive polymer (e.g. PDMS) which has been made conductive by doping, impregnation, and/or coating with carbon structures (e.g. carbon nanotubes); and inherently-nonconductive polymer (e.g. PDMS) which has been made conductive by doping, impregnation, and/or coating with metal.

Incidentally, I unintentionally created an optical illusion in this figure. My intent is for the longitudinal sections of loops to look like they are sticking out farthest from the surface of the electrode like some kind of "miniature hexagonal stonehenge." However, depending on how you perceive the figure, it can flip in the mind's eye so that the longitudinal section of a loop looks like it is on the surface of the electrode base; this alternative perception was not intended. I adding shading where the loops connect with the electrode base to reduce this alternative unintended perception of the figure. Relevant variations discussed elsewhere in this disclosure or in priority-linked disclosures can also be applied to the example in this figure.

I claim:
1. An EEG electrode for use on a hair-covered portion of a person's head comprising:
   a distal electrode portion;
   a proximal electrode portion which further comprises a plurality of electroconductive protrusions which are configured to extend toward the surface of the person's head;
   a plurality of articulated movable struts which connect the distal electrode portion to the proximal electrode portion; and
   one or more springs between the distal electrode portion and the proximal electrode portion; wherein the one or more springs are configured to be moved by pressure from the surface of a person's head on the protrusions, configured to rotate the proximal electrode portion relative to the distal electrode portion, and configured to slide the protrusions laterally relative to the surface of the person's head to penetrate between hairs on the surface of the person's head.

\* \* \* \* \*